US011423640B2

(12) United States Patent
Harrison et al.

(10) Patent No.: US 11,423,640 B2
(45) Date of Patent: Aug. 23, 2022

(54) METHODS AND SYSTEMS FOR AN AUTOMATED DESIGN, FULFILLMENT, DEPLOYMENT AND OPERATION PLATFORM FOR LIGHTING INSTALLATIONS

(71) Applicant: KORRUS, INC., Los Angeles, CA (US)

(72) Inventors: Benjamin James Harrison, Pasadena, CA (US); Shruti Koparkar, Pasadena, CA (US); Mark Reynoso, Encino, CA (US); Paul Pickard, Acton, CA (US); Raghuram L. V. Petluri, Cerritos, CA (US); Gary Vick, Northridge, CA (US); Andrew Villegas, Los Angeles, CA (US)

(73) Assignee: KORRUS, INC., Los Angeles, CA (US)

(*) Notice: Subject to any disclaimer, the term of this patent is extended or adjusted under 35 U.S.C. 154(b) by 0 days.

(21) Appl. No.: 16/664,213

(22) Filed: Oct. 25, 2019

(65) Prior Publication Data

US 2020/0066001 A1 Feb. 27, 2020

Related U.S. Application Data

(63) Continuation of application No. 16/601,711, filed on Oct. 15, 2019, which is a continuation of application No. PCT/US2018/029380, filed on Apr. 25, 2018.
(Continued)

(51) Int. Cl.
*G06T 15/10* (2011.01)
*G06T 19/20* (2011.01)
(Continued)

(52) U.S. Cl.
CPC ............ *G06V 10/751* (2022.01); *F21V 21/15* (2013.01); *G05B 13/0265* (2013.01);
(Continued)

(58) Field of Classification Search
USPC ......................................................... 348/135
See application file for complete search history.

(56) References Cited

U.S. PATENT DOCUMENTS 5,307,295 A 4/1994 Taylor
5,933,146 A 8/1999 Wrigley
(Continued)

FOREIGN PATENT DOCUMENTS

JP 2016086039 A 5/2016
WO 2014064629 A1 5/2014
(Continued)

OTHER PUBLICATIONS

PCT/US2018/029380, specification published Nov. 1, 2018, 263pp.
(Continued)

*Primary Examiner* — Christopher S Kelley
*Assistant Examiner* — Ana Picon-Feliciano
(74) *Attorney, Agent, or Firm* — Jay M. Brown

(57) ABSTRACT

A platform for design of a lighting installation generally includes an automated search engine for retrieving and storing a plurality of lighting objects in a lighting object library and a lighting design environment providing a visual representation of a lighting space containing lighting space objects and lighting objects. The visual representation is based on properties of the lighting space objects and lighting objects obtained from the lighting object library. A plurality of aesthetic filters is configured to permit a designer in a design environment to adjust parameters of the plurality of
(Continued)

lighting objects handled in the design environment to provide a desired collective lighting effect using the plurality of lighting objects.

20 Claims, 46 Drawing Sheets

Related U.S. Application Data

(60) Provisional application No. 62/562,714, filed on Sep. 25, 2017, provisional application No. 62/491,137, filed on Apr. 27, 2017.

(51) Int. Cl.
| | |
|---|---|
| *H04N 5/232* | (2006.01) |
| *G06F 16/953* | (2019.01) |
| *H05B 45/10* | (2020.01) |
| *G05B 13/02* | (2006.01) |
| *F21V 21/15* | (2006.01) |
| *G06F 3/01* | (2006.01) |
| *G06N 3/04* | (2006.01) |
| *G06F 3/04847* | (2022.01) |
| *G06V 10/75* | (2022.01) |
| *G06T 7/55* | (2017.01) |
| *G06T 7/73* | (2017.01) |
| *G06F 16/51* | (2019.01) |
| *G06N 20/00* | (2019.01) |
| *G06K 9/62* | (2022.01) |
| *G06N 5/04* | (2006.01) |
| *G06F 30/20* | (2020.01) |
| *G06F 30/13* | (2020.01) |
| *G06T 15/50* | (2011.01) |
| *G16H 50/20* | (2018.01) |
| *H05B 47/105* | (2020.01) |
| *H05B 47/175* | (2020.01) |
| *H05B 45/20* | (2020.01) |
| *H05B 47/11* | (2020.01) |
| *G06T 19/00* | (2011.01) |
| *G06T 7/00* | (2017.01) |
| *H04N 5/247* | (2006.01) |
| *G06T 15/08* | (2011.01) |
| *G06T 7/90* | (2017.01) |
| *G06F 16/583* | (2019.01) |

(52) U.S. Cl.
CPC ............. *G06F 3/011* (2013.01); *G06F 16/51* (2019.01); *G06F 16/5854* (2019.01); *G06F 16/953* (2019.01); *G06F 30/13* (2020.01); *G06F 30/20* (2020.01); *G06K 9/6215* (2013.01); *G06N 5/04* (2013.01); *G06N 5/047* (2013.01); *G06N 20/00* (2019.01); *G06T 7/55* (2017.01); *G06T 7/73* (2017.01); *G06T 7/90* (2017.01); *G06T 7/97* (2017.01); *G06T 15/08* (2013.01); *G06T 15/10* (2013.01); *G06T 15/50* (2013.01); *G06T 15/506* (2013.01); *G06T 19/006* (2013.01); *G06T 19/20* (2013.01); *G16H 50/20* (2018.01); *H04N 5/23229* (2013.01); *H04N 5/247* (2013.01); *H05B 45/10* (2020.01); *H05B 45/20* (2020.01); *H05B 47/105* (2020.01); *H05B 47/11* (2020.01); *H05B 47/175* (2020.01); *G06F 3/04847* (2013.01); *G06N 3/0409* (2013.01); *G06T 2200/24* (2013.01); *G06T 2207/20081* (2013.01); *G06T 2210/04* (2013.01); *G06T 2210/56* (2013.01); *G06T 2215/12* (2013.01); *G06T 2215/16* (2013.01); *G06T 2219/2012* (2013.01); *G06T 2219/2024* (2013.01)

(56) References Cited

U.S. PATENT DOCUMENTS

| | | |
|---|---|---|
| 6,166,496 A | 12/2000 | Lys |
| 6,211,626 B1 | 4/2001 | Lys |
| 6,292,901 B1 | 9/2001 | Lys |
| 6,445,814 B2 | 9/2002 | Iijima |
| 7,092,563 B2 | 8/2006 | Shiratani |
| 7,132,804 B2 | 11/2006 | Lys |
| 7,180,252 B2 | 2/2007 | Lys |
| 7,202,613 B2 | 4/2007 | Morgan |
| 7,221,104 B2 | 5/2007 | Lys |
| 7,221,374 B2 | 5/2007 | Dixon |
| 7,308,296 B2 | 12/2007 | Lys |
| 7,352,339 B2 | 4/2008 | Morgan |
| 7,353,071 B2 | 4/2008 | Blackwell |
| 7,453,217 B2 | 11/2008 | Lys |
| 7,495,671 B2 | 2/2009 | Chemel |
| 7,525,254 B2 | 4/2009 | Lys |
| 7,598,686 B2 | 10/2009 | Lys |
| 7,674,018 B2 | 3/2010 | Holder |
| 7,692,128 B2 | 4/2010 | Takizawa |
| 7,797,117 B1 | 9/2010 | Gordin |
| 7,845,823 B2 | 12/2010 | Mueller |
| 7,942,559 B2 | 5/2011 | Holder |
| 8,134,461 B2 | 3/2012 | Van Doorn |
| 8,138,000 B2 | 3/2012 | Keller |
| 8,432,438 B2 | 4/2013 | Ryan |
| 8,436,541 B2 | 5/2013 | Olson |
| 8,816,602 B2 | 8/2014 | Van Doorn |
| 8,847,257 B2 | 9/2014 | Keller |
| 8,905,597 B2 | 12/2014 | Holder |
| 8,938,468 B2 | 1/2015 | Morgan |
| 9,007,495 B1 | 4/2015 | Chin |
| 9,273,830 B2 | 3/2016 | Negley |
| 9,345,091 B2 | 5/2016 | Pickard |
| 9,554,447 B2 | 1/2017 | Rains, Jr. |
| 9,686,477 B2 | 6/2017 | Walters |
| 9,706,619 B2 | 7/2017 | Lim |
| 9,750,112 B2 | 8/2017 | Deese |
| 9,795,004 B2 | 10/2017 | Blum |
| 9,838,008 B2 | 12/2017 | Lark, Jr. |
| 9,857,867 B2 | 1/2018 | Kumar |
| 9,888,546 B2 | 2/2018 | Deese |
| 9,942,960 B2 | 4/2018 | Tylicki |
| 10,015,868 B2 | 7/2018 | Quilici |
| 10,076,011 B1 | 9/2018 | Amidi |
| 10,161,610 B2 | 12/2018 | Quilici |
| 10,171,780 B2 | 1/2019 | Shimizu |
| 10,210,664 B1 | 2/2019 | Chaturvedi |
| 10,244,228 B2 | 3/2019 | Millett |
| 10,375,794 B2 | 8/2019 | Wu |
| 10,420,185 B2 | 9/2019 | Biery |
| 10,465,869 B2 | 11/2019 | Keller |
| 10,495,295 B2 | 12/2019 | Van De Ven |
| 10,602,599 B2 | 3/2020 | Wouhaybi |
| 10,605,591 B2 | 3/2020 | Konno |
| 10,772,174 B2 | 9/2020 | Weaver |
| 10,772,177 B2 | 9/2020 | Mason |
| 2001/0021011 A1* | 9/2001 | Ono .................. G06T 7/586 356/3 |
| 2002/0176015 A1 | 11/2002 | Lichtfuss |
| 2002/0196415 A1* | 12/2002 | Shiratani ............ H04N 13/207 353/31 |
| 2005/0007035 A1 | 1/2005 | Sloan et al. |
| 2005/0205878 A1 | 9/2005 | Kan |
| 2007/0268585 A1 | 11/2007 | Santoro |
| 2008/0170755 A1 | 7/2008 | Nasser |
| 2008/0185969 A1 | 8/2008 | Vegter |
| 2009/0185173 A1 | 7/2009 | Ashdown |
| 2010/0084996 A1 | 4/2010 | Van De Sluis |
| 2010/0134050 A1* | 6/2010 | Engellen ............ H05B 47/175 315/312 |
| 2010/0245270 A1 | 9/2010 | Nako |

(56) References Cited

U.S. PATENT DOCUMENTS

| | | | |
|---|---|---|---|
| 2010/0290698 A1* | 11/2010 | Freedman | G06K 9/3241 382/154 |
| 2011/0026253 A1 | 2/2011 | Gill | |
| 2011/0035404 A1 | 2/2011 | Morgan | |
| 2011/0051420 A1 | 3/2011 | Gill | |
| 2011/0102681 A1 | 5/2011 | Lee et al. | |
| 2011/0169413 A1 | 7/2011 | Wendt et al. | |
| 2011/0307112 A1 | 12/2011 | Barrilleaux | |
| 2012/0050254 A1 | 3/2012 | Gordin | |
| 2012/0095745 A1 | 4/2012 | Le Guevel-Scholtens | |
| 2012/0230606 A1 | 9/2012 | Sugiyama | |
| 2012/0286699 A1 | 11/2012 | Yan et al. | |
| 2013/0009549 A1 | 1/2013 | Vinkenvleugel | |
| 2013/0009560 A1 | 1/2013 | Takeda et al. | |
| 2013/0129349 A1 | 5/2013 | Maxik et al. | |
| 2013/0134902 A1 | 5/2013 | Mahale | |
| 2013/0141009 A1 | 6/2013 | Jin | |
| 2013/0141013 A1 | 6/2013 | Kodama | |
| 2014/0009070 A1 | 1/2014 | Bouffay | |
| 2014/0035472 A1 | 2/2014 | Raj | |
| 2014/0070706 A1 | 3/2014 | Fushimi | |
| 2014/0139120 A1 | 5/2014 | Chien | |
| 2014/0175875 A1 | 6/2014 | Newman, Jr. | |
| 2014/0184100 A1 | 7/2014 | Yamada et al. | |
| 2014/0210357 A1 | 7/2014 | Yan | |
| 2014/0232297 A1 | 8/2014 | Chobot | |
| 2014/0265882 A1 | 9/2014 | Laski | |
| 2014/0304104 A1 | 10/2014 | Ladue | |
| 2014/0312780 A1 | 10/2014 | Vissenberg | |
| 2015/0061539 A1 | 3/2015 | Hirayama | |
| 2015/0126806 A1 | 5/2015 | Barroso | |
| 2015/0130355 A1 | 5/2015 | Rains, Jr. et al. | |
| 2015/0145431 A1 | 5/2015 | Ferrier | |
| 2015/0148871 A1 | 5/2015 | Maxik | |
| 2015/0189723 A1 | 7/2015 | Ogawa | |
| 2015/0205508 A1 | 7/2015 | Kawasaki | |
| 2015/0248228 A1 | 9/2015 | Seuntiens | |
| 2015/0278896 A1 | 10/2015 | Seuntiens | |
| 2015/0286724 A1 | 10/2015 | Knaapen | |
| 2015/0296589 A1 | 10/2015 | Melanson | |
| 2015/0296594 A1 | 10/2015 | Blum et al. | |
| 2015/0379594 A1 | 12/2015 | Sallee | |
| 2015/0382427 A1 | 12/2015 | Eisele et al. | |
| 2016/0063215 A1 | 3/2016 | Zamer | |
| 2016/0088708 A1 | 3/2016 | Anthony | |
| 2016/0128155 A1 | 5/2016 | Petluri | |
| 2016/0132030 A1 | 5/2016 | Marti | |
| 2016/0146927 A1* | 5/2016 | Hudman | G01S 17/894 356/5.01 |
| 2016/0169798 A1 | 6/2016 | Kostka et al. | |
| 2016/0227618 A1 | 8/2016 | Meerbeek | |
| 2016/0254416 A1 | 9/2016 | Cheng | |
| 2016/0270718 A1 | 9/2016 | Heneghan | |
| 2016/0291703 A1 | 10/2016 | Tokutake | |
| 2016/0324442 A1 | 11/2016 | Zdeblick | |
| 2016/0327227 A1 | 11/2016 | Green, Jr. | |
| 2016/0335698 A1 | 11/2016 | Jones | |
| 2016/0366746 A1 | 12/2016 | Van De Ven | |
| 2017/0064790 A1 | 3/2017 | Clark | |
| 2017/0078513 A1 | 3/2017 | Chang | |
| 2017/0127489 A1 | 5/2017 | Zulim | |
| 2017/0140145 A1 | 5/2017 | Shah | |
| 2017/0164440 A1 | 6/2017 | Hu | |
| 2017/0181252 A1 | 6/2017 | Wouhaybi | |
| 2017/0245340 A1 | 8/2017 | Chen | |
| 2017/0257925 A1 | 9/2017 | Forbis | |
| 2017/0269344 A1 | 9/2017 | Kato | |
| 2017/0281967 A1 | 10/2017 | Maxik | |
| 2017/0301143 A1 | 10/2017 | Gorumkonda | |
| 2017/0336253 A1 | 11/2017 | Barnard | |
| 2017/0349286 A1 | 12/2017 | Fehringer | |
| 2018/0077770 A1 | 3/2018 | Sooch | |
| 2018/0160490 A1 | 6/2018 | Li | |
| 2018/0160501 A1 | 6/2018 | Magielse | |
| 2018/0190011 A1 | 7/2018 | Platt | |
| 2018/0210185 A1 | 7/2018 | Kato | |
| 2018/0213206 A1 | 7/2018 | Price | |
| 2018/0235039 A1 | 8/2018 | Krajnc | |
| 2018/0279429 A1 | 9/2018 | Sadwick | |
| 2018/0324924 A1 | 11/2018 | Van De Sluis | |
| 2019/0019324 A1 | 1/2019 | Wu | |
| 2019/0057423 A1 | 2/2019 | Sallee | |
| 2019/0209806 A1 | 7/2019 | Allen | |
| 2019/0215931 A1 | 7/2019 | Magielse | |
| 2019/0254142 A1 | 8/2019 | Petluri | |
| 2019/0289697 A1 | 9/2019 | Meerbeek | |
| 2019/0340306 A1 | 11/2019 | Harrison | |
| 2019/0353839 A1 | 11/2019 | Krames | |
| 2020/0003944 A1 | 1/2020 | Di Trapani | |
| 2020/0045786 A1 | 2/2020 | Biery | |
| 2020/0045796 A1 | 2/2020 | Deixler | |
| 2020/0057828 A1 | 2/2020 | Harrison | |
| 2020/0058401 A1 | 2/2020 | Harrison | |
| 2020/0060007 A1 | 2/2020 | Harrison | |
| 2020/0066001 A1 | 2/2020 | Harrison | |
| 2020/0068686 A1 | 2/2020 | Harrison | |
| 2020/0068687 A1 | 2/2020 | Harrison | |
| 2020/0103102 A1 | 4/2020 | Harrison | |
| 2020/0104036 A1 | 4/2020 | Harrison | |
| 2020/0104432 A1 | 4/2020 | Harrison | |
| 2020/0104541 A1 | 4/2020 | Harrison | |
| 2020/0105054 A1 | 4/2020 | Harrison | |
| 2020/0107423 A1 | 4/2020 | Harrison | |
| 2020/0107424 A1 | 4/2020 | Harrison | |
| 2020/0110845 A1 | 4/2020 | Harrison | |
| 2020/0110910 A1 | 4/2020 | Harrison | |
| 2020/0134244 A1 | 4/2020 | Harrison | |
| 2020/0184122 A1 | 6/2020 | Harrison | |
| 2020/0184123 A1 | 6/2020 | Harrison | |
| 2020/0209712 A1 | 7/2020 | Hu | |
| 2020/0221022 A1 | 7/2020 | Wheeler | |
| 2021/0195706 A1 | 6/2021 | Vissenberg | |
| 2021/0262636 A1 | 8/2021 | Pyshos | |

FOREIGN PATENT DOCUMENTS

| | | |
|---|---|---|
| WO | 2018137868 A1 | 8/2018 |
| WO | 2018200685 A2 | 11/2018 |
| WO | 200685 A3 | 12/2018 |
| WO | 200685 A4 | 2/2019 |
| WO | 2019200685 | 10/2019 |

OTHER PUBLICATIONS

PCT/US2018/029380, Written Opinion of the International Searching Authority dated Nov. 8, 2018, 69pp.

PCT/US2018/029380, International Search Report dated Nov. 16, 2018, 12pp.

PCT/US2018/029380, International Preliminary Report on Patentability dated Oct. 29, 2019, 70pp.

PCT/US2018/029380, International Search Report, dated Nov. 9, 2018, 12pp.

U.S. Department of Health & Human Services/U.S. Food & Drug Administration, The BEST Resource: Harmonizing Biomarker Terminology, Jun. 2016, https://www.fda.gov/media/99221/download, 2pp.

Harrison et al, U.S. Appl. No. 16/702,727, filed Dec. 4, 2019, entitled "Methods and Systems for an Automated Design, Fulfillment, Deployment and Operation Platform for Lighting Installations," 266 pp.

Harrison et al, U.S. Appl. No. 16/702,825, dated Dec. 4, 2019, entitled "Methods and Systems for an Automated Design, Fulfillment, Deployment and Operation Platform for Lighting Installations," 266 pp.

Newsham et al., "Preferred surface luminances in offices, by evolution", Journal of Illuminating Engineering Society vol. 33, No. 1 (2004); pp. 14-29.

Totir, "The potential of computationally rendered images for the evaluation of lighting quality in interior spaces," Iowa State University Capstones, Theses and Dissertations, (2007), 90 pages.

Zhao et al., "A Multidimensional Continuous Contextual Lighting

(56) References Cited

OTHER PUBLICATIONS

Control System Using Google Glass," BuildSys'15, (Nov. 2015), pp. 235-244.
Kim et al., "An Intelligent Smart Home Control Using Body Gestures," IEEE 2006 International Conference on Hybrid Information Technology, (Nov. 9-11, 2006), 8 pp.
Califf, Robert, "Biomarker definitions and their applications," Experimental Biology and Medicine, 2018, vol. 243, pp. 213-221.
Strimbu and Tavel, "What are Biomarkers?", Curr. Opin. HIV AIDS, Nov. 2010; 5(6); pp. 463-466.
Sano et al., "Recognizing Academic Performance, Sleep Quality, Stress Level, and Mental Health using Personality Traits, Wearable Sensors and Mobile Phones", Oct. 19, 2015, 2015 IEEE 12th International Conference on Wearable and Implantable Body Sensor Networks (BSN), pp. 1-6 (Year: 2015).
Newsham et al., "Lighting quality research using rendered images of offices," Lighting Research & Technology, vol. 37, No. 2(2005), pp. 93-112.
Rohmer, Kai, et al. "Interactive near-field illumination for photo-realistic augmented reality on mobile devices." 2014 IEEE International Symposium on Mixed and Augmented Reality (ISMAR). IEEE, 2014. (Year: 2014).
Take3, "Area Light Distribution Pattern Types", Feb. 13, 2016, URL: https://www.takethreelighting.com/light-distribution-patterns.htmlpp 1-4. (Year: 2016).
Pritchard, E. H., and R. H. Simons High-speed photometer for measuring light intensity distributions. Lighting Research & Technology 24.2 (1992): 107-111. (Year: 1992).

\* cited by examiner

Requirements System 106

| Lighting Requirements 108 | Logistical Requirements 110 | Functional Requirements 112 | Control Requirements 114 | Health Requirements 126 |

FIG. 2

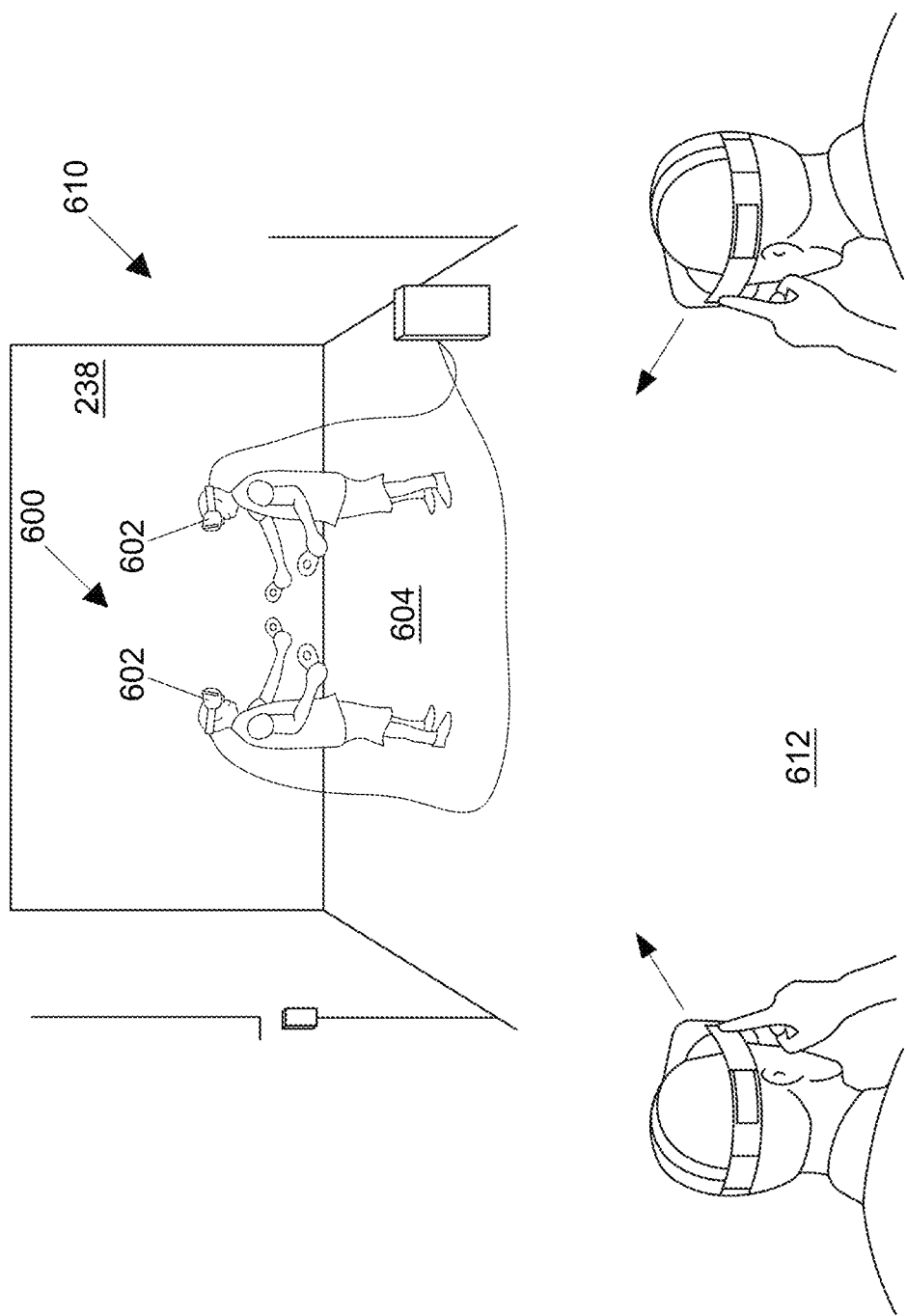

METHODS AND SYSTEMS FOR AN AUTOMATED DESIGN, FULFILLMENT, DEPLOYMENT AND OPERATION PLATFORM FOR LIGHTING INSTALLATIONS

CROSS-REFERENCE TO RELATED APPLICATIONS

This application claims priority to U.S. patent application Ser. No. 16/601,711, filed Oct. 15, 2019, entitled Methods and Systems for An Automated Design, Fulfillment, Deployment and Operation Platform for Lighting Installations, and to Patent Cooperation Treaty (PCT) International Patent Application Serial No. PCT/US2018/029380, filed Apr. 25, 2018, entitled Methods and Systems for An Automated Design, Fulfillment, Deployment and Operation Platform for Lighting Installations, and to U.S. Provisional Patent Application Ser. No. 62/491,137, filed Apr. 27, 2017, entitled Methods and Systems for An Automated Design, Fulfillment, Deployment and Operation Platform for Lighting Installations, and to U.S. Provisional Patent Application Ser. No. 62/562,714, filed Sep. 25, 2017, entitled Methods and Systems for An Automated Design, Fulfillment, Deployment and Operation Platform for Lighting Installations, each of which are commonly-owned and hereby are incorporated by reference as if fully set forth herein in their entirety.

BACKGROUND

This disclosure relates to the field of lighting, more particularly to an automated platform, with automation and machine learning features, for design, fulfillment, deployment, and operation of a lighting installation.

Typically, a critical component for the success of an architectural or interior design project is lighting design. Lighting elements may play a number of important functional roles in a space, including rendering (or failing to render) colors of walls, fabrics, furniture and other elements in a space that is illuminated, engendering emotional reactions of individuals in the space, causing biological effects on individuals in the space, and acting as fixtures that harmonize with other fixtures (or fail to do so) to establish an aesthetic design, among others. However, current workflows for lighting design can be significantly flawed. The market for lighting is highly fragmented, with thousands of fixtures and illumination sources being provided by many different suppliers. In many cases, information about lighting products is unavailable, limited, or inaccurate. For example, online searches, to the extent that they provide any technical information about a lighting fixture, typically provide only rudimentary information about characteristics of a light (such as via IES files that provide some basic information about the number of lumens a lighting product provides over a far field area). As a result, most designers of lighting installations need to use physical samples of a lighting product to determine its properties and evaluate its suitability for a given installation. Lighting fixtures tend to be collected in "sample closets" maintained by designers, sales representatives, and distributors, to which designers travel in order to characterize a lighting fixture in person. This process can take days or weeks for a large lighting installation, and even in that case often produces suboptimal results, because comparisons between products are unscientific, and designers often are not even aware of lighting products that may better suit the needs of a given installation. A need exists for fundamentally different lighting design workflows.

Meanwhile, lighting products and the environments in which they are located are increasingly intelligent. Many lighting fixtures are configured to operate as part of the Internet of Things (IoT), so that they can be connected to networks for communication with remote systems (such as in the cloud), can be controlled remotely, can communicate with each other and with other IoT devices in the same spaces (such as beacons and thermostats), and can operate with some degree of autonomy. However, due to the fragmented nature of the lighting market and the lack of expertise on the part of most designers, most lighting installations do little to take advantage of this increased intelligence. A need exists for methods and systems that enable lighting designers and occupants or owners (the term "occupant" or "owner" referring, except where context indicates otherwise, to encompass customers and clients of designers, building owners, tenants, workers and other parties occupying the spaces in which lighting systems are installed) to design, acquire, install, operate and maintain lighting installations that use intelligent features much more effectively to satisfy a wide variety of requirements.

SUMMARY

Systems and methods are described herein that use a variety of novel information technology components to enable coordination of a fundamentally different workflow for design, acquisition, installation, operation and maintenance of a lighting installation that leverages the intelligence of lighting fixtures, including lighting fixtures that use novel control capabilities that are coordinated with other system components as described herein. References to the platform are intended to encompass, except where the context indicates otherwise, the various methods, systems, components, modules, fixtures, data structures, workflows, and other elements that are coordinated, in various embodiments, to enable the workflow.

In embodiments, a platform for the design of a lighting installation that includes an automated search engine for retrieving and storing a plurality of lighting objects in a lighting object library. The platform includes a lighting design environment providing a visual representation of a lighting space containing lighting space objects and lighting objects. The visual representation is based on properties of the lighting space objects and lighting objects obtained from the lighting object library. The platform also includes a plurality of aesthetic filters configured to permit a designer in the design environment to adjust parameters of a plurality of lighting objects handled in the design environment to provide a desired collective lighting effect using the plurality of lighting objects.

In embodiments, methods and systems for generating a data structure that characterizes a near field illumination pattern generated by a light source includes disposing a surface at at least one distance of a plurality of distances in proximity to a light source so that a first side of the surface is illuminated directly by the light source, capturing, with at least a two-dimensional image sensor, a plurality of luminance values from at least one the side of the surface; and generating a data structure characterizing an illumination field generated by the light source including a pattern of luminance values on at least the first side of the surface for the at least one distance among the plurality of distances.

In embodiments, the data structure further characterizes a positioning of the two-dimensional image sensor. In embodiments, the methods include storing an image captured by the image sensor; and repeating the disposing of the surface, the capturing of the plurality of luminance values, and the generating of the data structure for a plurality of incremental distances between the light source and the surface. In embodiments, the repeating causes storing a plurality of incremental-distance differentiated images of the luminance of the light source.

In embodiments, the methods include storing the images for a plurality of light sources in a library that enables a user to search the library to identify a light source having a desired pattern of illumination. In embodiments, the methods include a pattern matching system for matching at least one image in the library to a specified pattern of illumination for a space and for facilitating identification of at least one light source that provides the specified pattern. In embodiments, the method includes a pattern matching system for matching a specified pattern of illumination for a space with portions of images in the library. In embodiments, the portions of images include an off-axis slice through a portion of the plurality of the incremental-distance differentiated images. In embodiments, the method includes a user interface configured to permit a user to at least one of specify and select a pattern of illumination for a space. In embodiments, the pattern of illumination is automatically provided as an input to the pattern matching system. In embodiments, the plurality of luminance values is stored for the side of the surface that is directly illuminated by the light source. In embodiments, the surface is translucent and wherein the plurality of luminance values is stored for a side of the surface that is opposite the first side that is directly illuminated by the light source. In embodiments, the method includes applying indirect measurement software to generate an area-source model of the light source. In embodiments, disposing a surface includes dynamically disposing the surface with a variable distance device that facilitates varying a distance between the light source and the surface.

In embodiments, the method includes generating a 3D volumetric luminance model from the two-dimensional measurements by arranging the plurality of incremental-distance differentiated images into a three-dimensional shape, in embodiments, each of the images represents a slice of the three-dimensional shape. In embodiments, the method includes converting with a processor at least one of the plurality of luminance values to a measure of luminous flux including values for $\theta$ and $\varphi$. In embodiments, near field illumination characterization includes luminous flux along $\theta$ and $\varphi$ directions for each of a plurality of points on a surface of a light source, and x and y image sensor location data of each of the plurality of luminance values.

In embodiments, the x and y image sensor location data maps to corresponding x and y location data of the light source. In embodiments, the near field illumination characterization is dependent on at least one of: (i) distance between the light source and the surface, (ii) an angle between a line projected from the light source and a position on the surface associated with one of the plurality of luminance values and a normal to the surface, (iii) an optical property of the surface, and (iv) the captured luminance value associated with the position of the surface. In embodiments, methods and systems for characterizing the near field illumination pattern generated by a light source include a positioning slide for holding a screen and moving the screen among a plurality of distances from the light source; at least a two-dimensional image sensor for capturing luminance values from at least one side of the screen when the screen is illuminated by the light source; and a storage system for storing a plurality of data structures, each data structure representing the luminance values captured by the at least two-dimensional image sensor at a given distance of the positioning slide for a given light source.

In embodiments, the plurality of data structures is stored in a searchable library. In embodiments, the method includes a user interface configured to permit a user to search for a light source having a desired pattern of luminance values. In embodiments, methods and systems of near-field illumination pattern matching, include capturing a plurality of two dimensional images of an illumination effect in an environment illuminated by a light source; storing a portion of the plurality of images in a digital data structure that facilitates distinguishing among the stored data values in each of the plurality of images by a two-dimensional location in an image of the plurality of images and an effective distance of the image from the light source; detecting a specified pattern of illumination of the environment in the digital data structure. In embodiments, the pattern includes a plurality of data values identified by a two-dimensional location value and light source distance value.

In embodiments, at least two of the data values in the specified pattern are located at different light source distance values. In embodiments, the light source distance value varies across a portion of the specified pattern of illumination. In embodiments, the plurality of two-dimensional images is non-co-planar. In embodiments, the images in the plurality of two-dimensional images are substantially parallel. In embodiments, the images in the plurality of two-dimensional images are substantially parallel. In embodiments, the illumination effect is an impact of illumination by the light source on at least one object in the environment. In embodiments, the two-dimensional images include data representing an impact of light from the light source on at least one object in the environment. In embodiments, the detecting includes extracting a plurality of data values from the digital data structure based on the two-dimensional location value and the light source distance value for each of the extracted data values. In embodiments, the light source distance value includes an image identifier. In embodiments, the image identifier facilitates identifying an image of the plurality of images.

In embodiments, methods and systems for identifying a desired lighting source, includes a library of lighting objects including at least one of lighting fixture objects and light source objects. In embodiments, the lighting objects are characterized by lighting properties. In embodiments, the lighting properties include at least one output bloom property that characterizes a luminance pattern provided by an output of a lighting object selected from the library; and a pattern matching system that identifies at least one lighting object in the library based on at least one output bloom property.

In embodiments, the output bloom property includes a shape of the output bloom. In embodiments, the shape of the output bloom is at a specified distance from the lighting object. In embodiments, the shape of the output bloom is determined at an intersection of the light bloom with a surface. In embodiments, the surface includes one of a plane, a column, and a slope. In embodiments, the shape of an output bloom includes a portion of a near field illumination pattern generated by a light object selected from the library.

In embodiments, the shape is a substantially continuous shape. In embodiments, the shape is a discontinuous pattern. In embodiments, the output bloom property includes a portion of at least one of a near field illumination pattern and a far field illumination pattern generated by a light object selected from the library. In embodiments, the output bloom property includes at least one of a color and an intensity of an output bloom. In embodiments, the output bloom property includes a reflection from a surface.

In embodiments, the output bloom property includes a transmission through a surface. In embodiments, the surface is a translucent surface. In embodiments, the surface is a shade of a lighting fixture. In embodiments, the method includes a user interface configured to permit a user to view and select a lighting object based on a display of the output bloom.

In embodiments, the method includes a user interface configured to permit a user to at least one of specify and select a desired output bloom property. In embodiments, the pattern matching system automatically matches at least one lighting object in the library to the desired output bloom property. In embodiments, the pattern matching system is an artificial intelligence classification system. In embodiments, the artificial intelligence system is trained to match output bloom patterns based on a training set of patterns matched by one or more human users. In embodiments, the methods and systems of electronic display rendering of lighting distribution in a three-dimensional space, include modeling light source emissions as a set of light ray-traces that represent light traveling between a light source and an element in the three-dimensional space, and reflections therefrom. In embodiments, the modeling of the reflections is based on the set of ray-traces and at least one reflection characteristic of the element in the three-dimensional space; capturing the light source emissions and the reflections as light volume-data; interpolating at least one of light source emissions and reflections for a plurality of points in the three-dimensional space; determining interactions among the ray-traces and reflections in the three-dimensional space; and rendering in the electronic display the volume-data with the interpolated plurality of points and the interactions among the ray-traces in the three-dimensional space.

In embodiments, modeling includes accounting for at least one of light transparency, absorption and reflection of the element in the three-dimensional space. In embodiments, the electronic display is controlled by a virtual reality display controller. In embodiments, the electronic display is an augmented reality display controlled by an augmented reality display controller. In embodiments, rendering includes rendering near-field lighting artifacts. In embodiments, the near-field lighting artifacts are rendered throughout the three-dimensional space. In embodiments, rendering includes accounting for effects relating to physical characteristics of the light source. In embodiments, the light source includes a plurality of distinct light elements, each distinct light element being associated with a corresponding set of ray-traces. In embodiments, rendering includes rendering effects from each of the plurality of distinct light elements. In embodiments, rendering includes rendering distance-based light source intensity. In embodiments, rendering distance-based light source intensity includes rendering light source intensity fall-off over distance from the light source for each ray-trace in the set of ray-traces.

In embodiments, methods and systems of capturing the light source emissions includes disposing a surface at at least one of a plurality of distances in proximity to the light source so that a first side of the surface is illuminated directly by the light source, capturing, with at least a two-dimensional image sensor, a plurality of luminance values from at least one side of the illuminated surface; generating a data structure characterizing the illumination field generated by the light source including the pattern of luminance values on at least one side of the illuminated surface for the distance among the plurality of distances; storing an image captured by the image sensor; and repeating the disposing, capturing, and generating a data structure steps for a plurality of incremental distances between the light source and the intermediate surface. In embodiments, the repeating causes storing a plurality of incremental-distance differentiated images of the luminance of the light source.

In embodiments, methods and systems of electronic display rendering of lighting distribution in a three-dimensional space, includes modeling light source emissions as a set of light ray-traces that represent light traveling between a light source and an element in the three-dimensional space, and reflections therefrom. In embodiments, the modeling of the reflections is based on the set of ray-traces and at least one reflection characteristic of the element in the three-dimensional space; capturing a plurality of two-dimensional images of at least one of the light source emissions and the reflections; storing a portion of the plurality of images in a digital data structure as light volume-data, the structure facilitates distinguishing among the light volume data in each of the plurality of images by a two-dimensional location in an image of the plurality of images and an effective distance of the image from the light source; interpolating at least one of light source emissions and reflections for a plurality of points in the three-dimensional space; determining interactions among the ray-traces and reflections in the three-dimensional space; and rendering in the electronic display the volume-data with the interpolated plurality of points and the interactions among the ray-traces in the three-dimensional space.

In embodiments, the modeling includes accounting for at least one of light transparency, absorption and reflection of the element in the three-dimensional space. In embodiments, the electronic display is controlled by a virtual reality display controller. In embodiments, the electronic display is an augmented reality display controlled by an augmented reality display controller. In embodiments, the rendering includes rendering near-field lighting artifacts. In embodiments, the near-field lighting artifacts are rendered throughout the three-dimensional space. In embodiments, the rendering includes accounting for effects relating to physical characteristics of the light source. In embodiments, the light source includes a plurality of distinct light elements, each distinct light element being associated with a corresponding set of ray-traces. In embodiments, the rendering includes rendering effects from each of the plurality of distinct light elements. In embodiments, the rendering includes rendering distance-based light source intensity. In embodiments, the rendering distance-based light source intensity includes rendering light source intensity fall-off over distance from the light source for each ray-trace in the set of ray-traces.

In embodiments, methods and systems for enabling custom tuning a lighting object, includes defining a custom tuning profile for the lighting object, the custom tuning profile specifying at least one of a color tuning profile, a dimming profile, and a lighting distribution profile for the lighting object; and automatically, under control of a processor, translating the defined custom tuning profile into a set of instructions for controlling the lighting object to behave according to the custom tuning profile in response to user input.

In embodiments, the custom tuning profile is a dimming profile that specifies a set of points on a color temperature gamut that defines a dimming curve along which the lighting object will dim in response to a control input from a dimmer. In embodiments, the dimming profile is specified to match a known dimming profile of a type of lighting object. In embodiments, the custom tuning profile is a color tuning profile that specifies a set of points on a color gamut through which a lighting object will progress in response to a variable voltage control input. In embodiments, the method includes a user interface configured to permit a user to define the custom tuning profile. In embodiments, the user interface allows a user to specify a dimming profile by tracing a curve on a gamut. In embodiments, the user interface allows a user to specify a color for a color tuning profile from a color gamut.

In embodiments, the method includes a library of stored profiles selectable by a user for tuning of a lighting object. In embodiments, the library of stored profiles includes at least one of a color quality profile, a circadian profile, a concentration profile, a relaxation profile, and an efficacy profile. In embodiments, the library is organized to provide custom tuning profiles that satisfy at least one of a performance requirement and an aesthetic requirement desired by a user. In embodiments, methods and systems of controlling a color of a light source independent of controlling dimming of the light source, include capturing at least one custom color curve for controlling a light source; controlling dimming of the light source through a first input that accepts a voltage that varies between 0 and 10 volts; controlling color of the light source through a second input that accepts a voltage that varies between 0 and 10 volts independent of the first input; and mapping the at least one custom color curve to the second input range of 0 to 10 volts.

In embodiments, the custom color curve is a dimming profile that specifies a set of points on a color temperature gamut that defines a dimming curve along which the light source will dim in response to a control input from a dimmer. In embodiments, the dimming profile is specified to match a known dimming profile of a type of lighting object. In embodiments, the custom color curve is a color tuning profile that specifies a set of points on a color gamut through which the light source will progress in response to a variable voltage control input.

In embodiments, the method includes a library of stored profiles selectable by a user for tuning of a lighting object. In embodiments, the library of stored profiles includes at least one of a color quality profile, a circadian profile, a concentration profile, a relaxation profile, and an efficacy profile. In embodiments, the library is organized to provide custom tuning profiles that satisfy at least one of a performance requirement and an aesthetic requirement desired by a user.

In embodiments, methods and systems for a light source control system for a light source that has independent color and dimming control inputs, and include a first output port of the system that is operatively coupled to the color control input of the light source; a second output port of the system that is operatively coupled to the brightness control input of the light source; and a processor of the system that accesses a light source tuning profile that characterizes a multi-dimensional lighting curve by mapping color output of the light to brightness of the light source so that a change in the brightness input causes a corresponding change in the color input.

In embodiments, the processor controls the first output and the second output based on information in the tuning profile. In embodiments, the controlling the brightness input results in the processor also controlling the color input to adjust the color of the light based on the tuning profile. In embodiments, the controlling the brightness to reduce the brightness results in a warmer color being output by the light source. In embodiments, the controlling the brightness to increase the brightness results in a cooler color being output by the light source. In embodiments, the tuning profile maps a plurality of target color and brightness output values to a corresponding plurality of two-dimensional voltage values, a first dimension controlling light color and a second dimension controlling brightness. In embodiments, the tuning profile maps values in the first dimension to a color control input voltage range. In embodiments, the tuning profile maps values in the second dimension to a brightness control input voltage range.

In embodiments, the tuning profile maps target output color temperatures of the light source to values in the first and second dimensions so that controlling the color input and brightness input based on the first and second dimensions configures the light source to output a target color temperature based on the tuning profile color temperature mapping. In embodiments, the tuning profile facilities maintaining a light color as the light is dimmed by adjusting the light color control based on a change in the light dimming control. In embodiments, the tuning profile is indexed by at least one of biologic impacts and physiological impacts of light so that at least one of the light color and the light brightness is specified for a plurality of biologic impacts and physiological impacts.

In embodiments, methods and systems of using emotional filters for lighting design, include capturing stylistic and aesthetic features from a visual representation of an environment; populating, with the captured features, an installation-specific emotional content data structure; applying machine learning to user feedback about at least one of emotional and aesthetic aspects of installation. In embodiments, the installation is characterized by the installation-specific emotional content data structure. In embodiments, the machine learning facilitates generating an understanding of factors that contribute to each emotional effect of a plurality of emotional effects; and updating at least a portion of the emotional content data structure based on the feedback.

In embodiments, the visual representation includes at least one of a photograph and a video. In embodiments, the method includes selecting at least one light source for the environment based on a similarity of a portion of an emotional content data structure for the light source with a corresponding portion of the installation-specific emotional content data structure. In embodiments, capturing features includes analyzing at least one of images, 3D models, renderings, and scans of the environment. In embodiments, populating includes storing at least one of cultural and geographical data associated with the environment in the installation-specific emotional content data structure. In embodiments, the emotional content data structure includes at least one of objects, classes, and properties including lighting properties selected from a group consisting of distribution of light on lighting space objects, distribution of lights on surfaces, illumination values, color and color temperature of light sources, spectral content, and fixture type. In embodiments, lighting space objects include at least one of desks, tables, and workspaces. In embodiments, the spectral content includes quality and intensity of light at certain spectral ranges. In embodiments, the fixture type includes at least one of modern, retro, industrial, romantic, suspended, embedded, and form factor.

In embodiments, methods and systems of a lighting design system using emotional filters, include a visual representation of an environment; a feature capture facility adapted to capture stylistic and aesthetic features of the environment from the visual representation and populate the captured features into an installation-specific emotional content data structure that is accessible to a processor; machine learning algorithms executing on a processor that receive user feedback about at least one of emotional and aesthetic aspects of an installation characterized by the installation-specific emotional content data structure, the machine learning algorithms generating an understanding of factors that contribute to each emotional effect of a plurality of emotional effects, the processor updating at least a portion of the emotional content data structure based on the feedback.

In embodiments, the visual representation includes at least one of a photograph and a video. In embodiments, the method includes the processor selecting at least one light source for the environment based on a similarity of a portion of an emotional content data structure for the light source with a corresponding portion of the installation-specific emotional content data structure. In embodiments, the feature capture facility is configured to capture stylistic and aesthetic features by analyzing at least one of images, 3D models, renderings, and scans of the environment. In embodiments, to populate the captured features includes storing at least one of cultural and geographical data associated with the environment in the installation-specific emotional content data structure.

In embodiments, the emotional content data structure includes at least one of objects, classes, and properties including lighting properties selected from a group consisting of distribution of light on lighting space objects, distribution of lights on surfaces, illumination values, color and color temperature of light sources, spectral content, and fixture type. In embodiments, lighting space objects include at least one of desks, tables, and workspaces. In embodiments, spectral content includes quality and intensity of light at certain spectral ranges. In embodiments, the fixture type includes at least one of modern, retro, industrial, romantic, suspended, embedded, and form factor. In embodiments, the method includes a library of light source emotional content data structures that describe stylistic and aesthetic features of a plurality of light sources.

In embodiments, the method includes a light source selection facility that compares at least one portion of emotional content data structures in the library with a corresponding at least one portion of an installation-specific emotional content data structure thereby generating a set of candidate light sources for satisfying at least one of aesthetic and stylistic aspects of the environment. In embodiments, information descriptive of at least one of the aesthetic and stylistic aspects of the set of candidate light sources is displayed on an electronic display to enable comparison with each other and with the at least one of aesthetic and stylistic aspects of the environment.

In embodiments, methods and systems of a near-field characterization system include a light source positioning support adapted to hold a light source disposed to distribute light in a first orientation; an intermediate screen disposed to receive on a first side the distributed light, the intermediate screen constructed to transfer a portion of the received light to a second side that is substantially parallel to the first side; a two-dimensional array illumination sensor disposed to capture an image of the second side of the intermediate screen, the image including a data value representing illumination at each of a plurality of image sensing positions in the array; a processor adapted to control the illumination sensor and store the data value and the two-dimensional location of the corresponding image sensing position in the array; and a data storage facility that works with the processor to store the data value and its corresponding position for a plurality of image sensing positions in the array.

In embodiments, to control the illumination sensor includes rotating the illumination sensor. In embodiments, the two-dimensional array illumination sensor includes a digital camera. In embodiments, the digital camera is a camera function of a smartphone. In embodiments, the intermediate screen is translucent.

In embodiments, the method includes a positioning system of the intermediate screen controlled by the processor to adjust a distance between the light source and the intermediate screen. In embodiments, the method includes a positioning system of the light source controlled by the processor to adjust a distance between the light source and the intermediate screen. In embodiments, the light source positioning support facilitates rotational and translational motion of the light source. In embodiments, the processor is further adapted to control at least one of position, rotation, and translational motion of the light source. In embodiments, the method includes a housing that mitigates the impact of ambient light on the intermediate screen and the area array illumination sensor.

In embodiments, methods and systems for a near-field characterization system include a processor controlled light source positioning support adapted to hold a light source disposed to distribute light in a plurality of orientations, the processor controlling at least a rotation of the light source about a longitudinal axis of the support; an intermediate screen including a first side and a substantially parallel second side, the intermediate screen disposed to receive the distributed light on the first side and constructed to transfer a portion of the received light to the second side; an area array illumination sensor disposed to capture light emissions from the second side of the intermediate screen; a controller adapted to control the illumination sensor and store the data value and the array location of the corresponding image sensing position in a data storage facility.

In embodiments, the method includes a housing that mitigates the impact of ambient light on the intermediate screen and the area array illumination sensor. In embodiments, the housing extends from the second side of the intermediate screen to the area array. In embodiments, the method includes a housing that encloses the light source, the intermediate screen, and the area array. In embodiments, the housing is configured to conditionally eliminate ambient light from reaching the enclosed system elements. In embodiments, the method includes a spectrometer disposed relative to the intermediate screen to capture spectral content of light proximal to the intermediate screen.

In embodiments, the spectrometer is disposed to capture spectral content of light between the light source and the intermediate screen. In embodiments, the spectrometer is disposed to capture spectral content of light between the intermediate screen and the area array sensor. In embodiments, a position and orientation of at least one of the light source, the intermediate screen, and the area array is adjustable under processor control. In embodiments, at least one of the position and orientation of at least one of the light source, intermediate screen, and the area array is adjusted between successive area array light distribution captures. In embodiments, an increment of the adjustment between successive light distribution captures is non-linear. In embodiments, an increment after a light distribution capture is based on an at least one of an entropy and an amount of information captured.

In embodiments, methods and systems for characterizing a near field illumination effect of a light source, the method includes iteratively capturing, with a multi-dimensional image sensor set, an illumination value for each of a plurality of image sensing elements in the image sensor set, for a plurality of distance-specific positions of the light source; storing, in a processor accessible electronic memory, a plurality of images captured by the image sensor set; producing a multi-dimensional representation of the near-field light distribution of light source by processing, with a multi-dimensional near-field illumination reconstruction algorithm, the plurality of stored images and their corresponding distance-specific position values; and storing the multi-dimensional representation in the processor accessible electronic memory.

In embodiments, the image sensor set is a two-dimensional array. In embodiments, the multi-dimensional representation includes four dimensions consisting of a first dimension of the two-dimensional array, a second dimension of the two-dimensional array, a theta component of the corresponding distance-specific position value and a phi component of the corresponding distance-specific position value.

In embodiments, the multi-dimensional representation includes five dimensions consisting of a first dimension of the two-dimensional array, a second dimension of the two-dimensional array, a value representing the distance-specific position of the light source, a theta component of the corresponding distance-specific position value and a phi component of the corresponding distance-specific position value. In embodiments, the reconstruction algorithm determines a relative contribution of each point source on a light source's surface to each pixel in the two-dimensional array image sensor. In embodiments, the producing a multi-dimensional representation includes applying at least one of the Kaczmarz method, numerical methods, machine learning methods, neural networks, and linear algebra. In embodiments, the multi-dimensional array image sensor set includes a smartphone camera. In embodiments, the multi-dimensional representation constitutes a high-fidelity model of the light source. In embodiments, the method includes controlling with the processor, a distance between the light source and the multi-dimensional array image sensor set. In embodiments, iteratively capturing includes capturing a light pattern visible on a secondary side of a translucent intermediate screen disposed between the light source and the array image sensor.

In embodiments, methods and systems for incrementally reconstructing a near-field illumination effect of a light source, the method includes capturing a first occurrence of multi-dimensional luminance of a light source with an indirect luminance collection device disposed at a first position relative to the light source; capturing a second occurrence of multi-dimensional luminance of the light source with the indirect luminance collection device disposed at a second position relative to the light source; producing a representation of the near-field illumination of the light source by applying a multi-dimensional near-field illumination reconstruction algorithm to the captured occurrences of multi-dimensional luminance of the light; storing the representation in a computer accessible non-volatile memory; and repeating the capturing, producing, and storing steps for a plurality of positions relative to the light source, thereby producing a model of near-field illumination of the light source.

In embodiments, the model of near-field illumination includes a plurality of data values for theta and phi luminance values for a plurality of three-dimensional locations in the near-field of the light source. In embodiments, a position relative to the light source includes a distance from the light source, a longitude relative to the light source and a latitude relative to the light source. In embodiments, the plurality of positions includes a plurality of distances for a given longitude and latitude. In embodiments, the plurality of positions includes a plurality of longitudes for a given distance. In embodiments, the plurality of positions includes a plurality of latitudes for a given distance. In embodiments, the reconstruction algorithm determines a contribution of a point source on a surface of the light source for each captured occurrence.

In embodiments, producing a representation of the near-field illumination includes applying at least one of the Kaczmarz method, numerical methods, machine learning methods, neural networks, and linear algebra to the captured occurrences of multi-dimensional luminance of the light. In embodiments, producing a representation of the near-field illumination includes applying at least two of the Kaczmarz method, numerical methods, machine learning methods, neural networks, and linear algebra to the captured occurrences of multi-dimensional luminance of the light. In embodiments, the indirect luminance collection device includes a smartphone camera adapted to capture indirect luminance from the light source. In embodiments, the smartphone camera adapted with a screen attached to the smartphone over the smartphone camera so that light from the light source impacts the smartphone camera indirectly.

In embodiments, a portion of light from the light source passes through the screen. In embodiments, the multi-dimensional representation constitutes a high-fidelity model of the light source. In embodiments, the method includes controlling with the computer, a distance between the light source and the indirect luminance collection device. In embodiments, capturing the occurrences of multi-dimensional luminance of a light source includes capturing a light pattern visible on a secondary side of a translucent intermediate screen disposed between the light source and the indirect luminance collection device.

In embodiments, the near-field illumination reconstruction algorithm produces a five-dimensional representation of the near-field. In embodiments, each value in the near-field is characterized by (i) a distance from a reference position on the indirect luminance collection device to the light source, (ii) a longitudinal offset from the reference point for the occurrence, (iii) a latitudinal offset from the reference point, (iv) a theta value of the illumination, and (v) a phi value for the illumination.

In embodiments, methods and systems include receiving a data structure representative of a desired lighting effect created by the incidence of illumination from a light source on at least one surface; determining characteristics and values thereof of a light source for producing the desired lighting effect; matching the light source characteristics to a library of light sources. In embodiments, at least a portion of the light sources in the library includes at least a portion of the light source characteristics; determining, from a result of the matching, a candidate set of light sources in the library; selecting a portion of the candidate set of light sources based on similarity of the values of the determined characteristics with values of corresponding characteristics in the candidate set of light sources; and presenting the selected light sources in an electronic user interface.

In embodiments, the data in the data structure includes a plurality of luminance values for a lighting effect region. In embodiments, the data in the data structure includes at least one of desired effect of the lighting effect, an aesthetic filter effect of the lighting effect and an emotional filter effect of the lighting effect. In embodiments, the characteristics include light color and light intensity. In embodiments, the electronic user interface facilitates visual comparison of the desired lighting effect and a lighting effect of at least one of the selected light sources. In embodiments, the electronic user interface facilitates presenting the desired lighting effect and a lighting effect of at least one of the selected light sources in an environment. In embodiments, the environment is a live view of an environment and the user interface utilizes augmented reality to present at least one of the desired lighting effect and a lighting effect of at least one of the selected light sources. In embodiments, the luminance values in the plurality of luminance values are dispersed throughout the lighting effect region. In embodiments, the lighting effect region is substantially planar. In embodiments, the user interface further enables a user to search through the library based on the desired lighting effect.

In embodiments, the determining characteristics and values thereof of a light source for producing the desired lighting effect is based on a result of machine learning applied to an algorithm that associates light source characteristics with lighting effects. In embodiments, selecting a portion of the candidate set of light sources based on similarity of the values of the determined characteristics employs weighting of the characteristics. In embodiments, the weighting is determined based on a degree of compliance by the light sources with the desired light lighting effect. In embodiments, a user specifies the degree of compliance through the user interface.

In embodiments, methods and systems include receiving a data structure representative of a desired lighting effect; determining characteristics and values thereof of the desired lighting effect; matching the characteristics to corresponding lighting effect characteristics in a library of lighting effects. In embodiments, each of the lighting effects in the library corresponds to a light source; determining from an output of the matching a candidate set of light sources in the library; selecting a portion of the candidate set of light sources based on similarity of the values of the determined characteristics with values of corresponding characteristics of lighting effects for light sources in the candidate set of light sources; and presenting the selected light sources in an electronic user interface.

In embodiments, the data in the data structure includes a plurality of luminance values for a lighting effect region. In embodiments, the data in the data structure includes at least one of desired effect of the lighting effect, an aesthetic filter effect of the lighting effect and an emotional filter effect of the lighting effect. In embodiments, the characteristics include light color and light intensity. In embodiments, the electronic user interface facilitates visual comparison of the desired lighting effect and a lighting effect of at least one of the selected light sources. In embodiments, the electronic user interface facilitates presenting the desired lighting effect and a lighting effect of at least one of the selected light sources in an environment.

In embodiments, the environment is a live view of an environment and the user interface utilizes augmented reality to present at least one of the desired lighting effect and a lighting effect of at least one of the selected light sources. In embodiments, luminance values in the plurality of luminance values are dispersed throughout the lighting effect region. In embodiments, the lighting effect region is substantially planar. In embodiments, the user interface further enables a user to search through the library based on the desired lighting effect. In embodiments, the determining characteristics and values thereof for producing the desired lighting effect is based on a result of machine learning applied to an algorithm that associates characteristics with lighting effects.

In embodiments, selecting a portion of the candidate set of light sources based on similarity of the values of the determined characteristics employs weighting of the characteristics. In embodiments, weighting is determined based on a degree of compliance by the light sources with the desired lighting effect. In embodiments, a user specifies the degree of compliance through the user interface. In embodiments, methods and systems include collecting data from a plurality of lighting installations; and classifying the lighting installations based on at least one lighting effect created by the installations; and storing at least one property for at least one of a lighting object based on the classification of the effect.

In embodiments, the method includes a library of lighting objects for which effects are classified. In embodiments, the method includes enabling a user to search for a lighting object based on a desired effect sought by the user. In embodiments, classifying is based on a measured effect on at least one of an individual and a group. In embodiments, the measured effect is a productivity effect. In embodiments, the measured effect is a health effect.

In embodiments, classifying includes classifying images of the lighting installations to establish at least one of an aesthetic filter and an emotional filter that characterizes a subset of the lighting installations. In embodiments, classifying occurs by an expert system. In embodiments, classifying occurs by an artificial intelligence system. In embodiments, the artificial intelligence system is trained based on a training set created by having human individuals classifying the lighting installations.

In embodiments, the filter includes a data structure indicating weights for lighting object properties that contribute to the filter. In embodiments, the method includes characterizing at least one lighting object property based on its contribution to the filter. In embodiments, the method includes characterizing at least one lighting object based on its contribution to the filter. In embodiments, methods and systems of lighting, include receiving as a user selection of a filter, an intent of the user; converting the user intent to a set of lighting control parameters; using a lighting control platform to adjust settings on a plurality of light sources in a target environment to reflect the set of lighting control parameters; applying user feedback associated with distributions of lighting in the target environment to a machine learning processor to facilitate developing an understanding of a relationship between user reactions of the lighting environment and the user's intent; and updating, based on the understanding, a data set that facilitates the converting of user intent to lighting controls.

In embodiments, a user intent is to promote user feedback indicative of one of alertness, happiness, and romance. In embodiments, methods and systems of near field metrics for evaluating light sources, includes taking a near field illumination characterization of a light source; processing the characterization with at least one of a pattern detecting algorithm and an artifact detecting algorithm; counting occurrences of detected patterns and artifacts; determining at least one of size and scale of detected artifacts; and aggregating at least one of size of artifacts, scale of artifacts, and occurrences of artifacts, thereby producing at least one near field metric of a plurality of distinct near field metrics for the light source.

In embodiments, the near field metrics are selected from a group consisting of a mixing distance metric, a scale of artifacts metric, and a contrast in near field metric. In embodiments, the scale of artifacts metric includes an indication of at least one of a size, a scale, and a frequency of occurrence of artifacts in a light pattern produced by the light source. In embodiments, mixing distance metric includes an indication of a distance from a light source at which a magnitude of artifacts drops below a threshold of artifact visibility. In embodiments, contrast in near field metric includes an indication of an intensity of at least one of patterns and artifacts detectable proximal to the light source. In embodiments, the indication of intensity includes a minimum to maximum ratio of at least one of detectable patterns and artifacts.

In embodiments, methods and systems for providing near field metrics for characterizing light sources, include accessing a data structure that captures a near field illumination characterization of a light source; calculating metrics for the near field including at least one of light quality rating, light output, color range, color temperature, lighting mixing characteristics and spectral characteristics by processing at least two of three-dimensional position, theta, and phi values for a plurality of data values in the data structure with near-field metrics algorithms; and storing the calculated metrics in a library of light sources so that accessing the light source in the library facilitates accessing the associated near field metrics.

In embodiments, near field metrics are selected from a group consisting of a mixing distance metric, a scale of artifacts metric, and a contrast in near field metric. In embodiments, the scale of artifacts metric includes an indication of at least one of a size, a scale, and a frequency of occurrence of artifacts in a light pattern produced by the light source. In embodiments, mixing distance metric includes an indication of a distance from a light source at which magnitude of artifacts drops below a threshold of artifact visibility. In embodiments, contrast in near field metric includes an indication of an intensity of at least one of patterns and artifacts detectable proximal to the light source. In embodiments, the indication of intensity includes a minimum to maximum ratio of at least one of detectable patterns and artifacts. In embodiments, calculating metrics is based on machine learning algorithms applied to algorithms that associate candidate metrics with a plurality of near field data sets.

In embodiments, methods and systems for augmented reality lighting methods, include a first device representing a light source, a position and orientation of the first device in an environment being detectable by a second device in the environment; the second device capturing an image of at least a portion of the environment based on the detected position and orientation of the first device and communicating the detected position and orientation of the first device and the captured image over a network to a lighting modeling server; the lighting modeling server accessing a lighting model of the light source and modeling an interaction of the light source with elements of the environment detected in the captured image based on the position and orientation of the first device; and the second device receiving the modeled interaction from the lighting modeling server and rendering the modeled interaction in an augmented reality representation of the environment.

In embodiments, the second device detects the orientation and position of the first device by capturing at least one image of the first device in the environment, analyzing the at least one image for indications of the position of the device and its orientation in the environment, and tracking changes to the position and orientation of the device. In embodiments, the second device detects the orientation and position of the first device by analyzing received position and orientation information from the first device. In embodiments, the first device includes a user interface through which a user is enabled to select a light source from a library of light sources and through which an image of the selected light source is presented. In embodiments, the first device is configured to communicate an identifier of the selected light source to the lighting model server. In embodiments, the lighting model server accesses the lighting model for the selected light source from the library.

In embodiments, methods and systems include a first computing device disposed in an environment and rendering in its user interface a selected light fixture, the first device communicating its location and orientation in the environment over a wireless network; and a second device rendering in its user interface an illumination effect of the selected light fixture on a portion of the environment in response to a model of luminance of the selected light fixture, at least one of surfaces and objects in the portion of the environment, and the location and orientation of the first device.

In embodiments, the second device captures at least one image of the portion of the environment based on the location and orientation of the first device. In embodiments, the second device is disposed in the environment. In embodiments, changes to at least one of the position and orientation of the first device cause corresponding changes to the rendering of the illumination effect in the second device. In embodiments, the model of luminance incorporates at least one of near-field and far-field luminance characterization of the selected light fixture.

In embodiments, the second device includes an augmented reality device that renders an illumination effect of the selected light fixture based at least in part on a position and orientation of the second device in the environment. In embodiments, the user interface of the first device is configured to facilitate selecting a light fixture from a light fixture library. In embodiments, the method includes a lighting space modeling server that generates a data set that describes the illumination effect of the selected light fixture on the portion of the environment that the second device uses for rendering. In embodiments, the first device is configured to communicate an identifier of the selected light fixture to the lighting space model server. In embodiments, the lighting space model server accesses the model of luminance of the selected light fixture from the library.

In embodiments, methods and systems of augmented reality-based lighting design, include detecting light sources in an augmented reality image; detecting at least one of surfaces and objects in the augmented reality image; facilitating disposition of at least one virtual light source in the augmented reality image, resulting in an updated augmented reality image; processing a near field and far field luminance characterization of the at least one virtual light source and the updated augmented reality image with a lighting space model; and depicting illumination of portions of the augmented reality image in response to the lighting space model.

In embodiments, portions of the augmented reality image include at least one of the detected surfaces and objects. In embodiments, the method includes detecting lighting effects of the detected light sources. In embodiments, illuminating portions of the augmented reality image is in response to the detected lighting effects.

In embodiments, methods and systems of illumination in an environment, include controlling a first light source in the environment, disposed to illuminate a first region of the environment, to mimic sky color based on at least one of a user input and a time of day; and controlling a second light source to mimic a window on a vertical wall of the environment. In embodiments, the second light source generates a color on the vertical wall that is consistent with the mimicked sky color.

In embodiments, the illuminated first region of the environment includes an area of a ceiling of the environment. In embodiments, the illuminated first region of the environment mimics a skylight. In embodiments, the illuminated first region of the environment includes a plurality of distinct areas of a ceiling of the environment. In embodiments, the illuminated first region of the environment mimics a plurality of distinct skylights. In embodiments, the illuminated first region changes colors based on an estimated position of the sun from sunrise to sunset. In embodiments, the illuminated first region mimics a lunar illumination effect based on a position of the moon. In embodiments, the method includes controlling a third light source to produce a melanopic flux ratio of at least 10:1 in a portion of the environment.

In embodiments, the first light source is disposed in the environment to produce cove lighting. In embodiments, the at least one of the first light source and the second light source is disposed in the environment to produce graze lighting. In embodiments, controlling the first light source and the second light source results in a melanopic flux ratio of at least 10:1 in a portion of the environment.

In embodiments, methods and systems of illumination in an environment, include controlling a first light source in the environment, the first light disposed to illuminate a first region of the environment, the controlled light mimicking sky color based on at least one of a user input and a time of day; and controlling a second light source to illuminate a second region of the environment, the second light source being selected from a library of light sources. In embodiments, the second region of the environment is a workspace.

In embodiments, the illuminated first region of the environment includes an area of a ceiling of the environment. In embodiments, the illuminated first region of the environment mimics a skylight. In embodiments, the illuminated first region of the environment includes a plurality of distinct areas of a ceiling of the environment. In embodiments, the illuminated first region of the environment mimics a plurality of distinct skylights. In embodiments, the illuminated first region changes colors based on an estimated position of the sun from sunrise to sunset and based on an estimated position of the moon from sunset to sunrise. In embodiments, the illuminated first region mimics a lunar illumination effect based on a position of the moon. In embodiments, the method includes controlling a third light source to produce a melanopic flux ratio of at least 10:1 in a portion of the environment.

In embodiments, the first light source is disposed in the environment to produce cove lighting. In embodiments, the at least one of the first light source and the second light source is disposed in the environment to produce graze lighting. In embodiments, controlling the first light source and the second light source results in a melanopic flux ratio of at least 10:1 in a portion of the environment.

In embodiments, methods and systems of illumination in an environment, include controlling a downlight light source in the environment to mimic sky color for at least one of sunrise, mid-day sun, and sunset; and controlling an uplight light source in the environment in response to the downlight control so that the illumination in the environment produces a melanopic flux ratio of at least 10:1 in the environment.

In embodiments, control of the uplight light source includes adjusting at least two channels of a multiple channel light. In embodiments, controlling the uplight source further produces a circadian action. In embodiments, the method includes controlling the downlight light source to shift a bias of light in the environment toward at least a first side, a central portion, and a second side of the environment. In embodiments, the environment is a room. In embodiments, coordinating control of the uplight light source in the environment in response to the downlight control includes mimicking sky color for at least one of sunrise, mid-day sun, and sunset.

In embodiments, methods and systems include receiving biomarker information from a plurality of wearable sensors from at least one user in a lighting control environment over a time frame; recording control settings for at least one light in the lighting control environment over the time frame; and using machine learning to determine correlations between biological states of the user and lighting effects in the environment based on the biomarker information and the record of lighting control settings.

In embodiments, methods and systems include receiving estimated future time zone and an activity schedule of a user for a plurality of sequential days; identifying an estimated future time zone of the user that is different than a current time zone; and controlling at least one light proximal to the user according to the estimated different future time zone prior to the user being located in the different estimated time zone.

In embodiments, methods and systems include receiving architecture information for a space into a lighting design system; processing the architecture information with a three-dimensional physical space modeling algorithm that produces a model of the space including at least one of objects and surfaces in the space; and applying a model of luminance for a light fixture to the model of the space, thereby producing an emulation of luminance in the space including an impact of luminance from the light fixture on at least one of the objects and surfaces in the space.

In embodiments, the method includes lighting control system that uses machine learning to adapt light control settings for at least one light in an environment based on at least one of a schedule of time zones of a user in the environment, a schedule of activities of the user in the environment, biomarker information received from wearable sensors worn by at least one user in the environment, feedback on lighting effects caused by the light control settings from users in the environment, and user generated light control settings for at least one light in the environment.

In embodiments, methods and systems of configuring a three-dimensional space for lighting simulation include capturing information descriptive of physical aspects of an environment as a three-dimensional point-cloud representation of the physical aspects; applying machine learning to the descriptive information to detect architectural features of the environment; determining light modeling aspects of the detected architectural features; configuring a digital library of the architectural features including at least one of the light modeling aspects of each architectural feature in the library; and configuring a lighting space model of the environment that references the library of architectural features and incorporates corresponding light modeling aspects of architectural features referenced in the library.

In embodiments, capturing information descriptive of the physical aspects of an environment includes use of one or more of a digital camera, three-dimensional sensor, camera-equipped personal computing device capturing images of the environment. In embodiments, capturing information descriptive of the physical aspects of the environment includes generating measurements of the detected architectural features and distances between them. In embodiments, applying machine learning to the descriptive information includes processing point clouds of the environment. In embodiments, the method includes generating at least one of a floor plan and a reflected ceiling plan of the environment.

In embodiments, the method includes presenting the lighting space model in an artificial reality interface. In embodiments, the method includes detecting at least one light source in the environment. In embodiments, configuring a lighting space model incorporates light modeling aspects of the light source. In embodiments, configuring a lighting space model includes incorporating a light source model for at least one light source in the environment. In embodiments, the light modeling aspects of the detected architectural features include reflectance by the feature of light directed a first angle. In embodiments, the light modeling aspects of the detected architectural features include surface type for at least one surface of the feature.

In embodiments, methods and systems of configuring a three-dimensional space model for lighting simulation include capturing visual information representative of physical aspects of an environment as a three-dimensional visual representation of the environment; detecting at least one of surfaces and edges between surfaces in the visual representation; determining physical relationships among the detected surfaces and edges. In embodiments, the physical relationships include relative orientation of a plurality of the detected surfaces; analyzing an impact of illumination on at least one of the surfaces and the edges to generate a reflective model of the analyzed surfaces and edges; and configuring a lighting space model of the environment that incorporates the detected surfaces and edges, their orientations, and their reflective model.

In embodiments, capturing visual information representative of the physical aspects of the environment includes use of one or more of a digital camera, three-dimensional sensor, camera-equipped personal computing device to capture at least one image of a portion of the environment. In embodiments, determining physical relationships includes generating measurements of surfaces and distances between the surfaces. In embodiments, the method includes applying machine learning to an output of the analyzing an impact of illumination on at least one of the surfaces and the edges to improve generating the reflective model.

In embodiments, the method includes generating at least one of a floor plan and a reflected ceiling plan of the environment. In embodiments, the method includes presenting the lighting space model in an artificial reality interface. In embodiments, the method includes detecting at least one light source in the environment. In embodiments, configuring the three dimensional space model includes incorporating light modeling aspects of the light source.

In embodiments, configuring the three dimensional space model includes incorporating a light source model for at least one light source in the environment. In embodiments, the reflective model of the analyzed surfaces and edges includes reflectance by the surface of light directed a first angle. In embodiments, the reflective model of the analyzed surfaces and edges includes a surface type for at least one of the surfaces.

In embodiments, methods and systems include receiving from a server blockchain-secured digital image content representative of a low resolution of an environment; rendering, via processing the received content, a low resolution image of an impact of a light disposed at a first location and oriented in a first orientation in the environment on elements in the environment; and in response to receiving an indication, from a user interface on which the low resolution image is rendered, of a subset of the environment to render in high resolution, rendering in high resolution and transmitting a blockchain-secured digital image of the indicated subset of the environment.

In embodiments, rendering the low resolution version is performed by a mobile device and wherein the rendering in high resolution is performed by a networked server. In embodiments, the method includes displaying the transmitted high resolution digital image on a user interface of a mobile device receiving the blockchain-secured transmitted high resolution image. In embodiments, the digital image content representative of the subset includes a full geometric model of the indicated subset.

In embodiments, the digital image content representative of the subset includes a high resolution image of the impact of the light on the element in the environment. In embodiments, the low resolution version is rendered in a virtual reality display of the environment. In embodiments, the digital image content includes at least one of a near field illumination model of illumination produced by a light source and a far field illumination model of illumination produced by the light source.

In embodiments, the blockchain secures a low resolution image of a portion of the environment rendered on a mobile device and a high resolution image of the portion of the environment rendered on a computing server device. In embodiments, methods and systems include receiving a first blockchain-secured digital image content representative of an environment; rendering, via processing the received content, a first resolution version of an impact on elements in the environment of a light disposed at a first location and oriented in a first orientation in the environment; receiving subsequent blockchain-secured digital image content of the environment; rendering a subsequent resolution version of the impact of light on the elements by combining the received subsequent digital image content with the most recently rendered resolution version; and repeating the receiving subsequent and rendering a subsequent resolution version until at least a portion of the next resolution version includes a resolution equivalent to a high resolution version of the environment.

In embodiments, rendering the first resolution version is performed by a mobile device and wherein the rendering of at least one of the subsequent resolution versions is performed by a networked server and streamed to the mobile device. In embodiments, the digital image content of the environment includes a full geometric model of the indicated subset. In embodiments, the next resolution version of the impact of light on the elements includes a high resolution image. In embodiments, the first content is rendered in a virtual reality display of the environment.

In embodiments, methods and systems include receiving on a first computing device a first multi-dimensional image of illumination produced by a light source and captured with an indirect near field illumination multi-dimensional image capture device; rendering on a user interface of the first computing device a first resolution representation of the near field illumination; receiving additional position differentiated multi-dimensional images of illumination from the light source captured by the indirect near field capture device; and in response thereto, rendering increasingly higher resolution representations of the near field illumination.

In embodiments, a count of additional position differentiated multi-dimensional images received is limited based on a performance aspect of the first computing device. In embodiments, a count of additional position differentiated multi-dimensional images received and rendered by a mobile device is less than a count of additional position differentiated multi-dimensional images received and rendered by a server. In embodiments, rendering at least one of the increasingly higher solution representations of the near-field illumination is performed by a computing device other than the first computing device.

In embodiments, receiving a first multi-dimensional image includes receiving a blockchain-secured message including the first multi-dimensional image. In embodiments, receiving additional multi-dimensional images includes receiving a blockchain-secured message including at least one of the additional multi-dimensional images.

In embodiments, methods and systems of producing a color tuning curve include controlling a first color control channel including setting an "x" value that corresponds to a first axis of a CIE diagram, based on a secondary control input; controlling a second color control channel including setting a "y" value that corresponds to a second axis of a CIE diagram, based on a secondary control input; controlling a third color control channel including setting a dim value that corresponds to a light output value; and controlling a fourth color control channel including setting at least one of the "x" value and the "y" value based on a primary control input.

In embodiments, the method includes producing the color tuning curve in an augmented reality lighting simulation environment. In embodiments, a lighting effect resulting from producing the color tuning curve is rendered throughout a three-dimensional space. In embodiments, the color tuning curve is applied to a lighting source in the three-dimensional space. In embodiments, the rendering includes accounting for effects relating to physical characteristics of light source. In embodiments, the rendering includes rendering distance-based light source intensity.

In embodiments, the rendering distance-based light source intensity includes rendering light source intensity fall-off over distance from the light source for each ray-trace in the set of ray-traces. In embodiments, the method includes providing a user interface that facilitates a user selecting a lighting fixture to control to produce the color tuning curve. In embodiments, the method includes providing a user interface that facilitate a user selecting at least one of a programmable dimming curve, programmable color tuning curve, a tuning curve start point, a tuning curve end point, a tuning curve dimming path, and a color tuning path.

In embodiments, in at least one of the turning curve dimming path and color tuning path is responsive to a level of dimming. In embodiments, the controlling steps are applied to a lighting system including three white light sources each with different CCTs to produce the color tuning curve. In embodiments, controlling steps are applied to a lighting system including a plurality of different color light emitting diode (LED) light sources to produce the color tuning curve. In embodiments, producing the color tuning curve is responsive to a user selection of a tuning curve start point, tuning curve end point and at least one tuning curve waypoint between the start and end points.

In embodiments, methods and systems for producing a single color of light across a plurality of color modes, include a four channel light emitting diode (LED) illumination source. In embodiments, each of the four channels are independently controllable for at least an amount of light output by the corresponding light emitting diode in the illumination source; a set of mathematical models that define features of each of a plurality of the color modes that, when processed with a map of LED illumination source channel control values for a plurality of target illumination colors by a processor produces a set of intensity information for each of the plurality of target illumination colors; and a computing architecture of the illumination source that receives an indication of a target color and a color mode and controls the four channels of the illumination source to produce the target color based on the set of intensity information and the indicated color mode.

In embodiments, a target color produced in power efficiency color mode is substantially the same color produced in a full power color mode. In embodiments, a common target color is produced by the system for each of a plurality of color modes consisting of a color quality mode, an efficacy mode, a circadian mode, a color bias mode, and a rest mode. In embodiments, a color quality mode is achieved by maximizing at least one of the color rendering index (CRI) and fidelity and gamut metrics.

In embodiments, an efficacy mode is achieved by maximizing output lumens per watt of consumed power. In embodiments, a circadian mode is achieved by maximizing equivalent melanopic lux (EML) content. In embodiments, a color bias mode is achieved by oversaturating a single color as a spectral component of a two-dimensionally indexed position on a color rendering index diagram. In embodiments, the rest mode is achieved by minimizing at least one of blue illumination and EML content.

In embodiments, the set of mathematical models facilitate producing a color tuning curve responsively to a user selection of a tuning curve start point, tuning curve end point and at least one tuning curve waypoint between the start and end points.

In embodiments, methods and systems of model-based rendering near-field effects of a light source, include modeling light source emissions as a set of direction-specific light ray-traces; capturing data at a plurality of positions along a portion of the set of direction-specific light ray-traces; determining interactions among the ray-traces; and rendering in an electronic display near-field effects of the light source, the effects derived from a lighting space model that incorporates the light volume-data, the interpolated plurality of points and the interactions among the ray-traces.

In embodiments, the lighting space model accounts for at least one of light transparency, absorption and reflection of elements in the three-dimensional space. In embodiments, the electronic display is controlled by a virtual reality display controller. In embodiments, the electronic display is an augmented reality display controlled by an augmented reality display controller. In embodiments, the rendering includes rendering near-field lighting artifacts. In embodiments, the near-field lighting artifacts are rendered throughout the three-dimensional space. In embodiments, the rendering includes accounting for effects relating to physical characteristics of a source of the light emissions. In embodiments, a light source of the light emissions includes a plurality of distinct light elements, each distinct light element being associated with a corresponding set of ray-traces.

In embodiments, the rendering includes rendering effects from each of the plurality of distinct light elements. In embodiments, the rendering includes rendering distance-based light source intensity. In embodiments, the rendering distance-based light source intensity includes rendering light source intensity fall-off over distance from the light source for each ray-trace in the set of ray-traces.

In embodiments, storing the captured data in a computer accessible memory as three-dimensional light volume-data and interpolating light source emissions for a plurality of points in a three-dimensional space characterized by the three-dimensional light volume data that are not present in the light volume-data.

In embodiments, the three-dimensional light volume data includes a shape of a lighting effect from a light source of the light emissions. In embodiments, a lighting effect property includes a shape of the lighting effect at a specified distance from the light source. In embodiments, the shape is a substantially continuous shape. In embodiments, the shape is a discontinuous pattern. In embodiments, the near-field data effects of the light source include at least one of a color and an intensity of a lighting effect. In embodiments, the near field data effects of the light source include a reflection from a surface.

In embodiments, methods and systems of the model-based rendering of a light field, include capturing a set of data representing a three-dimensional space proximal to a light source, the data set including data representing illuminance values of light at each of a plurality of locations in the three-dimensional space; extracting a multi-dimensional portion of the set of data; and generating a geometric model of the portion that facilitates modelling an impact of the illuminance of the light source on objects disposed in the space proximal to the light source.

In embodiments, the methods include interpolating a plurality of additional illuminance values within the multi-dimensional portion of the set of data. In embodiments, the three-dimensional data set includes a reflection from a surface. In embodiments, methods and systems for planning lighting in an augmented reality display, include representing physical features of an environment as a point cloud; using machine learning to generate a lighting space model of the environment from the point cloud; using the lighting space model to produce at least one of a floor plan and a reflected ceiling plan of the environment; coupling the lighting space model to an augmented reality view of the environment. In embodiments, light sources are added to the lighting space model by a user placing light sources in the augmented reality view of the environment; and rendering the environment through the augmented reality display including lighting effects of the placed light sources based on a near field illumination characterization of the placed light sources.

In embodiments, the rendering includes accounting for at least one of light transparency, absorption and reflection of at least one element in the environment. In embodiments, the rendering includes rendering near-field lighting artifacts. In embodiments, the near-field lighting artifacts are rendered throughout the three-dimensional space. In embodiments, the rendering includes accounting for effects relating to physical characteristics of at least one light source.

In embodiments, the at least one light source includes a plurality of distinct light elements, each distinct light element being associated with a corresponding set of ray-traces. In embodiments, the rendering includes rendering effects from each of the plurality of distinct light elements. In embodiments, the lighting effects of the placed light sources are based on an area-source model of the placed light sources. In embodiments, placing light sources includes selecting a model of a light source from a catalog of light sources presented in the augmented reality environment and indicating at least one of a position and orientation of the light source in the environment. In embodiments, the rendering is performed by a volumetric renderer.

In embodiments, methods and systems for planning lighting in an augmented reality display, include representing physical features of an environment as surfaces and edges; using machine learning to generate a lighting space model of the environment from the surfaces and edges. In embodiments, the lighting space model includes attributes for at least one of absorption and reflectance of each of the surfaces; using the lighting space model to produce a floor plan of the environment; coupling the lighting space model to an augmented reality view of the environment. In embodiments, light sources are added to the lighting space model and to the produced floor plan by a user placing light sources in the augmented reality view of the environment; and rendering the environment through the augmented reality display including lighting effects of the placed light sources based on a near field illumination characterization of the placed light sources.

In embodiments, the rendering includes accounting for at least one of light transparency, absorption and reflection of at least one surface in the environment. In embodiments, the rendering includes rendering near-field lighting artifacts. In embodiments, the near-field lighting artifacts are rendered throughout the three-dimensional space. In embodiments, the rendering includes accounting for effects relating to physical characteristics of at least one light source. In embodiments, the at least one light source includes a plurality of distinct light elements, each distinct light element being associated with a corresponding set of ray-traces. In embodiments, the rendering includes rendering effects from each of the plurality of distinct light elements.

In embodiments, the lighting effects of the placed light sources are based on an area-source model of the placed light sources. In embodiments, placing light sources includes selecting a model of a light source from a catalog of light sources presented in the augmented reality environment and indicating at least one of a position and orientation of the light source in the environment. In embodiments, the rendering is performed by a volumetric renderer. In embodiments, producing a floor plan includes use of a measuring facility in the AR interface to measure a space portrayed therein.

In embodiments, methods and systems for planning lighting in an augmented reality display, include representing physical features of an environment as a point cloud; using machine learning to generate a lighting space model of the environment from the point cloud; using the lighting space model to produce at least one of a floor plan and a reflected ceiling plan of the environment; coupling the lighting space model to an augmented reality view of the environment. In embodiments, light sources are added to the lighting space model by a user placing light sources in the augmented reality view of the environment by selecting a model of a light source from a catalog of light sources presented in the augmented reality environment and indicating at least one of a position and orientation of the light source in the environment; rendering the environment through the augmented reality display including lighting effects of the placed light sources based on a near field illumination characterization of the placed light sources; and populating a data object with item identification information for at least one of the placed light sources. In embodiments, populating causes automatic placement of at least one order into a supply chain for the at least one placed light source.

In embodiments, the rendering includes rendering near-field lighting effects in the environment of the placed light sources based on a near-file illumination model of the light source. In embodiments, populating includes obtaining the item identification information from the catalog of light sources. In embodiments, populating is in response to a user indicating in the augmented reality interface the at least one of the placed lights for automatic order placement. In embodiments, the methods include producing a lighting installation plan based on the floor plan and the position and orientation of the light source in the environment.

In embodiments, the method includes populating an automatic procurement data object with item identification information for at least one object identified in the floor plan. In embodiments, the rendering includes accounting for at least one of light transparency, absorption and reflection of at least one element in the environment. In embodiments, the rendering includes rendering near-field lighting artifacts. In embodiments, the near-field lighting artifacts are rendered throughout the three-dimensional space. In embodiments, the rendering includes accounting for effects relating to physical characteristics of at least one light source.

In embodiments, the at least one light source includes a plurality of distinct light elements, each distinct light element being associated with a corresponding set of ray-traces. In embodiments, the rendering includes rendering effects from each of the plurality of distinct light elements. In embodiments, the lighting effects of the placed light sources are based on an area-source model of the placed light sources. In embodiments, the catalog of light sources includes automated order light source identification information. In embodiments, the rendering is performed by a volumetric renderer.

In embodiments, methods and systems for planning lighting in an augmented reality display, include representing physical features of an environment as surfaces and edges; using machine learning to generate a lighting space model of the environment from the surfaces and edges. In embodiments, the lighting space model includes attributes for at least one of absorption and reflectance of each of the surfaces; using the lighting space model to produce a floor plan of the environment; coupling the lighting space model to an augmented reality view of the environment. In embodiments, light sources are added to the lighting space model and to the produced floor plan by a user placing light sources in the augmented reality view of the environment; rendering the environment through the augmented reality display including lighting effects of the placed light sources based on a near field illumination characterization of the placed light sources; and populating a data object with item identification information for at least one of the placed light sources. In embodiments, populating causes automatic placement of at least one order into a supply chain for the at least one placed light source.

In embodiments, the rendering includes rendering near-field lighting effects in the environment of the placed light sources based on a near-file illumination model of the light source. In embodiments, populating includes obtaining the item identification information from the catalog of light sources. In embodiments, populating is in response to a user indicating in the augmented reality interface the at least one of the placed lights for automatic order placement. In embodiments, the method includes producing a lighting installation plan based on the floor plan and the position and orientation of the light source in the environment. In embodiments, the method includes populating an automatic procurement data object with item identification information for at least one object identified in the floor plan. In embodiments, the rendering includes accounting for at least one of light transparency, absorption and reflection of at least one surface in the environment. In embodiments, the rendering includes rendering near-field lighting artifacts.

In embodiments, the near-field lighting artifacts are rendered throughout the three-dimensional space. In embodiments, the rendering includes accounting for effects relating to physical characteristics of at least one light source. In embodiments, the at least one light source includes a plurality of distinct light elements, each distinct light element being associated with a corresponding set of ray-traces. In embodiments, the rendering includes rendering effects from each of the plurality of distinct light elements. In embodiments, the lighting effects of the placed light sources are based on an area-source model of the placed light sources. In embodiments, the rendering is performed by a volumetric renderer.

In embodiments, methods and systems of control of modeled light sources in an augmented reality interface, include coupling a lighting space model of an environment to an augmented reality view of the environment. In embodiments, light sources are added to the lighting space model by a user placing light sources in the augmented reality view of the environment; rendering the environment through the augmented reality display including lighting effects of the placed light sources based on a near field illumination characterization of the placed light sources; and configuring a plurality of virtual lighting controls in the augmented reality user interface that control illumination from at least one of the placed light sources.

In embodiments, the plurality of virtual lighting controls includes user interface elements for controlling at least one of dimming level, fixture color, fixture finish, beam angles, light intensity, light color, and light color temperature. In embodiments, the plurality of virtual lighting controls includes user interface elements for controlling at least one of rotation, placement, orientation, and tilt of the placed light sources. In embodiments, the method includes interfacing the virtual lighting controls to wearable sensors that indicate a motion of a portion of a user wearing the wearable sensors.

In embodiments, the indication of motion from the wearable sensors is interpreted by the plurality of virtual lighting controls to control at least one of light intensity, light color, and light color temperature. In embodiments, the indication of motion from the wearable sensors is interpreted by the plurality of virtual lighting controls to control at least one of rotation and tilt of the placed light sources. In embodiments, the method includes rendering a marketplace of light sources in a portion of the augmented reality display from which a user selects the light sources to be added to the lighting space model.

In embodiments, methods and systems of control of modeled light sources in an augmented reality interface, include coupling a lighting space model of an environment to an augmented reality view of the environment. In embodiments, light sources are added to the lighting space model by a user placing light sources in the augmented reality view of the environment; rendering the environment through the augmented reality display including lighting effects of the placed light sources based on a near field illumination characterization of the placed light sources; and configuring a plurality of virtual lighting controls in a user interface of a handheld portable computing device that control at least one of the placed light sources.

In embodiments, the plurality of virtual lighting controls includes user interface elements for controlling at least one of light intensity, light color, and light color temperature. In embodiments, the plurality of virtual lighting controls includes user interface elements for controlling at least one of rotation and tilt of the placed light sources. In embodiments, the method includes interfacing the virtual lighting controls to wearable sensors that indicate a motion of a portion of a user wearing the wearable sensors. In embodiments, the indication of motion from the wearable sensors is interpreted by the plurality of virtual lighting controls to control at least one of light intensity, light color, and light color temperature. In embodiments, the indication of motion from the wearable sensors is interpreted by the plurality of virtual lighting controls to control at least one of rotation and tilt of the placed light sources.

In embodiments, the method includes rendering a marketplace of light sources in a portion of the augmented reality display from which a user selects the light sources to be added to the lighting space model. In embodiments, the virtual lighting controls include a touchable element on an electronic tablet display. In embodiments, the virtual lighting controls include an adjustable dial that represents a range of filter effects producible by the light. In embodiments, methods and systems of control of modeled light sources in an augmented reality interface, include coupling a lighting space model of an environment to an augmented reality view of the environment. In embodiments, light sources are added to the lighting space model by a user placing light sources in the augmented reality view of the environment; rendering the environment through the augmented reality display including lighting effects of the placed light sources based on a near field illumination characterization of the placed light sources; and configuring the lighting space model to receive input from a handheld portable computing device that control at least one of the placed light sources.

In embodiments, the input from the handheld portable computing device includes data that indicates at least one of an orientation and a movement of the handheld portable computing device. In embodiments, the orientation input indicates a new orientation in the environment for the at least one of the placed light sources. In embodiments, the movement input indicates a new position in the environment for the at least one of the placed light sources.

BRIEF DESCRIPTION OF THE FIGURES

FIG. 2 is a requirements system diagram of a platform for design, fulfillment, deployment, and operation of a lighting installation in accordance with the embodiments of the present disclosure.

FIGS. 26 and 27 are diagrammatic views that depict VR interfaces in accordance with the embodiments of the present disclosure.

DETAILED DESCRIPTION

Figure 1:
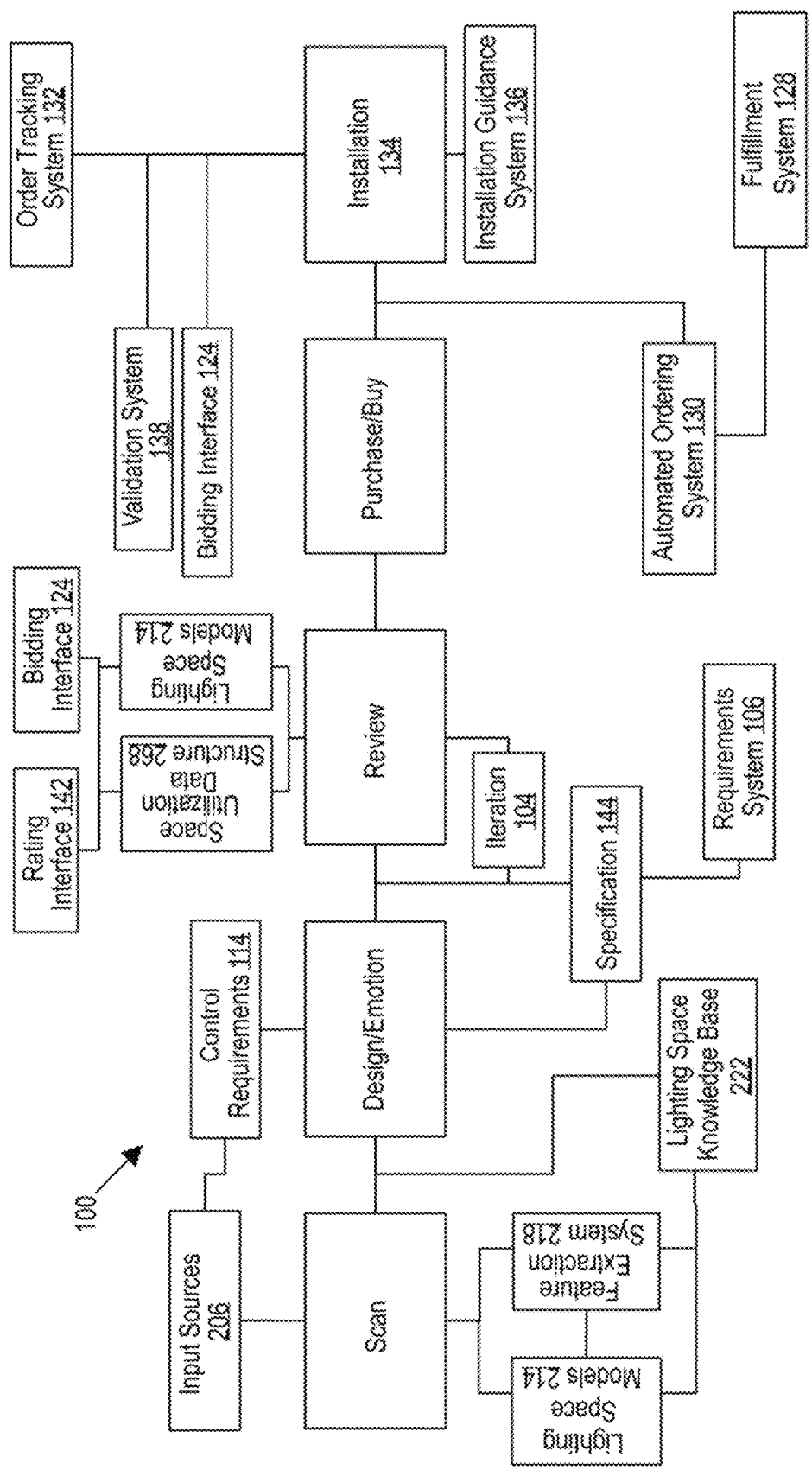
FIG. 1 is a schematic diagram of the main components of a platform for design, fulfillment, deployment, and operation of a lighting installation in accordance with the embodiments of the present disclosure.

FIGS. 1 through 8 depict a platform 100 for the design, fulfillment, deployment, and operation of a lighting installation. The platform 100 for the design, fulfillment, deployment, and operation of a lighting installation may include a lighting design environment 238, a control IT infrastructure 282 and a deployment environment 284. The deployment environment 284 may include a lighting installation 280. The lighting installation 280 may include a lighting installation sensor system 266 for sensing and collecting data from the environment of the lighting installation 280, using any of a wide range of sensor inputs, including motion sensors, temperature sensors, light sensors, flow sensors, chemical sensors, and others.

In embodiments, the lighting installation 280 may connect to or integrate with one or more scanning system input interfaces 202, input sources 206 and/or autonomous control systems, either directly, through a network, through a lighting installation sensor system, or the like. In embodiments, an autonomous control system 262 may connect to or integrate with various input sources 206, a workflow guidance system 242, an operational feedback system 264 and/or a control IT interface 282. Input sources 206 may also connect to or integrate with and provide input to the control IT infrastructure 282, the workflow guidance system 242 and/or the scanning system input interfaces 202. The workflow guidance system 242 may also connect to or integrate with the control IT infrastructure 282, the operational feedback system 264, the lighting design environment 238, a near field characterization system 270 and/or scanning system output interfaces 204.

In embodiments, the scanning system input interfaces 202 may also connect to or integrate with a scanning system 102. The scanning system input interfaces 202 may also connect to or integrate with a scan data store 208 and/or a scan alignment system 210. The scan data store 208 may also connect to or integrate with the scan alignment system 210. The scan alignment system 210 may connect to or integrate with a machine based alignment 212 system. Scanning system output interfaces 204 may also connect to or integrate with the near field characterization system 270, the lighting design environment 238, the operational feedback system 264, the workflow guidance system 242, the control IT infrastructure 282, the one or more input sources 206 and/or the autonomous control system 262. The near field characterization system 270 may also connect to or integrate with the operational feedback system 264, the lighting design environment 238, the workflow guidance system 242 and/or the control IT infrastructure 282.

In embodiments, the deployment environment 284 may connect to, include, or be integrated with the control IT infrastructure 282 and the lighting design environment 238. The deployment environment 284 may connect to or be integrated with the control IT infrastructure 282 through the autonomous control system 262, the input sources 206, the workflow guidance system 242, the scanning system output interfaces 204, the near field characterization system 270 and/or the operational feedback system 264. The deployment environment 284 may, moreover, connect to or be integrated with the lighting design environment 238, such as through the operational feedback system 264, the near field characterization system 270, the scanning system and output interfaces 204, the workflow guidance system 242, one or more input sources 206 and/or the autonomous control system 262.

Figure 6:
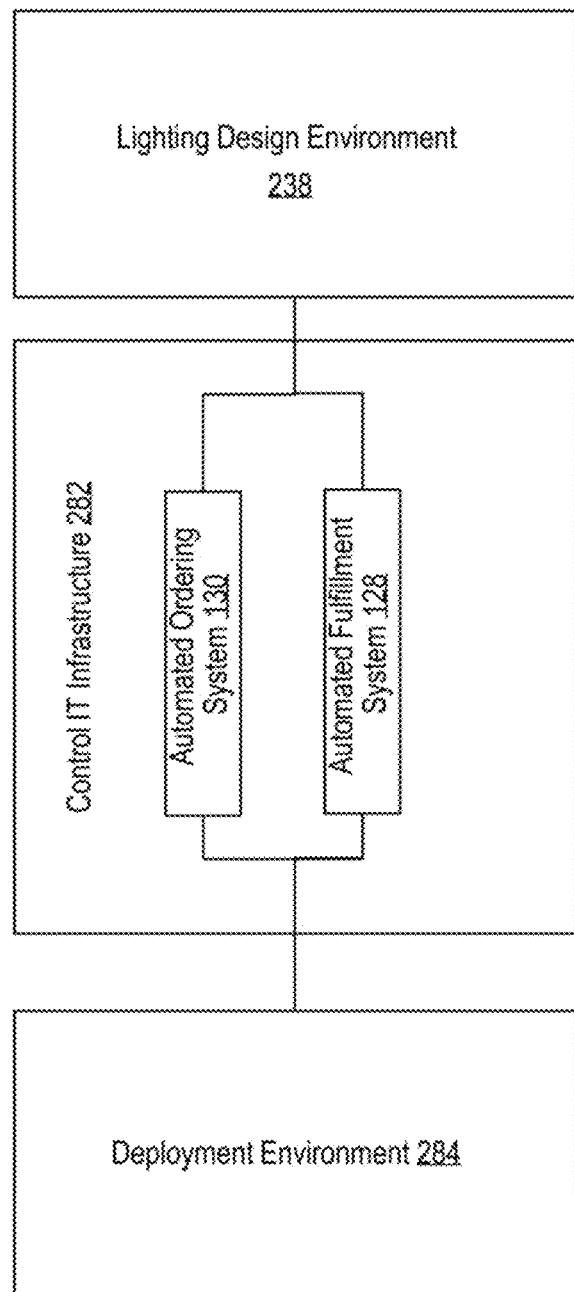
FIG. 6 is a control IT infrastructure diagram of a platform for design, fulfillment, deployment, and operation of a lighting installation in accordance with the embodiments of the present disclosure.

FIG. 6 provides an exemplary diagram of the control IT infrastructure for design, fulfillment, deployment and/or operation of a lighting installation. In embodiments, the control IT infrastructure 282 may include an automated fulfillment system 128 and an automated ordering system 130. The automated fulfillment system 128 may connect to the automated ordering system 130, the lighting design environment 238 and/or the deployment environment 284 or to the various elements, components, or sub-systems of each of them. The automated ordering system 130 may connect to or be integrated with the automated fulfillment system 128, the lighting design environment 238 and/or the deployment environment 284.

Figure 7:
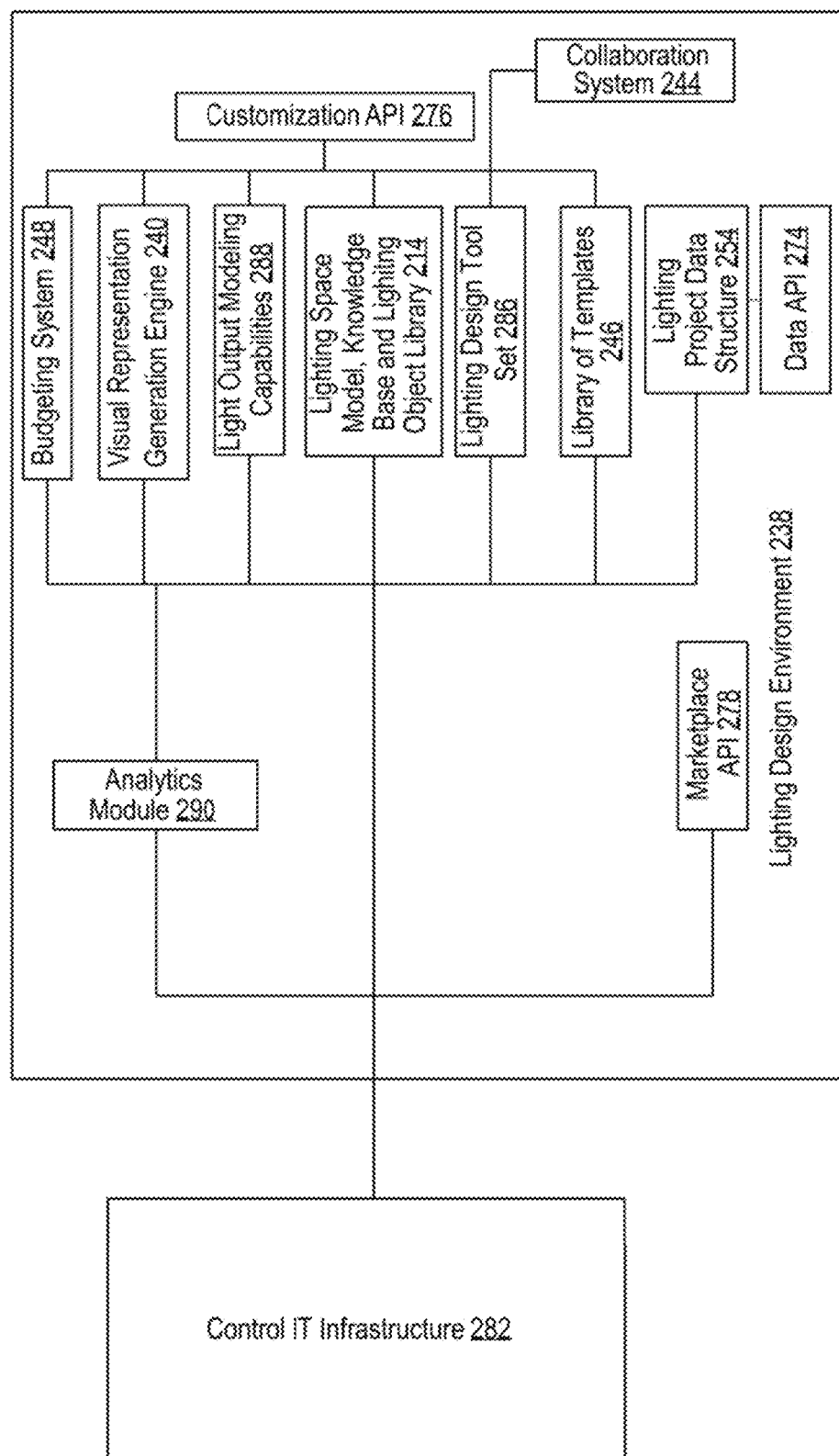
FIG. 7 is a lighting design environment diagram of a platform for design, fulfillment, deployment, and operation of a lighting installation in accordance with the embodiments of the present disclosure.

FIG. 7 provides the lighting design environment 238 diagram of a platform for design, fulfillment, deployment, and operation of a lighting installation. The lighting design environment 238 may include a marketplace API 278 that provides a programmatic interface to one or more sources of market-relevant information about lighting objects and lighting fixtures, such as specification information, pricing information, delivery information and the like. The marketplace API 278 may connect to or be integrated with one or more of the control IT infrastructure 282, a data API 274, a lighting project data structure 254, a library of templates 246, a lighting design tool set 286, a lighting space model, a knowledge base and lighting object library 214, a light output modeling system 288, a visual representation generation engine 240, a budgeting system 248 and/or an analytics module 290. The analytics module 290 may also connect to or integrate with the lighting project data structure 254, the library of templates 246, the lighting design tool set 286, the lighting space model, the knowledge base and lighting object library 214, the light output modeling system 288, the visual representation generation engine 240 and/or the budgeting system 248.

In embodiments, the platform 100 for the design, fulfillment, deployment, and operation of a lighting installation, referred to as the platform 100, may include or be integrated with various systems, components, features, methods, subsystems, and the like for enabling the lighting marketplace. The lighting marketplace may include the lighting marketplace API 278, as discussed elsewhere in this disclosure. The lighting marketplace may support real-time pricing and the various financial models that exist within the lighting design industry, such as project-based models, per-fixture models, cost-of-light models, cost-plus models, design-build models, fee-for-service models, and others.

The lighting marketplace may include a recommendation engine 122. The recommendation engine 122 may be integrated within the lighting design environment 238. The recommendation engine 122 may receive constraints from a project. The constraints from the project may be known when looking for lighting fixture objects 230 and may include pricing constraints (such as relating to an overall project budget or a budget for a particular item or line item within a budget), timing constraints (such as relating to when a project or portion of a project is supposed to be completed) and the like. The constraints of the project may also be specified in requirements system 106. The recommendation engine 122 may receive a complete lighting design (or portions thereof) and may suggest lighting fixture object 230 substitutions to support, for example, a value engineering design approach.

In embodiments, Augmented Reality and Virtual Reality (AR/VR) functionality may be integrated as a front end to a design stage and provide input to the lighting marketplace. For example, a user may experience the lighting design environment in a VR environment, such as seeing a virtual reality representation of a proposed lighting installation (including seeing fixtures and seeing illumination effects rendered in a 3D realistic environment) or an AR environment (such as seeing a room or other environment for which a lighting design is proposed, with overlays that represent lighting objects, fixtures or the like, as well as illumination effects. In embodiments, AR/VR functionality may obtain information from or provide input to the lighting marketplace of the platform 100 through the marketplace API 278. For example, the AR/VR system may allow a user to select items that are available for sale (optionally constrained to ones that fit within budgets and timelines for a project) and have those items represented in the AR/VR environment. Users may drag, drop, position, orient and move lighting objects to view the objects and their illumination effects, such as using gestures or speech as inputs to the AR/VR system.

The lighting marketplace may include support for product registration. Product registration may include providing enhanced support, such as accessing information about when a product was ordered, arrived, was delivered and the like. The marketplace API 278 may include a data feed into the lighting marketplace and provide benchmarking data regarding actual delivery dates for items over time. This information may allow the lighting marketplace to predict delivery times based on order history.

In embodiments, the lighting marketplace may include data collection elements that are not readily accessible in a standard B2B environment.

In embodiments, the lighting marketplace may deal with commercial freight while providing consumer-focused e-commerce features. For example, the lighting marketplace may allow customers to rate products once they have used the product. In embodiments, the lighting marketplace may include back-end data gathering for benchmarking supplier performance, such as benchmarking returns and delivery times. In embodiments, the lighting marketplace API 278 may provide a high level of data integration with a design process, by providing timing parameters, prices, ratings, lighting source objects 228, project requirements and the like as elements of or filters to the design process, such affecting what is viewed by a user of a platform in the design environment, in a dashboard for managing an installation, or the like.

By enabling rich visualizations, the platform allows lighting designers and lighting vendors to show the benefits of more expensive design features that are high impact in the design, potentially increasing sales of such features. Thus, the platform, by showing such benefits, may enable vendors and designers to sell certain aspects of the design that might have been omitted absent the visualization features of the platform 100. The term "designer" as used herein encompasses, except where context indicates otherwise, lighting designers, architects, interior designers, building contractors, and other individuals involved in designing, installing, operating and/or maintaining lighting installations.

In embodiments, the lighting marketplace may be integrated with the lighting design environment 238. The lighting marketplace may be built into the lighting design environment 238 so that if a user sets design targets and budget targets in a way that, if they cannot achieve the design targets in budget, the platform may recommend components of the lighting design environment 238 that purposely conflict with such constraints, rather than simply filtering components out of the lighting design environment 238 and coming out with "null" values. Instead, the platform may come back to the user and indicate that the user may achieve the effect with a larger budget as the primary answer, for example, rather than a "null" value if there are conflicting requirements, such as design and budget requirements. Providing recommended alternative components may encourage users toward higher quality designs, rather than just having them seek low-cost options that satisfy an original budget.

In embodiments, the lighting marketplace may be integrated with an Internet of Things (IoT) system, allowing a user to take advantage of an understanding made available by an IoT system, such as an understanding of how a lighting installation is used, helping a user of the platform 100, such as a designer, better understand the use of a space. For example, if customers in a restaurant are going to tables with a spotlight, then a platform may recommend ordering additional spotlights. In embodiments, the IoT integration may also allow the lighting marketplace to track users, by providing user tracking data as an input to the lighting marketplace, such as recommending an upgrade to the design. In these examples, IoT integration with the lighting marketplace may allow a user of a platform to gauge the impact of lighting on what is happening in a store, restaurant, and other locations.

In embodiments, the lighting marketplace may provide an enhanced sense of spatial awareness to a user, by extracting data for determining other elements of what is happening in a space. For example, for a retail user with a merchandising plan and a store, the platform 100 may allow the retail user to compare patterns and dwell times in the store, to gauge the effectiveness of influence on buying behavior of what is taking place in the store. In embodiments, one of the elements of the platform 100 that may interact with design, marketplace and implementation is an understanding of the lighting design environments 238 that products are being deployed in, allowing the user of the platform 100 to build a database of types of lighting design environments 238, regions of the country and the like, such as regarding how people are deploying and using light in predetermined regions or environments.

In embodiments, this understanding may indicate things like: "People in the Northwest like cooler color temperatures and downlights" or "Sushi restaurants deploy lighting like this." Because the lighting marketplace includes data on the type of space and what the space was designed for, the platform 100 may provide a user with an understanding of what lighting fixture objects 230 and deployments are typical for the lighting design environment 238.

In embodiments, lighting objects that include dynamic color tuning and dynamic lighting distributions may communicate with the platform 100, such as via two-way digital communication. This may include interactions with marketplace features of the platform 100. In these examples, if the lighting marketplace is aware of ten different pre-set ways for users to change the lighting distribution of the lighting design environment 238, the lighting marketplace may also be aware of what lighting distribution is most often chosen for that lighting design environment 238 and indicate that lighting distribution as the most preferred or most often implemented lighting distribution for that specific design environment. Also, such dynamic color and distribution tuning capabilities may be represented in the design environment, including in AR and VR interfaces, so that a user may see how a lighting object may be changed to create different effects in a given installation.

In embodiments, tuning information may be sent to the recommendation engine 122 and stored for future use. By way of these examples, a user may choose the preferred lighting distribution for the lighting design environment 238 in which the user is deploying. This information may indicate where and when users are using dynamic color, such as for lighting particular types of merchandise that appear more favorably under particular color tuning parameters. In embodiments, this information may also indicate other choices being made by users. In embodiments, the information may be collected over time by tracking the behavior of users of the platform 100 and using it in the recommendation engine 122 on the design side and in the lighting marketplace components of the platform 100.

In embodiments, the IoT integration with the platform 100 may include building integration. By way of these examples, the IoT building integration may include tracking people and understanding their dwell times, which may be used by a platform for purposes of occupancy sensing, space scheduling, and space optimization, among others. In further examples, the platform 100 may be integrated with a responsive HVAC system, providing health benefits to the lighting design environment 238. In these examples, the IoT integration may include ambient temperature, oxygen, and carbon dioxide sensing.

In embodiments, the IoT integration may include dynamic color and spectrum lighting sensing and detection. By way of these examples, dynamic color and spectrum lighting sensing and detection may indicate different access to daylight, versus not having daylight in a lighting environment. Dynamic color and spectrum lighting sensing and detection may also indicate different spectral content (such as during a sunny or cloudy day) and what ambient light is coming through to the lighting environment.

In embodiments, the IoT integration may provide a platform with access to elements of connected devices that may feed back into cloud-based systems, that may be responsive to people, such as providing biometric data from wearable devices, social media feeds, including Twitter™ feeds, Facebook™ posts, Pandora™ streams and the like. In these examples, this integration may allow a user of a platform to assess and use lighting as a method for altering mood, productivity, or the like based on non-lighting, building inputs.

In embodiments, a hotel may have spectrally dynamic, tunable lighting integrated with its reservation systems. By way of these examples, the reservation system may have a desired profile learned or programmed so that when a guest checks into the hotel, the user preferences, such as spectral content, for the hotel or hotel room are set. In further examples, a business traveler may be checking into a hotel having moved among a significant number of time zones. Using information from the traveler's calendar, including where the traveler has been historically, the platform 100 having the IoT integration may be able to adjust spectral control to manipulate the traveler's body clock, so the traveler is better able to wake and function at the times the traveler needs to be able to do that relative to time zone changes and travel. Spectral content may include visible light and other settings the traveler may not be aware of, based on the traveler's schedule, for example. Furthermore, the traveler could opt into being helped with their sleep patterns in this manner.

In embodiments, a restaurant may have down lights at tables. The tables may be moved, for example, to accommodate different group sizes. IoT integration with a platform could, when the operator of the restaurant moves the table, rearrange the down lights when the tables are moved, so a spotlight is shining on each table, even after a table is moved. In embodiments, dynamically applied ambient lighting and spot lighting may be controlled by IoT platform integration, so that, for example, when a large party comes enters a restaurant, spotlights shine on occupied tables, rather than the empty tables. In embodiments, when a table needs to be cleared (such as in a user interface that shows the environment and objects in it), the table may be tagged or otherwise prioritized in the lighting distribution map for the restaurant, such as to highlight it for workflow purposes, and the lighting of the table may be altered to highlight it (such as showing it with different color), such as to the staff person responsible for clearing tables. In embodiments, one or more of the lighting source objects 228, such as a spotlight, may be dimmed when not in use, saving energy and not highlighting the existence of empty tables.

In embodiments, filtered glasses and predetermined adjustment and readjustment of the gamut area in a particular space may be used to enable functionality where, without the filtered glasses, correlated color temperature (CCT), luminosity, or any of the chromaticities in the gamut area may appear to stay constant, but with the filtered glasses any of the changes become apparent. This may allow interesting situations in hotels and restaurants. In these examples, hotel and restaurant staff wearing the filtered glasses could be directed in a very subtle manner because the filtered glasses may allow the user to perceive the changes in the chromaticities of gamut area, luminosity, correlated color temperature (CCT), and the like while the customers are totally unaware (or at least sufficiently unaware) of the staff being directed.

In embodiments, a lighting project data structure 254 may also connect to or integrate with one or more of the data API 274, the library of templates 246, the lighting design tool set 286, the lighting space model, the knowledge base and lighting object library 214, the light output modeling system 288, the visual representation generation engine 240, and/or the budgeting system 248. The library of templates 246 may also connect to one or more of a collaboration system 244, a customization API 276, the lighting design tool set 286, the lighting space model, the knowledge base and lighting object library 214, the light output modeling system 288, the visual representation generation engine 240, and/or the budgeting system 248. The lighting design tool set 286 may connect to or integrate with one or more of the lighting space model, the knowledge base and lighting object library 214, the light output modeling system 288, the visual representation generation engine 240, the budgeting system 248, the collaboration system 244 and/or the customization API 276.

In embodiments, the lighting space model, the knowledge base, and the lighting object library 214 may also connect to or integrate with one or more of the collaboration system 244, the customization API 276, the light output modeling system 288, visual representation generation engine 240, and/or the budgeting system 248. The light output modeling system 288 may also connect to or integrate with one or more of the collaboration system 244, the customization API 276, the visual representation generation engine 240 and/or the budgeting system 248. The visual representation generation engine 240 may also connect to or integrate with one or more of the collaboration system 244, the customization API 276 and/or the budgeting system 248. The budgeting system 248 may also connect to or integrate with the collaboration system 244 and/or the customization API 276.

Figure 8:
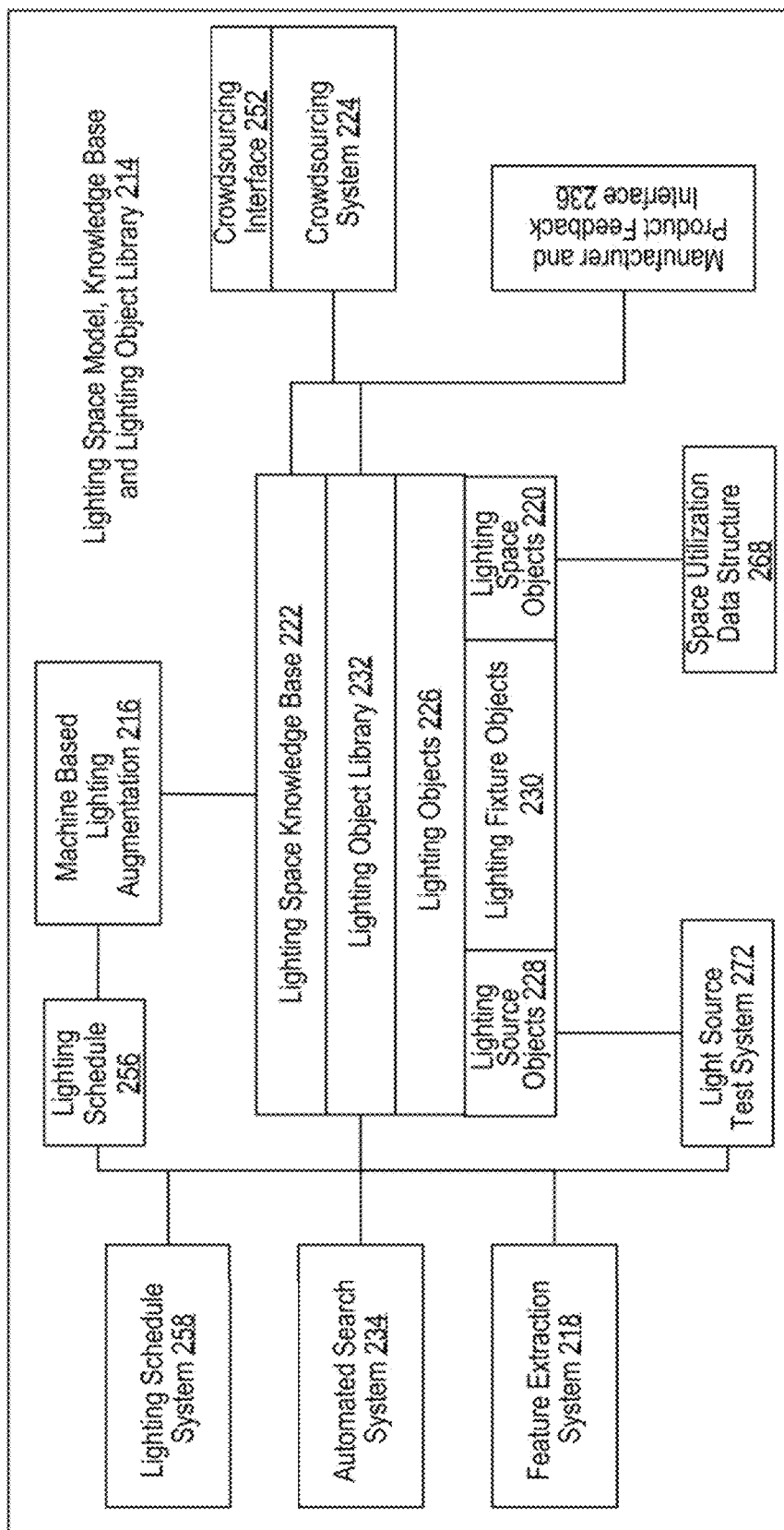
FIG. 8 is a lighting space model, knowledge base and lighting object library diagram of a platform for design, fulfillment, deployment, and operation of a lighting installation in accordance with the embodiments of the present disclosure.

FIG. 8 illustrates the lighting space model, the knowledge base, and the lighting object library 214 of the platform for design, fulfillment, deployment, and operation of a lighting installation. The lighting space model, the knowledge base, and the lighting object library 214 may include, connect to, or integrate with a lighting schedule system 258, an automated search system 234 and/or a feature extraction system 218. A lighting schedule system 258 may connect to one or more of a lighting schedule 256, the automated search system 234, a lighting object library 232, the feature extraction system 218 and/or a light source test system 272. The automated search system 234 may also connect to or integrate with one or more of the lighting schedules 256, the lighting object library 232, the feature extraction system 218 and/or a light source test system 272. The feature extraction system 218 may also connect to or integrate with one or more of the lighting schedule 256, the lighting object library 232 and/or the light source test system 272. The lighting schedule may also connect to or integrate with one or more of the lighting object library 232, the machine based lighting augmentation system 216 and/or the light source test system 272. In embodiments, the light source test system 272 may also connect to one or more lighting source objects 228. The machine based lighting augmentation system 216 may also connect to the lighting space knowledge base 222. The lighting object library 232 may also connect to or integrate with one or more of the lighting space knowledge base 222, one or more lighting objects 226, a crowdsourcing system 224 and/or a manufacturer and a product feedback interface 236. The lighting space knowledge base 222 may also connect to or integrate with the crowdsourcing system 224. The lighting objects 226 may also connect to or integrate with one or more of the lighting source objects 228, lighting fixture objects 230 and/or lighting space objects 220. The lighting space objects 220 may also connect to or integrate with one or more of a space utilization data structure 268. The crowdsourcing system 224 may include a crowdsourcing interface 252.

In embodiments, the platform 100 includes systems that enable efficient scanning of a space in which the lighting installation 280 is desired; automated conversion of a scan into a model or representation of the space that is displayed to a designer; specification 144 of various requirements for the space (including financial parameters, functional requirements 112 and aesthetic requirements 116, including relating to the desired emotional impact of the installation); automated search of a universal library of lighting products and filtering to a set that satisfies the requirements; automated generation of recommendations (including based on various filters, including emotive filters, collaborative filters, and others); manipulation of the model or representation to show the impact of various lighting products under different parameters or conditions; automated generation of a manifest or order for the lighting products required for the installation, automated ordering and fulfillment of the installation; remote operation and maintenance of the installation; and autonomous control of the installation (including self-commissioning and automated self-adjustment of the installation and including peer-to-peer and other configurations for control within the installation).

Figure 34:
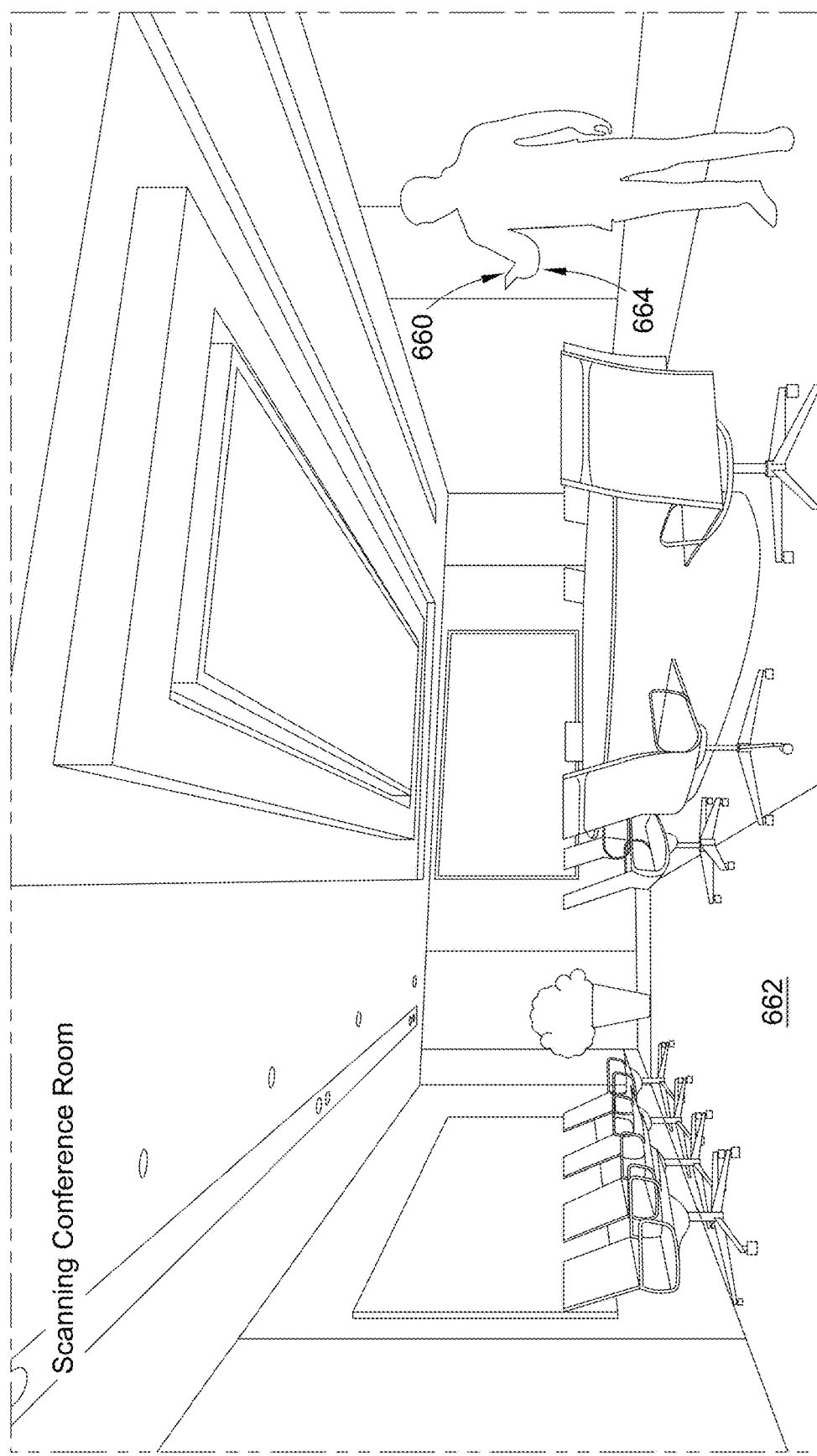
FIG. 34 is a diagrammatic view that illustrates scanning of an environment for which a lighting installation is to be designed in accordance with the embodiments of the present disclosure.

In embodiments, the platform may include methods, systems, modules, components and devices for scanning a space where the lighting installation 280 is to be deployed, all of which are collectively referred to as the "scanning system" 102. FIG. 34 illustrates user scanning 660 of an environment 662 for which a lighting installation is to be designed, such as using a mobile or handheld scanning device 664. In embodiments, the scanning system 102 may operate with various input sources 206, which may be loaded by one or more scanning system interfaces. Scanning system interfaces may include scanning system input interfaces 202 and scanning system output interfaces 204, which in embodiments may include a single, integrated interface. In embodiments, the input sources 206 may include images and video of a space captured by one or more cameras, spatial or point cloud scans conducted using infrared, acoustic, sonic or laser scanners (among others), scans using various types of sensors deployed on mobile units, such as drones and robots, floor plans, blueprints, drawings (which may be converted from paper form into design models or may exist in models, such as computer-aided design (CAD) models), and other sources. In embodiments, the scanning system interfaces may include application programming interfaces (such as allowing automated feeding of information into the scanning system 102 from another system) and various other types of interfaces used for extraction, transformation and loading of data or migration of data into the scanning system 102, including brokers, connectors, bridges, gateways, and the like, as well as data marts, data warehouses, micro marts, and other facilities for intermediate handling of data. In embodiments, the data from various input sources 206 may be normalized, such as by automatically converting it into a common format (such as a relational database format, an XML format, or the desired file format), so that it may be loaded into a scan data store 208 (which may be a distributed database in the cloud). In embodiments, information from various scanning input sources 206 may be aligned in the scan alignment system 210, such as by scaling representations from different sources (e.g., a CAD model and a point cloud scan) to a common spatial frame of reference. This alignment may include machine-based alignment 212 of the scans based on the automated extraction of features from the scans.

Lighting designers and architects may be required to survey an existing space, take measurements, and draw out a floor plan before they may begin to lay out a lighting design. To help accelerate and automate this process, the platform 100 may generate floor plans for existing spaces. In embodiments, the generating of floor plans for existing spaces may integrate with hardware and software such as the Matterport™ camera, Structure 3D™ sensor coupled with a tablet, Apple's ARKit™ on an iPhone™ or iPad™ wireless computing devices and the like, to scan an existing space and generate its point cloud representation. In embodiments, the Machine learning algorithms may then be used to process these floor plans in the form of point clouds and may detect and recognize the various structural/architectural elements and features in the space. By way of these examples, the machine learning may, in turn, construct a lighting space model 214 of the space. Such a system may output a floor plan or reflected ceiling plan as necessary. Alternatively, the system may directly process a point cloud to produce a floor plan.

In embodiments, if using a technology like ARkit™ by Apple™, the lighting schedule 256 may be added on top of floor plan generated by the platform 100. The platform 100 may allow a lighting designer to place lighting fixture objects 230 in the lighting space model 214 through an augmented reality (AR) interface as the lighting designer scans the lighting design environment 238. In embodiments, the lighting design environment 238, when viewed through an AR lens, may show the lighting fixture objects 230 and the lighting effects of the lighting fixture objects 230 as well. In the AR context, these lighting fixture objects may be permanent for the duration of a design session, unless removed or changed.

In embodiments, a generated floor plan may be registered to a real-world space, so lighting fixture objects placed in an AR interface and view may be correctly positioned on the floor plan without requiring additional input from a user. This may allow a lighting designer to create a lighting space model 214 on the go and visualize it in the lighting design environment 238. Once complete, the platform 100 may save a floor plan with the lighting fixture object 230 positions and note other fixture details to create the lighting schedule 256.

Figure 13:
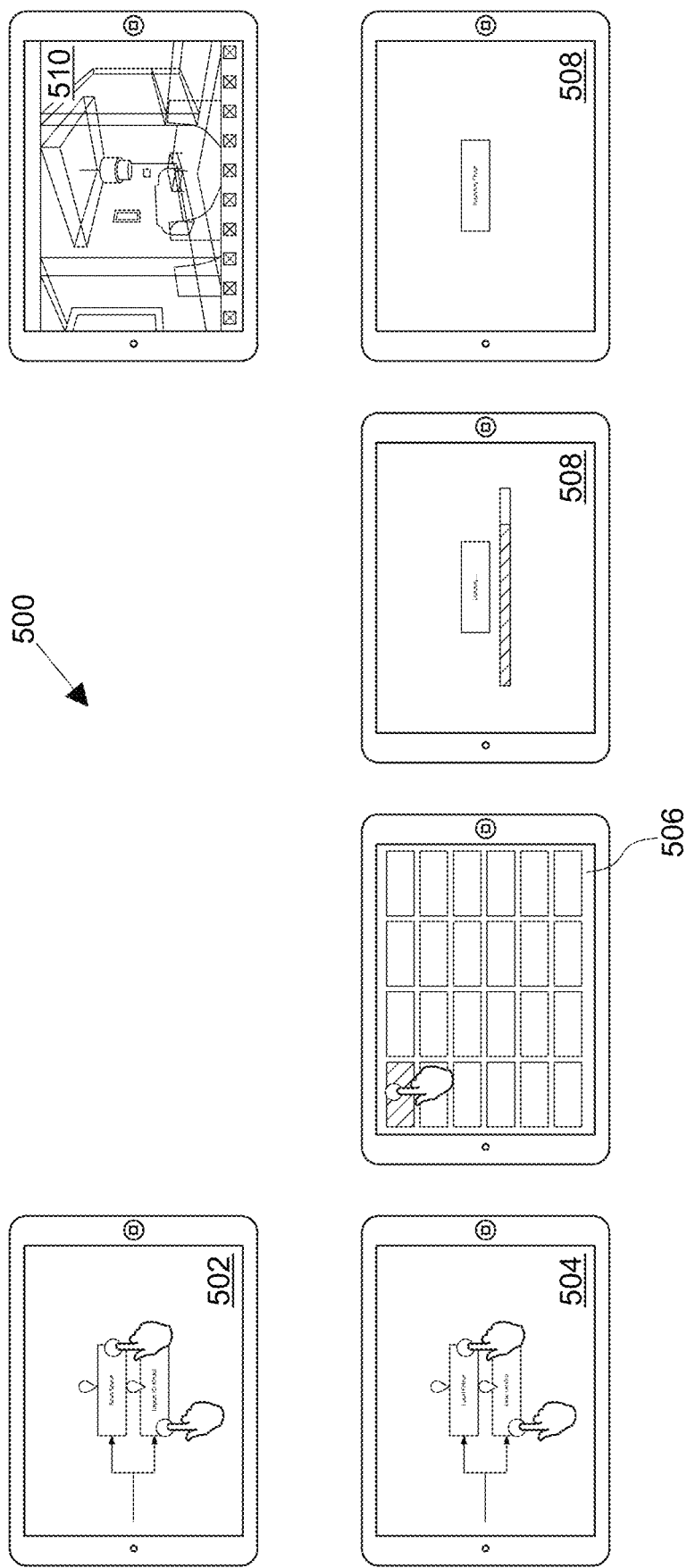
FIG. 13 is a diagrammatic view that depicts a user interface of the platform for a lighting space model selection process of a lighting design environment in accordance with the embodiments of the present disclosure.

FIG. 13 depicts a user interface of the platform for a scan process in accordance with embodiments of the present disclosure. A user interface for a scan process may include one or more of a scan initiation screen 452, scan progress screens 454, 458 and a scan output screen 460. In embodiments, the scan output screen 460 may present a first image rendering of a scanned space.

Figure 33:
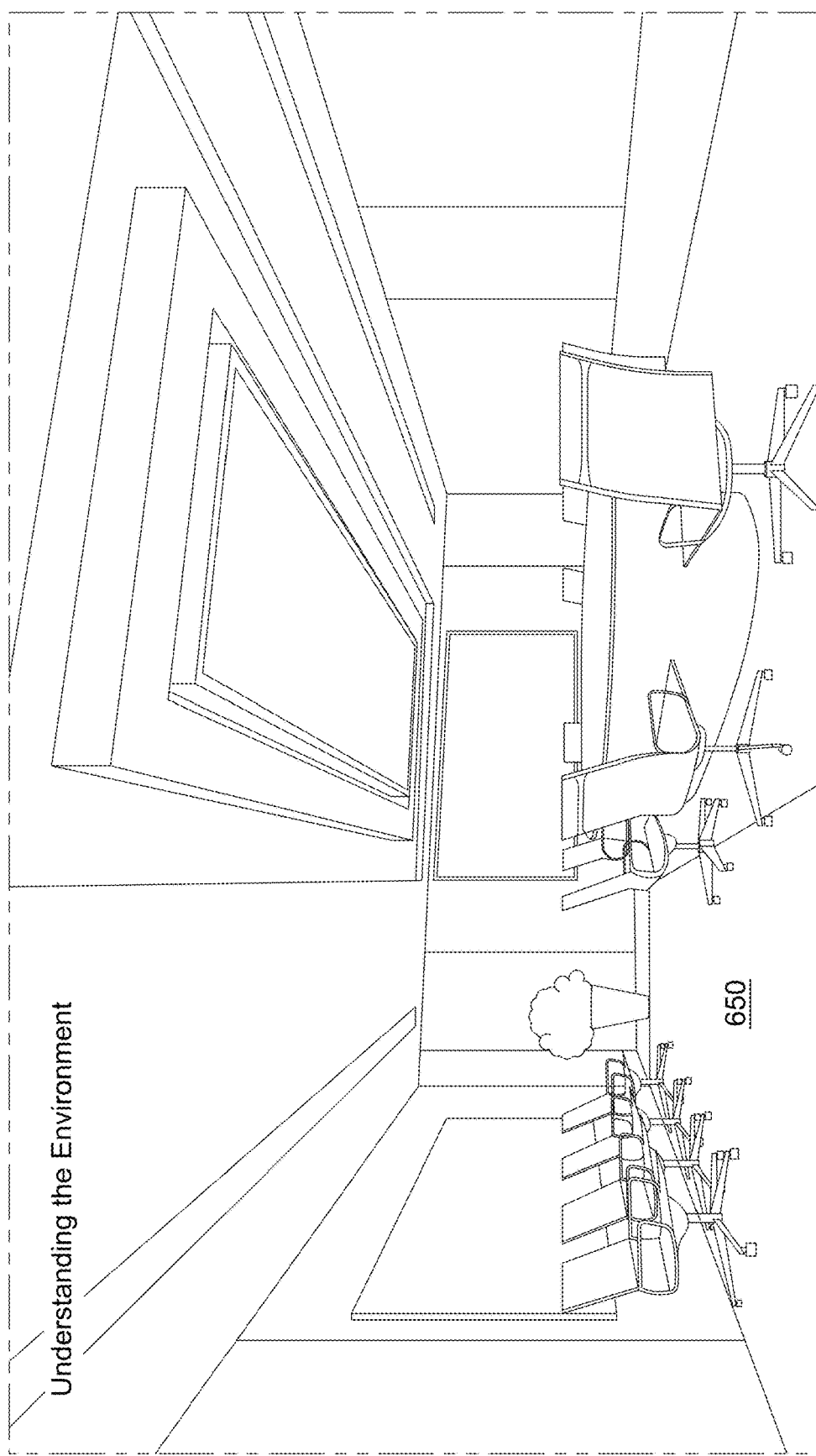
FIG. 33 is a diagrammatic view that illustrates the development of an understanding of the features of an environment using a feature extraction system in accordance with the embodiments of the present disclosure.

In embodiments, the scanning system 102 may populate or include one or more lighting space models 214, as depicted in FIG. 8, which may be based on features extracted from one or more input sources 206. By way of these examples, the lighting space models 214 depicted in FIG. 8 may be augmented (including automated, machine-based lighting model augmentation), such as based on an understanding of typical characteristics and parameters of buildings and interiors. In these examples, doorways, windows, columns, pillars, paints, carpets, wallpapers, hangings, objects of art, furnishings, fabrics, fixtures, and other elements of a space may be recognized by the feature extraction system 218 that may assign tags, labels, or other properties. Examples of such understanding for an interior office environment 650 (a conference room) are illustrated in FIG. 33. In embodiments, the model may thus store various lighting space objects 220 (which may be represented and stored in defined classes, with defined properties, attributes, fields, and parameters, such as in an object oriented programming languages like Java or C++), and each object may be assigned various parameters that are based on actual measurements (such as from the feature extraction system 218 or from a scan), may be based on inferences (such as populating the objects with common characteristics that are inferred from a lighting space knowledge base 222), or may be entered by a user, such as through a user interface. In embodiments, the feature extraction system 218 may include a self-learning, self-improving system that is capable of handling 2D and/or 3D spatial data (such as scan data, point clouds, CAD models, and others) and may use machine learning and artificial intelligence-based algorithms to extract features. In embodiments, the self-learning and self-improvement may occur under human supervision and/or via feedback (such as from any other system that contains information about the type or characteristics of a feature, such as an architectural or design model or blueprint), such as by verifying outcomes over multiple operations of the feature extraction system 218. In embodiments, the lighting space objects 220 may have various properties, such as dimensions, shapes, colors, reflecting characteristics, absorbing characteristics, surface characteristics, functional characteristics, and many others. Among many properties, ones that relate to interaction with light (such as transparency, reflectivity, opacity, surface characteristics, color, and the like) may be captured and characterized with sufficient detail to allow realistic rendering of the appearance of the lighting space objects 220 under different illumination conditions (including direction, intensity, color, color temperature, beam shape, and the like). In embodiments, object recognition technologies may be used to identify and characterize the lighting space objects 220, such as by type and by characteristics, such as specularity, diffusivity, reflectance, glare, and the like. In embodiments, machine vision and object recognition technologies may be used, such as to identify objects in photographs, videos or other scans. This capability may use and be improved by machine learning systems. The lighting space objects 220 may also include natural light sources, such as coming from windows. In embodiments, the lighting space knowledge base 222 may be constructed based on a series of scans, as well as by soliciting input from individuals, such as through the crowd-sourcing system 224 by which information about spaces may be solicited from individuals who experience or occupy spaces in general or the particular spaces that are to be modeled.

In embodiments, the platform 100 may use a vector field capture (VFC) system to capture and render the characteristics of light from a lighting object or fixture. Vector field capture is a 3D graphics rendering technique using volumetric data to realistically render effects, such as the lighting effects from the lighting fixture. With VFC, subtle three-dimensional detail may be accurately reproduced, and real luminaire light characteristics are accurately captured and rendered, such as in the lighting design environment (including, where applicable in VR and AR interfaces) using 3D graphics. Among other benefits, VFC may render the complete light-volume including subtle near-field artifacts throughout a three-dimensional space. In embodiments, the effects relating to the physical characteristics of a lighting fixture (such as light-clipping effects from the housing and/or lens assembly of a fixture) may be accurately reproduced. In embodiments, the VFC may also render the visual effects generated by multiple point light sources (e.g., LEDs) that may be contained in a fixture. It will be appreciated in light of the disclosure that conventional light rendering techniques typically measure a lighting object's intensity at various angles at a distance long enough, where the lighting object may be treated as a single point source, while VFC accounts for multiple point-sources effectively allowing for area and volume light sources. As a result, VFC may be shown to be more accurate than data from conventional IES representations of light sources or objects. In embodiments, using VFC, soft shadows are accurately recreated, such as rendering situations where real-world luminaires, especially LED-based luminaires that have multiple point sources that tend to have softer transitions between light and shadow. In many cases, the presence of multiple light origination sources may create complex interactions of shadows and lit areas, which cannot be reproduced when only a single point source is assumed, such as in the conventional IES specification of a lighting object. Using the VFC system, the intensity fall off of light over distance may be accurately captured and rendered, because intensity fall off may be explicitly included as part of the dataset. In contrast, conventional IES files do not capture falloff parameters. Also, in the VFC system, objects intersecting the light source (such as gobos, masks, filters, and physical objects like walls, coves, and the like) may be accurately illuminated. In embodiments, the light intensity may be calculated as a set of ray-traces from each light source to the intersecting element, and the light transparency, absorption, and reflection characteristics of each the intersecting object may be accounted for, such as to model intensity and color of each ray (including transmitted and reflected rays) in the overall 3D rendering environment.

In embodiments, the VFC may capture and reproduce the lighting distribution from a lighting object in various ways, such as the following. In embodiments, the light volume-data capture process may use either synthetically-rendered graphic image slices (such as from ray-set data) or may use photographs captured by photographing cross-sectional slices of the light from a lighting object, such as a luminaire. In embodiments, the captured illumination data is processed and then rendered as a three-dimensional volume. By way of these examples, interpolation is used to reconstruct the light-volume between known sample points for intensity. In embodiments, the three-dimensional intersections between the light-volume and illuminated geometry may be handled by z-depth comparisons from a "plane of projection." In these examples, arbitrarily complex 3D objects may be illuminated correctly (including concave objects) because the three-dimensional interpolation emanates from the light source(s) projection point(s). In embodiments, the rendering may be implemented using graphics-card shader-code, such as to enable high frame-rates. In these examples, the shader-code enables real-time rendering on platforms with a programmable GPU. Complex geometry may be illuminated with constant frame-rate performance. Rendering may integrate with other graphics techniques, such as one or more of bump, normal, displacement mapping, surface material properties, one or more bidirectional reflectance distribution functions (BRDF), and others. Shadows are accurately rendered for objects intersecting the light-volume.

In embodiments, the light illumination details may be accurately rendered across 3D object surfaces, such as objects represented in the lighting design environment. Subtle details and artifacts, such as caused by the lens/reflector assembly of a lighting fixture, may be reproduced in three dimensions. Most conventional 3D light rendering techniques are inaccurate even for only two dimensions (across a plane for example—they do not capture the artifacts present in a real light source), while VFC is accurate in three dimensions. Also, existing light-data descriptions, such as IES files, only capture the light luminance and angle information as if the light were a single-point source, while VFC may accurately render multi-point lighting objects, like LED arrays.

In embodiments, the platform 100 may use VFC-based rendering for various purposes. Embodiments include using VFC for photorealistic rendering. Photorealistic rendering applications such as 3DS Max™, Maya™, and Blender™ use ray-tracing to create photorealistic scene-renders; however, the light definition typically used is limited to a "single point source" definition. The standard light definition is the position, direction, intensity, falloff (assumed by model to be linear, quadratic, or the like). Using a VFC definition, these ray-traced lights become multiple point sources, with intensity and direction. In embodiments, the platform 100 may provide plugin support for these rendering packages (such as for reading VFC light definitions and rendering) to enable high-end rendering packages to more accurately render real-world luminaires, such as for architectural walk-throughs, movie and television 'virtual sets', etc.

In embodiments, lighting designers using the platform 100 need a way to examine luminaire characteristics. Usually, this is done by physically handling the luminaire and testing its output. Given the number of options for a luminaire (output intensity, light angle, light Kelvin temperature, etc.), manually examining one luminaire at a time is very limiting. Among other things, it requires a large inventory of sample luminaires. A better option is to use a software capability of the platform 100 (optionally with an interface on a smartphone, tablet, PC, or Mac) that integrates the VFC technology to realistically simulate a luminaire's light output. Using the software capability, numerous luminaire options may be experimented with and visualized in the lighting design environment. While the lighting object is moved around in a virtual environment, options such as beam angle, color temperature, and the like may be quickly adjusted and accurately rendered. By interactively trying different light options, and seeing them realistically rendered, a lighting designer will be better informed about lighting objects being considered for an installation.

In embodiments, VFC rendering of lighting objects may be integrated into any software application where real-world subtle characteristics of lighting fixture output are required to be viewed. For example, by creating the library of existing lighting objects (from numerous manufacturers), the dominant luminaire model choices may be cataloged and viewed within an application. This lends itself well to building a "virtual catalog" (optionally associated with the lighting marketplace elements of the platform 100), where the end-user may narrow choices down by using either standard "filter options" or by using machine learning to suggest possible luminaire choices for specific environments. The end-user may then visually see the options from a large set of possible choices in the lighting design environment within minutes.

In embodiments, VFC rendering allows any lighting designer or software developer to accurately render outputs from a lighting object. Providing a VFC-based rendering pipeline for lighting objects may be used to enable an "open architecture" for software development, such as involving a light-volume capture tool that creates image slices from a lighting object. In embodiments, the resulting dataset may be downloaded from, for example, a luminaire manufacturer; a software application to process the image slices into one or more data files (in embodiments such a data file may be provided by luminaire manufacturer); and a rendering plugin that may be added to the rendering pipeline as a "material" applied to the rendered objects. These objects may be used in the platform 100 enabling representation of a wide range of objects from many manufacturers.

Among other benefits, VFC rendering reproduces light ray information as individual source vectors. In embodiments, the light source-position and direction is accounted for, and subtle light effects based on multiple source-origins such as crossing shadows (and shadows within the light volume) are reproduced. When creating 3D rendered synthetic images, whether for 'architectural walkthroughs', movies, television, advertising, video games etc., the images are more photo-realistically accurate than using conventional information like IES files, because the "current best approximation" of an IES file only represents the light as a single point source viewed from a distance. The conventional IES measurement cannot account for internal volume details. Also, light gobos, masks, filters and the like may only be roughly approximated when assuming a single point source; for example, a LED luminaire that includes multiple LEDs along a narrow strip will not accurately show the light masking that results when the luminaire end is abutting a wall cove. In such a situation, the LEDs on the end will be completely obstructed but the LEDs toward the middle will be unobstructed, but a conventional rendering based on the IES specification (which assumes a single point source) cannot account for cases like these.

It will be appreciated in light of the disclosure that VFC rendering typically requires a larger data set definition than other light-rendering techniques (such as IES based rendering). In embodiments, the VFC data set may be compressed using various compression techniques. In embodiments, VFC may be used to account for direct lighting and indirect-lighting (bounced light). In embodiments, the platform 100 may include various facilities and systems for machine learning and analytics. In embodiments, the machine learning and analytics may include learning for design decisions, to find fixtures, to characterize fixtures, to price fixtures, to recommend fixtures and to tune them. In embodiments, the tuning under machine learning may include tuning of colors, color temperatures, timing, lighting distributions, intensities, beam angles and the like. Tuning may also include tuning emotional or aesthetic filters and the like.

In embodiments, the machine learning and analytics may be integrated with the recommendation engine 122. Designers today are used to searching through lighting fixture objects 230 in a very basic way, such as searching by voltage, dimming technology and the like. This type of searching includes very little, if any, comprehension of what the designer actually wants. In embodiments, the machine learning and analytics may allow a designer using a platform to search within a design context; for example, the platform 100 may recognize that the designer is trying to highlight a walkway through a space, for example, and may start to recommend suitable lighting fixture objects 230 and light space models 214.

In embodiments, the platform 100 may access and use information about the technical capabilities of lighting fixtures and lighting objects, including capabilities for custom color tuning, custom dimming curves, and custom lighting distribution effects, collectively referred to herein as a custom tuning system. By way of these examples, the custom tuning system may include multiple channels, providing a platform user with many ways to achieve a certain color and intensity. In embodiments, the custom tuning system may sit between a user choosing color and intensity levels and the drivers setting chosen color and intensity levels in a given lighting object or fixture in the lighting design environment 238.

In embodiments, a custom tuning system may include various tuning modes. By way of these examples, tuning modes may be user-selectable tuning modes. In these examples, a user may indicate to a custom tuning system, by selecting a tuning mode, a bias in terms of how the system is going to choose to make a color indicated by the user. In embodiments, the bias may include luminosity, efficacy, color quality, such as best color on metrics, intensity, such as maximum or minimum melanopic flux ratios, and the like.

If a user selects a tuning mode, there are many methods to analyze and manage information related to a bias. In most instances, users choose and set a single method. Unless the user is dynamically adjusting the tuning mode, the user has typically picked a given set of parameters for adjusting channels, and that set flows through to control of a lighting object. Instead, a custom tuning system may allow a user to optimize for a preference and have the biases in the system configured to implement the preference in the lighting design environment 238. This may include, for example, having the light move through a selected curve of lighting control parameters as the light is dimmed.

Typically, efficacy, color quality, and intensity may be preselected at the software or firmware level and not otherwise selectable or changeable by a user. For example, a user may choose a 2700K CCT setting and the platform 100 may use its predetermined bias to achieve the correct output according to the selected 2700K CCT setting. The user selectable tuning modes, such as user selectable tuning modes that may be available to a user in the platform 100, may allow the platform 100, either at the software or firmware level, to dynamically and algorithmically determine the correct balance of four color channels, based on the user selectable tuning modes available to the user. Each mode may have an associated algorithm. When a mode is selected by a user, the platform 100 may engage the algorithm associated with the selected mode. In embodiments, the platform 100 may engage the algorithm in a way that is transparent to the user and does not require the user to have an awareness of the underlying algorithm.

In embodiments, a custom tuning system may include a warm dim setting that covers color points. A warm dim setting may include red, green, blue, and white (RGBW) elements. By way of these examples, the warm dim setting may include programmable curves and a user interface to manage programmable curves. In embodiments, the programmable curve may include a start point, an end point, and a configurable path between the two. The programmable curve may be programmed to provide control based on input from a 0-10 volt dimming system, a DALI control system, or the like. In embodiments, the custom tuning system may allow a platform to dynamically reassign lighting direction and its intensity at particular points, readjusting where light is directed and tuning the spectral characteristics of the light, such as efficacy, luminosity, color quality and melanopic flux.

In embodiments, dynamically reassigning lighting direction and intensity using a custom tuning system may include a capability to readjust where the light goes and to adjust the content of the light to make it responsive to the lighting design environment 238. This may effectively disaggregate the resulting light distribution or other illumination effects from a particular light fixture object 230, which also may disaggregate a lighting experience from installed lighting fixture objects 230. In embodiments, this disaggregation (created by making any given lighting fixture object 230 much more flexible) in turn provides much better flexibility in the design of a lighting installation because many more lighting fixture objects 230 may satisfy the design constraints of a given installation.

In embodiments, the custom tuning system may connect lighting variables to filters, such as aesthetic filters; for example, it may be observed that for a given application, like lighting a desktop used for detailed work, maximizing luminosity is a key parameter for a "desktop filter." For a filter that intends to create a given mood (e.g., a "romantic filter"), parameters may be tuned to provide warm color temperatures and a palette of colors that are perceived as being more romantic. In embodiments, connections between lighting control parameters for a custom tuning system and one or more filters may be learned through the machine learning capability of a platform, such that over time the system recommends and enables the design, purchasing (such as through the lighting marketplace) and control of custom tuned lighting objects and fixtures that satisfy desired emotional and aesthetic characteristics as represented by filters selected by a user. In these examples, connections among lighting variables and filters may allow a platform to tune to different scenes, such as lunch, cocktail hour, or dinner scenes, translating the filters to the variables. In embodiments, the connections may create an abstraction layer between the technology that enables a desired filter or effect and the intent of the user. By way of these examples, the user's intent (which may be embodied in selecting a filter) may include keeping people alert, making people feel happy, supporting romance and the like. In embodiments, the platform 100, under machine learning, may learn to embody that intent by variation, selection and promotion of custom tuning parameters for lighting objects and fixtures, based on feedback from users as to whether a given object, fixture or installation achieves the desired intent.

A lighting space model 214 may also include one or more of the lighting objects 226, including the lighting source objects 228 and lighting fixture objects 230. In embodiments, the lighting source objects 228 and the lighting fixture objects 230 may include novel data structures, which may be represented and stored in defined classes, with defined properties, attributes, fields and parameters and may be collectively referred to except where context indicates otherwise as "properties", such as in an object oriented programming languages like Java or C++ that characterizes light sources and lighting fixtures by many different properties that may be relevant to the use of light sources and lighting fixtures in a lighting installation. In these examples, the lighting object properties may include physical dimensions (i.e., length, width, height, volume, and weight); lighting properties (i.e., output levels in lumens, Color Rendering Index (CRI) properties, color properties, color temperature properties, spectral characterization properties, output bloom properties, and many others); financial properties (e.g., prices, discounts, costs of operation, rebates, energy usage projections, installation costs, servicing costs, shipping costs, taxes, and others); performance properties (e.g., power levels, predicted life spans, battery life, operating temperatures); functional properties (e.g., installation type, type and shape of connectors, etc.); control properties (such as for controlling light source outputs, networking features, IoT integration, remote control, autonomous control, etc.); and many others. In embodiments, light sources and corresponding lighting source objects 228 may include a wide variety of types of light sources, as well as light sources in combination with optics, filters, and similar accessories. In these examples, the light sources may be, for example, incandescent, fluorescent, semiconductor, LED, halogen, laser, inductive and other light sources, and may be combined with filters, phosphors, and the like. In further examples, a laser diode with a single crystal phosphor may provide a highly variable distribution from a light source that is projected into a room. In embodiments, lighting may include laser-driven sources, such as using an array of reflective elements to distribute light to a space. In embodiments, the light sources and fixtures may be adjustable or controllable, and the lighting objects 226 may include properties, fields, metadata, and the like that enable dynamic adjustment or control of the light source so that the lighting design environment 238 may model and display such control characteristics.

In embodiments, the lighting fixture objects 230 may include functional elements of lighting fixtures, including without limitation robotic elements, such as where a lighting fixture is positioned on a gimbal or similar mechanism to allow directional control of the lighting fixture, where a lighting fixture is positioned for movement (such as along a supporting line), and the like.

In embodiments, the lighting objects 226, with their properties, may be stored in the lighting object library 232, which may include a universal database of light sources and lighting fixtures from various manufacturers. In embodiments, the automated search system 234 of the platform may search public sources, such as websites of lighting manufacturers, sales representatives, and distributors, among many others, to find new lighting objects 226 for the library and to find updated information (such as pricing and specification information) about the lighting objects 226 that are in the library. In these examples, the automated search system 234 may use a web crawler, spider, bot, or similar facility to find sources of information needed for the lighting object library 232. Where available, the automated search system 234 may find and configure one or more application programming interfaces to establish an ongoing feed of information to the lighting object library 232, such as a feed of updated pricing or specification information. The automated search system 234 may be configured to search for keywords relevant to lighting products (such as "lumens," "illumination," or the like, as well as terms used in engineering standards like ISO standards for lighting products), for file types that are relevant (such as IES files that are used to characterize the far field illumination characteristics of lighting products, as well as proprietary data formats used by various manufacturers to characterize their lighting products), for known brand names and product names, and the like. In embodiments, the automated search system 234 may be trained to find and classify lighting products, such as into categories, such as using machine learning under human supervision. In embodiments, the crowd-sourcing system 224 may be used to populate the lighting object library 232, such as by allowing users to identify and add additional light sources and lighting fixtures, and by allowing users to populate various properties or fields of the lighting objects 226.

It will be appreciated in light of the disclosure that the marketplace for lighting products is not transparent, as many products are promoted with limited, often inaccurate technical information, and pricing information is often absent. Obtaining real pricing information, reflecting discounts, rebates, and the like often requires extended research and negotiation. Similarly, availability and delivery information is often unreliable. Accordingly, an operator of the platform, by virtue of the handling of many projects on the platform, may accumulate, via repeated use of the automated search system 234, via independent testing of the lighting objects 226 and via feedback solicited from users and from the public, may accumulate, in the lighting object library 232, information about the validity of technical specifications, information that may augment technical specification, information about real product costs, and information about turnaround times and the like. In embodiments, this information may be solicited by the crowdsourcing interface 252 described elsewhere herein or via a manufacturer and the product feedback interface 236 through which users or the public may provide information about their experiences with products and manufacturers. In embodiments, the resulting information (such as technical lighting information, pricing information, rating information, and the like) may be stored in the lighting object library 232 (such as in properties of each lighting object) or elsewhere for access by the platform.

In embodiments, the lighting design environment 238 may allow a user of the platform to select a lighting space model 214. FIG. 13 depicts a user interface 500 of the platform for a lighting space model selection process of the lighting design environment 238. In embodiments, the user interface 500 for a lighting space model selection process may include one or more of a lighting space model selection initiation screen 502, lighting space model source selection screen 504, lighting space model source selection screen 506, lighting space model loading progress screens 508 and a lighting space model selection output screen 510. In embodiments, the lighting space model selection output screen 508 may present or render an output image of a scanned space.

Figure 15:
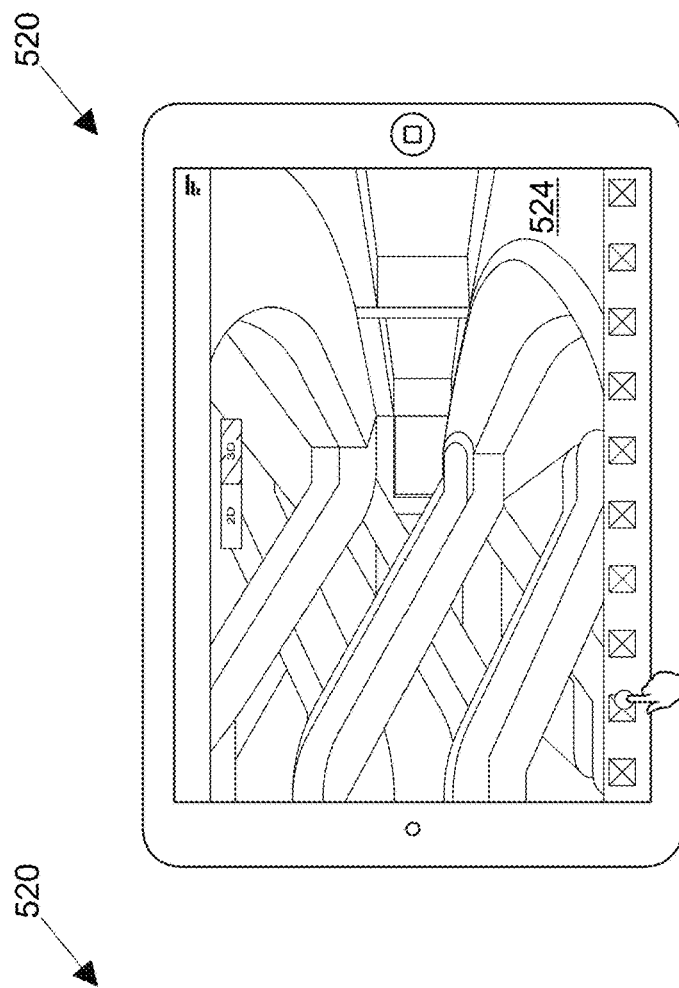
FIGS. 14, 15, 16, and 17 are diagrammatic views that depict lighting space model design renderings in accordance with the embodiments of the present disclosure.
Figure 14:
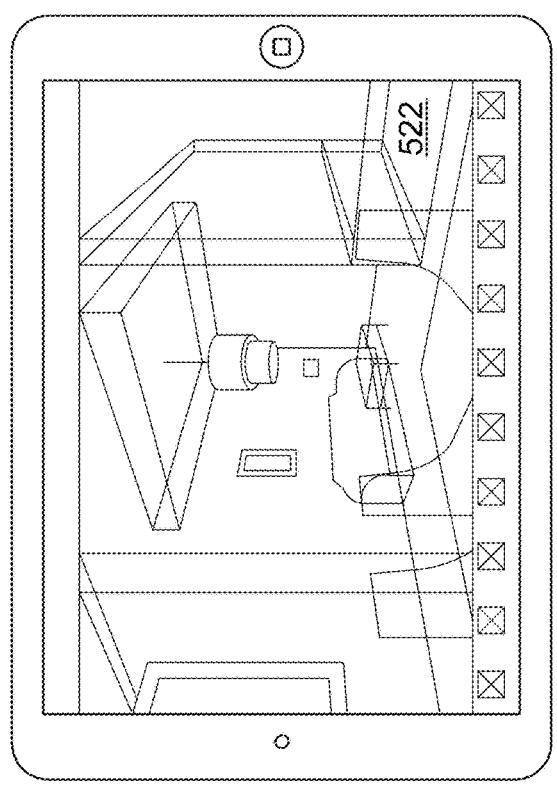
Figure 17:
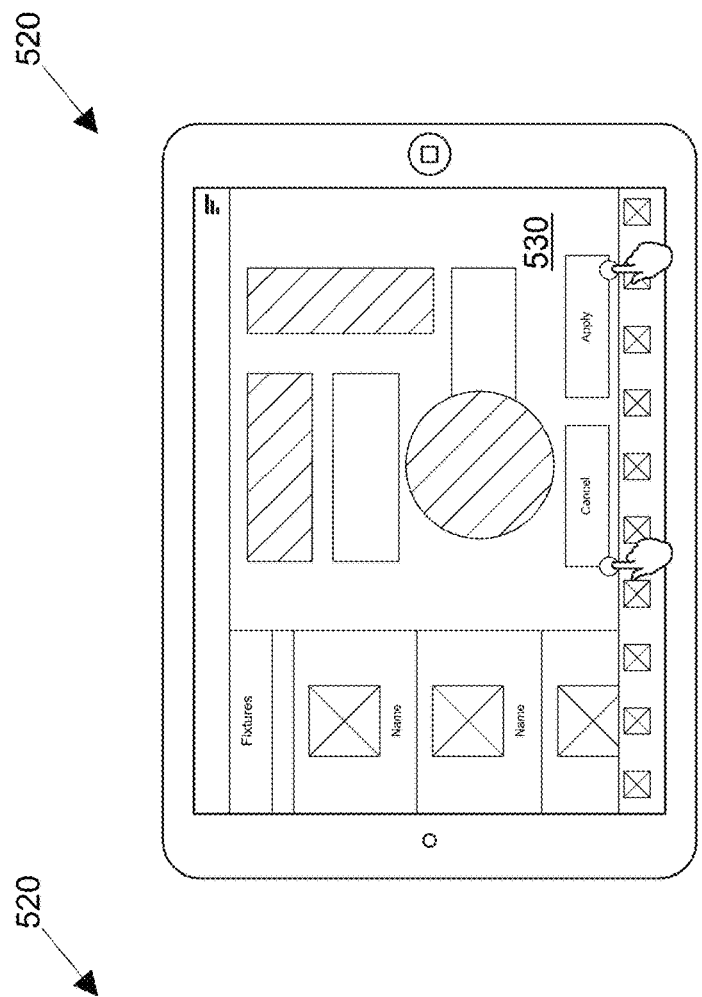
Figure 16:
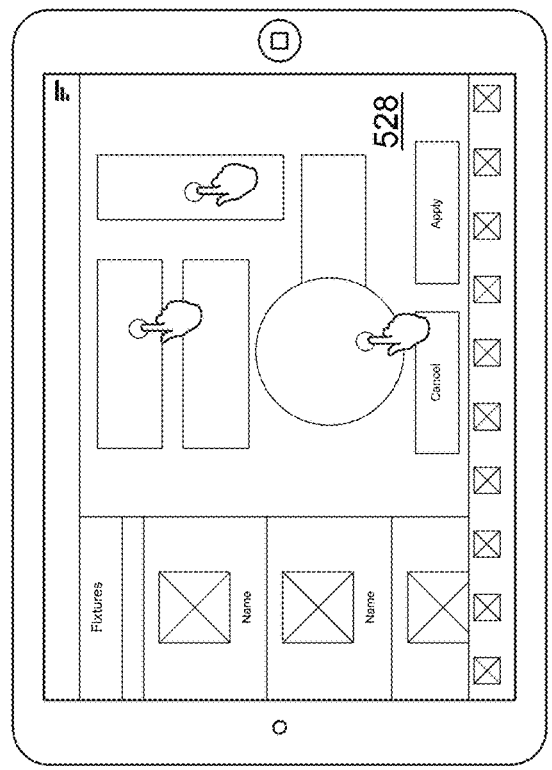

FIGS. 14, 15, 16, and 17 depict lighting space model design renderings provided in a user interface 520 in accordance with many embodiments of the present disclosure. FIG. 14 depicts a design rendering 522 that conveys an understanding of a space in terms of individual structural elements. FIG. 15 depicts a final 3D design rendering of a space 524. FIGS. 16 and 17 depict 2D views 528, 530 of a design rendering.

Figure 19:
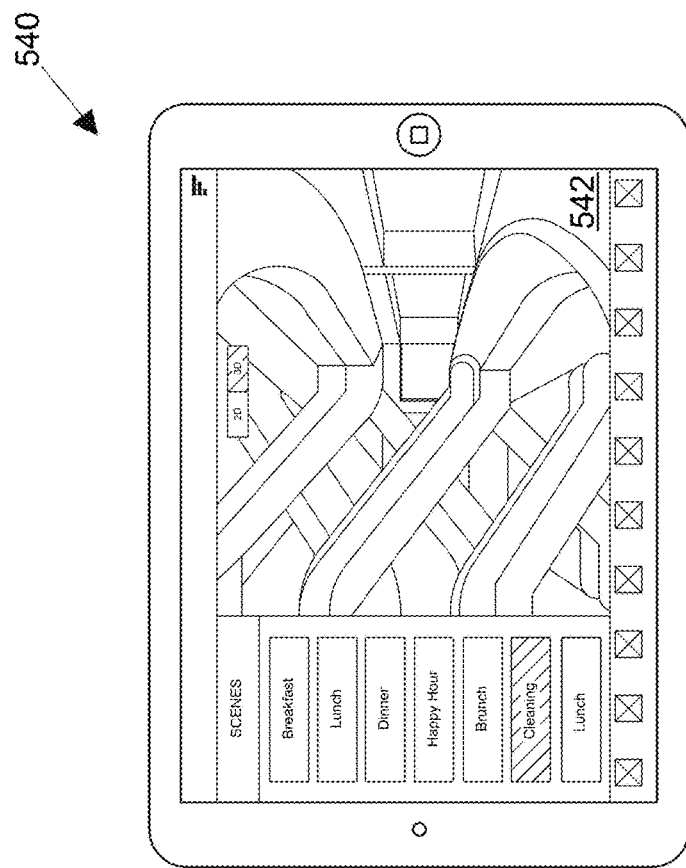
FIGS. 18 and 19 are diagrammatic views that depict scene renderings for a scene that includes lighting elements in accordance with the embodiments of the present disclosure.
Figure 18:
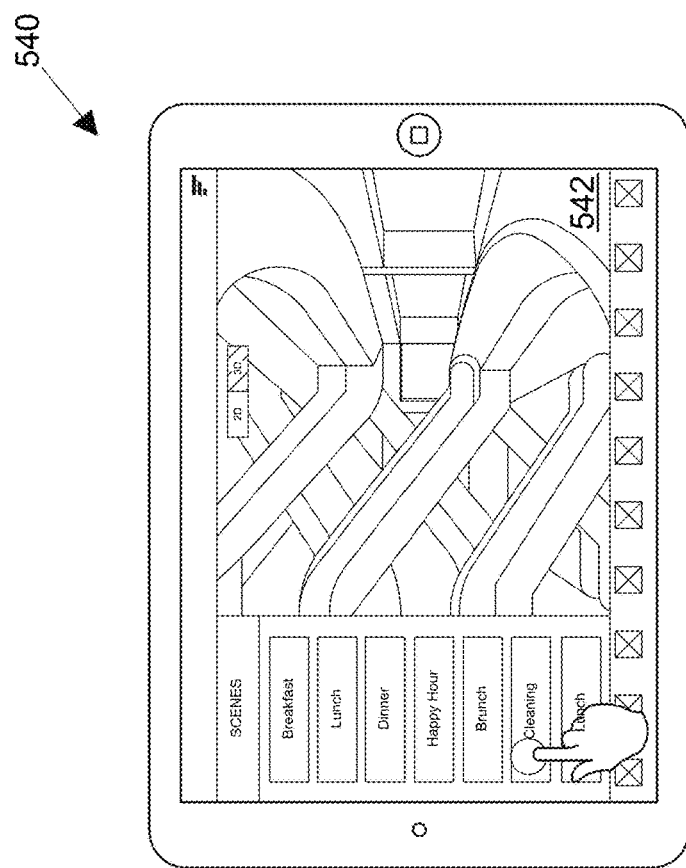

FIGS. 18 and 19 depict scene renderings 540 in accordance with embodiments of the present disclosure. In the examples depicted in FIGS. 18 and 19, a user of the platform chooses a cleaning scene 542 rendering to be displayed by the platform.

Figure 21:
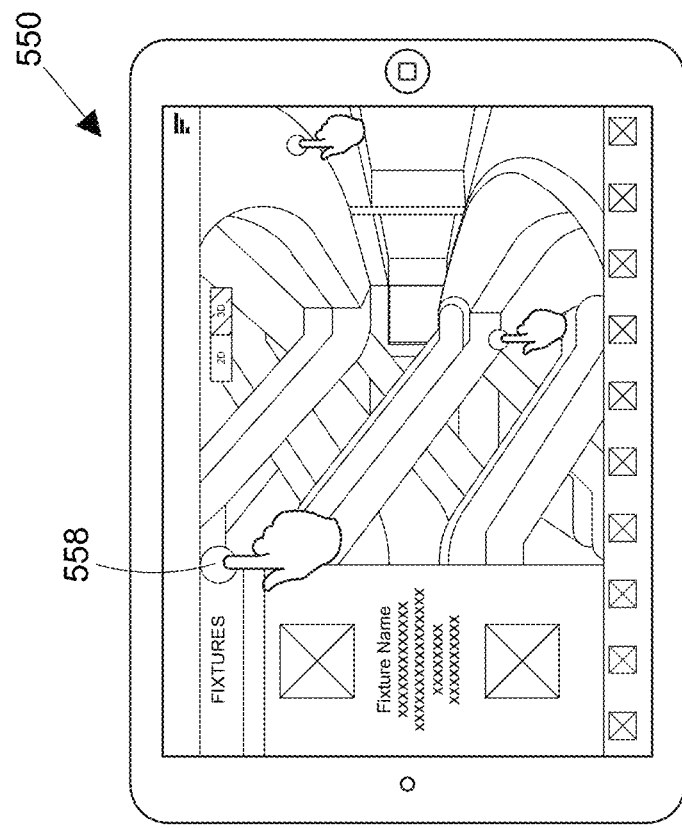
FIGS. 20 and 21 are diagrammatic views that depict a user interface for a lighting fixture object selection in accordance with the embodiments of the present disclosure.
Figure 20:
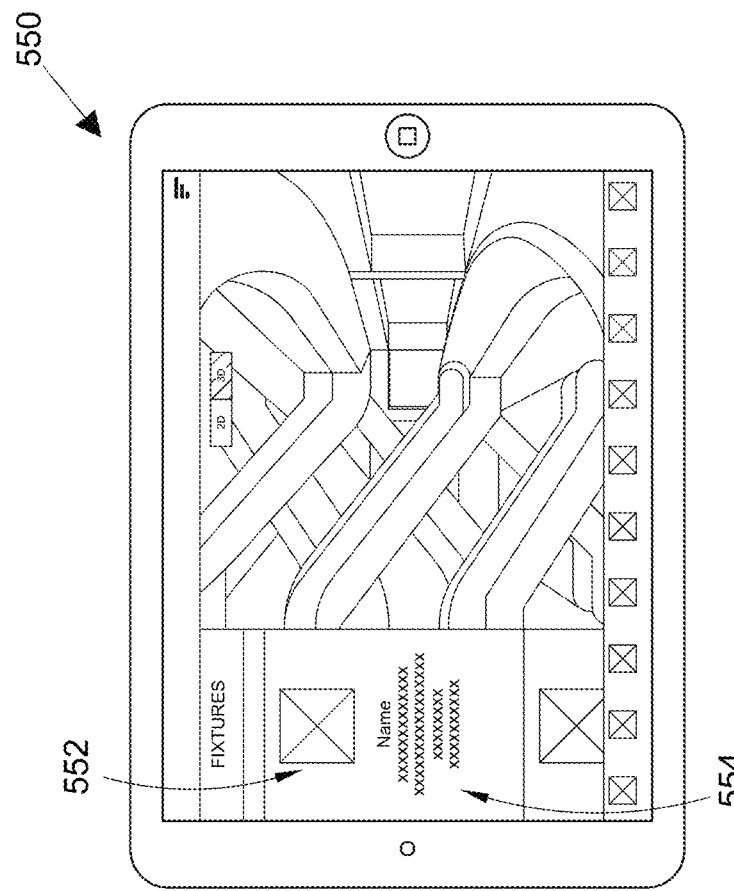

FIGS. 20 and 21 depict a user interface 550 for selection of lighting fixture objects 230 in accordance with the embodiments of the present disclosure. FIG. 20 depicts the UI 550 in which the platform tells a user the name 552 and specifications 554 of a lighting fixture object 230, as well as presents options to modify 558 the selected lighting fixture object 230. FIG. 21 depicts the UI 550 that allows a user to rearrange lighting fixture objects across a design.

Figure 22:
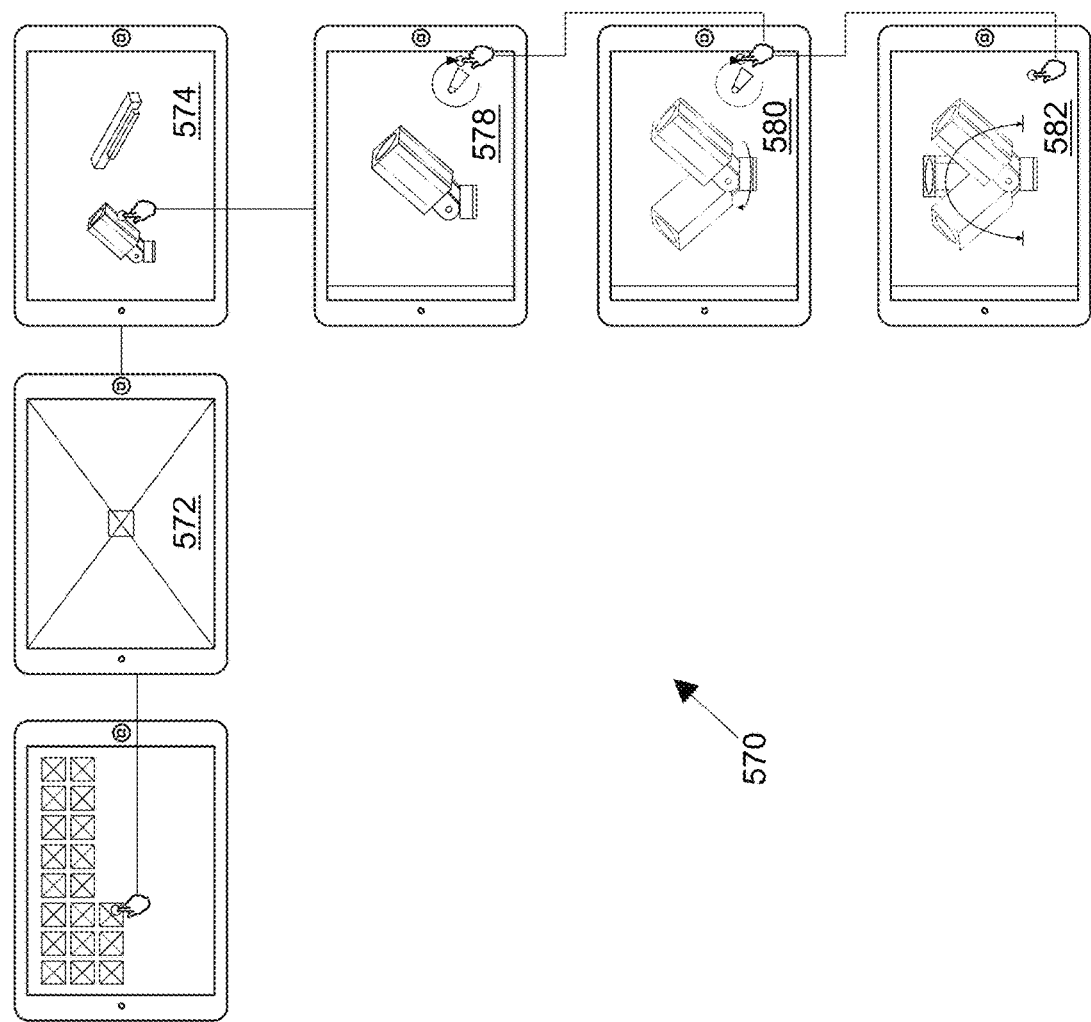
FIGS. 22 and 23 are diagrammatic views that depict a user interacting with AR functionality in accordance with the embodiments of the present disclosure.
Figure 23:
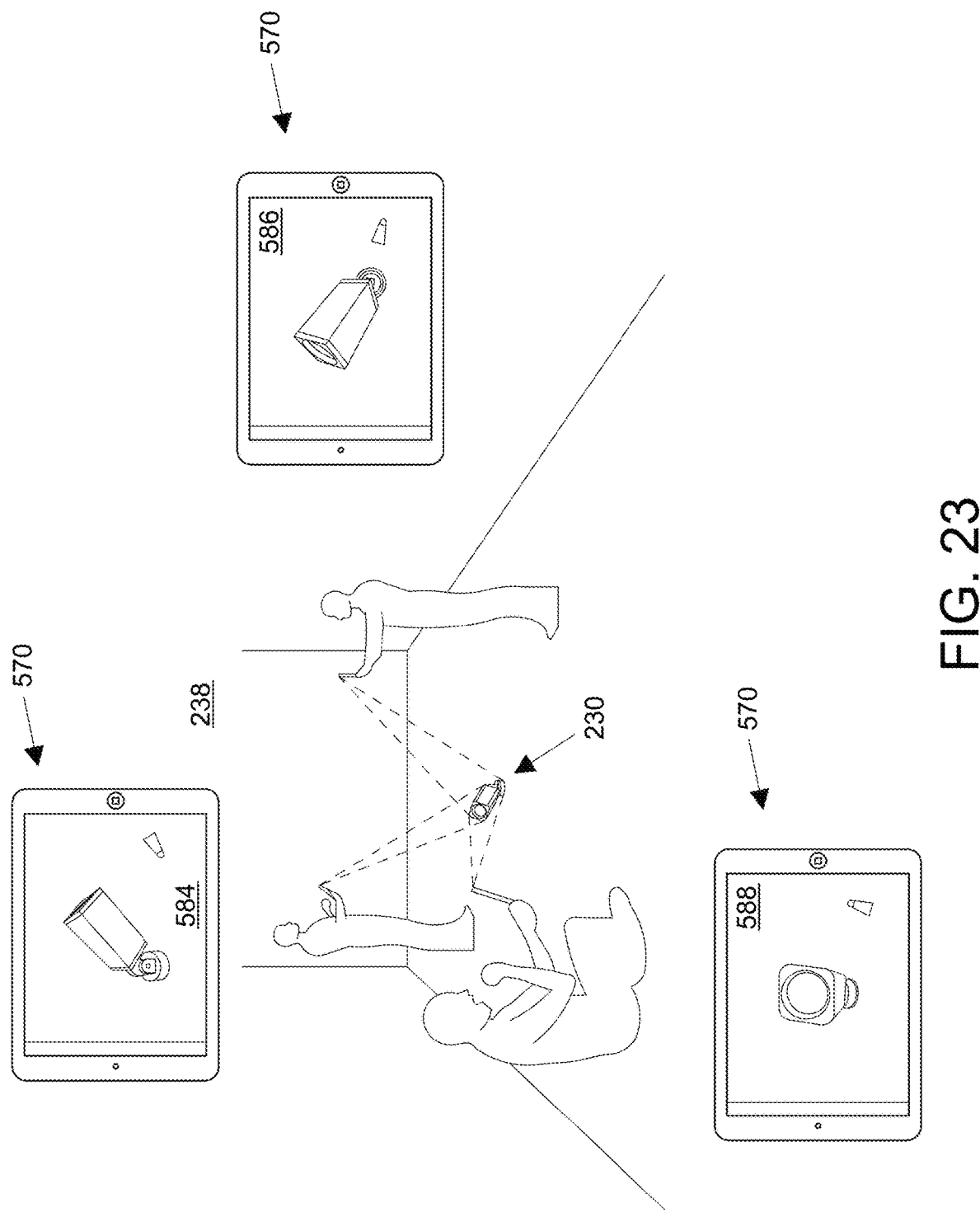

FIGS. 22 and 23 depict various user interfaces 570 for AR functionality for user selection and modification of lighting fixture objects 230. Users of the platform 100, such as lighting designers, may desire to inspect and evaluate lighting fixture objects 230 by examining them and their light. To support this function, the platform 100 may allow a user to digitally inspect both the physicality and the light from a given lighting fixture object 230.

In embodiments, the platform 100 may allow a user to digitally inspect a lighting fixture object 230 using augmented reality (AR). Using AR, a user may inspect a lighting fixture object 230 with all its relevant details in the current lighting design environment 238 by viewing the lighting design environment 238 through a camera. By way of these examples, the platform 100 may modulate illumination intensity in a space on a screen to show how a light from the lighting fixture object 230 may affect the lighting design environment 238. This may allow a user to inspect both the physicality and the light of the lighting fixture object 230. FIG. 22 depicts the many examples of the user interfaces for selecting and inspecting controlling the movement of a lighting fixture object 230 in the augmented reality context depicted in FIG. 23.

Near Field

Figure 24:
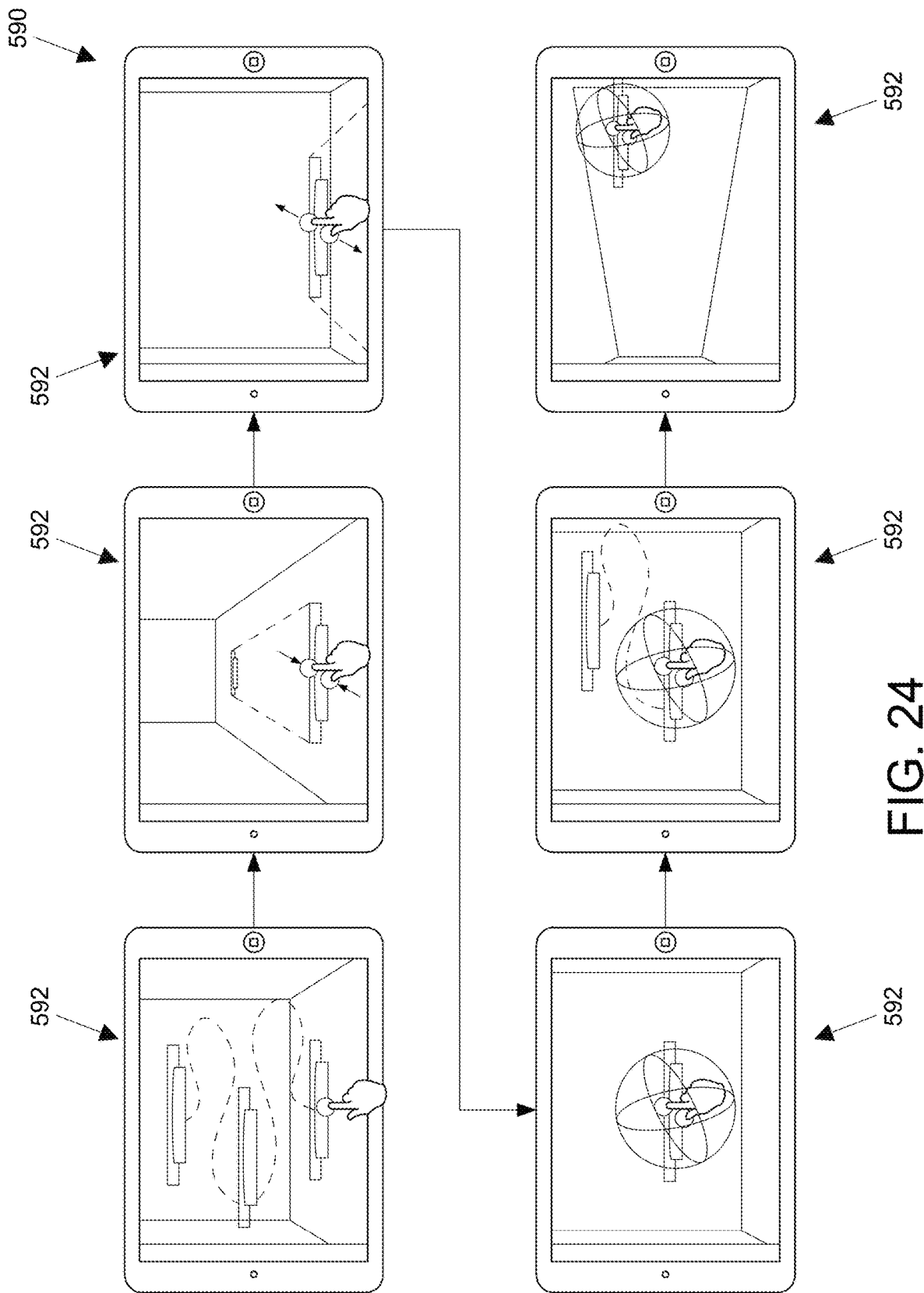
FIGS. 24 and 25 are diagrammatic views that depict a user interacting with near field functionality in accordance with the embodiments of the present disclosure.
Figure 25:
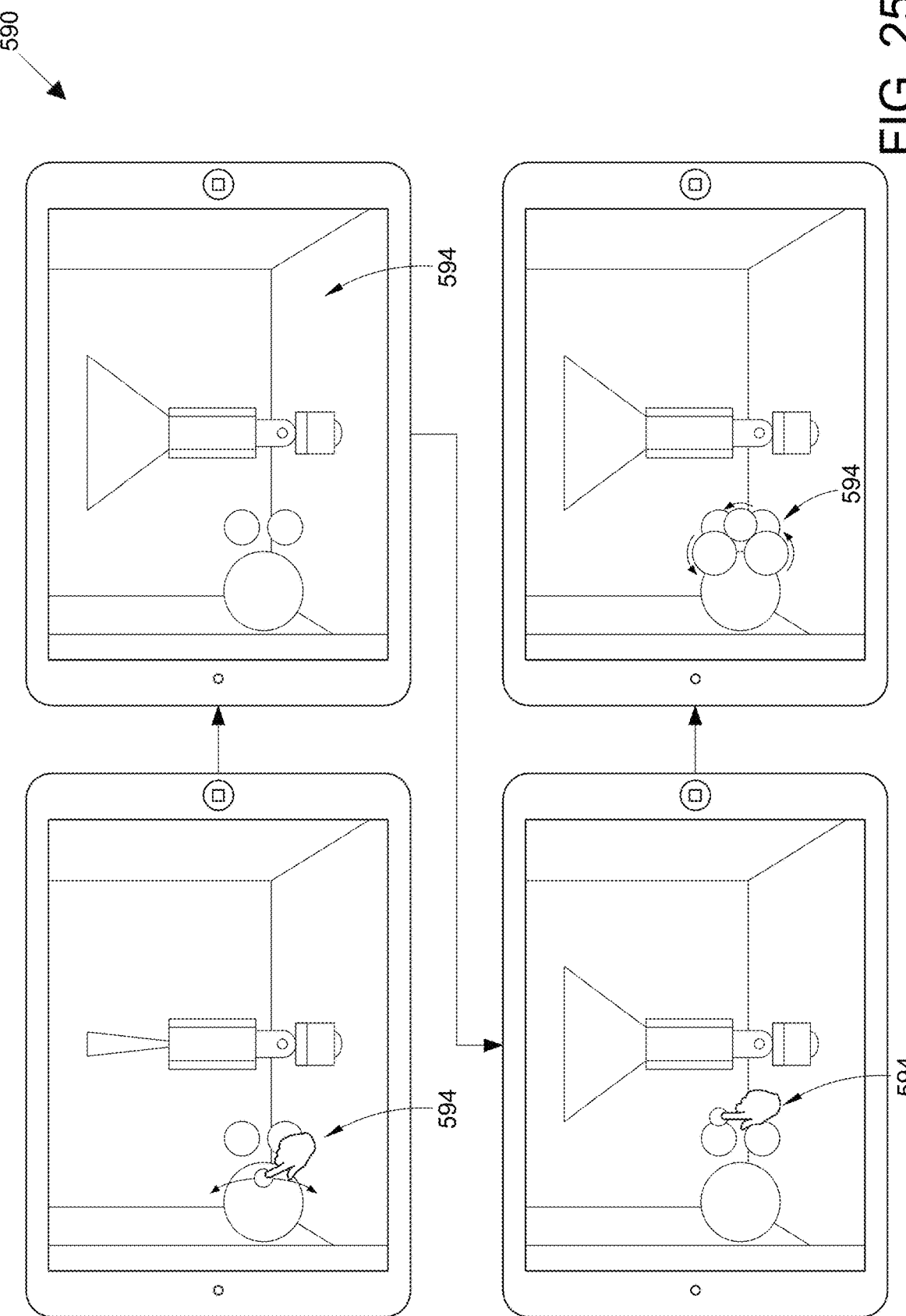

FIGS. 24 and 25 depict various user interfaces 590 for near field functionality for the user-selection and modification of lighting fixture objects 230. In embodiments, the platform 100 may also allow a user to inspect a near field light characterization 200 of a lighting fixture object 230. Users, such as lighting designers, may desire to shine a lighting fixture object 230 on a white wall to be able to inspect it. In further examples, users, such as lighting designers, may desire to shine a lighting fixture object 230 on any digital surface for exploration of one or more of other shapes, colors, textures, and the like. The user may explore and perform these activities from various distances and angles. FIG. 24 depicts controls 592 of the platform 100 that a user may use to move a lighting fixture object 230 and inspect the light patterns the lighting fixture object 230 creates on a digital white wall, or a digital surface, or the like. FIG. 25 depicts controls 594 of the platform 100 that a user may use to change attributes of a lighting fixture object 230 and inspect the light patterns the lighting fixture object 230 creates on a digital white wall, or a digital surface, or the like. These light patterns on the wall may change if various parameters such as the beam angles, CCT and the like are changed.

In embodiments, the platform 100 may support changing these and other parameters and then render the light on the digital wall based on the changed parameters. FIG. 25 depicts user interfaces 590 of the platform 100 that a user may use to change such parameters. In embodiments, the information handled by the platform, such as information associated with or used by one or more lighting space models 214, the lighting space knowledge base 222, various lighting space objects 220, the lighting object library 232, and other aspects of the platform, may be used to support the lighting design environment 238, which may include a user interface supported by various information technology components, including processing systems, data storage facilities, operating system elements, programs, applications, and the like. By way of these examples, the user interface may provide one or more visual displays of a lighting installation, showing the lighting space containing various lighting space objects 220 and the lighting objects 226. In embodiments, the visual representation generation engine 240 of the platform may generate views for the interface based on the various input data sources, object properties, and the like. Views from different input sources 206 of the scanning system 102 may be presented in various forms, such as in the native formats from the input sources 206 (e.g., showing a point cloud from a laser scan, a photograph, a video, or a view generated from a CAD model, such as a 3D model), in normalized formats (such as a 3D animation view or photorealistic view that is generated by the visual representation generation engine 240), in aligned formats (such as showing overlays of different types of content that have been aligned, such as by the scan alignment system 210), so that mixed content may be viewed in the interface including showing an object from an infrared scan in the same space as a 3D modeled object and a photographed item.

In embodiments, the visual representation generation system may be configured to allow user manipulation, such as by various tools, menu elements, mouse movements, touchscreen interactions, auditory inputs, or the like. In these examples, a user may drag and drop various elements into the lighting design environment 238 (such as objects retrieved from the lighting object library 232 or the lighting space knowledge base 222), position elements in the interface, size and resize elements, direct elements (such as directing a beam or bloom of light from a lighting object in a desired direction), set properties of elements (such as setting desired colors from a color palette), and the like. Information about the properties of the lighting space objects 220 and the lighting objects 226 may be used to inform how those objects are represented in the environment; for example, a lighting fixture that generates a given beam shape may be automatically represented as delivering that shape, and a light source with a given range of properties (such as intensity, hue, color saturation, CRI, dimming, or the like) may be presented in the interface such that a user may adjust the light source in the interface within the range of available properties. In embodiments, the user may, therefore, place a lighting fixture with a given light source into the environment, adjust its position and direction, and tune its intensity level, color, and the like to a desired setting, or may configure it to be adjusted within a range of settings, such as setting it to dim along a given dimming curve as described elsewhere in this disclosure.

In embodiments, the lighting design environment 238 may include or enable a virtual reality (VR) interface 600, such as providing an immersive, 3D interface in which a user may experience the lighting space, such as while wearing virtual reality headgear 602, or the like. In embodiments, the lighting design environment 238 may also include or enable an augmented reality (AR) interface, such as allowing a user to view an actual space (such as through a lens or camera) with overlay elements that represent the lighting space objects 220 and/or the lighting objects 226. By way of these examples, a user may look at a space through glasses or headgear, and the lighting design environment 238 may supply one or more overlays that represent how a lighting fixture might appear in the space (with the location being indexed to one or more features of the space by the visual representation generation engine 240) and how the beam or bloom of illumination from the fixture might illuminate other objects, etc. To support the interface (including VR and AR interfaces), the visual representation generation engine 240 may be configured to handle various aspects of 3D object generation and manipulation, such as rendering hue, saturation, transparency/opacity, surface textures, shadows, specular/reflective effects, and many others.

Figure 26:
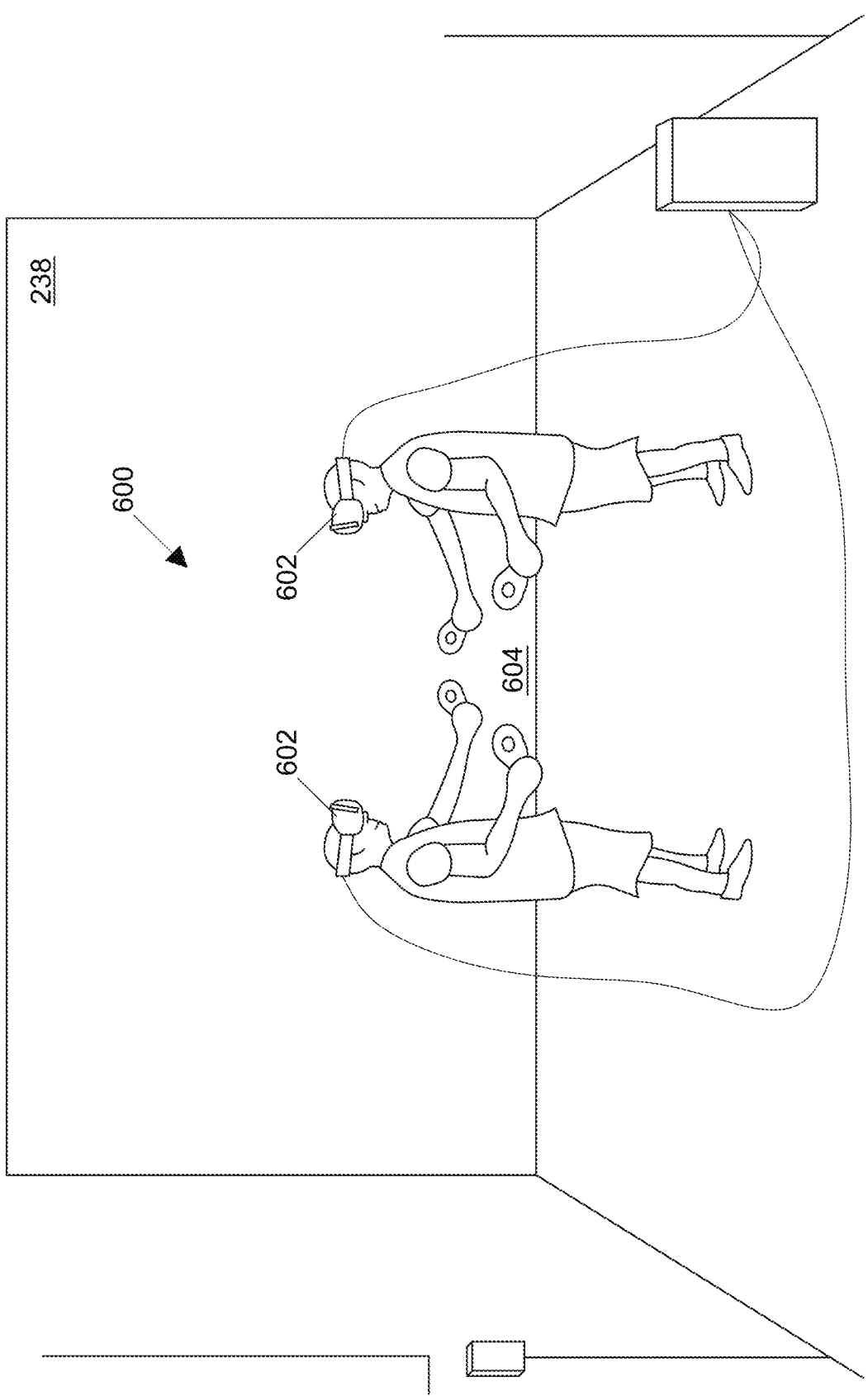

FIGS. 26 and 27 depict VR interfaces 600 in accordance with the embodiments of the present disclosure. FIG. 26 depicts users of the platform sharing a virtual reality (VR) space 604 to experience and modify a lighting design in a space. FIG. 27 depicts users of the platform observing a design process 610 using a VR experience 612.

As noted above, the platform for the design, fulfillment, deployment, and operation of a lighting installation, referred to as the platform 100, may include augmented reality and virtual reality (AR/VR) functionality. In the examples, AR/VR functionality may demonstrate to a user of the platform how objects may be illuminated. In embodiments, the AR/VR functionality may show a user how a light distribution looks in a space, by modeling the light distribution in a lighting space model 214, when a user desires to highlight a lighting object 226, such as a painting, within the space. In examples, a user may desire to mount one or multiple lighting source objects 228 on a ceiling to highlight the painting hanging on a wall. In embodiments, the AR/VR functionality of the platform may recognize objects or markers to build a virtual space within the lighting space model 214, where the virtual space then gets layered on top of a camera feed to create an augmented reality world.

In these examples, the platform 100 may take a marker and position it flush with the base of a wall that is going to have the lighting object 226 of interest placed on it. This provides the ground plane and the location of the wall that supports the lighting object 226, specifically the painting in these examples while allowing a user to input the ceiling plane information. Alternatively, the platform may determine the ceiling plane information. Continuing with these examples, the user may position the one or more lighting source objects 228 where it makes sense in the ceiling plane, for example avoiding ducts, or other objects that might interfere with the light. The light may project as a layer onto the surface that has the painting on it.

In embodiments, the user may see the light distribution as an alpha channel laid on top of a video feed. By way of these examples, the platform may modulate illumination intensity in a space on a screen to show how a light would affect the scene. In further examples, this may be achieved using an alpha mask over the passthrough video. The platform 100 may then allow the user to see how different products might look in real time in the space.

In embodiments, the AR/VR functionality may also include handling faithful video color rendering. AR/VR functionality may handle faithful video color rendering to develop an overlay by addressing nuances of color perception and nuance of a video. AR/VR may do this by applying an alpha map concept to render the video color as effectively as possible. An alpha map concept may include a color filter and an intensity map.

Lighting design may be only part of an experience when a user is in a space. Toward that end, interior design may also contribute to the experience of a user in a space. In embodiments, the user may enter a space and desire to view the space when redecorated according to a specific aesthetic requirement 116. The AR/VR functionality of a platform may, therefore, allow a user to visualize a space redecorated according to the aesthetic requirements 116. A user may interact with the AR/VR functionality of the platform in this and other examples using a phone 302, a phone accessory 304, such as an AR/VR headset, and the like.

In embodiments, the AR/VR functionality may interact with the marketplace API 278 and fulfillment system 128 of the platform. Continuing with the previous examples, the AR/VR functionality may interact with the marketplace API 278 and fulfillment system 128 to order the lighting source objects 228 required to meet the aesthetic requirements 116.

When a lighting designer has a design, while the designer may desire a client to understand a design, the designer may not want to communicate the design to a client using line drawings. Toward that end, AR/VR functionality of a platform may allow a designer and client to exist in a lighting space model 214 together virtually, such as with the Vive™ or the Oculus Rift™ AR/VR devices, or the like. AR/VR functionality may also allow a user, such as a designer or a client, to move freely within a room-sized lighting space model 214. The hands of the user may be tracked, allowing the user to do things within the room-sized lighting space model 214.

In embodiments, the designer may be the master in a lighting space model 214 and may have a high-end system that allows them to interact with the lighting space model 214 using the platform 100 connected to or integrating with an AR/VR platform or device. For example, a client or clients may join the designer in the lighting space model 214 on any AR/VR platform, for example, Google Cardboard™, as a platform may support any and all VR systems or just a video feed being displayed on a phone or laptop.

In additional examples, designers and clients in the same lighting space model 214 may be able to talk to each other. As designers and clients walk through the lighting space model 214, such as the lobby of the hotel, the clients may be able to say, "I don't like the way the sign looks and I want to change it." In embodiments, the designer may bring up a virtual palette of lighting fixture objects 230, make the changes suggested by the clients, allowing the designer and clients to experience everything about the space together in real time. In this way, the designer may affect the lighting design, as well as showing various scenes, such as lunch, dinner, cocktail hour, etc. As such, the client will have a complete understanding of the lighting design and ask the designer to make changes while having a complete understanding of the space and what is being offered. Toward that end, the designer and client may obtain a richer understanding of how the lighting space model 214 will look when implemented in a physical space.

In embodiments, the AR/VR functionality may include virtual showrooms. The virtual showrooms may operate as light-experiencing "caves" where a user may have their hands tracked. In these examples, the virtual showrooms may allow a user to pick up a lighting fixture object 230, look at the near field characterization system 270 and see the effects of the near field characterization system 270 on the lighting fixture object 230. The virtual showrooms may allow a user to control a lighting fixture object 230 in a multitude of environments, including being up at the level of a cove and seeing how the scene may change as they adjust the angle and position of the lighting fixture object 230.

With the Vive™ AR/VR device, for example, where a user has two tracked controllers, each with multiple inputs, a user may create a situation where a lighting fixture object 230 may be fixed to or "welded" onto the end of the controller in a virtual sense, so that the user may shine it on a wall and move it around a lighting design space model 214. By way of this example, the user may control a light in a multitude of environments. In addition, the user may position themselves up at the level of a cove and away from the ground to see how the scene changes when the angle and position of the light are adjusted in the environment.

In embodiments, the AR/VR functionality may include projecting light from lighting source objects 228 in an AR environment onto an object which exists on a physical surface in the physical (real) world. For example, a user of an AR device may be able to place furniture into a lighting space model. In further examples, a user of AR/VR functionality may be able to place furniture into lighting design space model 214. In these examples, a user may drop one or more of the lighting space objects 220 in a living room as the user looks through an AR device, while the AR/VR functionality scales the one or more lighting space objects 220 for previewing the piece of furniture. In these examples, the lighting space object 220 may be a piece of paper being dropped on a table so the user may manipulate a lighting fixture object 230 in the lighting design space model 214 without having to physically have the lighting fixture object 230.

In embodiments, the lighting fixture object 230 acts like it is supposed to, including dropping a beam of light on the area around it. The user may touch the lighting fixture object 230 to aim it. If the lighting fixture object 230 is aimed at the wall, then the user can, therefore, see beam angles, change beam angles and the like. This provides an effective method for seeing how a lighting fixture object 230 would look in the lighting design space model 214. In embodiments, the AR/VR functionality may include support for lighting fixture objects 230 that may articulate around two different axes. While the lighting fixture object 230 may be static, it may have multiple degrees of freedom. In embodiments, the AR/VR functionality may be controlled by a joystick that looks like an aerial view of a device that maintains its orientation to a lighting fixture object 230. For example, if a user walks around a lighting fixture object 230, the joystick may do a loop on screen, so the user is always dragging their thumb in a consistent direction.

FIGS. 22 and 23 depict a user interacting with VR functionality to interact with lighting fixture objects 230 that may articulate around two different axes. As depicted in FIG. 22, a user may open an app by selecting the app from a plurality of apps, displayed on a mobile device in this example. Continuing to refer to FIG. 22, a splash screen may load after the app is selected, as depicted in 572. Once the splash screen is finished loading, the app may display different lighting source objects 228 from which a user may select.

In these examples and as depicted in 574, an app displays "Rise" and "Troy" lighting fixture objects 230 to the user. As further depicted in 326, the user may then select a lighting fixture object 230 from the options presented. In this example, the user selects the "Rise" option. The selected lighting fixture object 230 and the lighting fixture object controller may then load, as depicted in 578. Continuing with the example, the lighting fixture object controller allows the user to move the selected lighting fixture object 230 in a 360-degree panning movement as depicted in 580 and a 180-degree tilt movement as depicted in 582.

FIG. 23 depicts a user in the lighting design environment 238 interacting with a lighting fixture object 230 according to the process depicted in FIG. 22. A lighting fixture object 230 pointing to the right of a user is depicted in 584. A lighting fixture object 230 pointing to the left of a user is depicted in 586. A lighting fixture object 230 pointing toward the user is depicted in 588.

In another example, augmented-reality (AR) functionality or visual reality (VR) functionality may allow designers and clients in different physical locations to conduct a virtual walkthrough of a completed design, providing for an enhanced interactive experience between a designer and clients. As illustrated by this example, AR/VR functionality may provide a shared space collaborative environment where users may view things on the fly, with a director controlling experiences of viewers.

The lighting design environment 238 may be configured with the workflow guidance system 242 that may include workflow features that enable management of projects (including multiple projects, such as for multiple lighting installations). The workflow guidance system 242 may support various workflow features, such as organizing a flow of work from initial concept work and ideation to finalizing a lighting installation, with many steps between. Workflow features may include checklists, prompts, approvals, and the like that guide a user or group of users through the end-to-end process, and various sub-steps, that are described herein. The lighting design environment 238 may include a collaboration system 244, such as enabling various collaboration features, including version control (such as allowing a designer to store various candidate designs, and versions thereof) for a given lighting installation 280 project, features for shared viewing of designs, and other features that allow designers, owners and occupants to collaborate on a design for a lighting installation. The term "occupant" or "owner" referring, except where context indicates otherwise, to encompass customers and clients of designers, building owners, tenants, workers and other parties occupying the spaces in which lighting systems are installed.

In embodiments, the library of templates 246 may be provided on the platform with content that facilitates the development of a lighting design. Templates may be created for types of environments (offices, lobbies, guest rooms, bathrooms, etc.), for industries, for workflows, for overall aesthetic effects, and for many other purposes. Templates may be linked to requirements, such as various requirements described below. In embodiments, the library of templates 246 may include ones for hotels, high-end residential lighting installations, restaurants, casinos, educational environments, healthcare environments, enterprise workplaces, manufacturing facilities, warehouses, and many others.

Whether starting with a template or not, the lighting design environment 238 may be used to explore various design elements and variations. The user may discover, for example, by trying different lighting objects 226, that a particular lighting design will work with a given lighting space object (such as seeing that a given lighting design works well with a particular carpet or paint color depicted in the display of the design). For example, as the lighting design is changed in the lighting design environment 238, including controlling dimming or intensity of a given lighting object, changes may be shown in the environment itself, such as how colors of paints and carpets appear, how shadows appear, and the like. Thus, the user may experiment with various settings and configurations of the lighting objects 226 to explore the environment. In embodiments, the user may also change lighting space objects in the lighting design environment 238, such as changing paint colors, carpet colors, and the like.

Figure 4:
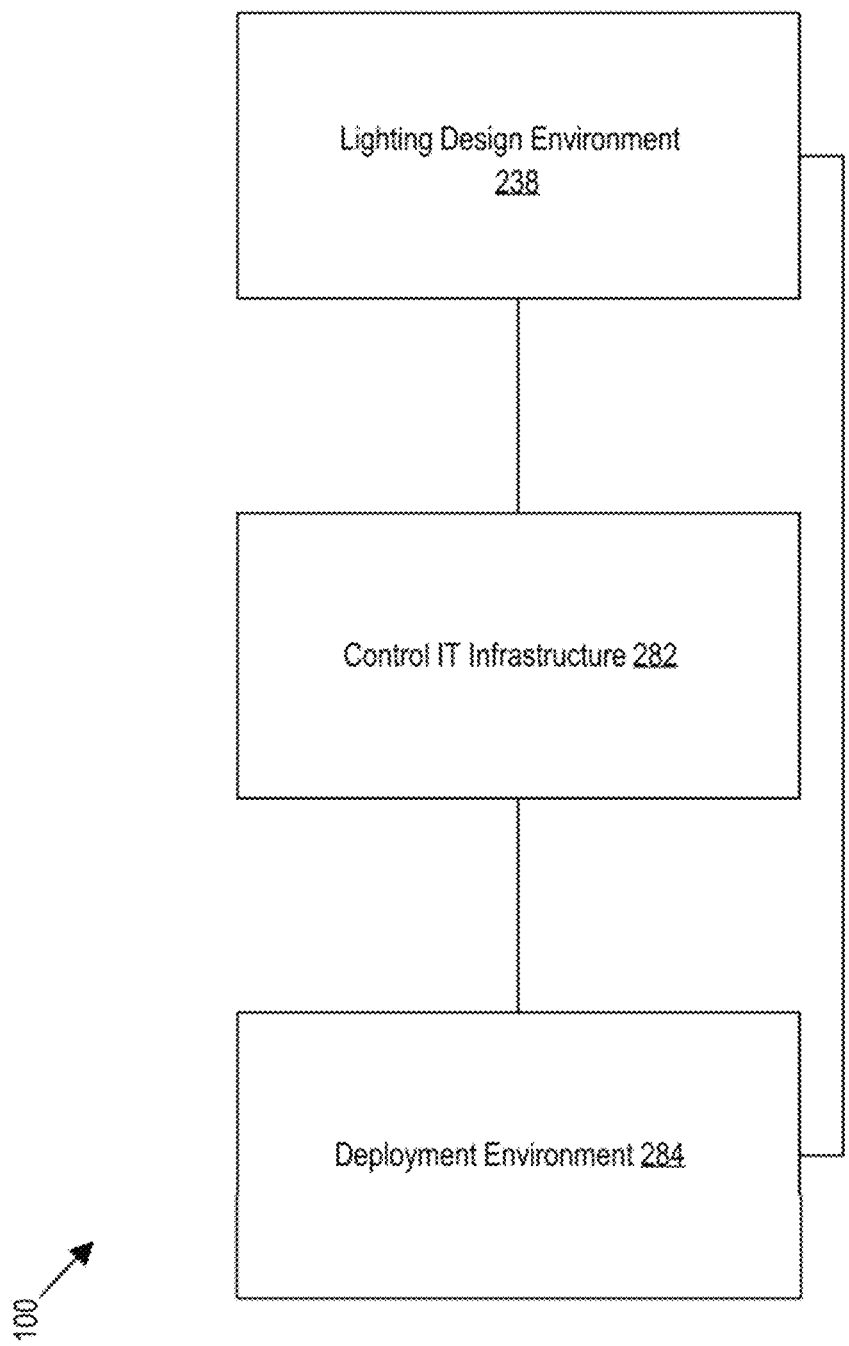
FIG. 4 is a system diagram of the main systems of a platform for design, fulfillment, deployment, and operation of a lighting installation in accordance with the embodiments of the present disclosure.
Figure 5:
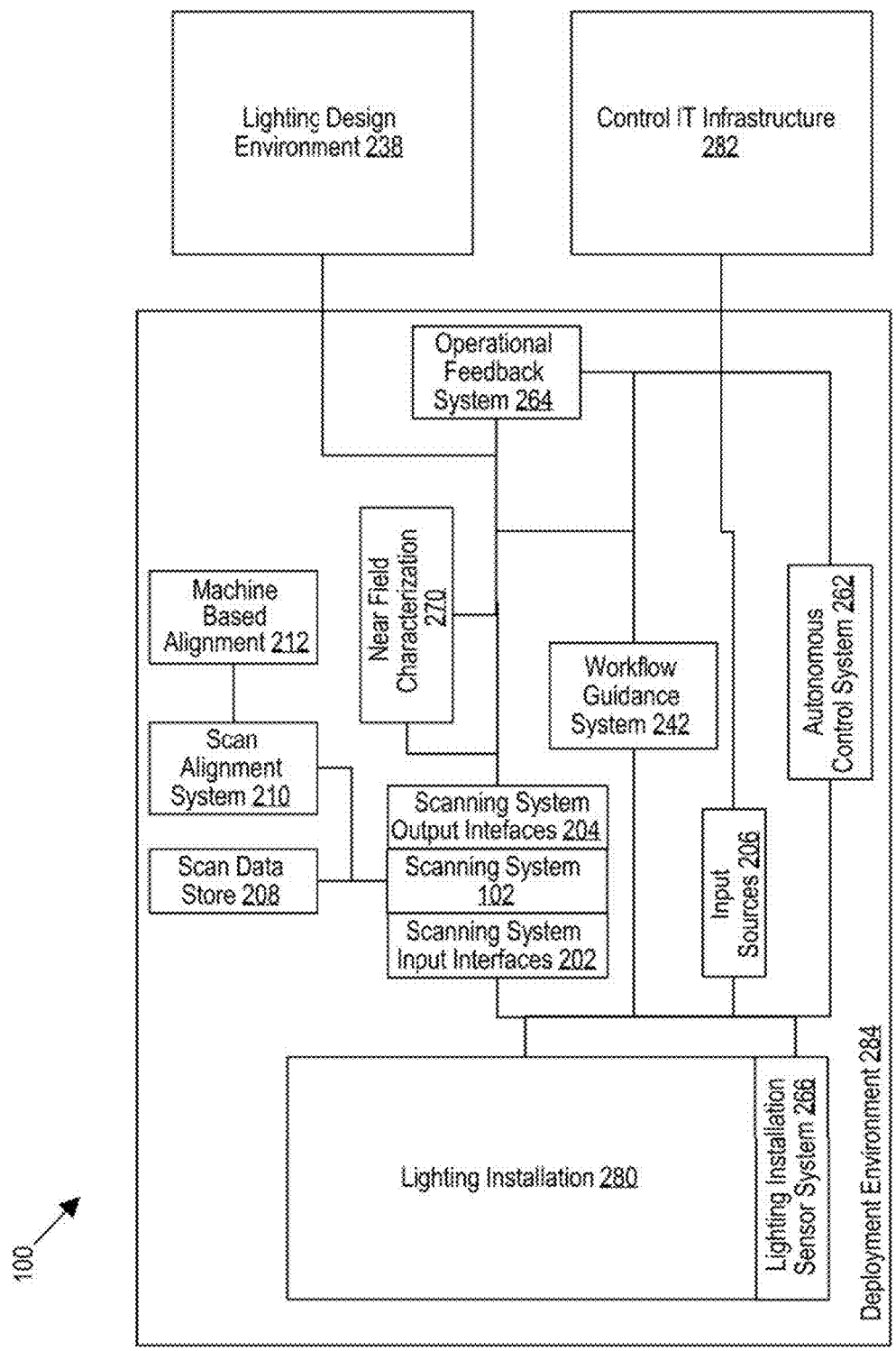
FIG. 5 is a deployment environment diagram of a platform for design, fulfillment, deployment, and operation of a lighting installation in accordance with the embodiments of the present disclosure.

As depicted in FIG. 4, the lighting design environment 238 may include a requirements system 106, where one or more requirements for the lighting installation 280 may be handled. Users, such as designers, owners, and occupants, may collaborate to develop requirements. Requirements may include financial requirements, which may be handled in the budgeting system 248 of the platform, into which a user may enter a target budget for a lighting installation. In embodiments, the budgeting system 248 may receive data (such via one or more APIs, by pulling data using queries, by data migration techniques, by structured feeds, or the like) such as from the lighting object library 232, such as pricing information for various light sources and fixtures that are of interest for a lighting installation. In these examples, APIs may include a data API, customization API, marketplace API and the like.

In embodiments, the requirements may also include technical lighting requirements 108, such as relating to a number of fixtures, an amount of illumination, a location of illumination, and many others. These may be captured in the requirements system 106, depicted in FIG. 4, for use in the lighting design environment 238 and elsewhere in the platform. In these examples, lighting requirements 108 may relate to required intensity levels, contrast, CCT values, color temperature, colors, near field effects, far field effects, beam shapes, shadow patterns, reflected light characteristics, and many others. In embodiments, the lighting requirements 108 may be defined at the fixture level and also at the system level, such as based on the combined intensity generated from multiple fixtures at a defined position and based on the distribution and types of light sources and lighting fixtures within a space. In embodiments, the technical lighting requirements 108 may be associated with particular objectives, including functional and aesthetic requirements 116 described elsewhere in this disclosure. In the examples where lighting is for an office space, lighting may be made directional, such as to provide consistent illumination throughout a space by having significant horizontal components in the direction of light sources. Thus, lighting requirements 108 may include requirements for the overall composition of the lighting objects 226 and the lighting space objects 220 in the space.

In embodiments, the requirements may include logistical requirements 110, such as reflecting the planned timing of a project (including various milestones for construction, renovation, move-in, and the like) for which the lighting installation 280 is relevant (such as indicating the required timing for installing a lighting system within the overall workflow of a construction or renovation project).

Figure 3:
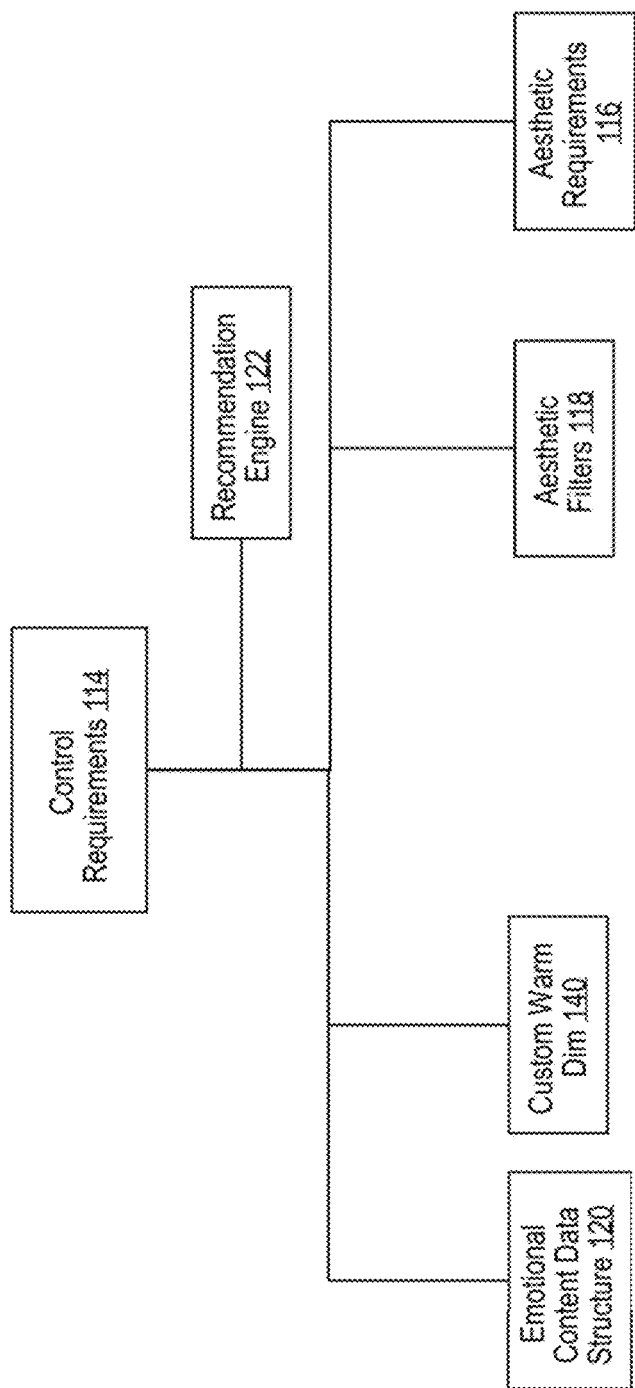
FIG. 3 is a control requirements diagram of a platform for design, fulfillment, deployment, and operation of a lighting installation in accordance with the embodiments of the present disclosure.

In embodiments, the requirements may include the functional requirements 112, such as reflecting functions to be supported or performed by a lighting installation. The functional requirements 112 may include requirements associated with defined work functions, processes, and workflows, such as specifying high quality work lights for desks, tables and other areas where work is performed, specifying appropriate levels of general or ambient lighting suitable for a given type of environment (such as warm ambient lighting for a restaurant), specifying appropriate spot lights for highlighting elements (such as works of art), specifying lighting systems for guidance of users in a space (such as to produce a desired traffic flow), and many others. In embodiments, the functional requirements 112 may be captured in the requirements system 106 for use in the lighting design environment 238 and elsewhere in the platform. As depicted in FIG. 3, the functional requirements 112 may include control requirements 114, such as for controlling lighting fixtures (such as for motion, rotation and the like), for controlling light sources (such as for dimming, changing colors, changing color temperatures, and the like), and for controlling intelligent features of the lighting objects 226 or lighting space objects, such as networking features (including use of routers, switches, gateways, bridges, mesh networking features, peer-to-peer networking features, optical networking features, Wi-Fi, Bluetooth, NFC and others), communication features (such as enabling remote control, such as from the cloud and enabling communication with other IoT devices), sensor features (such as using motion sensors, proximity sensors, and the like) and the like. In embodiments, each of these functional or control requirements 114 may correspond to one or more properties of a lighting object that may be stored in the lighting object library 232.

Figure 29:
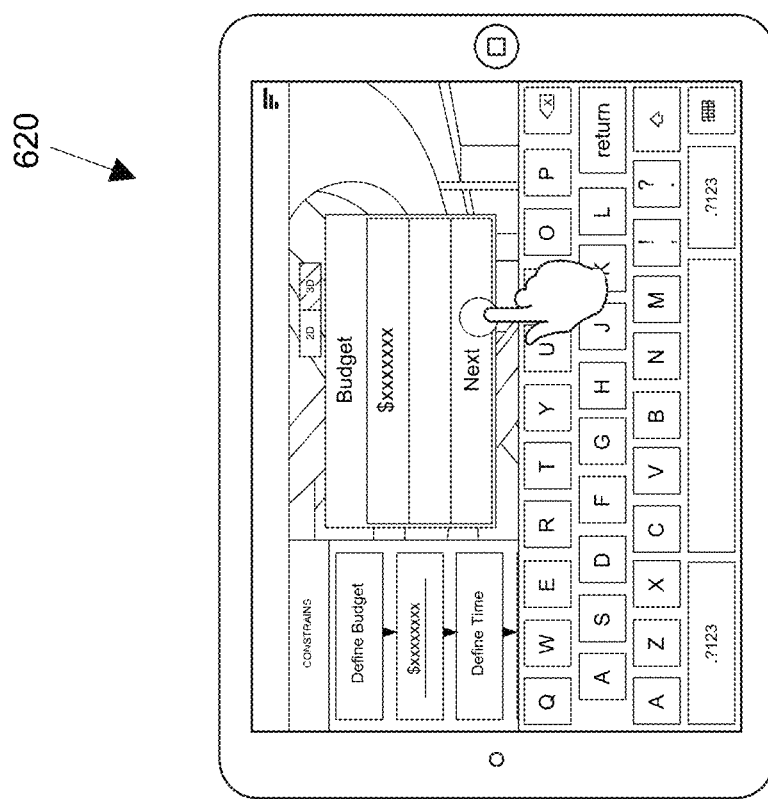
FIGS. 28 and 29 are diagrammatic views that depict a user interface of a requirements system in accordance with the embodiments of the present disclosure.
Figure 28:
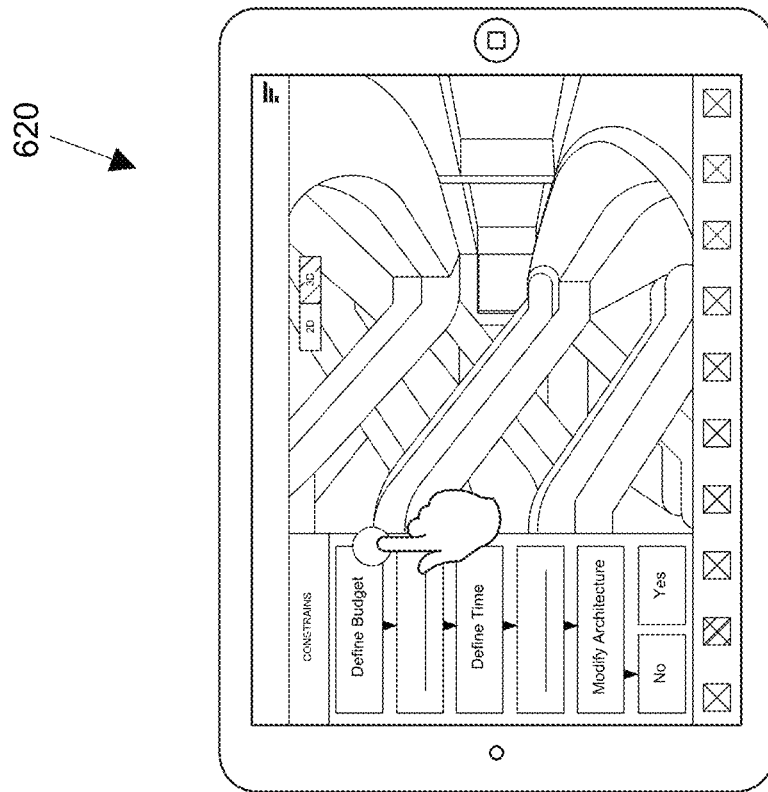

FIGS. 28 and 29 depict a user interface 620 of a requirements system 106. In embodiments depicted in FIGS. 28 and 29, a user of the platform may set a budget requirement and/or various functional or aesthetic requirements for a design, using the budgeting system 248. While design and deployment of the lighting installation 280 involve many technical, functional, financial and logistical requirements 110, the lighting of an environment is may also have aesthetic, emotional, and health impacts.

It will be appreciated in light of the disclosure that lighting may have a strong aesthetic impact. For example, painters and portrait photographers develop distinctive lighting "set-ups" to create distinctive aesthetic effects, as with the "Rembrandt set-up" that fully illuminates one side of a subject's face and leaves a triangle of illumination below the eye on the other side that is otherwise in shadow. Similarly, some restaurants may place spotlights in greeting areas and along pathways to tables to illuminate staff and patrons in a favorable way, while keeping ambient light levels low and warm to provide a suitable atmosphere, while others might use brighter illumination and accent lighting to encourage a lively atmosphere. It will also be appreciated in light of the disclosure that lighting may have a significant emotional impact; for example, as incandescent light sources are dimmed and become warmer, they are perceived by many as providing a more romantic environment, while cooler light sources, such as fluorescent lights, are perceived as reflecting a colder, more clinical emotional state. Lights are often thought of as having "soft" or "hard" impacts on users. In embodiments, the various aesthetic and emotional impacts may be characterized by one or more aesthetic requirements 116, such term encompassing various aesthetic and emotional factors that may be intended for a lighting installation. In these examples, aesthetic requirements 116 may include a wide variety of factors and parameters. For example, where the lighting installation 280 is intended to illuminate individuals, aesthetic requirements 116 may indicate how individuals should be illuminated in various locations within the environment. In other examples, lighting for seats at a high-quality restaurant could be configured to use flattering lighting setups, such as portrait lighting setups (e.g., split lighting setups, loop lighting setups, Rembrandt lighting setups, butterfly lighting setups, broad lighting setups and short lighting setups, among others).

In embodiments, the lighting for a stage may be defined according to various stage lighting setups (including side lighting setups, front lighting setups, colored lighting setups, flood lighting setups, beam lighting setups, spot lighting setups, and many others). Aesthetic requirements 116 may be captured in the requirements system 106 for use in the lighting design environment 238 and elsewhere in the platform. Such requirements may be specific (such as indicating use of a specific type of spotlight of a given color temperature to achieve an aesthetic effect at a defined position in an environment); however, as with most things that have artistic or emotional impact, it may be difficult for users to specify in detail what the lighting objects 226 will achieve a desired overall aesthetic or emotional effect. In embodiments, requirements may include compositional elements for rendering humans in expected locations in a lighting environment. This may include various elements that may make people look better, such as in the seats of a restaurant, or the like.

Figure 35:
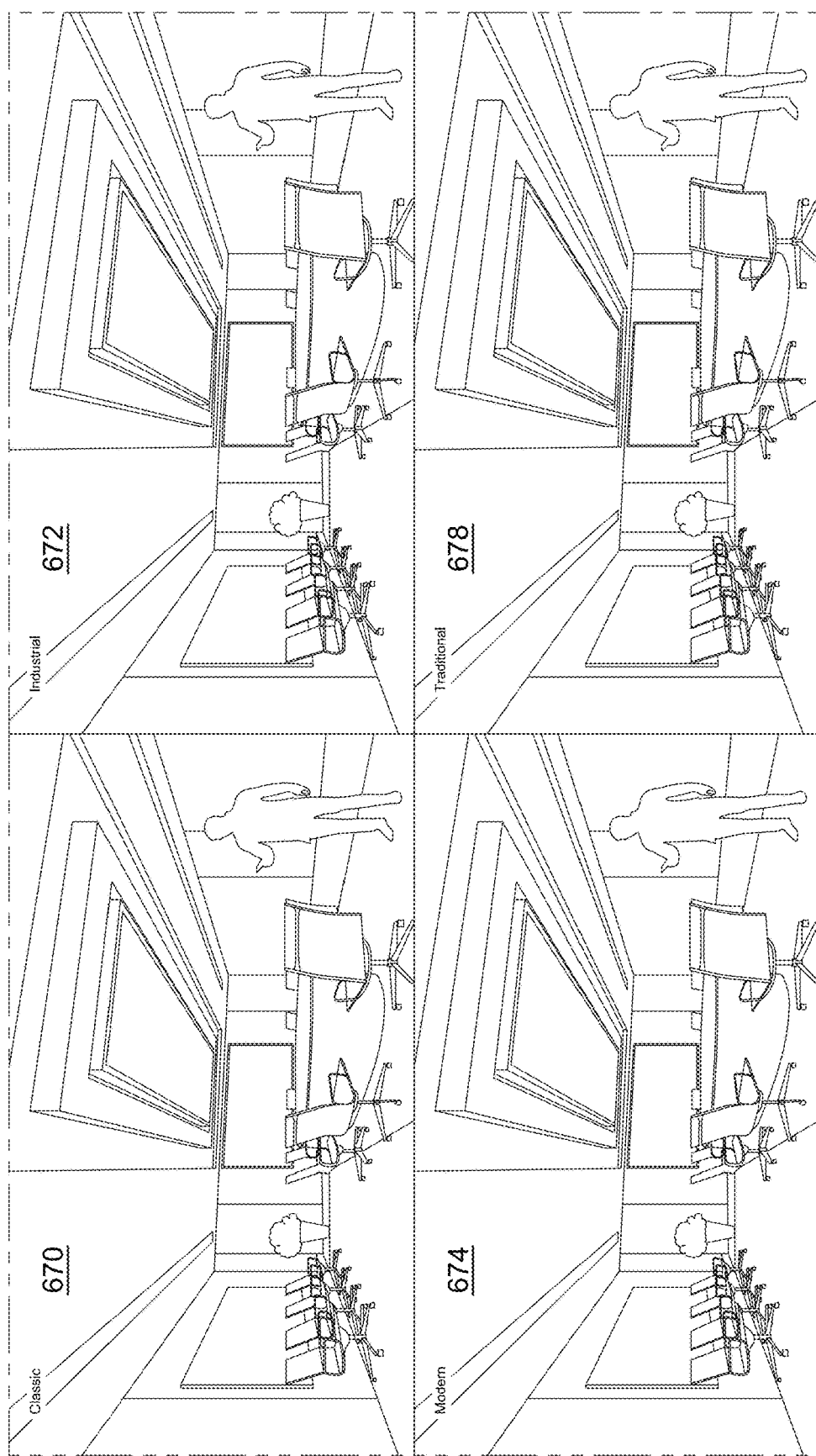
FIG. 35 is a diagrammatic view that illustrates various filters that may be used to determine control parameters and other characteristics of a lighting design for an environment in accordance with the embodiments of the present disclosure.
Figure 36:
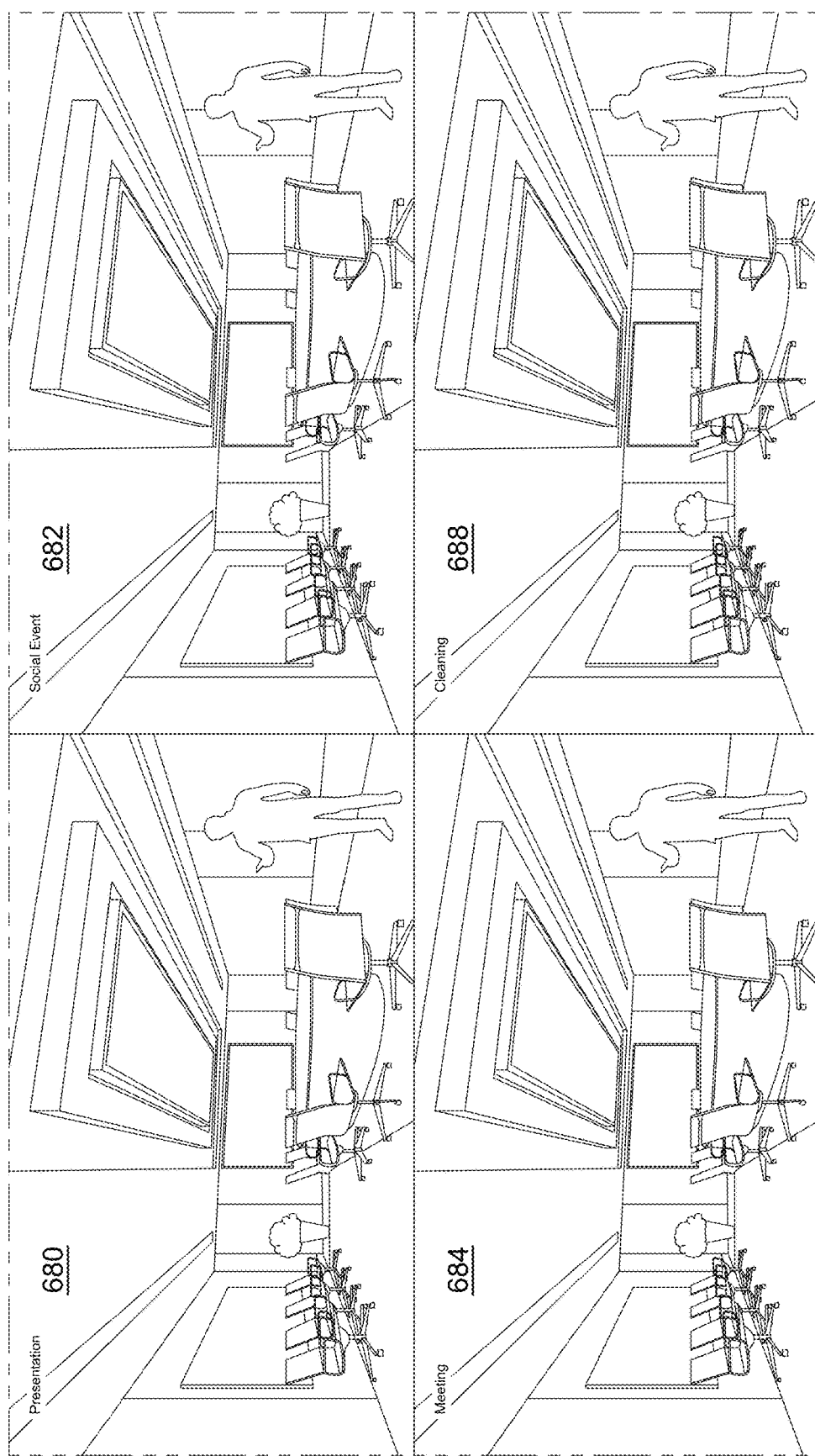
FIG. 36 is a diagrammatic view that illustrates alternative scenes that may be produced using aesthetic filters in a lighting design in accordance with the embodiments of the present disclosure.

In embodiments, the compositional elements may be informed by information about the impact of lighting setups for various photographic styles. As with lighting setups for photography, stage lighting, and the like, the platform may define a set of aesthetic filters 118, each of which defines a coordinated set of characteristics of a lighting installation, such as providing desired colors, color temperatures, contrast ranges, sharpness, illumination range, and the like. Similar to photograph filters popularized by Instagram™, each aesthetic filter may be used to specify or modulate one or more factors in a lighting installation, so that the lighting achieves a desired overall aesthetic effect. In embodiments, an aesthetic filter may include a data object of a defined class, the class defining various properties or fields that may be varied to produce an aesthetic impact of the lighting installation 280 in an environment. In embodiments, aesthetic filters 118 may be developed by users; for example, an owner of a brand (such as a hotel chain), may develop and define one or more aesthetic filters 118 that define the aesthetic lighting properties for lobbies, guest rooms, conference rooms, and retail spaces for the chain. Similarly, an artist, designer, or the like may define lighting setups or aesthetic filters 118 that are associated and branded by that designer, as with designer clothing, shoes and jewelry, such that a given lighting installation 280 aesthetic may be obtained from that designer, such as via one or more templates that are controlled by the designer. FIG. 35 illustrates examples of various filters 670 672, 674,678 that may be used to determine control parameters and other characteristics of a lighting design for an environment. FIG. 36 illustrates examples of alternative scenes 680, 682, 684, 688 that may be produced using aesthetic filters in a lighting design.

In embodiments, aesthetic filters 118 may be crowd-sourced and/or curated, such as by having users submit their own filters and/or by having users classify, rate, or comment upon filters. The owner of the brand may further specify other elements, such as colors, objects, and the like, which may be coordinated as an overall set of design requirements for the brand. As with other requirements, aesthetic requirements 116 may be processed by the platform, such as to automatically search for and find light sources or lighting fixtures that satisfy the aesthetic requirements 116.

It will be appreciated in light of the disclosure that emotional and aesthetic effects may be quite complex, involving the interaction of various factors to produce an overall effect. To facilitate understanding of emotional and aesthetic impacts of a lighting installation, an emotional content data structure 120 may be created, stored, and used in the platform, such as consisting of one or more objects or classes with various properties that may impact the emotional impact of a design. Relevant properties may include lighting properties, such as the distribution of light on the lighting space objects 220 (such as the distribution of light on tables, desks, or workspaces), distribution of lights on walls, ceilings and floors, illumination values, color and color temperature of light sources, spectral content (e.g., the quality and intensity of light at certain spectral ranges), and the like. In embodiments, the lighting fixture properties may also be included in the emotional content data structure 120, such as reflecting the impact of a given type of fixture (e.g., where the fixture has a given style or mood, such as "modern," "retro," "industrial," "romantic," or the like). Different types of fixtures may have different impacts, such as suspended fixtures versus embedded fixtures. It will also be appreciated in light of the disclosure that the form factor of a fixture may also be important (and may reflect trends in fashion that shift over time). Metadata for fixtures characterizing general type, shape, and form factor may be included in the lighting fixture object data structures and the emotional content data structure 120 used by the platform. In embodiments, various features such as stylistic and aesthetic features, may be extracted from images, 3D models, renderings, scans, or the like of existing installations or designs that are enabled or handled by the platform 100 for use in characterizing an aesthetic filter 118 or for populating a related emotional content data structure 120. Because a design style or aesthetic filter 118 may be a function of space, culture, geography and the like, these factors and related parameters may be extracted and/or taken into consideration in creating and/or characterizing an aesthetic filter 118 and/or emotional content data structure 120.

In embodiments, varying properties of the emotional content data structure 120 may be used to develop or evaluate aesthetic filters 118, the lighting objects 226, lighting space objects, or other factors of a design, such as using machine learning with feedback from users about what emotional or aesthetic impressions are created by various configurations, so that various factors may be understood as tending to produce a given set of emotional and aesthetic reactions. This may include training a machine learning facility to algorithmically detect various characteristics that indicate an aesthetic or emotional effect. In these examples, a machine learning facility may be trained to discover patterns of light and shadows that the lighting installation 280 will create on faces, such as to identify known patterns (such as a butterfly shape around the nose in a butterfly lighting setup or a triangle of light under the eye in a Rembrandt lighting setup), so that emotional impacts may be predicted.

In embodiments, machine learning may be used to improve aesthetic filters 118, lighting space models 214, or the like based on various measures of feedback. These examples may include feedback based on reviewing displays of lighting designs in the lighting design environment 238 and feedback on lighting installations in the real world (including, without limitation, installations design and/or operated using the platform). Feedback measures may include feedback on social impact, mood, activity levels, revenues, returns on investment, beauty, usefulness, and many others.

Figure 31:
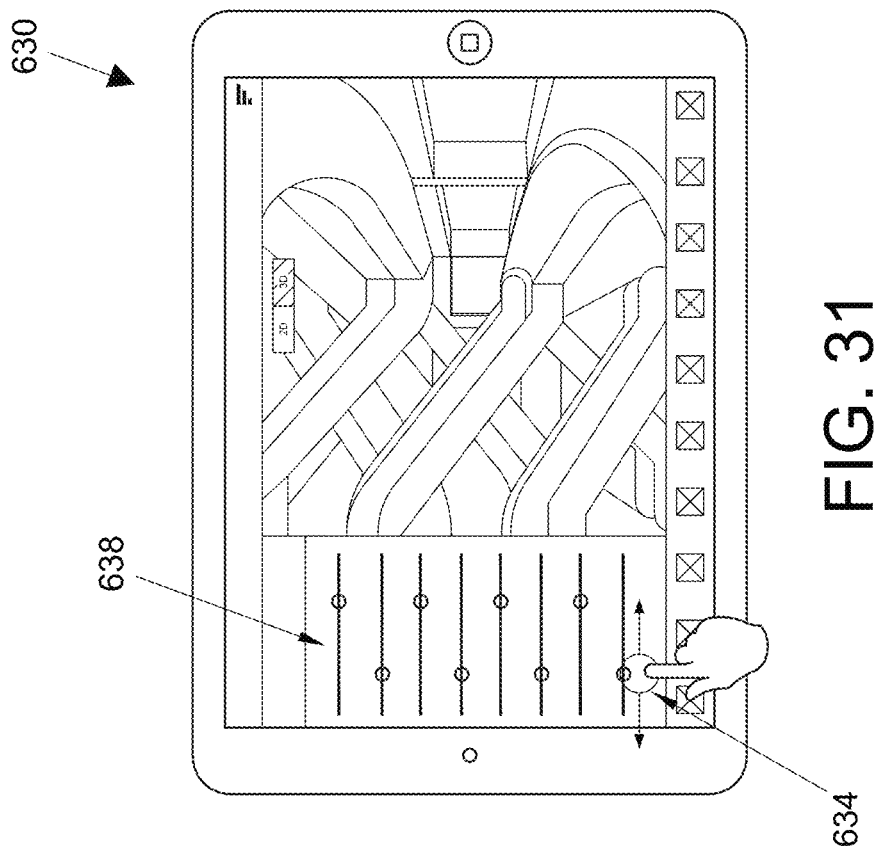
FIGS. 30, 31, and 32 are diagrammatic views that depict a user interface for setting filters and emotions of a design in accordance with the embodiments of the present disclosure.
Figure 30:
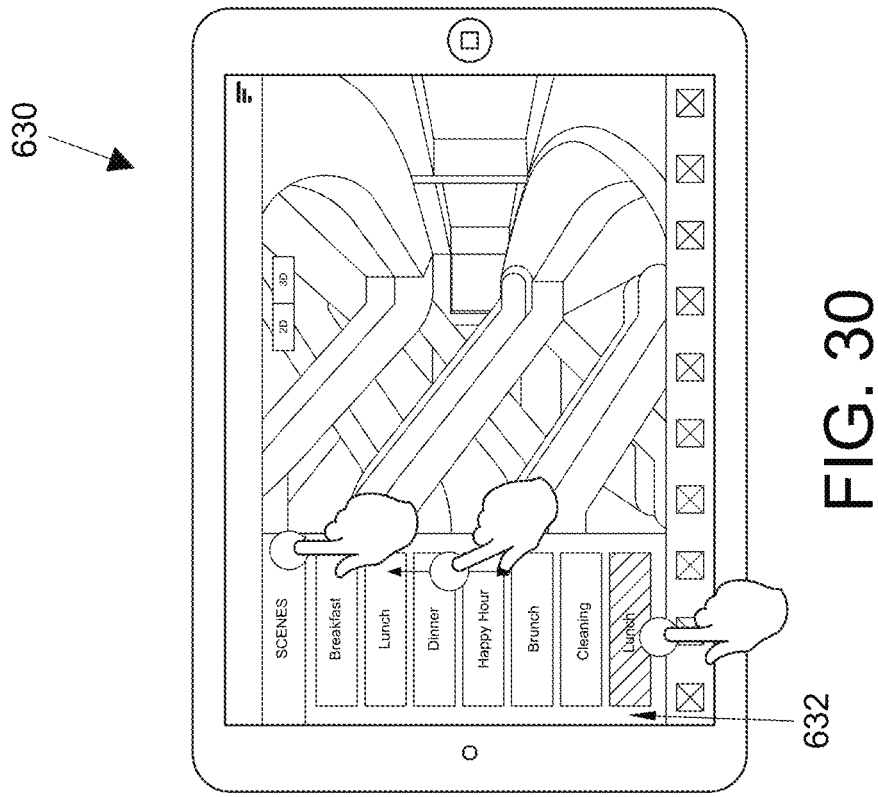
Figure 32:
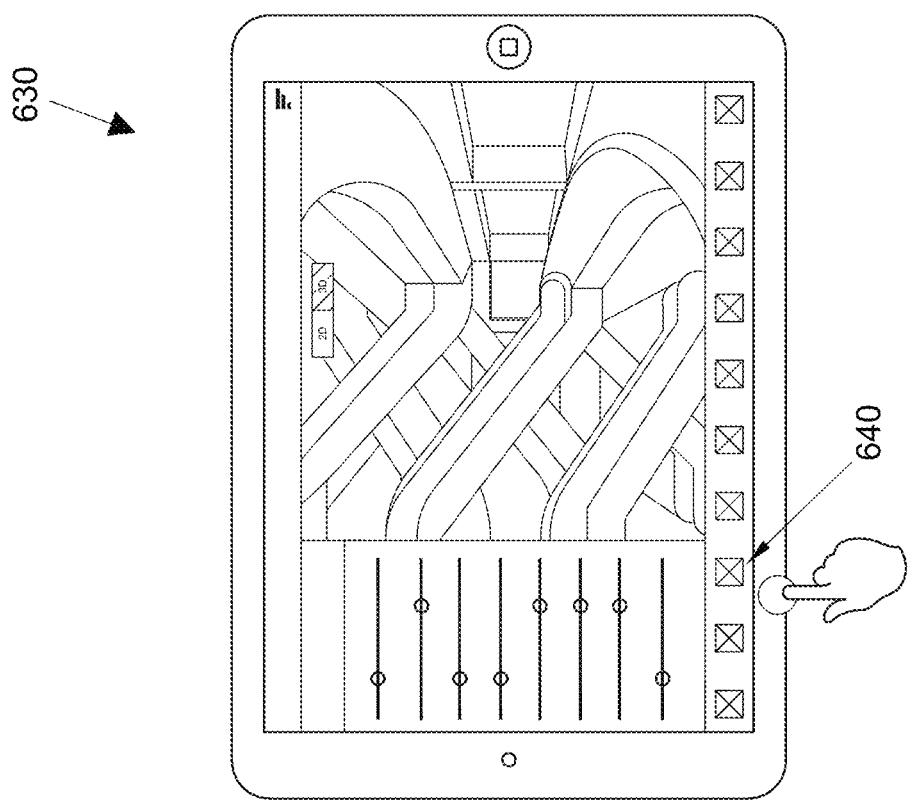

FIGS. 30, 31, and 32 depict a platform user interface (UI) 630 for setting filters and emotions of a design. FIG. 30 depicts a user selecting an experience emotional/aesthetic filter 632. FIG. 31 depicts a user adjusting a preset parameter 634 of a selected filter 638. FIG. 32 depicts a user selecting fixtures 640 to which the selected filter will be applied. In embodiments, the platform may include the recommendation engine 122, which may recommend light sources, lighting fixtures, or the like, using one or more machine-automated processes. In these examples, recommendations may be made based on history (such as by presenting items that have been frequently specified in other lighting installations, items that have been reviewed most frequently in searches, and the like). Recommendations may be based on ratings, such as from other users, such as collected in a rating interface 142 of the platform. Recommendations may also be based on similarity, such as using collaborative filtering or similar approaches, such as based on similarity of an environment where the lighting installation 280 is planned with other environments on various dimensions that are included in lighting space models 214 and the lighting space objects 220 (such as by assigning weights to differences and similarities in two environments based on the presence of similar objects in them). In embodiments, similarity for purposes of recommendations may also be determined based on the requirements of users, such as by performing calculations on objects in the requirements system 106. Similarity may also be determined based on the users, such as based on psychographic, demographic, preference and geographic factors.

In embodiments, the information about the preferences of a user may be accumulated through interactions with a user, such as through the rating interface 142. By way of these examples, a user may be asked to rate a collection of lighting installations (such as being presented photographs or videos of installations in pairs, where the user is asked to select a preferred member of the pair, as in A/B testing). In embodiments, a user may be asked to indicate preferences via a survey, such as with toggles or filters by which the user may indicate agreement or disagreement, or an extent to which one or more factors is important to the user. In embodiments, lighting designs may be compared using the active measurements of emotional reaction, such as by collecting input from a physiological monitor, affect recognition system or other devices for measuring emotional reaction. In embodiments, the system may learn which types of installations the user prefers, either based on a hierarchy or classification of types of installations or by a machine-based learning, such as developing a self-organizing map. These and other techniques may be used to help sort and recommend one or more items to a user. In embodiments, the recommendation engine 122 may recommend one or more aesthetic filters 118 based on any of the foregoing factors.

In embodiments, the platform may include a user interface where a user may scan or upload a digital representation or indicator of a space, such as one the user likes. By way of these examples, a user may scan a magazine photo that shows a space that is appealing, from which the system may automatically extract features, including the lighting space objects 220, the lighting objects 226, and other features (including aesthetic features), which may be used to inform the system of the characteristics or preferences of the user, such as to help identify and recommend one or more aesthetic filters 118 to the user, or the like.

As noted, the design process may be iterative. In embodiments, the users may be prompted, such as in a workflow managed by the platform and reflected in the user interface, to enter information about budgets and other factors, such as the culture of a workplace, the preferred style of a design, and the like. The system may automatically populate sets of fixtures and light sources that generally satisfy various requirements within a given budget. In embodiments, manufacturers, such as owners of lighting brands, may sponsor one or more products, and the lighting design environment 238 may have locations for presenting one or more sponsored or non-sponsored products. In embodiments, a designer or manufacturer may sponsor an aesthetic filter or lighting template. In embodiments, a designer may mandate the use of particular fixtures or fixtures from a particular manufacturer. As a prototype design is developed, the automated search engine may operate in the background of a design project to suggest alternative light sources, fixtures, and the lighting space objects 220, such as ones that better fit requirements, that are available for a lower cost, that offer earlier delivery times, or the like. In embodiments, a user may be able to specify a light source of lighting fixtures that are not found by the automated search engine, such as by defining various form factors and other properties, to create a request for a custom light source, which may be published, such as by a bidding interface 124 for bids by manufacturers.

For example, a user may request an alternate color for a fixture, use of a different bulb as a light source in a fixture, a new control property for a fixture, or the like.

It will be appreciated in light of the disclosure that lighting may also have a health impact. It is well known that light may impact circadian rhythms, affect mood, impact sleep, ameliorate seasonal affective effects, impact concentration and performance (such as in educational and work environments), feed photosynthesis, and have various other physiological effects on humans, animals, and plants. Thus, the functional requirements 112 may include health requirements 126 related to any of the foregoing, which may be captured in the requirements system 106 for use in the lighting design environment 238 and elsewhere in the platform. By way of these examples, a designer of the lighting installation 280 for an educational environment may specify a given quality of lighting for teaching spaces, such as one that improves focus and concentration or diminishes seasonal affective disorder. Similarly, a healthcare facility may specify lighting that improves mood during the day and improves the quality of sleep at night. As with other requirements, the health requirements 126 may be processed by the platform, such as to automatically search for and find light sources or lighting fixtures that satisfy the health requirements 126 in accordance with the embodiments of the present disclosure.

As noted above, various items may be solicited through a crowdsourcing interface by which members of the public may be asked to provide information that improves one or more capabilities of the platform. This may include data on light sources and the lighting objects 226 (such as where manufacturers may populate such information to improve the quality of information in the platform). In embodiments, the crowd sourcing may also include feedback and ratings, such as on lighting fixtures, light sources, lighting designs (such as candidate designs and templates handled by the platform), lighting installations (including ones designed with the platform and others), aesthetic filters 118, prices, and other factors. In embodiments, the crowd sourcing may provide verification, such as indicating whether a product is in fact what it claims to be.

As noted above, designers, building owners, occupants, and other relevant parties may iterate, such as using collaboration features of the lighting design environment 238, to develop a lighting space model 214 that reflects a series of passes at a lighting design and layout for the lighting installation 280 in a space. In embodiments, an end customer may provide feedback, such as that the design is "too romantic," and the designer may modify a design, such as by selecting different lighting objects 226 or applying a different aesthetic filter to modify the emotional or aesthetic impact of a design, such as by modulating control parameters for the lighting objects 226 that are included in the lighting space model 214 or by substituting other lighting objects 226. In the many examples, the designer, owner, occupant, or other involved parties may see each variant of a design in a realistic and immersive way, so that the overall aesthetic or emotional impact, and individual elements, may be experienced.

After iteration 104 (FIG. 1), a final design may be determined and captured in the lighting space model 214 for the project, with a lighting project data structure 254 that represents all of the lighting space objects and the lighting objects 226 in the model, along with their respective properties, as well as information about positions and orientations of the objects, functional and operational capabilities, and the like. In embodiments, the lighting project data structure 254 may be used as an information source for the lighting schedule 256 for the product, as well as for generating instructions, such as for installation, operation, and maintenance of the lighting installation. In embodiments, a lighting schedule system 258 may store a schedule, list, manifest, or the like (referred to herein as the "lighting schedule" 256) that contains information identifying the lighting fixtures and light sources that are included in a design (such as the ones that are currently represented in a display in the lighting design environment 238 or that are currently represented in a version of a lighting design for the lighting installation 280 project). In embodiments, the lighting schedule 256 for a version of a lighting design may list the fixtures and light sources currently under consideration (such as ones shown in a visual representation in the lighting design environment 238 that was created by the designer) along with other information, such as availability information, lead times, pricing information (including factoring in volume discounts, rebates, and the like) and other information that is relevant to budget requirements, lighting requirements 108, scheduling requirements and other requirements described throughout this disclosure. In embodiments, the automated search system 234 may search for light sources and lighting fixtures that may meet the requirements of the project, such as by searching the lighting object library 232 or public sources for the lighting objects 226 that could satisfy the requirements. In embodiments, the lighting schedule system 258 may include automation features, such as for filtering the lighting schedule 256 to include only items that satisfy one or more requirements, highlighting items that violate one or more requirements, highlighting the extent to which items satisfy requirements to a better or worse degree (e.g., including quality ratings for light sources or fixtures, or highlighting lower price versions of items of comparable quality), and the like. In embodiments, the lighting schedule system 258 information may automatically feed into the budgeting system 248, such as by providing a total cost or various sub-costs associated with a version of a design. In embodiments, a user may interact with the lighting design environment 238 and the lighting schedule system 258 by adding or subtracting elements and viewing the impact on an overall budget and timing of a project until a design is finalized. Upon finalizing a given design, the lighting schedule system 258 may generate the lighting schedule 256 for the project, which may include all of the information necessary to order the light sources, light fixtures, and associated shipping and installation services, for the design. In embodiments, the lighting schedule 256 may be shared in the collaboration system 244, such as to allow approvals of particular light sources, fixtures, services, or the like, and to allow approvals of budgets. The lighting schedule 256 may also be analyzed automatically by the requirements system 106, such as to confirm that the proposed lighting schedule 256 satisfies the requirements for the project. As noted above, the lighting schedule 256 may evolve through one or more rounds of iteration 104 among designers, clients, and others, until a design for the lighting installation 280 is complete.

In embodiments, the lighting schedule 256 and/or the lighting project data structure 254 may be used in a fulfillment system 128 of the platform, optionally along with other data sources, for automated ordering and fulfillment for a lighting installation. Using information stored in the lighting schedule 256, a set of orders may be automatically placed by an automated ordering system 130 of the platform, including setting delivery dates and locations that correspond to the timeline for a project, such as dates of installation of different components of a projects (e.g., different delivery dates may be configured for overhead lighting for the space that is integrated into ceilings versus accent lights that may be installed later in a project). In embodiments, a fulfillment system 128 and automated ordering system 130 may be included in the control IT infrastructure 282. As depicted in FIG. 7, the control IT infrastructure 282 may also include the lighting design environment 238. An order tracking system 132 of the platform may track information, such as from shipping companies and carriers, such as to flag any issues in delivery that may require changes to the schedule for a project. In embodiments, the automated ordering system 130 may automatically order substitute items for any items that are delayed, including on an expedited basis, or may automatically alert users to issues and offer alternatives, such as alternate items, expedited shipping, and the like. Thus, the fulfillment system 128 may automatically undertake steps to keep a project on time and on budget.

In embodiments, an installation guidance system 136 of the platform may guide contractors, sub-contractors, installers, and the like to install the lighting installation 280 according to the design that was created in the lighting design environment 238. This may include providing step-by-step guidance in locations, positions, control configurations, network connections, power connections, data interfaces, and other aspects of each of the lighting objects 226 specified in the domain. In embodiments, the installation guidance system 136 may access the lighting project data structure 254 to obtain information, such as installation instructions, configuration instructions, power requirements, and the like, for each of the specified lighting objects 226 for a project. Guidance instructions may include visual representations, video instructions, audio instructions, links to manuals, and the like. In embodiments, the installation guidance system 136 automatically configures an order of installation instructions for the installer.

In embodiments, as the lighting objects 226 are installed in the environment of a lighting installation, networking features automatically engage upon powering up one or more the lighting objects 226, and the lighting objects 226 may automatically commission themselves, such as by connecting to the platform and/or to other lighting objects 226. Thus, the lighting objects 226 in an installation may self-commission and self-configure to create a network connection between the lighting objects 226 in the environment and a remote operator (such as in the cloud). The lighting objects 226 may configure in a master/slave, ring, mesh, or peer-to-peer network, by which autonomous control features may be engaged in the environment. In embodiments, remote control features may be engaged using the network connection to the platform or other remote operators.

Figure 37:
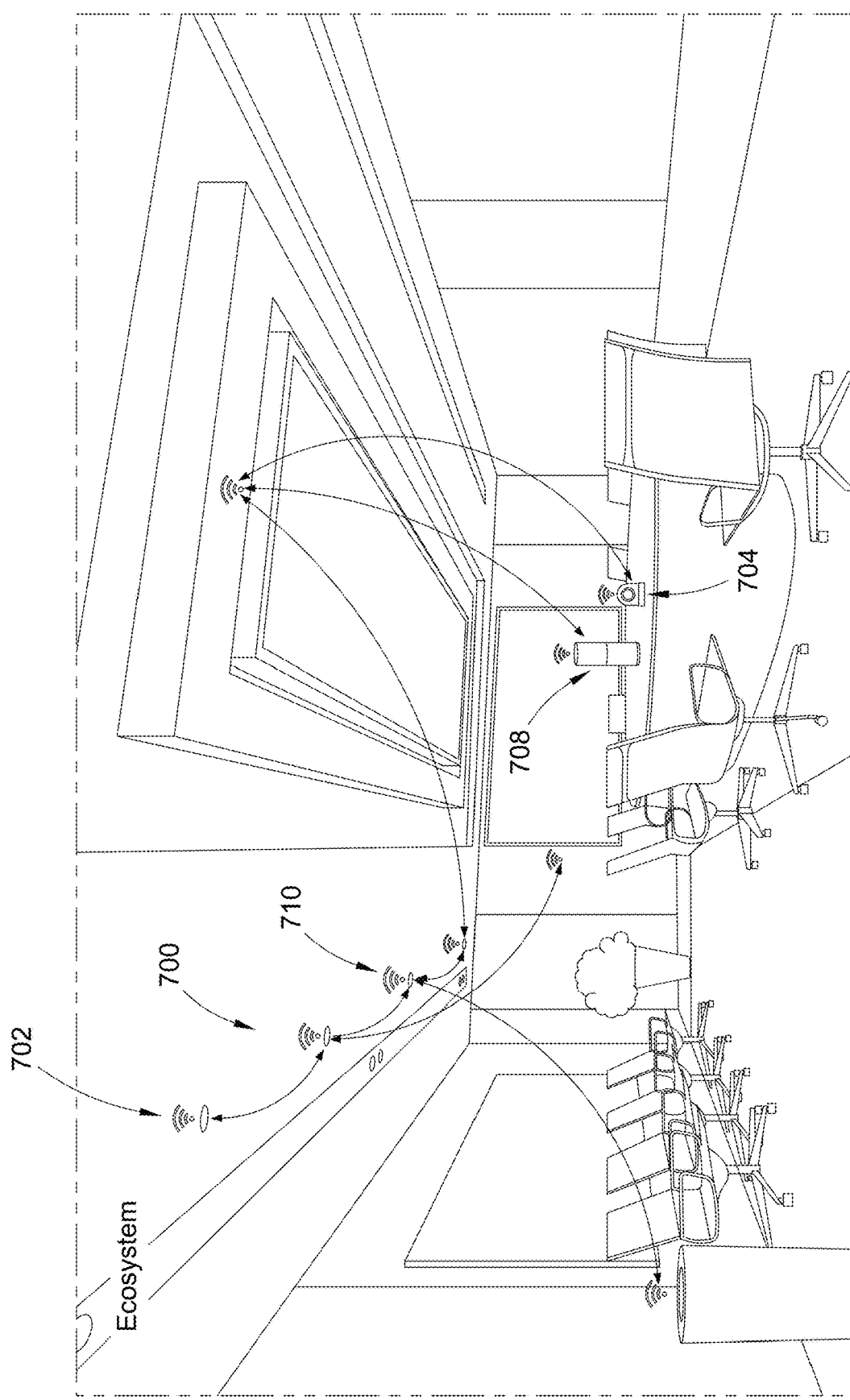
FIG. 37 is a diagrammatic view that illustrates communication among components in a deployed lighting installation in accordance with the embodiments of the present disclosure.

FIG. 37 illustrates exemplary embodiments of networked communication 700 among components in a deployed lighting installation 702. Once installed and commissioned control of the lighting installation 280 may be handed over to an operator of a platform, such as a building owner, occupant, landlord, tenant, or the like. In embodiments, handoff may include using identity and authentication features, such as using keys, passwords, or the like that allow operation of the lighting installation 280 by permitted users. In embodiments, the remote-control interface 704 of the platform may be used by an operator for remote operation of the lighting installation. The remote-control interface may use the lighting project data structure 254 as a source of knowledge about the properties, configurations, control capabilities, and other elements of a lighting installation, so that the same platform used for the design of the lighting installation 280 may be used to control the lighting installation. The remote-control interface may include operational guidance features, such as guiding users through the operation of a lighting installation.

In embodiments, the autonomous control system 262 may be provided for a lighting installation, by which the lighting installation 280 may control various features of the lighting system, such as based on information collected locally in the environment, such as from one or more sensors. For example, the autonomous control system 262 may automatically adjust control parameters for a light source to achieve improved adherence to the overall specifications for a lighting installation, may adjust timing variables based on detected usage patterns in a space, may adjust lighting properties based on changes in a space (such as changes in colors paints, carpet and fabrics), and the like.

Under operation, the lighting installation 280 may include the operational feedback system 264, configured to collect information about the lighting installation, which may include interfaces for soliciting and receiving user feedback (such as regarding satisfaction with the installation or indicating desired changes) and which may include the lighting installation sensor system 266, such as including light sensors, motion sensors, temperature sensors, and others to collect information about the actual lighting conditions in the environment, activities of occupants within the environment, and the like. Information collected by the lighting installation sensor system 266 may be relayed to a validation system 138 of the lighting platform, such as for validation that an installation is operating as designed, including by comparison of light properties at various locations in the environment with the specifications and requirements provided in the lighting design environment 238, such as reflected in the lighting project data structure 254. In embodiments, the variances from the specifications and requirements may be provided to the autonomous control system 262 and/or the remote-control system, so that adjustments may be made, either autonomously or by a local or remote operator of the lighting installation, to enable adjustments (such as to colors, intensities, color temperatures, beam directions, and other factors), such as to cause the lighting installation 280 to better meet the specifications and requirements. The operational feedback system 264 may also capture feedback that leads to revisiting the lighting design in the lighting design environment 238, which may induce further iteration 104 as noted above, resulting in changes to control parameters for the lighting objects 226, as well as automated ordering of additional or substitute lighting objects 226, with updated installation and operational guidance.

In embodiments, remote control may enable field programmable lighting systems, such as for transitional environments like museums (where art objects change regularly), stores (where merchandise shifts) and the like as well as for customizable environments (such as personalizing lighting in a hotel room according to a specification 144 for a guest (which may include having the guest select an aesthetic filter). Such features may enable the lighting installation 280 to change configurations (such as among different aesthetic filters 118) for multi-use environments, multi-tenant environments, and the like where lighting conditions may need to change substantially over time.

In embodiments, a lighting system may include navigation features, such as being associated with beacons, where the lighting system interacts with one or more devices to track users within a space. The lighting objects 226 and their locations may be associated with a map, such as the map of the lighting space in the design environment. The map may be provided from the lighting design environment 238 to one or more other location or navigation systems, such that locations of lights may be used as known locations or points of interest within a space.

In embodiments, the lighting installation 280 may be designed for an operation that is coordinated with one or more external systems, which may serve as inputs to the lighting installation, such as music, video and other entertainment content (such as to coordinate lighting with sound). Inputs may include voice control inputs 708, which may include systems for assessing tone or mood from vocal patterns, such as to adjust lighting based on the same.

In embodiments, inputs may also include inputs from wearable devices, such as enabling adjustment of lighting control parameters (autonomously or with remote or local control features) based on physiological factors, such as ones indicating health conditions, emotional states, moods, or the like. Inputs from wearable devices may be used in the operational feedback system 264, such as to measure reactions to lighting conditions (such as to enable automated adjustment of a lighting installation), as well as to measure impacts on mood, health conditions, energy, wellness factors, and the like.

In embodiments, the platform 100 may be configured to change settings or parameters for a lighting installation (including various lighting objects and fixtures, such as using a custom tuning system) based on a variety of real time data, with a view to having the lighting installation best suit its environment in a dynamic way. In embodiments, data may be obtained that serves as an indicator of the emotional state or the stress level of an environment, and the lighting installation may respond accordingly to that state or stress level. In embodiments, data about the environment may be collected by a wearable device, such as a smartwatch, armband, or the like; for example, data may be collected on acceleration, location, ambient light characteristics, and heart rate, among other possibilities. In embodiments, the data may be provided to the platform 100 for analysis, including using machine learning, such as to observe physiological indicators of stress, mood, or the like under given lighting conditions. The analysis may enable model-based controls (such as where a given mood or state of the users in a room are linked to a set of control parameters appropriate for that state). In embodiments, machine learning may be used; for example, over time, by variation of parameters for lighting objects and fixtures (such as color, color temperature, illumination patterns, lighting distributions, and many others), a machine learning system may, using feedback on outcomes based at least in part on physiological data and other data collected by a wearable device, select and/or promotion lighting installation parameters that improve various measures of stress, mood, satisfaction, or the like. This may occur in real time under control of a machine learning system based on the current conditions of users or the environment. In embodiments, data collected at least in part by a physiological monitor or wearable device may be used as an input to processing logic on a lighting object that changes lighting levels or other parameters to accommodate the 'emotional state' of the users in an environment where the lighting object is located. In embodiments, there is memory that retains and manages function with no appreciable drain on the battery.

In embodiments, inputs may include systems that take data harvested from sensors 710 in the lighting installation environment as well as sensors that reflect information about users, such as one or more of physiological sensors (including wearable devices, such as armbands, wrist bands, chest bands, glasses, clothing, and the like), sensors on various devices used by a user, ambient sensors, and the like. These may include sensing one or more of temperature, pressure, ambient lighting conditions, localized lighting conditions, lighting spectrum characteristics, humidity, UV light, sound, particles, pollutants, gases (e.g., oxygen, carbon dioxide, carbon monoxide and radon), radiation, location of objects or items, motion (e.g., speed, direction and/or acceleration). Where one or more wearable or physiological sensors are used, they may sense one or more of a person's temperature, blood pressure, heart rate, oxygen saturation, activity type, activity level, galvanic skin response, respiratory rate, cholesterol level (including HDL, LDL and triglyceride), hormone or adrenal levels (e.g., cortisol, thyroid, adrenaline, melatonin, and others), histamine levels, immune system characteristics, blood alcohol levels, drug content, macro and micro nutrients, mood, emotional state, alertness, sleepiness, and the like.

In embodiments, the platform may connect to or integrate with data sources of information about users, such as including social networks (Facebook™, LinkedIn™, Twitter™, and the like), sources of medical records (23&Me™ and the like), productivity, collaboration and/or calendaring software (Google™, Outlook™, scheduling apps and the like), information about web browsing and/or shopping activity, activity on media streaming services (Netflix™, Spotify™, YouTube™, Pandora™ and the like), health record information and other sources of insight about the preferences or characteristics of users of the space of a lighting installation, including psychographic, demographic and other characteristics.

In embodiments, the platform may use information from sources that indicate patterns, such as patterns involving periods of time (daily patterns, weekly patterns, seasonal patterns, and the like), patterns involving cultural factors or norms (such as indicating usage patterns or preferences in different regions), patterns relating to personality and preferences, patterns relating to social groups (such as family and work group patterns), and the like. In embodiments, the platform may make use of the data harvested from various sources noted above to make recommendations and/or to optimize (such as automatically, under computer control) the design, ordering, fulfillment, deployment and/or operation of a lighting installation, such as based on understanding or prediction of user behavior. This may include recommendation or optimization relating to achieving optimal sleep time and duration, setting optimal mealtimes, satisfying natural light exposure requirements during the day, and maintaining tolerable artificial light exposure levels (such as during night time). In embodiments, the platform may anticipate user needs and optimize the lighting installation to enhance productivity, alertness, emotional well-being, satisfaction, safety and/or sleep.

In embodiments, the platform may store a space utilization data structure that indicates, over time, how people use the space of the lighting installation, such as indicating what hallways are more trafficked, and the like. This may inform understanding of a space, such as indicating what is an entry, what is a passage, what is a workspace, and the like, which may be used to suggest changes or updates to a lighting design. In embodiments, sensors may be used to collect and read where people have been in the space, such as using one or more video cameras, IR sensors, microwave sensors. LIDAR, ultrasound or the like. In embodiments, the platform may collect and read what adjustments people have made, such as task lamp activation and other activities that indicate how a lighting fixture is used by an individual in a space. By way of these examples, aggregate usage information may be used to optimize a lighting design and adjust other lighting designs. Based on these factors, a space may be dynamically adjusted, and the lighting model for an installation may be updated to reflect the actual installation.

In embodiments, control capabilities of the lighting objects 226 may include dynamic configuration of control parameters, such as providing a dimming curve for a light source that is customized to the preferences of a designer or other user. This may include a selection from one or more modes, such as ones that have desired effects on mood or aesthetic factors, that have desired health effects, that meet the functional requirements 112, or the like. By way of these examples, when using a four-channel color changing system with both uplight and downlight components, the platform may include multiple modes, such as two modes that may help mimic outdoor lighting. In these examples, a first mode may include a downlight portion of the light that may be set in a circadian mode, such as being set at warm or very warm (1800-2500K CCT) around sunrise and sunset and transitioning to cool to very cool (5000-10000K CCT) around noon. In embodiments, these could be white or slightly hue-adjusted white color points. Additionally, an up-light portion may be made to mimic sky color. When a downlight portion is lighting a room with a warm CCT like 2500K, an up-light portion may be used in further examples to broadly illuminate the ceiling, such as in a shade of orange to mimic the sunrise or sunset. During the middle of the day, while the down-lighting is a cool white CCT, an up-light may in further examples illuminate the ceiling in a cyan shade to mimic a mid-day sky.

In order to truly achieve circadian action, prolonged exposure may be required, however, a melanopic flux may, in many embodiments, need to be at least 10:1 and in further embodiments, may need to be 20:1, 50:1, 100:1, or a greater ratio. It will be appreciated in light of the disclosure that most conventional systems simply adjust from a warm CCT to a cool CCT, which may only provide a 2:1 or 3:1 ratio of melanopic flux, which may not be enough to provide health benefits. In embodiments, the platform may include spectral tuning targets for a multiple channel system (e.g., a four-channel system) that may optimize this ratio for a white only ceiling and/or a white plus sky color ceiling, among examples. These targets, along with adjustments intensity of light (e.g., 4:1) may provide a higher ratio, such as a 10:1 ratio or greater, and thus provide greater melanopic flux ratios.

In a second mode and either in combination with the above mode or not, the platform may include adjustable down-facing optical distributions to support an ability to shift the bias of light in a room. In embodiments, the user may synchronize the general illumination (middle of the room) lights to start off with most of the light bias "left" (looking at a linear fixture end-on), shift to being primarily pushing down the middle, and then biasing the light to the "right" over the course of the day. These modes may support an ability to have the diffuse shadows cast in a room mimic the movement of the sun across the sky in examples where the room may not align with the East-West movement of the sun but the modes may nevertheless support generating a lighting bias typical of being outside.

Figure 38:
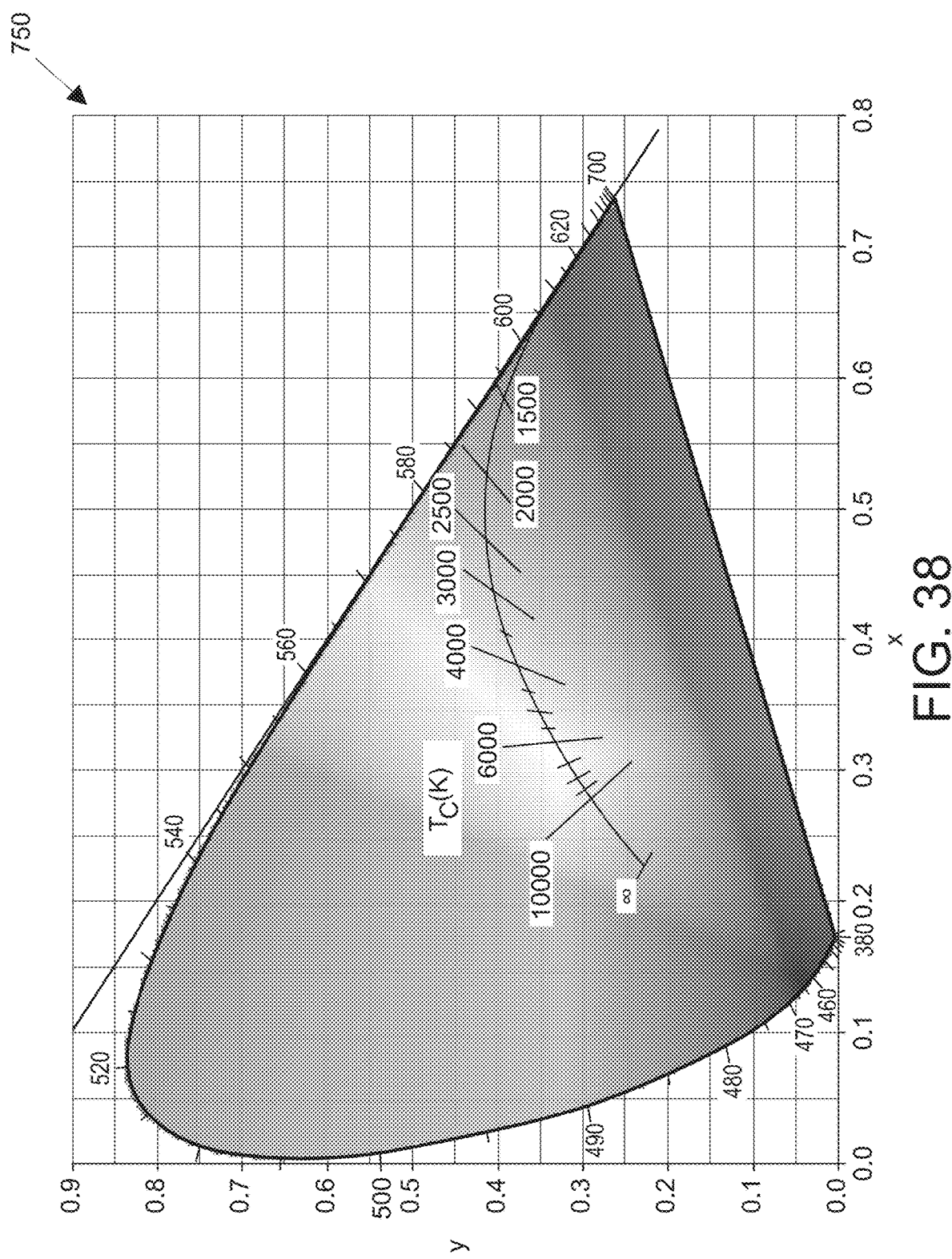
FIG. 38 is a diagrammatic view that illustrates alternative spectral tuning curves that may be enabled, such as for programmable dimming or color tuning modes in accordance with the embodiments of the present disclosure.
Figure 39A:
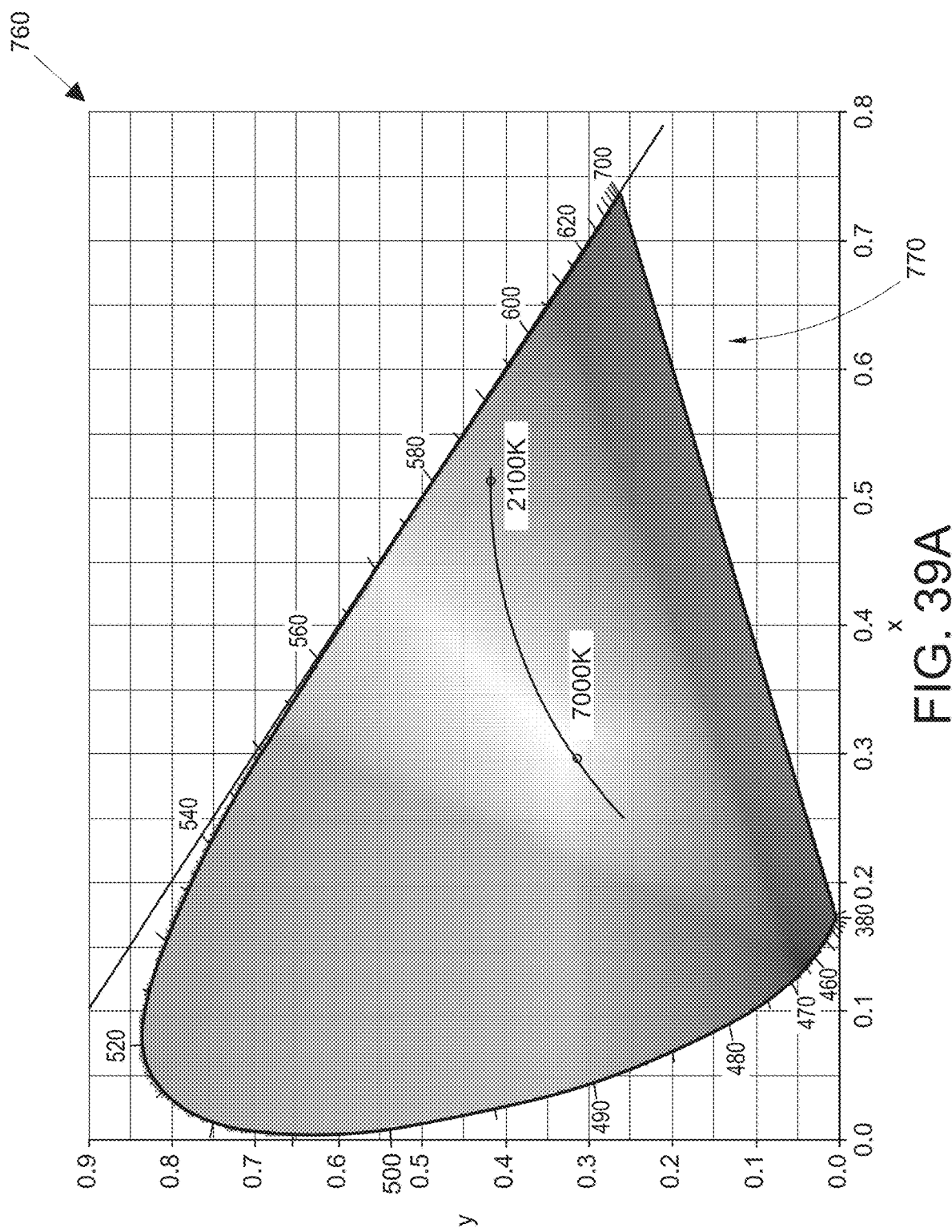
FIGS. 39A, 39B, 39C, 39D, 40, and 41 are diagrammatic views that depict embodiments of spectral tuning of lighting curves for lighting fixtures, as may be specified or selected using an interface of the platform or a related system in accordance with the embodiments of the present disclosure.
Figure 39B:
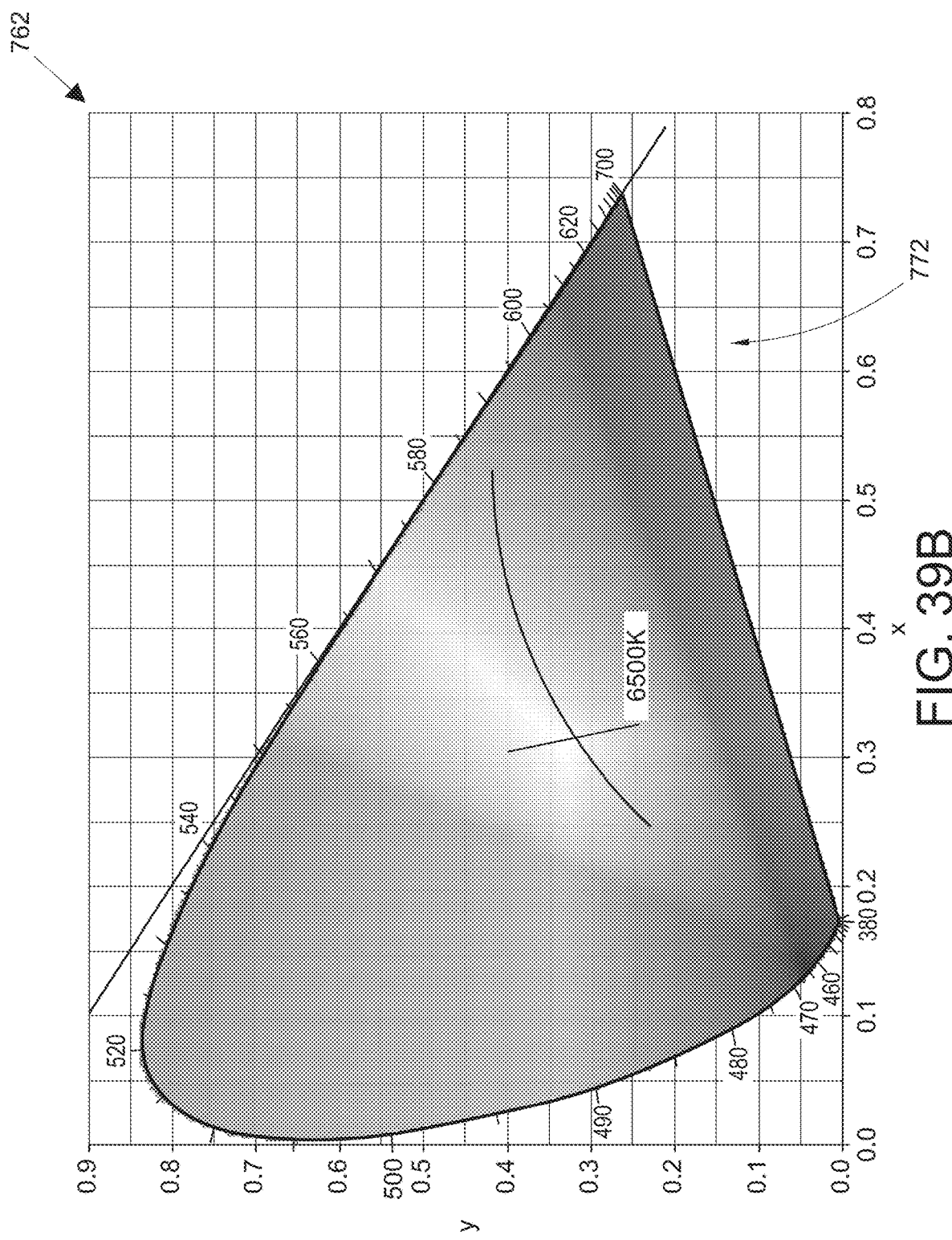
Figure 39C:
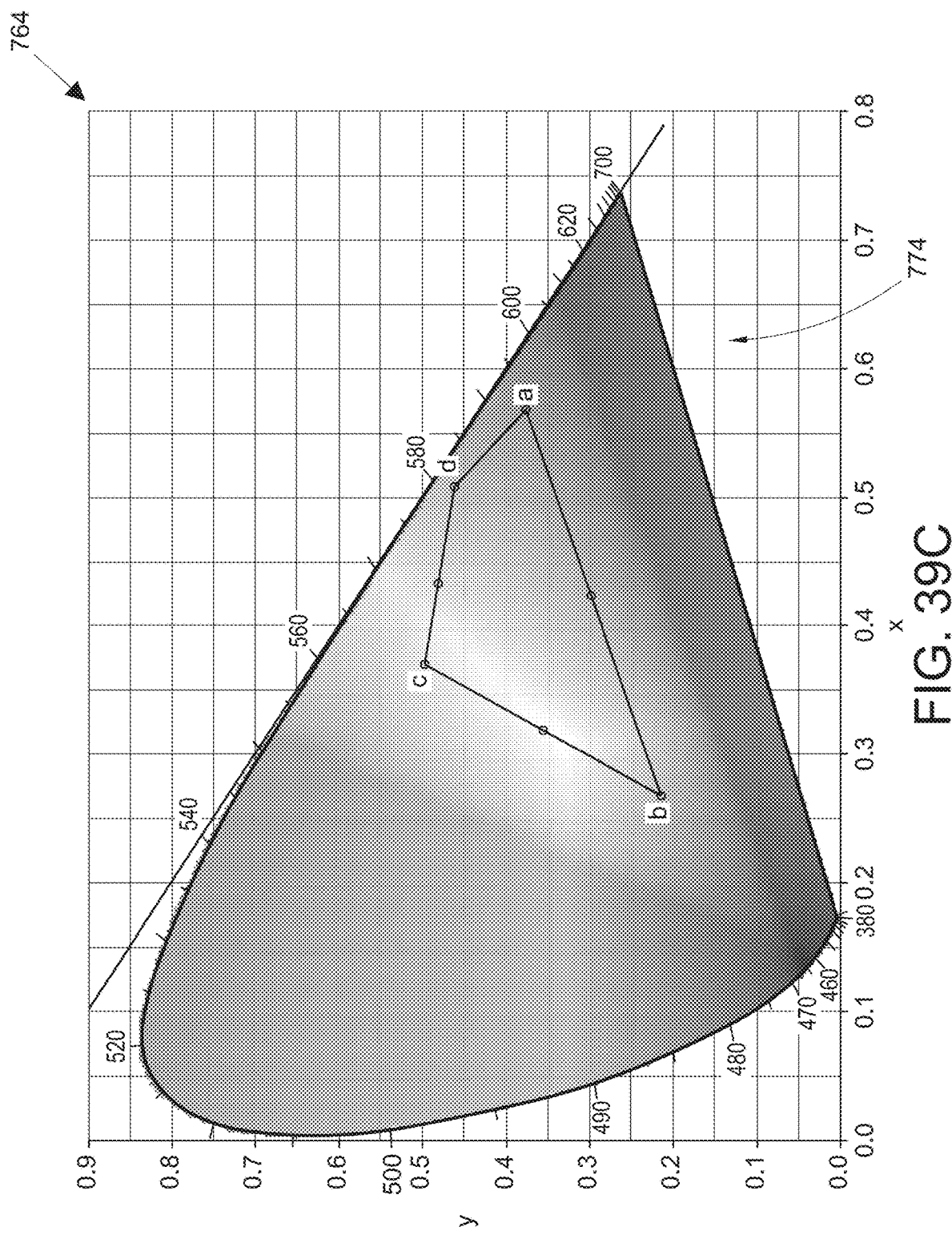
Figure 39D:
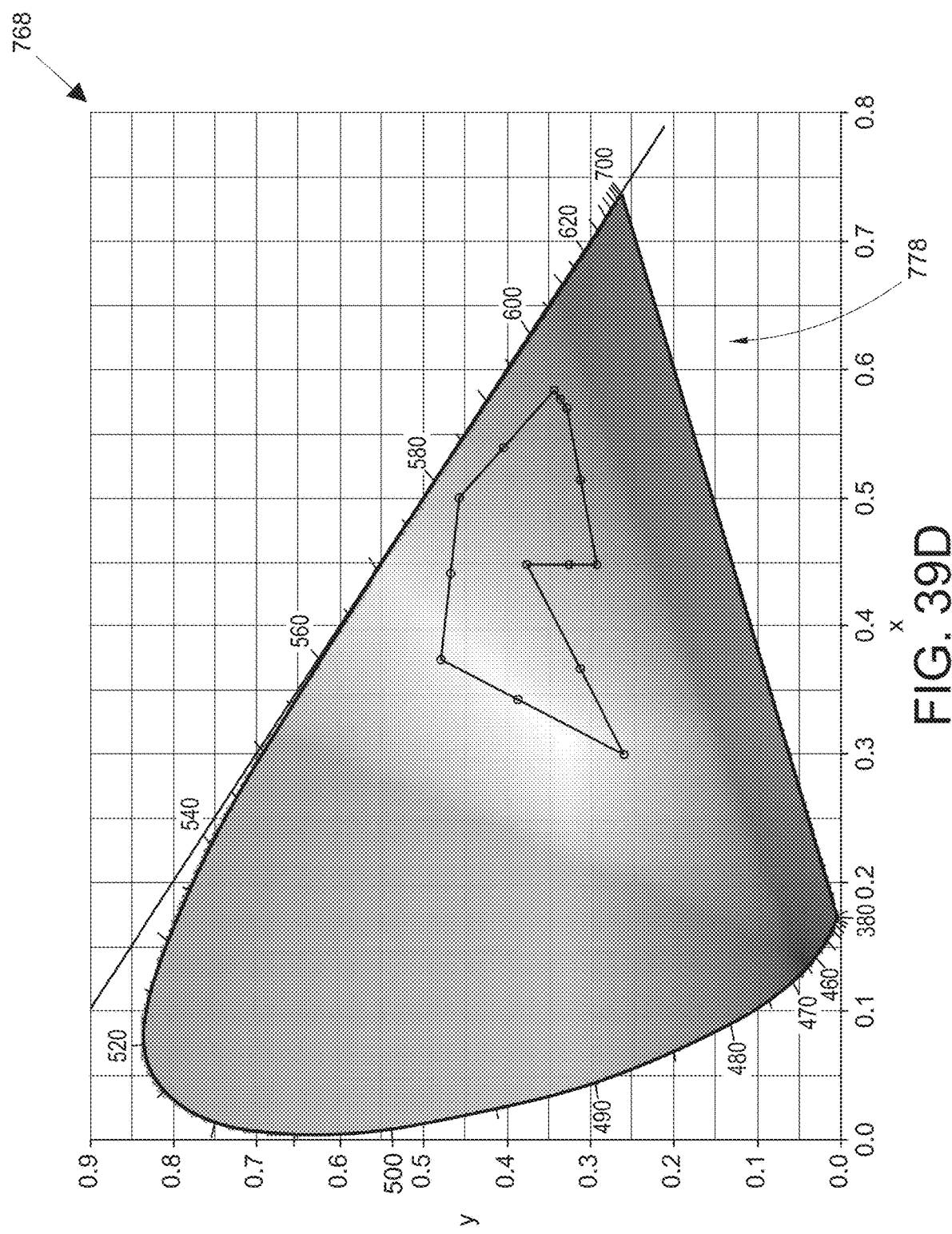
Figure 40:
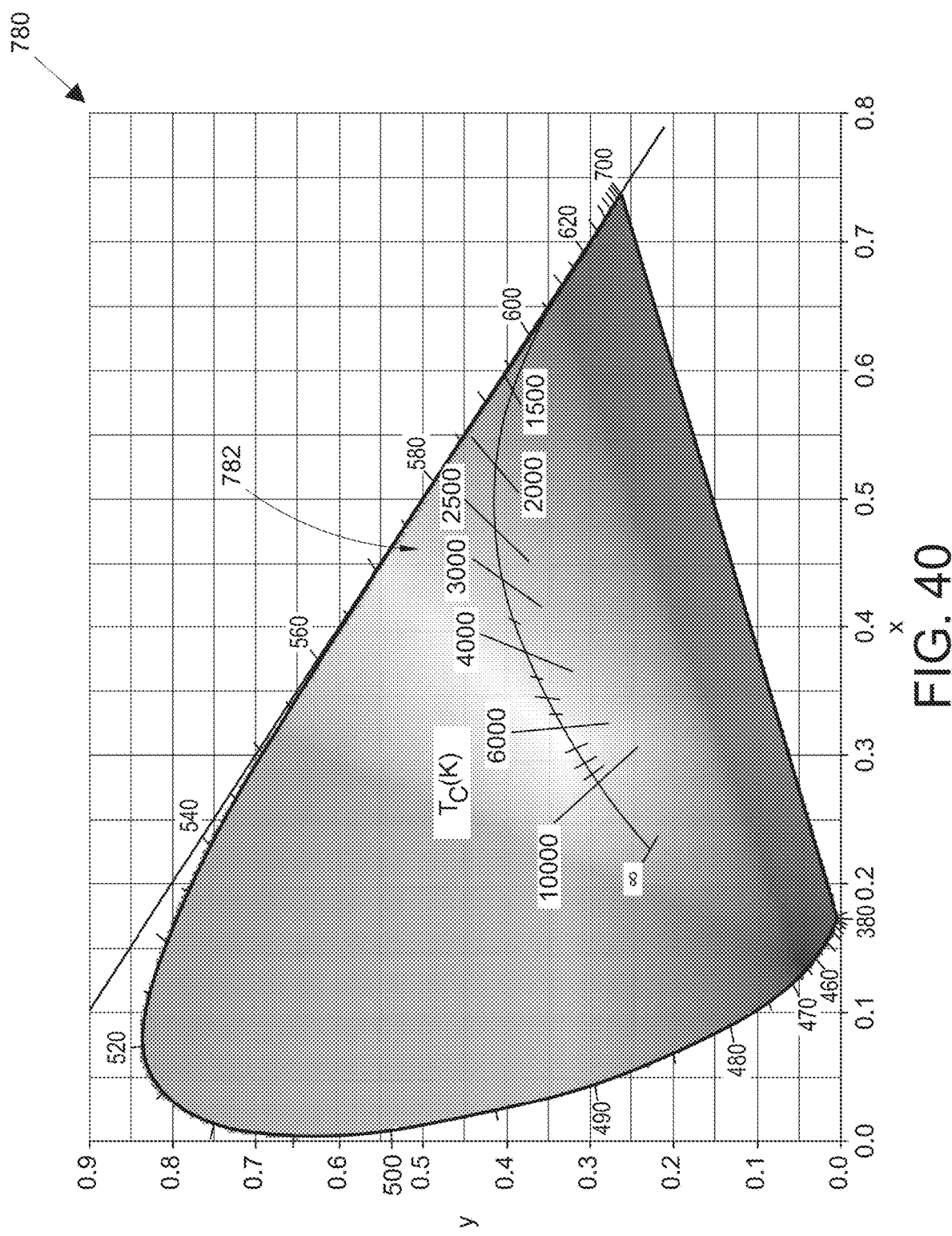

In embodiments, various other programmable modes may be provided, such as fixture settings where using different combinations of color light sources to achieve a given mixed color output may be optimized for efficacy, efficiency, color quality, health impact (e.g., circadian action), or to satisfy other requirements. In embodiments, the programmable modes may also include programmable dimming curves, color tuning curves, and the like (such as allowing various control interfaces, such as extra-low voltage (ELV) controllers or voltage-based dimmers to affect fixture colors, such as where a custom tuning curve provides a start point, an end point and a dimming and/or color tuning path in response to a level of dimming). In embodiments, programmable modes may use conventional tuning mechanisms, such as simple interpolation systems (which typically use two or three white color LEDs, are dimmable on a zero to ten-volt analog system, and have a second voltage-based input for adjusting the CCT of a fixture between warm and cool CCTs. FIG. 38 illustrates a system 750 using three white sources with CCTs at 2700K, 4000K and 6500K. In embodiments, various spectral tuning curves 760, 762, 764, 768 may be provided, as illustrated in FIGS. 39A, 39B, 39C and 39D. In embodiments, FIG. 39A depicts a black body curve 770. By way of this example, FIG. 39B depicts a curve 772 having a constant CCT at 6,500K. FIG. 39C depicts a curve 774 having a color space perimeter. FIG. 39D depicts a curve 778 having a random color tour. In embodiments, programmable modes may also be provided for fully tunable systems, which may include various light sources, such as various combinations of red, green, blue, white and amber LEDs, such as RGB, RGBW, RGBWA (red, green, blue, white and amber), and other three-channel or greater color combinations. Because of the wide range of potential white or non-white colors produced by such systems, they may be controlled by the platform 100 that may specify a particular x, y coordinate on the CIE diagram 780, as illustrated in FIG. 40. Lighting control protocols like DMX™ and Dali 2.0™ may achieve this result. The black lines 782 show the available CIE area covered by an RGB system, with the white lines representing the color contributions from each channel.

Figure 41:
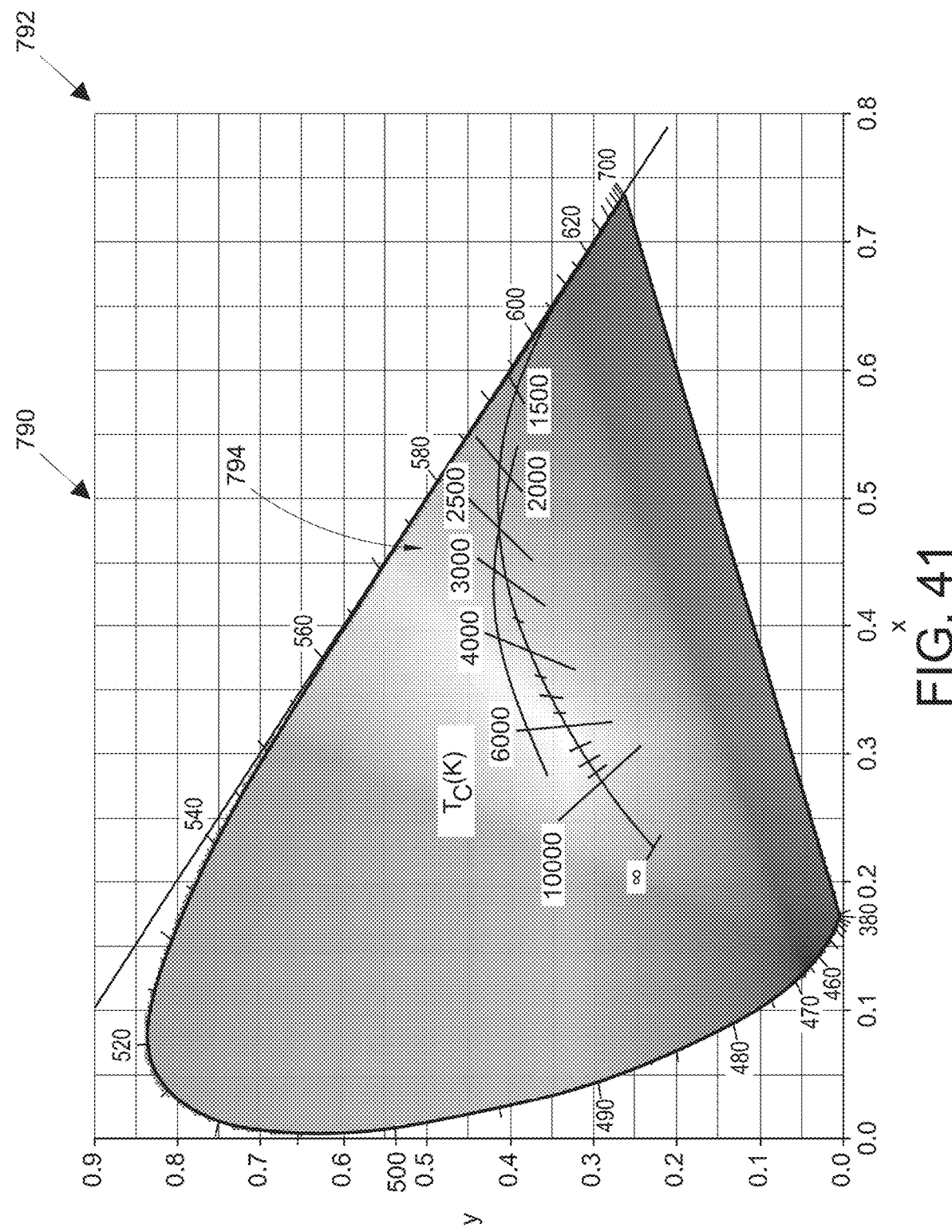

In embodiments, a programmable color curve 790 for an LED driver may be input, such as through an interface 792 of the platform 100, or through a desktop software interface, a mobile phone, a tablet app, or the like, that enables a user to define a start and stop point to a color tuning curve and to specify how it will be controlled by a secondary input, such as a voltage-based input (e.g., a 0 to 10-volt input) to the fixture. These may include pre-defined curves, as well as the ability to set start, end, and waypoints to define custom curves. Referring to FIG. 41, the color curve 794 shows a starting point around 8000K biased above the black body curve, the color curve crossing the black body around 2700K, and finishing around 1800K below the black body curve. Similarly, a curve could be programmed such that the start was 4000K well above the black body, with the end being 4000K well below the black body. By way of these examples, any adjustment would be in hue only, not CCT. Further examples may include a curve that never produces a white color, such as starting in the purple and finishing in orange. In any of these cases, these curves may be programmed into lighting fixtures via the interface of the platform 100, the desktop, mobile phone or tablet. In embodiments, the curves may be designed, saved, and then activated, such as using the secondary (supplemental) 0 to 10-volt input.

In embodiments, a three-channel warm dim mode may be used, such as for target applications where the "fully on" CCT falls between 3000K and 2500K. By way of these examples, as the fixture dims (via ELV control or in response to the 0 to 10-volt input) the CCT may be gradually decreased to between 2500K and 1800K. In embodiments, the hue adjustment may all occur below the black body curve. Alternative embodiments may use the "Green" and "Red" points, such as of a four-channel system, plus 4000K to achieve a warm dimming mode that allows for adjustment both above and below the black body curve.

Where a four-channel color system includes 3000K to 1800K CCT white within its range, a programmable mode may be included within the driver that adjusts color with the dimming percentage as well. In some aspects, this may be similar to a conventional control mode, except that the color control would not be on the secondary 0 to 10-volt channel, but may be activated through the primary 0 to 10-volt input channel or ELV controller. In embodiments, the "starting" color point may be the one when the fixture was "fully on." In embodiments, the "ending" color point may be the one where the fixture is maximally dimmed. It is thus possible to make full range color change, such as purple to orange, that is slaved to the 0 to 10-volt or ELV dimming signal.

In embodiments, an optimized mode may be provided. With a 4-channel color system, there are many ways to create a single x-y point on the CIE diagram. In embodiments, the maximally efficient mode may typically be one that uses the colors that have x, y coordinates closest to the target x, y coordinate. But for best color quality, utilizing a fourth channel (and thereby requiring more light from the color in the opposite "corner") may help provide a desired spectral power distribution. For the maximum melatonin suppression (for systems hoping to mimic circadian lighting), a higher cyan channel content may be required for CCTs of 3500K and above and minimizing cyan and blue content below 3500K. It will be appreciated in light of the disclosure that conventional systems either require expert users to understand the color balances necessary to achieve these effects (who then implement the color balances channel-by-channel) or are designed for maximum efficiency with color quality as a byproduct.

In embodiments, a digital power system is provided herein (including firmware-driven power conversion and LED current control) that controls a multichannel color system, such as a 4-channel color system, and allows for the inclusion of "modes" which may calculate the correct color balance between the various channels to provide optimized outputs. In embodiments, optimization may occur around one or more of efficacy, color quality, circadian effects, and other factors. Other modes are possible, such as optimizing for contrast, particular display requirements (such as red-emphasized colors for displaying meats or green-emphasized colors for displaying produce, among many others). It will be appreciated in light of the disclosure that this is not an exhaustive list but is representative of potential modes that could be engaged through an interface of the platform (or of a mobile, tablet or desktop application) where a color tuning curve may be specified, such that the curve is used to specify an interface between a controller and the Digital PSU in a lighting fixture. In embodiments, these modes may account for actual measured colors for each fixture and calculate the correct balance of for the chosen modes, such as based on algorithms loaded into the Digital PSU microprocessor.

In embodiments, machine learning may be used, such as based on various feedback measures, such as relating to mood (stated by the user or measured by one or more sensors), noise levels (such as indicating successful utilization of a space based on a desired level of noise), returns on investment (such as where lighting systems are intended to promote retail merchandise), reported pain levels, measured health levels, performance levels of users (including fitness, wellness, and educational performance, among others), sleep levels, vitamin D levels, melatonin levels, and many others. In embodiments, the lighting installations may be operated or controlled based on external information, such as based on seasonal lighting conditions, weather, climate, collective mood indicators (such as based on stock market data, news feeds, or sentiment indices), analyses of social network data, and the like. This may include controlling a system to reflect, or influence, the mood of occupants.

It will be appreciated in light of the disclosure that most lighting products are characterized by IES files that provide far field data about light output; however, the near field characterization system 270 is usually absent or inaccurate. Moreover, lighting fixture objects 230 may be modeled with Illuminating Engineering Society (IES) data but IES data may lack near field fidelity making a lighting simulation incomplete and in some cases, inaccurate. In embodiments, the platform 100 may include a solution, a near field characterization and/or testing system, to capture near field light distribution, so that the platform 100 may more completely and accurately model lighting.

It will also be appreciated in light of the disclosure that lighting fixture object manufacturers may provide IES files for their lighting fixtures. IES files may typically consist of far field light distribution data. IES files may include a two-dimensional characterization I ($\theta$, $\varphi$), which may represent the luminous flux in a given direction defined by $\theta$ and $\varphi$. In embodiments, this data may be gathered using a goniophotometer to measure light at different angles and at large distances relative to the size of a lighting fixture such as more than 10× the size of a lighting fixture object 230. By definition, the far field characterization may assume that a lighting fixture object 230 is a point source, which may be a valid assumption as long as the lighting fixture object 230 is at a large enough distance from the measurement system. It will be appreciated in light of the disclosure that in practice many lighting fixture objects 230 are area sources with highly varying light distributions in different directions. With this in mind, their characterization as a point source may frequently fail to capture the lighting field patterns that may be observed at shorter distances from the fixture, which are referred to herein as the near field. Near field light distribution is defined as the luminous flux in a given direction per unit area of a source. In embodiments, near field light distribution may be characterized by four dimensions in a function L (x, y, $\theta$, $\varphi$) which accounts for the spatial extent of the source. Because this is a significantly richer characterization, the tools in the many embodiments may be used to capture the lighting field patterns observed in the near field as well as in the far field. Toward that end, far field characterization may be calculated by integrating over x, y. In embodiments existing near field measurement systems may be used, employing the same concept as a goniophotometer. The approach may include rotating a lighting fixture object 230 to measure the luminance of a lighting fixture object 230 at all angles. For example, the PM-NFMS™ from Radiant Vision Systems™ consists of a two-axis goniophotometer to rotate a lighting fixture object 230 and a stationary imaging colorimeter that is placed in the near field to view the lighting fixture object 230 directly. In embodiments, the high resolution of the CCD sensors in the imaging colorimeter enables distinguishing of individual rays and the system may then produce a near field model of luminance. It will be appreciated in light of the disclosure that this method, although accurate, has the following disadvantages: (a) slow speed as it may take anywhere between 2-5 hours to measure near field light distribution for a lighting fixture; (b) high cost as the system may cost tens of thousands of dollars or more; (c) limited portability; and (d) long setup time. In embodiments, the platform 100 may, in contrast, use an indirect measurement system. An indirect measurement system may include indirect measurement hardware and indirect measurement software.

Figure 9:
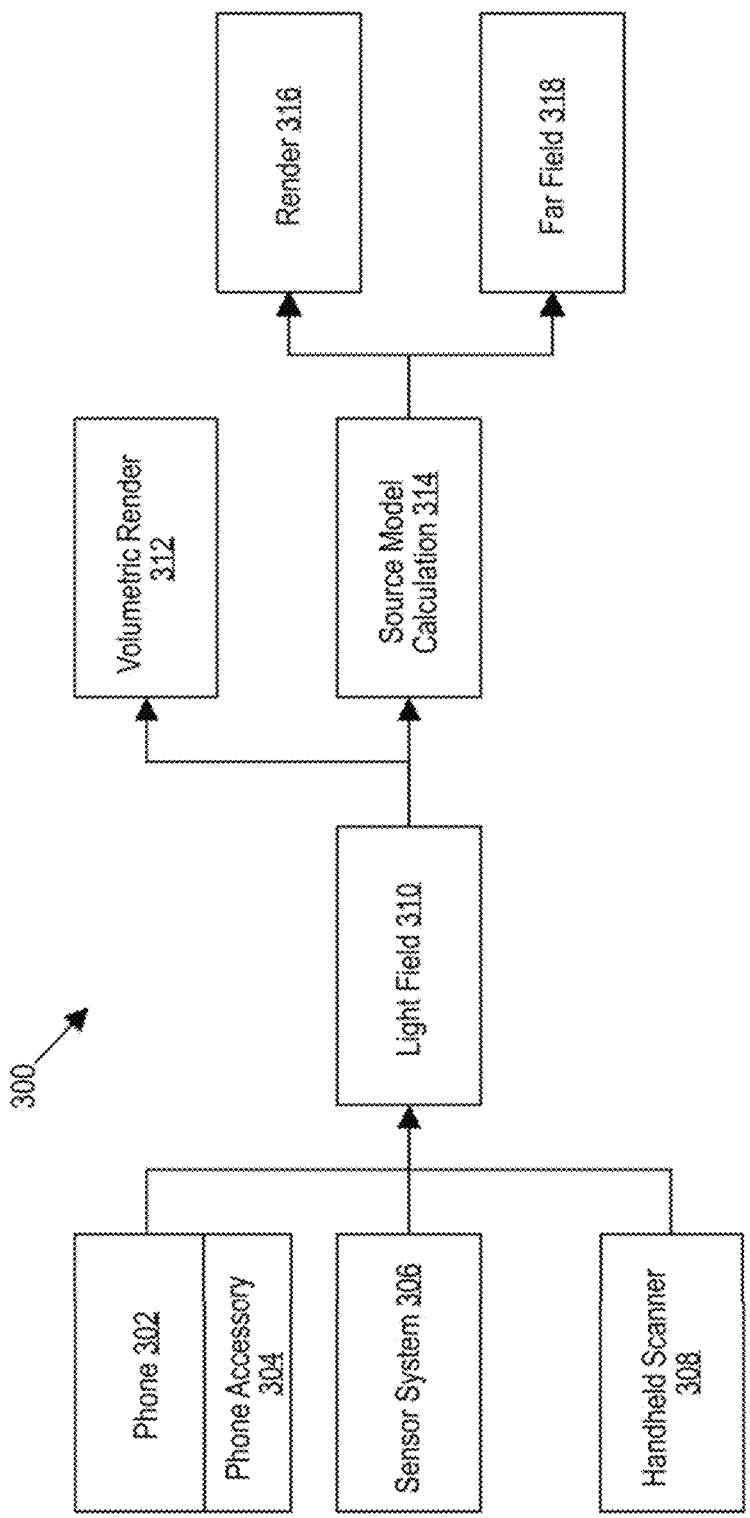
FIG. 9 is a diagrammatic view that depicts flow for characterization of the near field illumination characteristics of a lighting source or lighting fixture in accordance with the embodiments of the present disclosure.

FIG. 9 depicts a near field characterization flow 300, which may be integrated with or may provide information to the platform 100 in accordance with the embodiments of the present disclosure. In a near field characterization flow 300, a light field 310 may be measured, such as using inputs from a camera-enabled phone 302, a sensor-based system 306, a handheld scanner 308, or the like. In embodiments, a phone may include the phone accessory 304. Measurement of the light field 310 may be provided as an output to other elements of the platform 100, such as to a volumetric render 312, a source model calculation 314, or the like. In embodiments, the source model calculation 314 may then be provided to a renderer 316 and/or a far field system 318.

Figure 10:
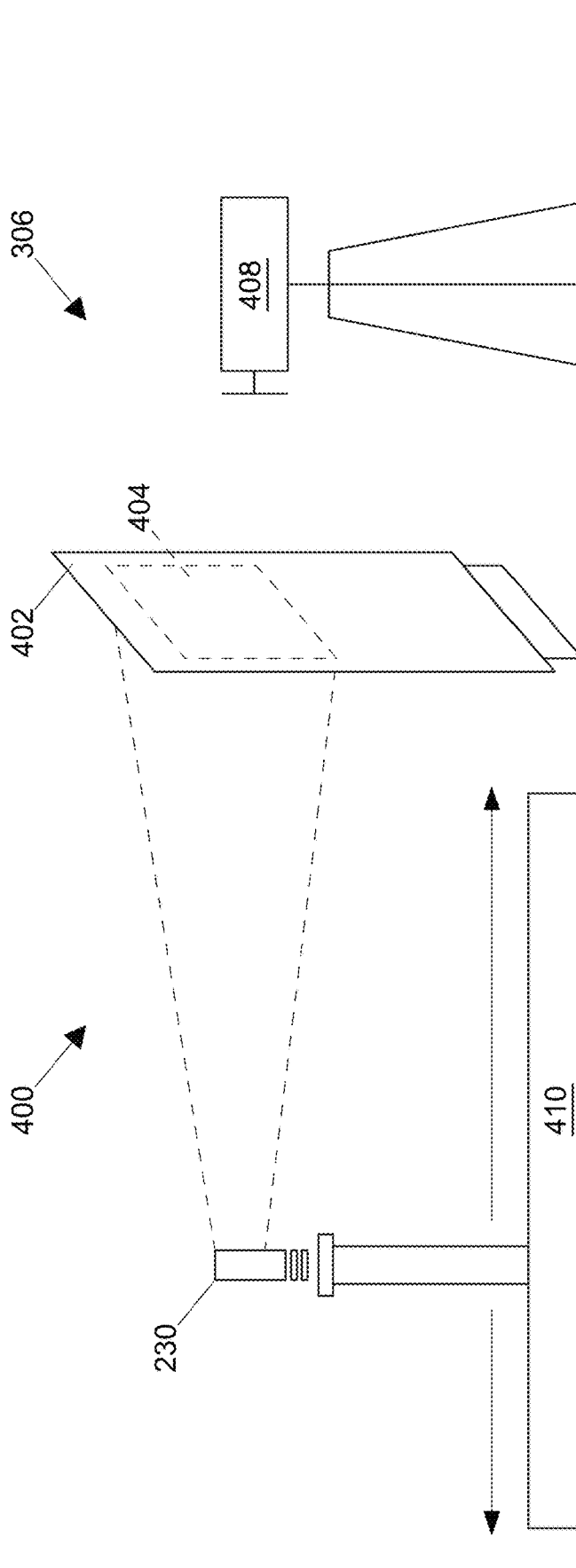
FIG. 10 is a diagrammatic view that depicts a lighting fixture object moving along a single axis in an indirect measurement system in accordance with the embodiments of the present disclosure.

As depicted in FIG. 10, an indirect measurement system 400 may include examples of a sensor-based system 306. Using the indirect measurement system 400 instead of measuring the luminance of a lighting fixture object 230 directly, a lighting fixture object 230 may be set-up in indirect measurement hardware to illuminate an intermediary or intermediate surface. In embodiments, the intermediary or intermediate surface may be an imaging screen 402 that may be translucent. In embodiments, the lighting fixture object 230 may light up one side of the screen 402 and may create an illuminance pattern 404 which may be visible on the other side of the screen 402. This illuminance pattern 404 may then be captured via a camera 408. In embodiments, the lighting fixture object 230 may sit on a positioning slide 410 to enable it to move, in order to vary the distance between the lighting fixture object 230 and the screen 402.

As depicted in FIG. 10, the platform 100 may begin by placing a lighting fixture object 230 as close to the screen 402 as possible and then move it in small increments through a certain distance, while capturing the illuminance pattern 404 at every distance increment. Because each measurement is a 2D image, the set of measurements may give rise to 3D volumetric illuminance data. Once the indirect measurement hardware captures 3D volumetric illuminance data, the indirect measurement software may use reconstruction techniques to create a near field characterization of the source. The indirect measurement software may model a lighting fixture object 230, as an area source that includes a certain number of point sources depending on the desired accuracy, the higher the number of point sources, greater the accuracy of the system.

Each point source may be characterized by I ($\theta$, $\varphi$), namely, the luminous flux it gives out in every direction. That characterization combined with the (x, y) position of each point source on the fixture surface, may provide the near field characterization L (x, y, $\theta$, $\varphi$). In embodiments, the relative contribution of each point source to each pixel in an illuminance pattern may be a function of: (i) the distance between a physical location of a point source on a lighting fixture object 230 and a physical location of a pixel on a screen; (ii) the angle a line connecting the above two points makes with a normal to a screen; (iii) optical properties of a screen; and (iv) luminance of a point source in a direction of a pixel. Because the items (i), (ii), and (iii) in this list may be known quantities, this problem may be formulated as a system of linear equations, which may relate unknown luminance and measured illuminance. In these examples, Ax=b, where "A" is a (m×n) matrix determined by the above three factors: (i), (ii), and (iii), "x," a (n×1) vector is a collection of variables—each unknown value of L (x, y, $\theta$, $\varphi$), and "b", a (m×1) vector is a collection of each pixel value from the 3D volumetric illuminance data.

In the above system example, "A" is known, "b" is measured and hence "x" may be calculated. In embodiments, the platform 100 may use numerical methods to solve linear systems involving a large number of variables. For example, an iterative algorithm may be used to solve a system of linear equations, the Kaczmarz method being one possible example. This indirect measurement system 400 may be much faster than existing systems and may be less expensive than current systems of the art. In embodiments, the indirect measurement system 400 may use smartphone cameras. Use of smartphone cameras may make the indirect measurement system 400 very portable and democratize access to near field light distribution data. Near field light distribution may be a high-fidelity model of the one or more lighting source objects 228 (FIG. 8), which may enable much more accurate renderings of spaces using the lighting source objects 228. In embodiments, this may have applications from architecture to Hollywood. Additionally, a near field may be used to define certain lighting fixture object 230 evaluation metrics.

Figure 11:
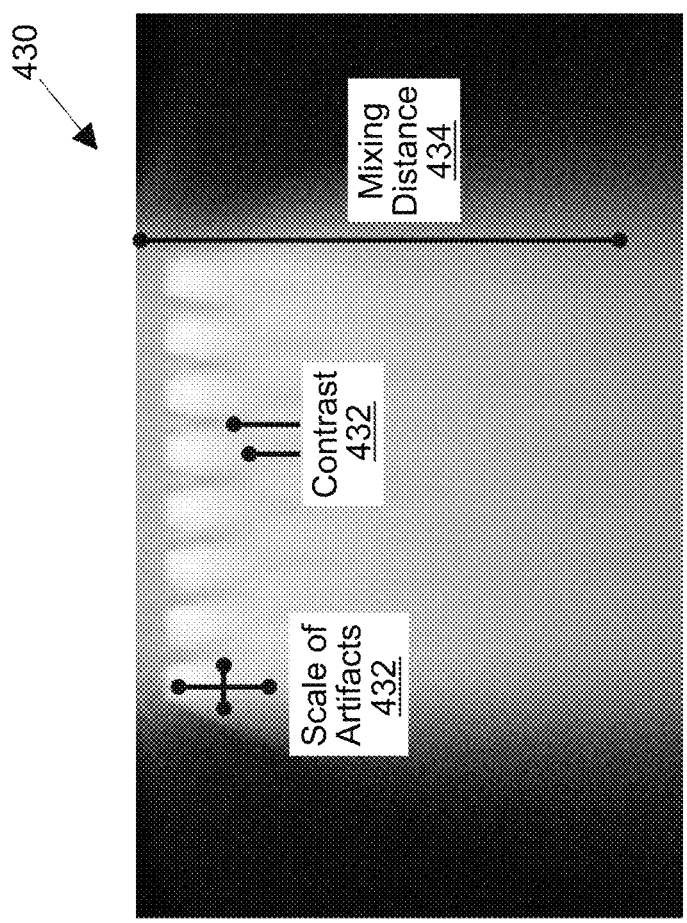
FIG. 11 is a diagrammatic view that illustrates near field metrics that may be characterized in a near field measurement system in accordance with the embodiments of the present disclosure.
Figure 12:
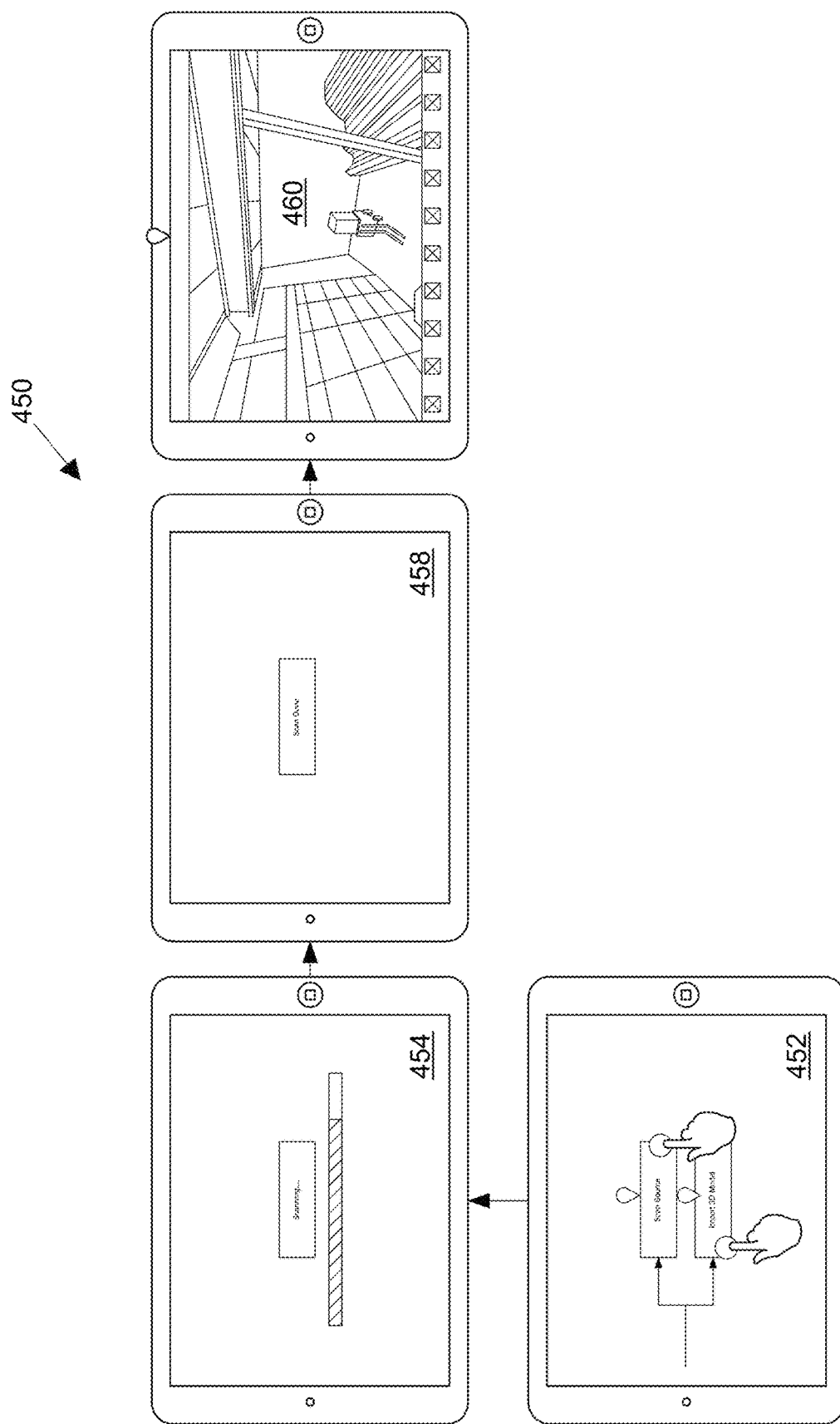
FIG. 12 is a diagrammatic view that depicts a user interface of the platform for a scan process in accordance with the embodiments of the present disclosure.

Referring to FIG. 11, based on a near field light distribution 430, new near field metrics may be developed that may be used to evaluate lighting fixture objects 230. In embodiments, these metrics may depend on the distance and angle to a lighting fixture object 230, so having a rich characterization through the near field light distribution 430 may be useful for many situations. Exemplary metrics may include: (a) a scale of artifacts metric 432 such as indicating the size and scale of artifacts and/or the frequency with which they appear in the light pattern; (b) a mixing distance metric 434 such as indicating the distance from a lighting fixture object 230 at which the light mixes well and has zero or minimal artifacts; and (c) a contrast in near field metric 438 (e.g., indicating the min-to-max intensity ratio in the near field that shows how dramatic the lighting patterns/artifacts are). In embodiments, the light source test system 272 (FIG. 8) of the platform may be used to test the lighting objects 226 and augment their properties with complete near field and far field data, so that illumination effects may be accurately characterized in the lighting design environment 238 for objects at varying distances from a light source.

Near Field: Observing a Light Field and not Point Sources on the Light Source

In embodiments, illumination data for or about a light source may include near field data, far field, and a combination thereof, reflecting the nature of illumination of the environment surrounding the light source at different distances. Near field data may be captured proximal to a light source and may generally describe illumination effects that tend to be non-uniform in distribution as a result of the proximity to the source. For example, a lighting fixture with multiple light sources may have a near field illumination pattern that represents the super-position of the light from each bulb, which may vary significantly at different angles from the light source. Meanwhile, for most light sources, such as fixtures with multiple bulbs, far field data may represent the distribution at greater distances, where illumination patterns become more uniform, such that a distribution approximates the light source as if it were a single, point-based light. Far field data is often used to measure and characterize light sources, but such far field data is usually missing potentially valuable information about a light fixture, including how the illumination from the light source is likely to interact with surfaces, objects and the like in the nearby environment. Relevant information, such as how each bulb in a fixture may contribute to a lighting effect, can be lost in far field data, as the contributions from multiple bulbs tend to merge at a distance from the light source. At any given location in the near field, illumination data may represent illumination effects from one or more light sources in the fixture, as well as how other elements of a fixture, such as lenses and other optical elements, filters, shades, reflective surfaces, and the like may impact certain aspects of directionally oriented light from one or more bulbs. Therefore, methods and systems are provided herein for capturing illuminance patterns that may be present at various locations and distances proximal to the light fixture, including to allow characterization of the light fixture, such as for use in a lighting design system, a lighting marketplace or other system or process described throughout this disclosure.

In embodiments, methods and systems for capturing and handling near field illumination information may include one or more methods of generating a near field illumination data structure. Such a data structure may characterize near field patterns and the like generated by a light source, including, in embodiments, a multi-bulb source. Gathering the data for the data structure may be accomplished by disposing a surface in the near field of the light fixture so that at least one side of the disposed surface is illuminated by the light source. The surface may be positioned at a range of locations, such as different orientations relative to and distances from the light source, so that illumination data for a range of portions of the near field may be captured, optionally including or representing different slices of the surface through the near field illumination pattern around the light fixture. In embodiments, one or more two-dimensional image sensors may be disposed relative to the surface, such as in front of the surface, behind the surface, adjacent to the surface, above the surface, below the surface, and the like, to capture light in the near field. In various embodiments, light reflected from the surface may be captured, light that passes through the surface may be captured (such as if the surface is at least semi-translucent), light that illuminates the two-dimensional sensor directly may be captured, or combinations of the above may be used. In embodiments, light captured by a two-dimensional image capture array may be converted by the array into digital values representing at least a measure of light brightness for each cell in the array. This illumination data may be populated into the data structure, such as in a planar image. As the location and distance of the surface and/or sensor is changed, illumination data for a plurality of distances and positions (including angular orientations) in the near field can be populated into the data structure. In this way, the data structure can capture the light intensity, color, color temperature value (e.g., CCT) and the like for each cell along with a distance from the light source, an orientation of the sensor, an orientation of the surface associated with the sensor, and the like.

In embodiments, the orientation of the sensor may remain fixed while the distance from the light source is varied. This may be accomplished with a variable distance device that facilitates varying a distance between the light source and the sensor and/or surface. Data captured in this way can represent a directional catalog of illumination data, effectively producing a plurality of incremental-distance differentiated images of luminance of the light source. When distance variances are combined with position, such as latitudinal or longitudinal position, angular position or the like, data in the data structure can accurately represent the near field illumination as it would occur at particular locations in an environment, such as where light would interact with a surface that is positioned at a given distance and orientation relative to the light source. When latitudinal and longitudinal position variations are both included, an omni-directional volume of illumination data may be captured.

In embodiments, storing the near field images for a plurality of light sources in a digital library, such as a database, may facilitate a user searching the library to identify a light source having a desired pattern of illumination, at least for a near field. The digital library may include or interface with a pattern matching system for matching at least one image in the library to a specified or desired pattern of illumination for a space. Such a pattern matching system may facilitate identifying at least one light source (e.g., fixture) that can provide the specified pattern. In embodiments, a user may, such as by interacting with a software-based user interface, draw an image of a pattern (such as outlining a shape, selecting a color and the like) or select an image of a desired pattern of light (such as a "bloom" of light on a wall), and the pattern matching system may search for matching images in the digital library. In embodiments, pattern matching may use machine learning, such as by training the system to find matching patterns based on a training data set created by human users and/or supervision of a series of trials by a machine learning system, such as a neural network. Machine learning may operate on feature vectors of the images of an illumination pattern, such as intensities, colors, shapes and the like. The pattern matching system may in embodiments be adapted to facilitate matching a specified pattern of illumination with any portion of the data in the images in the library, such as data from multiple two-dimensional images. In embodiments, pattern matching may account for patterns that result from illumination of surfaces that are positioned at an angle from a light source, such as by specifying an off-axis slice through a portion of the data that is used to generate or characterize planar images of illumination patterns.

In embodiments, pattern matching may be based on determining, for a given position in the near field illumination space (e.g., for a given distance, and/or longitudinal and/or latitudinal orientation) whether the luminance data values in the library captured for at least one light source match those in the specified pattern. For example, a user may seek a spot light that provides a substantially circular, three-foot diameter circle of light with an intensity level between a minimum threshold and a maximum threshold at a distance of ten feet from the light source, and the pattern matching system may filter light sources that in the library to the subset that satisfy those requirements. Rather than having to match all the values, various matching thresholds may be devised to support matching similar patterns, such as a minimum number of matches in the pattern, a minimum number of near-matches in the pattern e.g., values in the library being within a range of values (e.g., a tolerance band) relative to the pattern, and the like. In an example of near-matching, a pattern may include a specific value for a location in the pattern (for example, a value may be 0x92) plus a range of values that would satisfy a near-match criteria (e.g., +/−0x08) so that any value in the location within the range of 0x84-0x100 may be deemed to be a near-match. In embodiments, the pattern matching may be based on a match tolerance value that is specified independently of the pattern to match. In embodiments, pattern matching may be based on a total differential of values between the specified pattern and position-corresponding values in a library. In embodiments of a pattern matching technique, a shape and set of values may be specified in the pattern. Any matching set of values in the library that conforms to the shape of the pattern (e.g., a rectangle, an oval, a circle and the like) may be selected. In this approach, a user may be interested in determining the portion of the near field space of the light fixture that matches the pattern. Other techniques for matching may be included in the methods described herein including matching a hash and/or signature value derived from the pattern to hash values generated for portions of the data in the near field luminance library, and the like.

In embodiments, generating a near field characterization of light fixture luminance may include a user interface through which a user may specify and/or select a pattern of illumination for the space. The user specified and/or selected pattern may be automatically provided as an input to the pattern matching system.

In embodiments, near field luminance data may be processed with indirect measurement software to generate an area-source model of the light fixture or source. An area-source model of the light fixture may take into consideration aspects of the fixture that may not be included in a point-source model, such as may be obtained with far field data. Aspects such as differences in light radiating from different portions of the fixture may be modeled in this way.

In embodiments, generating a near field characterization of light fixture luminance may include generating a three-dimensional volumetric luminance model from the two-dimensional images. A three-dimensional volumetric luminance model may be generated by arranging a plurality of the incremental distance differentiated images into a three-dimensional shape, such that each of the images represents or corresponds to a two-dimensional slice of the three-dimensional shape. Once such a three-dimensional volumetric luminance model is created, capturing luminance values and other lighting parameters at various points in 3D space around a light fixture, the model can be used to generate other two-dimensional slices, including ones that are different from the images used to generate the model. Thus, the illumination cast by the fixture onto various surfaces (including flat and curved surfaces) can be modeled in the three-dimensional volumetric luminance model, such as for purposes of representing in a lighting design user interface the appearance that would be created by using a lighting fixture within a given environment, including what illumination it would cast upon surrounding surfaces. As further described elsewhere in this disclosure, illumination parameters may be maintained in the three-dimensional luminance model that allow for modeling of interaction with surface characteristics or other optical characteristics of the objects in an environment, such as for modeling the effect of color, reflection, absorption, refraction, and the like, of an object when impacted by the illumination provided by a light fixture at a given point and angle within the 3D space modeled by the model.

In embodiments, luminance values captured by the two-dimensional sensor may be converted to a measure of luminous flux including values for $\theta$ and $\varphi$ of the light source.

In embodiments, the near field luminance characterization may include $\theta$ and $\varphi$ luminous flux for each of a plurality of positions as well as x-coordinate and y-coordinate area image sensor location data. The x-coordinate and y-coordinate image sensor location data may be mapped to a corresponding area location on the light source, based, for example, on a distance from the sensor array, a position of the sensor array, an angle of the sensor array relative to the light source, and the like.

In embodiments, data representing the near field illumination characterization in the library is dependent on at least one of: (i) distance between the light source and the surface or surfaces used for generation of the library, (ii) an angle between a line projected from the light source and a position on the surface(s) associated with one of the plurality of luminance values and a normal to the surface, (iii) one or more optical properties of the surface(s), and (iv) the captured luminance value associated with the position of the surface(s).

In embodiments, a system for capturing a near field illumination pattern generated by a light source may include a positioning slide for holding a screen and facilitating moving the screen among a plurality of distances from the light source. The positioning slide may also rotate around the light source both longitudinally and latitudinally to facilitate capturing light output from the light source at a range of locations and distances. The system may also include an image sensor with at least two-dimensions for capturing luminance values from at least one side of the screen when the screen is illuminated by the light source. The system may also include a computer accessible digital data storage system for storing a plurality of data structures, each data structure representing the luminance values captured by the at least two-dimensional image sensor at a given distance, and or position of the positioning slide for a given light source. In embodiments, the plurality of data structures may be stored in a searchable library. The system may further include a user interface through which a user may search for a light source having a desired pattern of luminance values, such as by specifying a desired pattern of luminance values and other relevant criteria about a desired light source.

In embodiments, a method of near field illumination pattern matching may include capturing a plurality of two-dimensional images of an illumination effect in an environment illuminated by a light source. The method may include storing a portion of the plurality of images in a digital data structure that facilitates distinguishing among the stored data values in each of the plurality of images by a two-dimensional location in an image of the plurality of images and an effective distance of the image from the light source. The method may also include detecting a specified pattern of illumination of the environment in the digital data structure. In embodiments, the pattern includes a plurality of data values identified by a two-dimensional location value and light source distance value. To support detecting patterns that are off-axis relative to the direction of light emanating from the light source, at least two data values in the specified pattern may be located at different light source distance values. Also, the light source distance value may vary across a portion of the specified pattern of illumination to facilitate representing a pattern that may be non-planar. The plurality of images may each be captured so that at least two of the images are non-co-planar; however, the images may be substantially parallel. In embodiments, data in the digital data structure represents an impact of light from the light source on at least one object in the environment, such as a wall, column, furniture, floor, window, and the like. Each of the plurality of captured images may be labeled with an identifier that may facilitate referencing a captured image directly, such an identifier may be included in and/or referenced by the specified pattern of illumination.

Figure 42:
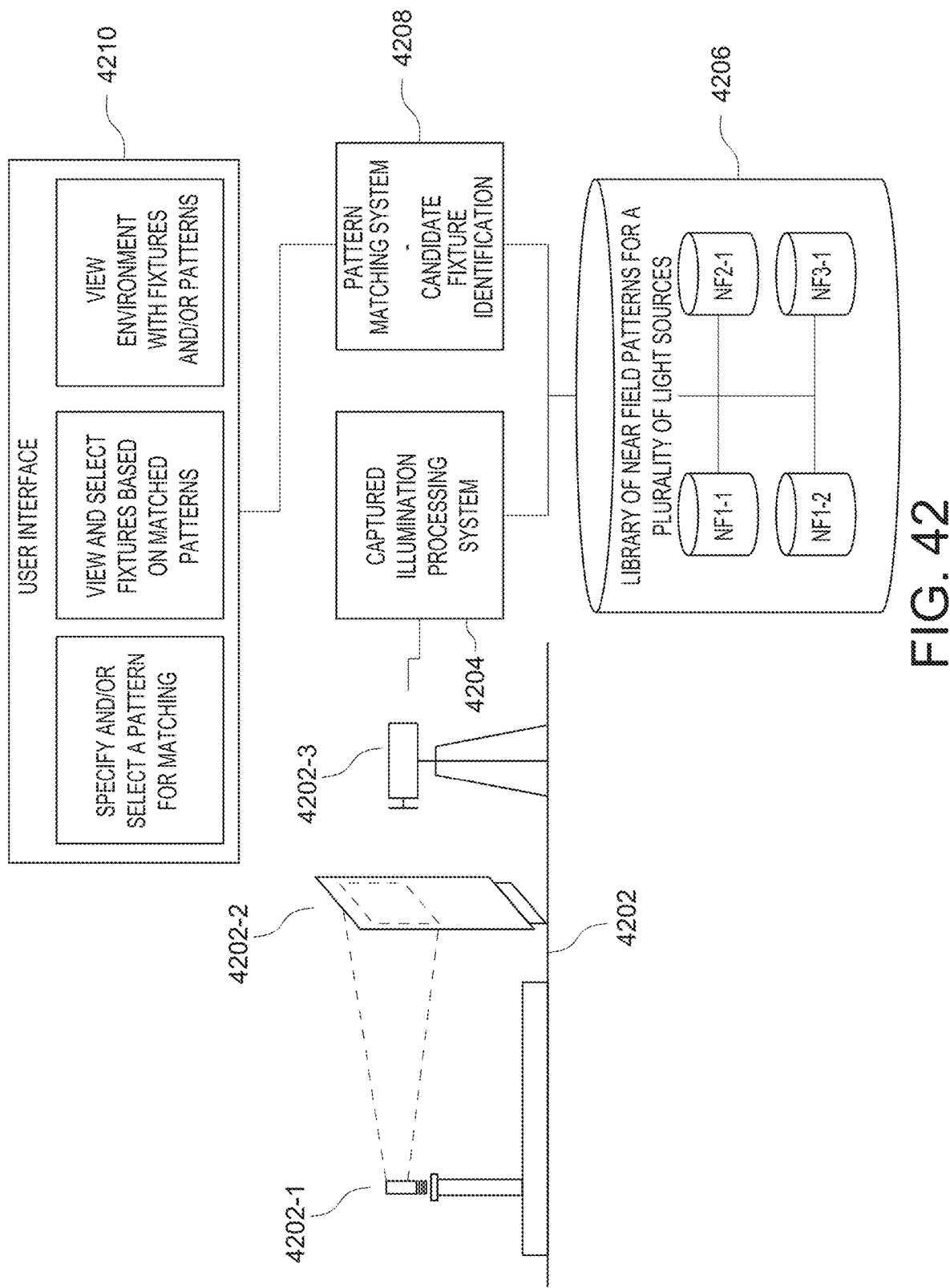
FIG. 42 is a diagrammatic view that depicts embodiments of a near-field characterization system in accordance with the embodiments of the present disclosure.

Referring to FIG. 42, an embodiment of a near-field characterization system 4200 is depicted. An illumination capture system 4202 as described herein may include a light positioning device 4202-1, an intermediate screen 4202-2 and an area array illumination sensor 4202-3. System 4202 may communicate with a capture illumination processing system 4204 that may process data from the illumination capture system 4202 and store it as a data structure (NF1-1 and the like) in near field data structure library 4206. A pattern matching system 4208 may interface with the library 4206 and a user interface 4210 to facilitate matching at least portions of near field patterns as described herein. The pattern matching system 4208 may also facilitate identifying candidate fixtures that may produce patterns similar to a pattern to be matched. The pattern matching system 4208 may also interface with the user interface 4210 through which a user may specify and/or select a pattern for matching; view and/or select one or more fixtures that may be presented in the user interface by the pattern matching system and the like based on a similarity of patterns produced by the one or more light fixtures with a pattern to be matched, such as one that the user has specified and/or selected through the user interface 4210. The user interface 4210 may further facilitate viewing an environment, such as with one or more fixtures selected by the pattern matching system and/or the user and the resulting near field light distribution from the one or fixtures in the environment. The user interface 4210 may use two-dimensional, three-dimensional, and/or virtual reality display systems.

Lighting Distributions: Bloom to Bloom Match

In embodiments, achieving consistency in lighting within an environment or across a plurality of environments may be accomplished by ensuring that light fixtures that provide consistent and/or desired lighting bloom effects are utilized. The term "bloom" is used herein to generally describe the illumination pattern emanating from a light fixture and/or being cast by a light fixture on surfaces and objects in its environment and should be understood to encompass any of a wide variety of lighting characteristics (including shape, color, intensity, and the like) described throughout this disclosure, except where context indicates otherwise. In embodiments, a design for lighting in an environment may prescribe a certain bloom effect from a light source to be added to the environment. A desired bloom effect from a light source may be localized to a portion of an environment in which the light source is deployed, such as a target area of illumination (e.g., a painting hanging on a wall, an object, a walk way, a façade, and the like). Bloom effects from a light source may also be composed of bloom properties that help characterize and distinguish among a range of bloom effects. However, a bloom effect of a light fixture can be impacted by a range of factors, such as other light sources, bulbs used in the fixture, a shape and/or orientation of a shade, lens, mirror, or filter of the fixture, and the like. Therefore, starting with a consistent bloom effect from a light fixture may improve the chances of achieving a desired bloom effect.

In embodiments, determining a fixture that can produce a preferred bloom effect may be accomplished by comparing a digital characterization of the preferred bloom effect to digital characterizations of known bloom effects, such as those produced by other light fixtures. Therefore, a system for matching bloom effects, such as one for facilitating identifying a light source based on a bloom effect may include a library of lighting objects that may represent lighting fixture objects and/or light source objects. In embodiments, at least some aspect of a bloom effect of the lighting objects can be accessed in the library. In embodiments, a bloom effect may be generated from a light source model, such as a near field characterization of the light source and the like. Therefore, bloom effects for lighting objects in the library may be generated and matched to desired bloom effects. In embodiments, models of lighting objects in the library that have lighting properties similar to properties of a desired bloom effect may be used to generate bloom effects that may be used when selecting among (e.g., filtering, and the like) candidate lighting objects in the library. The lighting objects in the library may be characterized by lighting properties, such as output bloom properties that characterize at least a portion of a luminance pattern provided by a lighting object selected from the library. This library may be accompanied by a pattern matching system that facilitates matching bloom effects, such as by matching bloom properties of different bloom effect stored in the library. In embodiments, the library may include a collection of bloom effects represented by digital data structures of the bloom properties and the like. The bloom effects in such a library may be associated with one or more light objects, such as light fixtures, that may produce a specific bloom effect or a bloom effect that is substantially close to a bloom effect in the library. Therefore, the pattern matching system may facilitate identifying at least one lighting object in the library based on at least one output bloom property. The pattern matching system may match bloom effects, properties and the like to facilitate matching a first (e.g., preferred) bloom effect to bloom properties in the library to determine a subset of lighting objects that produce a bloom effect similar to the preferred bloom effect. In embodiments, the pattern matching system may identify just one lighting object in the library that sufficiently matches the desired bloom effect.

In embodiments, an output bloom property may describe a shape of an output bloom from the lighting objects. The output bloom shape may be specified for a given distance from the lighting object, such as when the output bloom intersects with a surface of an object in the environment, such as a plane (e.g., wall, floor, door), column (e.g., a vertical surface that may not extend as far as a wall, and a slope (e.g., a stairway, escalator, ramp, exterior sloped surface, and the like). In embodiments, a shape of an output bloom, or the output bloom itself may be captured by a portion of a near field illumination pattern or of a far field illumination pattern generated by a light object selected from the library. The output bloom shape may be continuous, discontinuous, and the like. A given light fixture may produce a range of light blooms based on, for example, a type or wattage of bulb being used in the fixture, a color of a shade, and the like; therefore, a plurality of blooms may be saved for each lighting object. Data descriptive of the bloom, the lighting object, and the conditions that impact the bloom may be accessible in or through bloom-specific data sets. Determining if an output bloom of a lighting object matches to a desired bloom may include matching multi-dimensional data sets that each include data for luminance proximal to a light source. A preferred output bloom may be represented by a three or greater dimensional data set where at least a measure of light output is stored in cells of the data set. A lighting object output bloom may also be represented by a near-field characterization of the light, that may also include a three or greater dimensional data set where at least a measure of light output is stored in cells of the data set. In embodiments, comparing bloom effects may include comparing portions of near-field characterizations of light sources.

In embodiments, light output bloom properties may include color, intensity, diffusion over distance, reflection from a surface in the environment, transmission through a surface in the environment, and the like. A surface in the environment may be translucent. The surface may be a shade of a lighting fixture, and the like.

In embodiments, the system for facilitating identifying a desired light source based on a bloom effect may include a user interface whereby a user can view and select a lighting object based on a display of the output bloom. The user interface may render to a user, via a computer interface such as a virtual reality interface and the like, the preferred output bloom effect in an environment, such as an environment selected by the user. The user may select among lighting objects in the library, and the output bloom for the selected lighting object may be rendered. The user interface may further facilitate a user selecting and/or specifying a desired output bloom property, such as by referencing a lighting object with certain conditions, identifying an existing bloom with the property, entering the property directly (e.g., a color or the like). The user interface may allow a user to view bloom effects from, for example, a library of lighting object bloom effects in an environment and then select one as a preferred bloom effect. For conditions that may impact the bloom if varied, such as ambient light in the environment, the user interface may allow the user to adjust such conditions.

In embodiments, the bloom pattern matching system of the system that may facilitate identifying a desired light source based on a bloom effect may automatically identify at least one lighting object in the library based on a desired output bloom property, such as by matching an output bloom property of the lighting object with the desired output bloom property. In an example, an output bloom property may include how a bloom of illumination from a lighting object may illuminate other objects in the environment. Automation and bloom matching may be enhanced by performing artificial intelligence classification that may be trained to match output bloom patterns based on a training set of patterns. Such a training set may be matched by one or more human users, and the like.

Near Field: Volumetric Renderer

In embodiments, a near field volumetric rendering facility may facilitate displaying a representation of lighting distributions from a light source in an arbitrary, three-dimensional environment. A rendering facility that has access to near field light fixture data, which may include data that represents illumination of a three-dimensional region around a light source, may apply light emission modeling techniques to generate a rendering of light impacting an environment that correlates to the near field functioning of the light fixture. In a three-dimensional space, rendering of near field data may include modeling light source emissions as a set of light ray-traces. In embodiments, near field illumination data may be stored as light ray-trace data. It may also be converted from a format that is not a light ray-trace data format into a light ray-trace data format for modeling. In an example, a near field data set that represents measures of light luminance proximal to a light source may include data for a range of locations in the light source's near field. The data may be configured as a set of planar area segments of the near field space, where each segment represents the near field effect of the light source at a given distance in a given direction from the light source. Data in this format, essentially may be represented as a three dimensionally indexed array of light measures, may be converted into light ray-trace data by, for example, selecting a ray that originates from a point on the surface of the light source and ordering the values found in a cell that the ray passes through in each of the area segments intersected along the path of the ray trace.

The modeled light emission set of ray-traces may represent light that travels from a light source disposed relative to the three-dimensional space and that travels through the three-dimensional space to an element in the three-dimensional space, such as a wall and the like. The modeling may further include reflections of the light off elements in the space. The reflections may be modeled based on a set of ray-traces and at least one reflection characteristic of the element in the three-dimensional space. In this way, if the surface is rough or matte, the reflection characteristic will result in a different effect of the light than would a shiny, smooth surface. The modeled ray-trace data (emissions and reflections) may be converted and/or captured as light volume data. Any data in the volume that may be missing may be interpolated based on, for example, nearby light ray-trace data values and/or nearby converted volume data values. The modeled data may then be processed to determine interactions among the ray-traces and reflections in the three-dimensional space. The interpolated data may be added to the volume data, the ray-tracing data, and the like so that the rendering facility may render the composite volume data, interpolated data, and interactions among the ray traces in the three-dimensional space.

In embodiments, modeling may account for light transparency, absorption, reflection, refraction, filtering, and the like of elements in the three-dimensional space. Modeling may further consider near field lighting artifacts, such as physical characteristics of the light source (e.g., a fixture shade, bulb orientation, stand, hanging chain, accessories such as snoots, barn-doors, cross hair baffles, cell louvers, screens, pattern templates, hoods, spread lenses, color lenses, and the like). Rendering may apply the modeled aspects, such as near field lighting artifacts, element features (e.g., transparency, and the like) to the three-dimensional space so that the impact of these modeled aspects may be realistically rendered in the electronic view of the space. Because the three-dimensional space may be a virtual space or a real space and may be presented as captured images or as live images, the near field volumetric rendering may be presented on a virtual reality display by, for example, interfacing with a virtual reality display controller, an augmented reality display controller and the like.

In embodiments, the light source may be made up of a plurality of distinct light elements, such as bulbs, and each light element may have a corresponding set of ray traces to be modeled. The data representing the near field of the light source may include data for each light element. Alternatively, a near field data set for each light element may be processed into one or more sets of ray-traces to be modeled. The near field volumetric rendering facility may render multiple sets of ray traces for the one or more light element so that interactions among the ray traces in each set may be considered and presented in the rendered display.

In embodiments modeling and/or rendering may account for distance-based light source intensity, so that, for example, a measure of light intensity (e.g., brightness and the like) may be greater for a position along the ray-trace that is closer to the light source than for a distal position along the ray trace. This distance-based light source intensity may be captured in the ray trace data and/or may be generated during modeling, rendering, and the like. In an example of distance-based light source intensity modeling and/or rendering, light source intensity fall-off over distance from the light source for each ray-trace in the set of ray-traces may be presented in the resulting rendered display of the three-dimensional space.

In embodiments, various techniques for capturing light emissions to be modeled may be employed. One exemplary technique includes disposing a surface at a plurality of positions with different distances from the light source along a ray-trace path and capturing at least luminance values of the light interacting with the surface at each of the disposed positions. The collected luminance values may, for example, be a set of two-dimensional values for each disposed surface position. The collected luminance values may be stored as two-dimensional image slices of a portion of a near field space of the lighting fixture, effectively resulting in a three-dimensional collection of near field data, where each two-dimensional image slice may be associated with a unique distance along the ray-trace from the light source so that each data value captured in each slice may represent a three-dimensional location in the near field of the light source. By repeating the disposing, capturing, and storing steps, a volumetric representation of the near field of the light source may be produced for modeling and rendering.

In embodiments, a method of electronic display rendering of a lighting distribution in a three-dimensional space may start with capturing a plurality of two-dimensional images of at least one of light source emissions and reflections of light originating from a light source disposed in an environment. The method may continue by storing a portion of the plurality of images in a digital data structure as light volume-data. The structure may be adapted to facilitate distinguishing among the light volume data in each of the plurality of images by a two-dimensional location in an image of the plurality of images and an effective distance of the image from the light source, essentially a third dimension. Light emissions and reflection for positions in this volume data that are not directly captured may be interpolated. The updated volume data, as well as any detected reflections (that may be included in the volume data) may be modeled as a set of light ray-traces that represent light traveling from a light source to an element in the three-dimensional space. Modeling reflections may be based on the set of ray-traces and at least one reflection characteristic of the element in the three-dimensional space. The modeled volume data, interpolated points, reflections, and interactions among the ray-traces may be rendered for display in an electronic display of the environment, which may be an arbitrary three-dimensional space.

In embodiments, modeling and/or rendering may account for light transparency, absorption, reflection, refraction, filtering, and the like of elements in the three-dimensional space. Modeling may further consider near field lighting artifacts, such as physical characteristics of the light source (e.g., a fixture shade, bulb orientation, stand, hanging chain, and the like). Rendering may apply the modeled aspects, such as near field lighting artifacts, element features (e.g., transparency, and the like) to the three-dimensional space so that the impact of these modeled aspects may be realistically rendered in the electronic view of the space. Because the three-dimensional space may be a virtual space or a real space and may be presented as captured images or as live images, the near field volumetric rendering may be presented on a virtual reality display by, for example, interfacing with a virtual reality display controller, an augmented reality display controller and the like. In embodiments, an experience with near field volumetric rendering may be enhanced through the use of a virtual reality controller, and the like.

In embodiments, the light source may be made up of a plurality of distinct light elements, such as bulbs, and each light element may have a corresponding set of ray traces to be modeled. The data representing the near field of the light source may include data for each light element. Alternatively, a near field data set for each light element may be processed into one or more sets of ray-traces to be modeled. The near field volumetric rendering facility may render multiple sets of ray traces for the one or more light element so that interactions among the ray traces in each set may be considered and presented in the rendered display.

In embodiments modeling and/or rendering may account for distance-based light source intensity, so that, for example, a measure of light intensity (e.g., brightness and the like) may be greater for a position along the ray-trace that is closer to the light source than for a distal position along the ray trace. This distance-based light source intensity may be captured in the ray trace data and/or may be generated during modeling, rendering, and the like. In an example of distance-based light source intensity modeling and/or rendering, light source intensity fall-off over distance from the light source for each ray-trace in the set of ray-traces may be presented in the resulting rendered display of the three-dimensional space.

Figure 43:
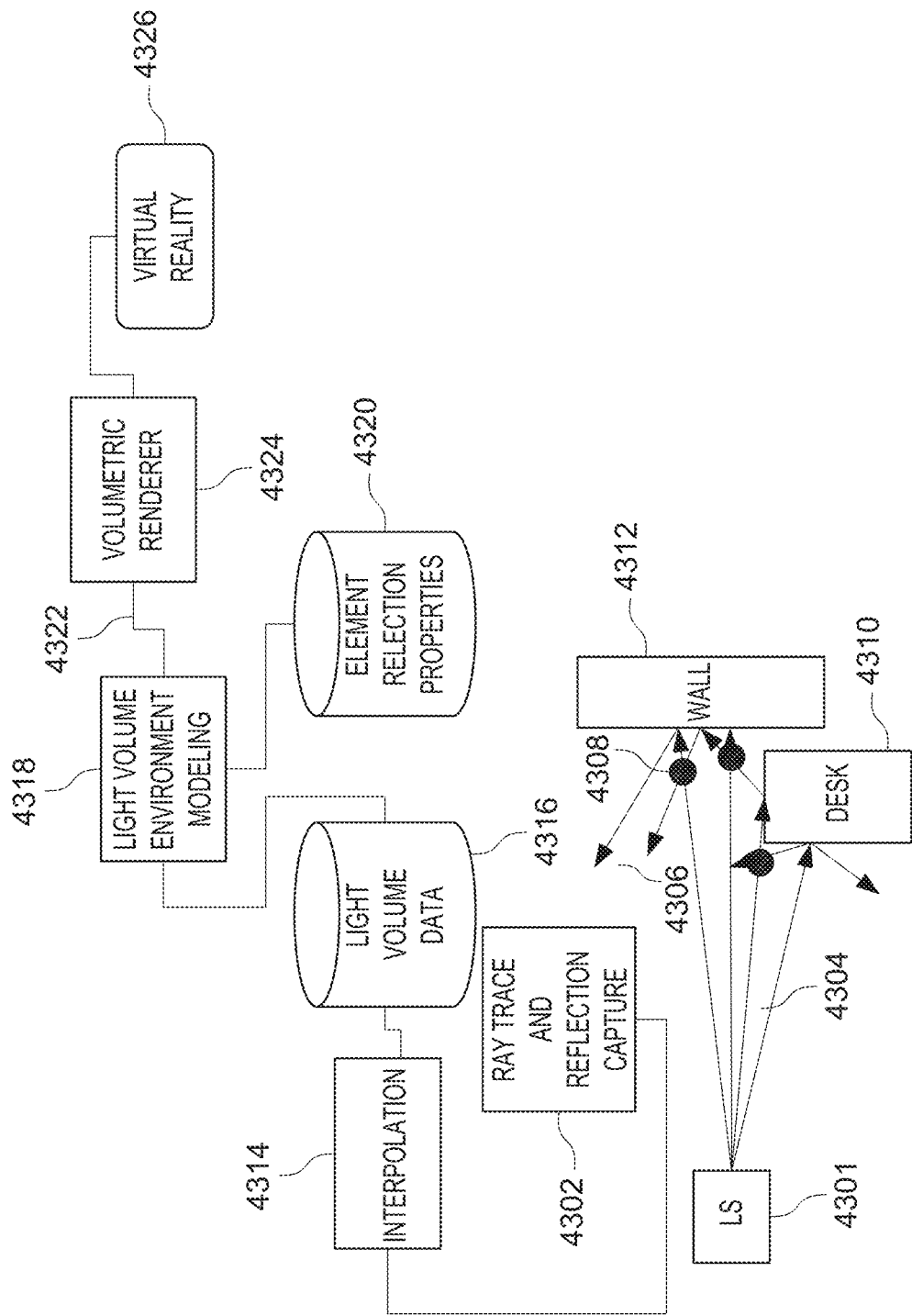
FIG. 43 is a diagrammatic view that depicts an embodiment of volumetric rendering in accordance with the embodiments of the present disclosure.

Referring to FIG. 43, an embodiment of volumetric rendering is depicted. Volumetric rendering, which may be described herein, may include capturing with an area array sensor 4302 ray traces 4304, reflections 4306, and interactions among ray traces and reflections 4308 for light being transmitted from a light source 4301 in an environment including features such as a desk 4310, wall 4312 and the like. The captured ray trace and reflection day may be processed to interpolate 4314 missing data. The captured and interpolated data may be stored in a storage facility for light volume data 4316 from which a light volume modeling facility 4318 applies the captured light volume data 4316 with element light interaction properties 4320 to produce ray trace data 4322 that a volumetric rendering facility 4324 turns into a visual representation of a space being illuminated by the light source 4301 and displayed in a virtual reality or the like display 4326.

Color: Legacy Control of Programmable Curves

In embodiments, lighting fixtures may be controllable for color and intensity independently, such as through separate control inputs. In embodiments, control inputs may be based on a voltage input range, where different values within the range map to different colors and intensities. It may be desirable to provide a control function for such lighting fixtures that can provide coordinated control of these separate inputs so that the impact of changing one (e.g., brightness via dimming, for example) on the other (e.g., color of a light will typically change due to the intensity of light being produced) can be mitigated or eliminated. Additionally, a control protocol, which may be a tuning profile or the like may be configured to emulate a legacy light bulb brightness versus color performance, such as an incandescent bulb, gas lamp, compact fluorescent and the like. A control input range, which may be a range of voltage placed on an input to the light element may be mapped over any range of color or brightness. In an example, a fixed range, such as over 10 volts, may be mapped in a first color curve to adjust color from 2000K to 2900K, whereas a second color curve may map the range of 10 volts to adjust color from 1700K to 4500K. In an example, an input voltage range for dimming a light in a specific scene may be mapped to a one-volt range (e.g., 2V-3V) and the like. This may limit the range of light intensity to a subset of the full range of control possible with the light. In embodiments, mapping a dimming range for a specific scene to 2V-3V may facilitate interfacing with devices that have limited voltage output capability. In this example, a control device that is limited to 3V maximum output could be used without limiting the desired degree of dimming. In each case, both the range of the curve and the individual points may be customized to provide a desired transition of color as input proceeds over the voltage range.

Through the use of different, customizable color curves, a range of light performance can be accomplished for color programmable lights. In embodiments, a color curve may be configured to support human biological rhythms, such a circadian rhythm and the like. A cool color curve may be configured at the start of a day to produce a range of cool color light to encourage wakefulness and activity. The same programmable light may be configured with a warm color curve that produces a range of warm colors in the evening to promote restfulness. By configuring a custom color curve for a programmable light, a legacy controller, such as a conventional dimmer, may be used while still enabling the desired output color type or effect. In embodiments, color curves may be configured to support non-visual light such as ultraviolet, special purpose light such as plant biologic, ultraviolet for sterilization, infrared for security, and the like.

In embodiments, enabling custom tuning, such as color and/or brightness of a lighting object may be performed by various methods including defining a custom tuning profile and, under control of a processor, controlling one or more lights to comply with the tuning profile. In an example of such custom tuning, the custom tuning profile may specify a color tuning profile, a dimming profile, a light distribution profile, and the like for a lighting object to be controlled. In the example, the processor may translate the custom tuning profile into a set of instructions, such as a range of voltages, for controlling the lighting object to behave per the profile. User input, such as through a dimmer, via voice input, and the like may be accepted by the processor and used as a guide to determine which portion of the tuning profile to follow. In embodiments, the custom tuning profile may be a dimming profile that specifies a set of points on a color temperature gamut that defines a dimming curve along which the light object will dim in response to a control input, such as a dimmer. In this way, adjusting a dimmer will cause a change in the color output of the light object, such as to achieve a desired color for a given light output. As noted above, the dimming profile may be specified to match a legacy or other known dimming profile of a type of lighting object, such as an incandescent light, a gas light, a halogen light, and many others. In embodiments, the custom tuning profile may be a color tuning profile that specifies a set of points on a color temperature gamut that defines a color curve along which the light object will adjust in response to a control input, such as a variable voltage control input. In this way, adjusting the voltage input will cause a change in the color output of the light object, such as to achieve a desired color for a given light output.

In embodiments, a user interface may be employed to facilitate a user defining a custom tuning profile. A user may specify a custom dimming profile by tracking curve on a brightness gamut. A user may, for example, specify a custom color tuning profile by tracking a curve on a color gamut. A user of the user interface may, for example, select an input value, such as a maximum or minimum input control voltage, and select a color from the gamut to apply to the selected control input voltage.

In embodiments, a library of stored profiles may be available to a user when configuring a custom tuning profile. A user may, such as through the user interface, select a stored profile from the library. Stored profiles may include at least one of a color quality profile, a circadian profile, a concentration profile, a relaxation profile, an efficacy profile, a security profile, and the like. The library may also be organized to profile custom tuning profiles that satisfy a performance requirement, such as energy savings, an aesthetic requirement, such as avoiding blue light, and the like.

In embodiments, lighting objects with independent brightness and color control variable voltage inputs may be configured to satisfy a preferred color performance by referencing a custom tuning profile, such as a color curve and assigning the color curve to a fixed voltage control input range for the color control input so that each incremental voltage value applied to the input will result in a color specified on the color curve by mapping the color curve to the fixed voltage range. In embodiments, the custom color curve may be a dimming profile that specifies a set of points on a color temperature gamut that defines a dimming curve along which the light source will dim, so that changes to a dimming control input will cause a coordinated color output from the light. The coordinated color output from the light may be a consistent color. To achieve this consistent color over a range of dimming control values, the color voltage control values may be adjusted accordingly. The dimming profile may be selected to match an existing light object, such as an incandescent bulb and the like.

In embodiments, the custom tuning profile may be a color tuning profile that specifies a set of points on a color temperature gamut that defines a color curve along which the light object will adjust in response to a control input, such as a variable voltage control input. In this way, adjusting the voltage input will cause a change in the color output of the light object, such as to achieve a desired color for a given light output.

In embodiments, a library of stored profiles may be available to a user when configuring a custom tuning profile. A user may, such as through the user interface, select a stored profile from the library. Stored profiles may include at least one of a color quality profile, a circadian profile, a concentration profile, a relaxation profile, an efficacy profile, a security profile, and the like. The library may also be organized to profile custom tuning profiles that satisfy a performance requirement, such as energy savings, an aesthetic requirement, such as avoiding blue light, and the like.

In embodiments, legacy control of programming profiles may be accomplished by a light source control system for a light with independent color and dimming control inputs may include a first output port that is operatively coupled to a color control input of a light source and a second output port that is operatively coupled to a dimming control input of the light source. The system may further include a processor sub system that accesses a light source tuning profile that characterizes a multi-dimensional lighting curve by mapping color output of the light source to brightness of the light source so that a change in the brightness input causes a coordinated change in the color input based on the curve. In embodiments, the processor controls both the first and second outputs based on information in the tuning profile, so that changing the brightness input results in the processor also changing the color input to adjust the color of the light based on the tuning profile. In an example of coordinated input control, controlling the dimming control input to reduce the brightness causes a coordinated change in color control input that results in a warmer color being output by the light. Similarly, increasing the brightness results in a cooler color being output by the light.

In embodiments, the tuning profile may map a plurality of target color and brightness output values to a corresponding plurality of two-dimensional voltage values, a first dimension controlling light color and a second dimension controlling brightness of the light source. The profile may map values in the first dimension to a color control input voltage range. The profile may map values in the second dimension to a brightness control input voltage range. The tuning profile may map target output color temperatures of the light source to values in the first and second dimensions so that controlling the color input and brightness input based on the first and second dimensions configures the light source to output a target color temperature based on the tuning profile color temperature mapping. A two-dimensional mapping of the tuning profile may facilitate maintaining a light output color as the light is dimmed by, for example, adjusting the light color input control voltage based on a change in the light dimming control input voltage.

In embodiments, the tuning profile may be indexed by at least one of biologic impacts and physiological impacts of light so that at least one of the light color and the light brightness is specified for a plurality of biologic impacts and physiological impacts. This may facilitate a user selecting a tuning profile that has a preferred biologic impact throughout a control range, such as if the user were to dim a light under control of this profile, the resulting color would comply with the preferred biologic impact.

Figure 44:
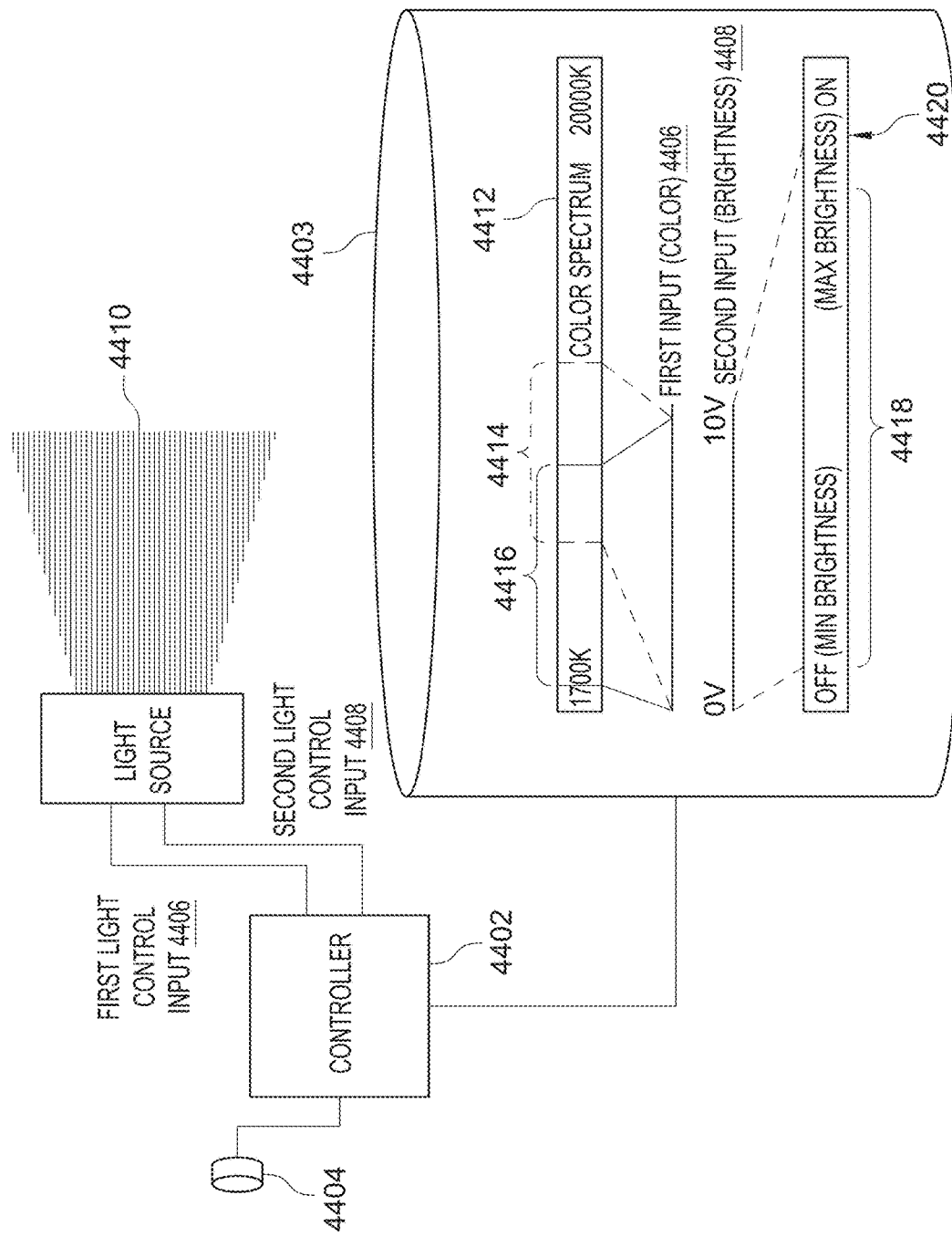
FIG. 44 is a diagrammatic view that depicts embodiments of legacy color programmable control in accordance with the embodiments of the present disclosure.

Referring to FIG. 44, an embodiment of legacy color programmable control is depicted. A light controller 4402 accesses a data set of custom tuning profiles 4403 and a user control 4404, such as a dimmer to control light emissions 4410 from a light source to provide legacy control of light color 4406 and brightness 4408 using a custom tuning profile. Light source control inputs for controlling, for example, light color 4406 and light brightness 4408 may be mapped via a custom tuning profile to adjust color and brightness of a light source over custom ranges. In the embodiment of FIG. 44, a first custom color tuning profile 4416 may map a portion of the entire color spectrum 4412 to the full input 4406 control range to adjust the color output from the light source from approximately 1700K to 6500K. A second custom color tuning profile 4414 may map the full input 4406 control range to adjust the color output from the light source from approximately 3300K to 10000K. Depending on the custom color tuning profile selected, the controller would be configured to control the light color output over the custom tuning range of color. Likewise, a custom dimming profile 4418 may map a portion of the entire brightness capability of the light 4410 to a custom subset that is slightly less than the full range. In this embodiment, adjusting the dimming dial 4420 through its full range would cause light output from the light source to range from nearly dark (but not fully off) to nearly maximum brightness (but not fully bright). In embodiments, either of the color tuning profiles 4414 and 4416 may be coordinated with the custom dimming profile 4418 so that an adjustment of the dimmer 4414 may cause a coordinated change in the color control input 4406 to, for example, substantially maintain the color output from the light source for a range of brightness values in the custom dimming profile 4418.

E: Main: Emotional Filter

In embodiments, emotional filters may be useful for lighting design. Filters that relate to stylistic, aesthetic, and perceptive aspects of lighting in an environment may provide value to a lighting design process. In embodiments, an exemplary technique for using emotional filters may include configuring, populating, maintaining, and using an emotional content data structure for emotional filter-related information about light sources, environments, and the like. Emotional content information about an environment may be captured from processing a live capture of the environment with an emotional filter feature capture facility. An emotional filter feature capture facility may also process a visual representation of an environment, such as a live stream, a set of one or more still images (e.g., photograph), a video of the environment, a text description of the environment, and the like.

In embodiments, using emotional filters in a lighting design process may include capturing stylistic, aesthetic, and other features from a visual representation of an environment, such as a room in a private home, an office, exterior space, and the like. Capturing features may include analyzing at least one of images, 3D models, renderings, and scans of the environment. The captured emotional filter-related features maybe populated in an installation-specific instance of an emotional content data structure that may provide structured access to emotional filter-related data suitable for use in lighting design. Populating may include storing at least one of cultural and geographical data associated with the environment in the installation-specific emotional content data structure. Over time, feedback about emotional aspects of installations, such as physical installations, virtual renderings of installations, and the like that may be characterized by an installation-specific emotional data structure may be captured. The feedback may be processed by machine learning algorithms to develop an understanding of factors that contribute to each of a plurality of emotional effects. The processed feedback may then be used to update portions of the installation-specific instance of the emotional data structure. Emotional content data structures for lighting fixtures used in the environment for which feedback is captured may also be updated based on the feedback. Feedback may include quantitative and qualitative data that may impact data items in the emotional content data structure for the environment and/or for the lighting fixtures, if any, deployed in the installation-specific instance.

In embodiments, using emotional filters in a design lighting process may include selecting at least one light source for the environment based on a similarity of a portion of an emotional content data structure for the light source with a corresponding portion of the installation-specific emotional content data structure.

In embodiments, the emotional content data structure may be configured to support objects, classes, and properties including lighting properties, such as distribution of light on lighting space objects, distribution of lights on surfaces, illumination values, color and color temperature of light sources, spectral content, fixture type, and the like. Lighting space objects may include any object in the environment, such as, without limitation desks, tables, appliances, drapery, walls, columns, doors, staircases, furniture, vehicles, toys, televisions, and the like. In embodiments, spectral content may include quality and intensity of light at certain spectral ranges. In embodiments, fixture type may include any of a wide range of fixture types including, without limitation modern, retro, industrial, romantic, suspended, embedded, and the like.

In embodiments, a lighting design system using emotional filters may include a display, such as a computer display, virtual reality display, augmented reality display, 3D display and the like for presenting a visual representation of an environment. The visual representation may include a photograph, live stream, video, and the like and may be analyzed by a feature capture facility adapted to capture stylistic and aesthetic features of the environment from the visual representation. The feature capture facility may be adapted to capture stylistic and aesthetic features by analyzing at least one of images, 3D models, renderings, and scans of the environment. The system may also include an installation-specific emotional content data structure that is accessible to a processor into which the captured features are populated. The system may employ machine learning algorithms executing on a processor to receive user feedback about emotional and/or aesthetic aspects of an installation characterized by the installation-specific emotional content data structure, thereby generating an understanding of factors that contribute to each of a plurality of emotional effects. This feedback may be used to update at least a portion of the emotional content data structure of the environment and/or of lighting sources deployed in the environment.

In embodiments, the system may include a light source selection facility that may facilitate identifying at least a candidate set of light sources (e.g., fixtures, and the like) for satisfying emotional features of the environment based on similarity of a portion of an emotional content data structure for light sources with a corresponding portion of the installation-specific emotional content data structure. The emotional data structure may support storage of cultural and/or geographical data. Such data associated with the environment may be stored in the installation-specific emotional content data structure. In embodiments, the emotional content data structure may support, without limitation objects, classes, and properties including lighting properties selected from a group consisting of distribution of light on lighting space objects, distribution of lights on surfaces, illumination values, color and color temperature of light sources, spectral content, fixture type, and the like. Examples of lighting space objects include, without limitation desks, tables, appliances, drapery, walls, columns, doors, staircases, furniture, vehicles, toys, televisions, and the like. In embodiments, spectral content may include quality and intensity of light at certain spectral ranges. In embodiments, fixture type may include any of a wide range of fixture types including, without limitation modern, retro, industrial, romantic, suspended, embedded, and the like.

In embodiments, a system for emotional filter-based lighting design may further include a library of light source emotional content data structures that describe stylistic and aesthetic features of a plurality of light sources. The system may also include a light source selection facility that compares at least one portion of emotional content data structures in the library with a corresponding at least one portion of an installation-specific emotional content data structure thereby generating a set of candidate light sources for satisfying at least one of aesthetic and stylistic aspects of the environment. In embodiments, information descriptive of the aesthetic and/or stylistic aspects of the set of candidate light sources may be displayed on an electronic display to enable comparison with each other and with aesthetic and/or stylistic aspects of the environment.

Near Field: Hardware—Manifestations of the Hardware

In embodiments, capturing light from a light source may be used to characterize a near field illumination of the light. Near field illumination capture may be performed with equipment that enables locating a light source, and at least an illumination-sensitive sensor (e.g., a camera and cover screen combination and the like) at a plurality of known locations and orientations relative to each other. A goal of capturing near field illumination is to capture the illumination at a wide range of locations, including different distances, longitudinal and latitudinal positions, and the like in the near field of the light. A near field characterization system may include a light positioning device, a light filtering device, a light capture device, and a processing system for processing and storing the captured light data so that it can be used in algorithms that help characterize near field illumination effects of the light source. In embodiments, a near field characterization system may include a light source positioning support that may be adapted to hold a light source (e.g., a light fixture and the like) disposed in one of a plurality of orientations to facilitate distributing light in the near field at least to other elements of the system. The system may also include an intermediate screen that may be disposed at one of a plurality of intermediate positions (e.g., between a light source and a light sensor array) in the near field. The screen may be disposed so that a first side receives the distributed light. The screen may be constructed to transfer a portion of the received light to a second side that may be substantially parallel to the first side (e.g., the intermediate screen may be at least two-sided and at least partially translucent). The system may include a two-dimensional array illumination sensor that may be disposed, such as in the near field, to capture an image of the screen, preferably the second side of the screen. The captured illumination image may include data values representing illumination captured at each of a plurality of sensing elements distributed substantially uniformly across the two-dimensional array. Each of the plurality of sensing elements may be queried to provide a digital representation of the captured illumination. The system may also include a processor that may be adapted to control the illumination sensor and store the captured illumination data value and the location (x and y) within the array. The x and y location may correspond to a pixel or other type of individual sensing element in the array. In embodiments, there may be "x times y" sensing elements in the array. The system may further include a data storage facility that works with the processor to facilitate storing the data value and a corresponding array position for a plurality of image sensing positions in the array. Additionally, the data storage facility may store information descriptive of the data value, such as its relative location in the array (x and y value), position of the array, orientation of the array, distance of the array relative to the screen and/or to the light source, an index that identifies the data value and all other data values in the array as an image group, a date/time stamp of capturing the data, ambient light conditions, whether an enclosure was employed, and the like. In embodiments, control of the illumination sensor may include resetting the sensor, such as between capture events, accessing the data stored in the individual elements of the sensor, adjusting an exposure mode of the sensor, configuring the sensor, such as for adjusting for ambient light, and the like, positioning the sensor, rotating the sensor, changing an orientation of the sensor, and the like. In embodiments, the two-dimensional array illumination sensor may be a digital camera sensor, such as a digital camera feature of a smartphone and the like. In embodiments, the intermediate screen may be translucent so that light impacting the first side is visible on the second side. In embodiments, the intermediate screen may be patterned so that a pattern of the light impacting the first side is visible on the second side. In embodiments, the intermediate screen may be an active screen, such as an LCD screen and the like that can be adjusted by a processor to cause a controlled amount of light to pass from the first side to the second side.

In embodiments, the system may include a positioning system of the light source, the intermediate screen, or the sensor array that may, under processor control configure these three elements into a plurality of different relative orientations. In embodiments, a processor controlled light source positioning system may facilitate fixing the position of the screen while adjusting the distance of the light source from the screen, and a position of the light source in any longitudinal and latitudinal position (e.g., any spherical position), including rotation and translation. Likewise, a processor controlled intermediate screen positioning system may vary the distance and spherical position of the screen relative to the light source. Additionally, a processor controlled illumination sensing array positioning system may vary the distance and spherical position of the screen relative to the light source. In embodiments, the intermediate screen may be optional so that only the light source and sensor array positions would need to be controlled.

In embodiments, a near field light source characterization system may include an enclosure that mitigates an impact of ambient light, or other light sources, on the intermediate screen and the area array illumination sensor.

In embodiments, a near-field light source measurement and characterization system may include a processor controlled light source positioning support adapted to hold a light source disposed to distribute light in a plurality of orientations. The processor may control the rotation of the light source about a longitudinal axis of the support. The processor may control the rotation of the light source about a latitudinal axis of the support. The processor may control translation of the light source in any of three directions. The near-field light source measurement and characterization system may include a two-sided intermediate screen that has a first side and a substantially parallel second side. In an exemplary deployment of the system, the intermediate screen may be positioned relative to the light source to receive the distributed light on the first side and it may be constructed to transfer a portion of the received light to the second side, such as by passive means, such as being translucent and the like. The near-field light source measurement and characterization system may also include an area array illumination sensor disposed relative to the screen to capture light emissions from the second side of the intermediate screen. The near-field light source measurement and characterization system may also include a controller that may be adapted to control the illumination sensor and store the data value, the array location of the corresponding image sensing position, and information descriptive of the sensing event in a data storage facility. The near-field light source measurement and characterization system may further include a housing that mitigates the impact of ambient light on the elements of the system so that ambient light can be ignored when determining a characterization of the near field illumination of the light source. In embodiments, the housing may extend from the second side of the intermediate screen to the array sensor. In embodiments, the housing may enclose the light source, the intermediate screen and the area array sensor. In embodiments, the housing may be configured to conditionally eliminate ambient light from reaching the enclosed system elements, such as through the use of a door, adjustable screen or shade, active housing elements, such as LCD-based enclosure segments, and the like.

In embodiments, the near-field light source measurement and characterization system may further include a spectrometer disposed relative to the intermediate screen to capture the spectral content of light proximal to the intermediate screen. When the spectrometer is disposed between the light source and the screen, spectral content of light being distributed by the light source may directly be captured by the spectrometer. When the spectrometer is disposed between the screen and the area array sensor, spectral content of light passing through the intermediate screen may be captured by the spectrometer. In embodiments, the spectrometer may be moved between these positions to capture spectral content on both sides of the intermediate screen to facilitate analysis of the spectral filtering impact of the screen, and the like.

In embodiments, operating the near-field light source measurement and characterization system to capture near field data may include repeatedly adjusting the position of at least one of the screen and/or the area array sensor relative to the light source while capturing illumination data at each adjusted position until enough data is captured to enable characterization of at least a portion of the near field of the light source. The increment of adjustment may be based on factors, such as the size of the light source, the size of the array sensor, the optical properties of the array sensor, a specified degree of resolution of the near field data, and the like.

In embodiments, characterization of the near field of the light source by the near-field light source measurement and characterization system may include calculating an effective distance between the light source and the area array. Such an effective distance may be calculated as a logarithm of the physical distance. In embodiments, effective distance values may be applied to functions that determine, for example, a fall-off of luminance for a range of effective distances.

In embodiments, successive captures of illumination may be performed with varying relative orientations, positions, and distances of the lighting source and the near field illumination capture elements (e.g., the intermediate screen and/or the array sensor, and the like). The variations for any of position, orientation, distance, and the like between captures may be non-linear, such as logarithmic and the like. In embodiments, an increment of any of the relative position, orientation, distance, and the like may be determined for each successive capture. In embodiments, the increment may be determined based on an entropy or an amount of information captured in a prior capture event, such as the immediately prior event, a capture event earlier than the immediately prior event, a calculation of multiple prior capture events (e.g., an average of two or more capture events), and the like. Therefore, for any given pair of increments between successive captures, the pair of increments may be linear or non-linear based on the increment determination.

In embodiments, the intermediate screen and the area array sensor may be integrated so that movement of either causes a corresponding movement of the other. In embodiments, the screen may be an attachment to a smartphone camera feature so that for any orientation of the smartphone, the relationship between the screen and the camera remains unchanged. In embodiments, the screen may be a universal smartphone camera feature attachment that can be adapted by a user to conform to a range of smartphone enclosures. Such a screen adapter may be configured to eliminate ambient light from the region between the screen and the smartphone camera feature.

Near Field: Software—Reconstructive Algorithms—Iterative or Otherwise

In embodiments, characterizing a near field illumination generated by a light source, such as a light fixture and the like, may be performed with one or more light sensing devices disposed proximal to the light source and a set of reconstructive algorithm(s) that can take the information from the one or more light sensing devices, such as a multi-dimensional (e.g., two-dimensional) set of image sensors (e.g., an array of image sensors, one or more cell phone cameras, and the like) and produce a three-dimensional data set of values that represent the illumination produced by the light source at a plurality of locations (e.g., distances and directions from the light source) in the near field of the light source. Reconstructive algorithms may work, for example, on a collection of two-dimensional data points, such as a set of images that capture the illumination at multiple locations (e.g., image planes) within a volume proximal to the light source. Reconstructive algorithms may also operate iteratively, constructing and updating a three-dimensional near-field data set for a light source as additional data (e.g., from two-dimensional planar images) is made available. In embodiments, while the data may be termed two-dimensional or three-dimensional, these dimensions merely refer to the location within the near-field at which illumination data from the light source is collected (i.e., distances and directions in a coordinate system). The data values themselves may be multidimensional, including aspects such as color, intensity (e.g., brightness), color temperature, saturation, and the like, including any of the characteristics attributed to light sources, lighting objects, and the like as described throughout this disclosure.

In embodiments, an exemplary method for characterizing a near field illumination effect of a light source by applying a reconstructive algorithm to a collection of two-dimensional illumination data sets (e.g., two-dimensional images) may include iteratively capturing the illumination data with, for example, a two-dimensional array image sensor so that each of the image sensor elements in the array captures at least one aspect of illumination, such as intensity, brightness, color, color temperature, saturation, and the like. Each image iteratively captured may be differentiated by at least one of a distance from and a relative position (e.g., direction) of the two-dimensional sensor array relative to the light source. Information that facilitates determining position, and orientation, such as longitude and latitude relative to the light source for each two-dimensional image, or a distance and angle in polar coordinates, may be used by the reconstructive algorithm to produce a data set that represents the illumination of the light source at a set of points within a volume. In embodiments, a reconstruction algorithm may generate a data set that links one or more values in one or more two-dimensional images with one or more other values in one or more two-dimensional images to facilitate processing the resulting volume data (e.g., as ray-trace data and the like). In embodiments, the resulting volume data set output by the reconstructive algorithm may include a multi-dimensional representation of the near-field illumination of the light source. The dimensions may include a first dimension of the two-dimensional array, a second dimension of the two-dimensional array (e.g., x and y values of the array), a theta component of the illumination value, a phi component of the illumination value at each x/y location, a value representing the distance from the light source, a longitude value and a latitude value, and the like.

In embodiments, a reconstructive algorithm may determine a relative contribution of each point source of a light source (e.g., each individual bulb, lens, and the like) such as on a surface of a light fixture to each location in the volume of near field data. Reconstructive algorithms, and the like, for producing a multi-dimensional near field data set that may include methods such as Kaczmarz, numerical, machine learning, neural networks, linear algebra and the like. In embodiments, data captured and used to generate a multi-dimensional near field data set of a light source may result in a high-fidelity model of the light source. In embodiments, a reconstructive algorithm may make use of, or be used to facilitate generation of, a model of the illumination pattern from a light source, such as where a model recognizes the presence of two (or more) point sources (e.g., a pair of bulbs or LEDs) in a lighting fixture that produce different lighting effects in different directions from the lighting fixture by virtue of variations in the mixing/interference of the light from the point sources at different angles from the lighting fixture. A model, such as a ray trace model, may be constructed by which the presence of different light sources within a lighting fixture may be understood and based which values of illumination may be interpolated for locations within a three-dimensional space around a lighting fixture for which measured data does not yet exist. Such a model may be iteratively updated, such as using machine learning techniques, as additional data is acquired, such as using the image sensor sets described herein. A collection of such models may be generated and stored by the system, such as to allow recognition of common patterns, such as pairs of bulbs, triplets, and the like, thereby allowing generation of three-dimensional representations of the illumination around a light source that represents a combination of measured data from image sensor sets (e.g., two-dimensional arrays) and data that is estimated, such as by interpolation, from a model.

In embodiments, a relative position of a light source, a sensor array and other elements used to capture near field illumination data may be controlled by a processor. Aspects such as distance, orientation, location in three dimensions, exposure time, and the like may be controlled. When an intermediate screen is used to facilitate indirect illumination capture, the reconstructive algorithms may process light pattern data that is visible on a side of the screen opposite the light source.

In embodiments, incrementally reconstructing a near field illumination effect of a light source may use reconstructive algorithms as described herein adapted to incrementally develop a three-dimensional (e.g., volume-based) set of data for a three-dimensional region proximal to the light source. Such an approach may include capturing a first two-dimensional image with an image sensor disposed at a first location relative to the light source. Upon capturing a second image at a second location (e.g., a further distance from the light source) the reconstructive algorithm may process the two images with their position data to produce a three-dimensional data set of the near field illumination of the light source. As successive two-dimensional images are captured, the reconstructive algorithm may incrementally enlarge the three-dimensional data set based on the position of the newly captured image. This process can be repeated for a full range of distances, longitudes, latitudes and the like throughout any portion of the spherical volume proximal to the light source. In embodiments, the captured data values may include luminance values for theta and phi as well as data values representing brightness, color, and the like. In embodiments, producing a three-dimensional space data set of near field illumination may include processing two-dimensional images captured at a plurality of distances for a given longitude and latitude, images captured at a given distance and longitude but with incrementally adjusted latitudes, images captured at a given distance and latitude but with incrementally adjusted longitudes, and the like. Examples referencing longitudes and latitudes should be understood to encompass similar concepts of distance and direction as expressed in other coordinate systems, such as X-Y coordinates, polar coordinates, and the like. Similarly, various mathematical/geometric transformations from point data collected in one coordinate system (e.g., a two-dimensional image sensor) to volumetric data in another coordinate system (e.g., polar coordinate data for a volume around a light source) should be understood to be encompassed herein. Other combinations of distance, longitude and latitude may be incrementally captured and processed.

In embodiments, reconstructive algorithms may process data captured by various devices including without limitation an indirect luminance collection device that includes a smartphone camera adapted to capture illumination from the light source indirectly. In such embodiments, the smartphone may be adapted with a screen or filter, such as attached to the smartphone over the smartphone camera or disposed to reflect light to the smartphone camera, so that light from the light source impacts the smartphone camera indirectly. Other arrangements involving indirect illumination (such as by a pass-through filter or a reflective screen) are encompassed herein, including ones that use various types of image sensors, including CMOS sensors.

Figure 45:
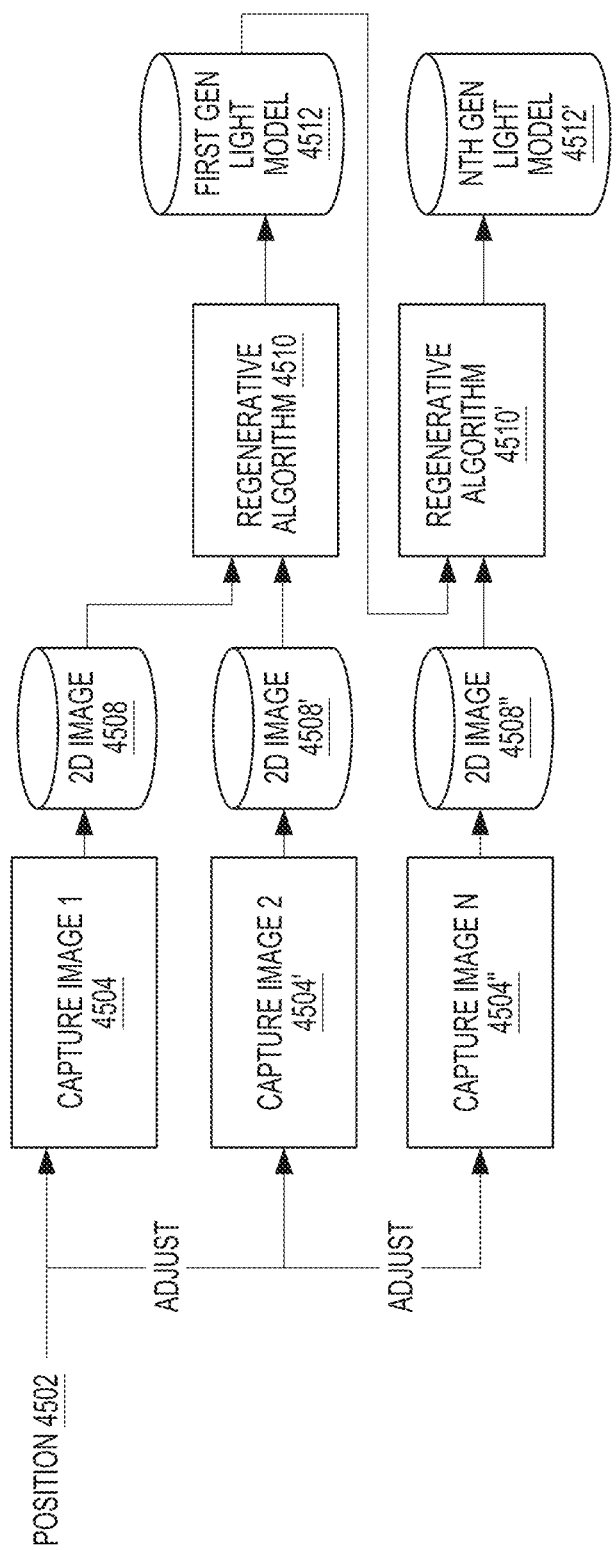
FIG. 45 is a diagrammatic view that includes a flow diagram that depicts incremental light model generation using an iterative image capture and regenerative algorithm in accordance with the embodiments of the present disclosure.

Referring to FIG. 45, a flow diagram depicting incremental light model generation using an iterative image capture and regenerative algorithm as described herein. An initial position 4502 of a luminance sensor is used in an image capture process 4504 that captures, such as through an indirect near field data collection process described herein an initial 2D image 4508 of luminance from a light source. The initial position 4502 is adjusted, a second image capture process 4504' is performed and a second image 4508' is captured. The two captured images 4508 and 4508' are processed by a regenerative near field lighting model algorithm 4510 that produces, for example a first-generation light model 4512, such as a near field characterization model of the light source. Successive adjustments to position and/or orientation are made along with captures of corresponding 2D images (e.g., 2D Image 4508" and the like). The regenerative algorithm 4510' is applied for each acquired image to produce successively richer lighting models, ultimately producing a model that is configured to emulate a portion of a near field luminance volume space of the light source after the final image 4504" is captured and processed.

Figure 46:
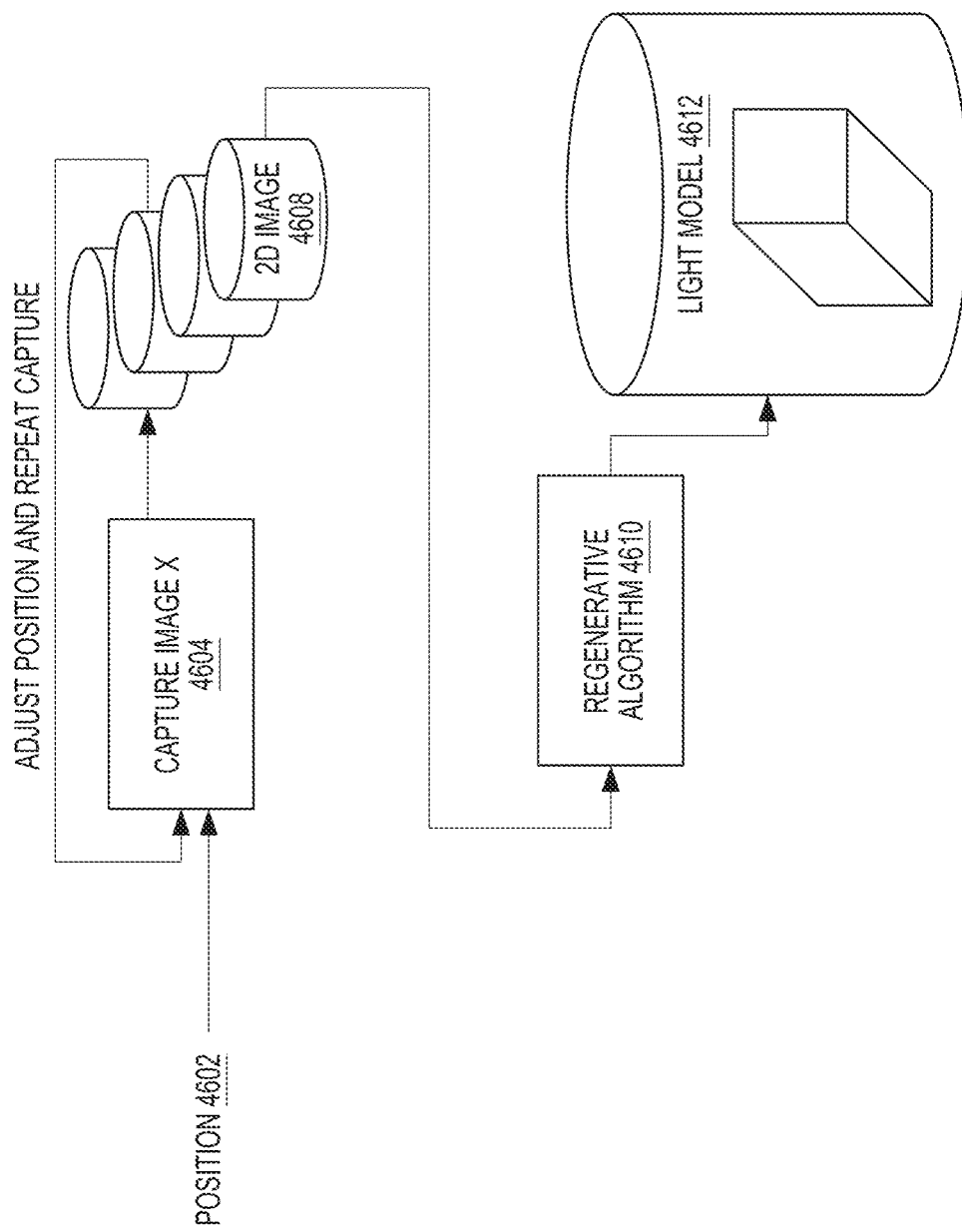
FIG. 46 is a diagrammatic view that includes a flow diagram that depicts incremental image capture and aggregated image processing by a regenerative algorithm that produces a near field volume luminance model of a light source in accordance with the embodiments of the present disclosure.

Referring to FIG. 46, a flow diagram depicting incremental image capture and aggregated image processing by a regenerative algorithm that produces a near field volume luminance model of a light source. An initial position and/or orientation of a luminance capture device, such as an indirect luminance capture device described herein, relative to the light source is used to facilitate capturing, storing, and tracking near field data captured by the device. The sequence of adjusting a position/orientation and image capture is repeated, resulting in a plurality of images, typically 2D images with location and orientation information for each image being stored in a near field data set. The collection of 2D images may be accessed by a regenerative algorithm 4610 that processes the image data and location data to generate a light model of the light source 4612

Lighting Distributions: Match to Desired Effect

In embodiments, users may indicate a desired lighting effect in a portion of a room or the like, such as through a real-time augmented reality user interface. A user may want light of a color or range of colors with a range of intensities to illuminate a space, such as a wall, ceiling, hallway, piece of art, and the like. A lighting designer may utilize lighting effect user interface to capture the user's preferences in a structured set of values, such as light color range, light (e.g., lumens and the like) intensity, light direction, distance and the like. In embodiments, a data structure representative of the desired lighting effect, which may alternatively be referred to herein for convenience as a "bloom effect," may be captured from the structured set of values or indicated by a user viewing and selecting among virtual emulations of lighting effects. In embodiments, a designer or the like may attempt to find a light source (e.g., fixture) that can produce the desired lighting effect while meeting other criteria such as size, location, cost and the like.

In embodiments, a system that facilitates determining characteristics and values thereof of light sources that produce the desired lighting effect may process the structure data that is descriptive of the desired bloom effect as noted above to generate one or more light source characteristics that are indicative of a light source that may produce the desired effect. In embodiments, machine learning may be used to improve on matching light source characteristics with desired bloom effects. A matching algorithm may be employed that matches the light source characteristics to a library of light sources that may facilitate identifying light sources based on certain characteristics and one or more values for those characteristics. In embodiments, a light source characteristic may be a color range, such as a warm color range, and a value for such a range may be a subset of warm color values. Therefore, a matching system may first detect light sources that produce warm colors. This subset may be further analyzed to match lights that produce the desired subset of warm color value. In embodiments, light source characteristics may include shape characteristics, such as shapes of or within the pattern of illumination and shadow produced by a light source, and a value may include a name for the pattern (e.g., a "butterfly" shape) or values (e.g., geometric data) that represent the shape of the pattern (e.g., a circle, a cone, a triangle, a square, etc. having one or more stated dimensions). Shape characteristics may be measured and stored for different distances from a light source and for different surfaces upon which illumination is cast. For example, a fixture may cast a butterfly shape at three feet from the light source on a planar surface that faces the light source, but the fixture may cast an even, or "unshaped," illumination pattern further away, as directional effects from individual bulbs diminish farther away from the fixture. Additional attributes, such as cost, size, and the like may be included in a light source characteristic search (e.g., lights costing greater than $X may be excluded from further assessment as candidate light fixtures). A user may view and select among the candidate light sources in a user interface. In embodiments, matching a light source to a bloom effect may be based on similarity of values of the identified characteristics with values of corresponding characteristics of light fixtures. In this way, lights that may not exactly match a specific color value or a specific shape of illumination may be classified as candidate light fixtures for further review by a human, such as the user and the like. To facilitate differentiation among light sources, some characteristics may be weighted more heavily than others. In an example, a color output by a light may be weighted more heavily than a cost for lights so that a user may be presented with lights whose cost is outside of a cost range characteristic. A user interface may be configured to allow a user to determine the weighting of characteristics as a degree of compliance by the light sources with the characteristics of the desired bloom effect.

In embodiments, a bloom effect data structure may include information that facilitates determining a desired effect of the bloom (e.g., illuminating a walkway), an aesthetic filter effect of the bloom (e.g., washing along a wall), an emotional filter effect (e.g., developing a welcoming and friendly atmosphere), and the like. This information may be coded, such as on a scale for an emotional filter from friendly to business-like.

In embodiments, a user interface of a system that facilitates matching light sources to a desired bloom effect may facilitate visual comparison of the desired lighting bloom effect and a bloom effect of at least one light source. In embodiments, the user interface may facilitate presenting the desired lighting bloom effect and a bloom effect of at least one light source in an environment, such as in a virtual reality rendering of a bloom effect of a light source on an image of a specific environment (e.g., the user's hallway). The user interface may also facilitate a user scrolling through a library of light fixtures by viewing their bloom effects. In embodiments, the presentation may include a live view of an environment that the user interface processed through an augmented reality rendering system to present either the desired lighting bloom effect or a bloom effect of a light source. In embodiments, a user may specify a bloom effect region within an environment, such as a wall, floor, or other substantially planar surfaces.

In embodiments, light source selection may be based on matching desired bloom effects to light source bloom data in a library of light sources. Light source bloom data in a library may include characteristics that may be like those determined for a desired bloom effect, such as aesthetic filter effects, emotional filter effects, and the like. A bloom matching system may seek bloom effects in the library that have comparable characteristics and values thereof. By searching for comparable bloom effects, a set of candidate light fixtures, specifically those fixtures that produce the bloom effects that are most similar to the desired bloom effect may be identified and presented to the user. The user may be presented the desired bloom effect and candidate bloom effects side-by-side to facilitate visual comparison. Once a candidate set of light fixtures is determined based on the bloom effect matching, other factors such as cost, size, and the like may be used to further filter the candidate set. In embodiments, a single light fixture may produce multiple different bloom effects, such as due to use of different light bulbs. Therefore, by searching based on bloom effect rather than fixture characteristics, fixtures that have light-bulb dependent bloom effects may be detected.

In embodiments, to facilitate, for example, searching through a library of light fixtures based on a desired light bloom effect, light bloom effects for light fixtures need to be accessible. This may be accomplished by capturing light data from many different light fixture installations, including virtual installations that may be generated by a human user and/or through automated machine learning-based approaches, such as artificial intelligence and classifying the installations (including, the light fixtures, bulbs being used and the like) according to one or more lighting effects created by the light fixtures in the installations. The captured light data and the classification may be stored in a light fixture library as properties of the lighting object used in each installation. When searching for lighting effects that contain certain properties, these captured light effects may be searched directly for the properties. In embodiments, classifying the lighting effects may be based on a measurable effect on a group or an individual, such as a productivity effect, a health effect and the like. In embodiments, classification may be done by an expert system, an artificial intelligence system and the like. In embodiments, training for an artificial intelligence system may be based on a training set of lighting effects created by, for example, humans classifying lighting installations.

Figure 47:
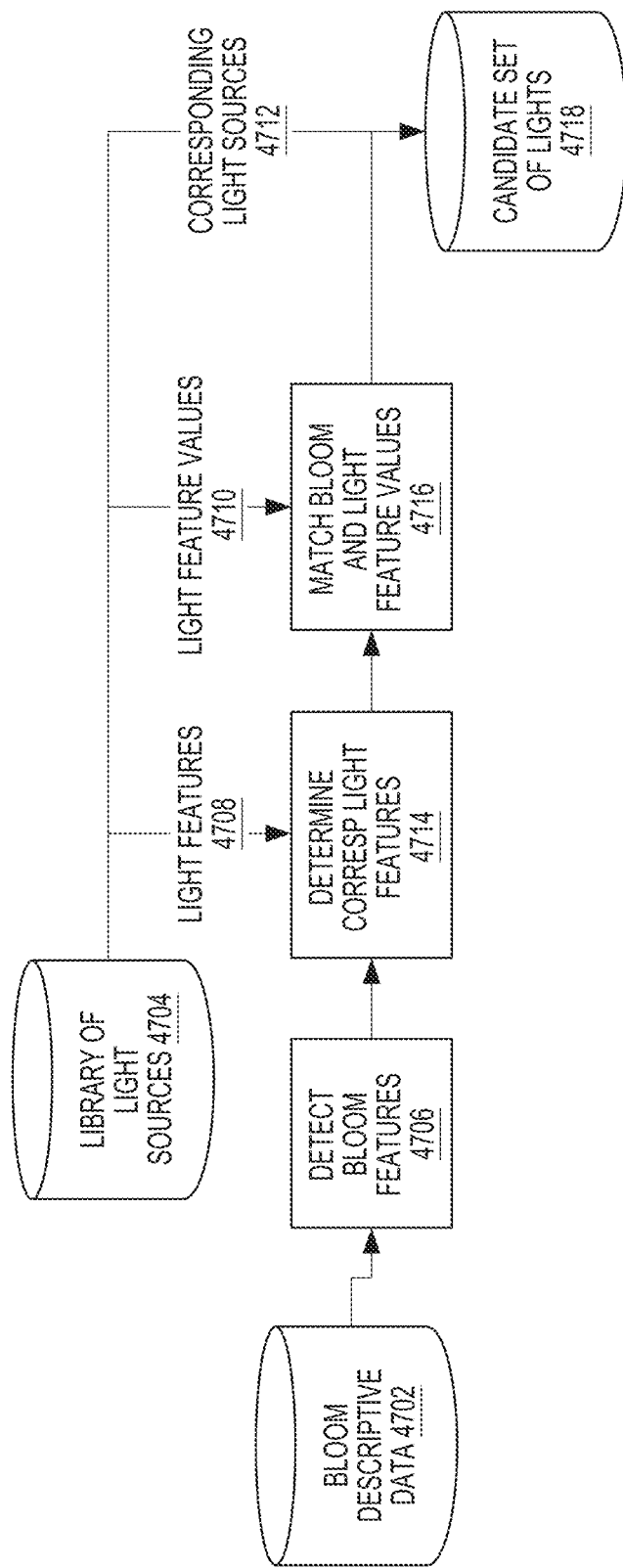
FIG. 47 is a diagrammatic view that includes a flow diagram that depicts generating a candidate set of light sources based on attributes of a desired bloom effect being compared to light source features in accordance with the embodiments of the present disclosure.

In embodiments, a user's intent in selecting a light bloom effect (e.g., establish a warm setting in a space) may be mapped to light fixture controls in play when the user expresses his intent. In this way, the light fixture controls that produce the user intent may be applied to one or more light sources in other spaces. User feedback from experiencing these other spaces may be applied to a machine learning function that facilitates developing an understanding of a relationship between user reactions of the controlled light sources in the other spaces with the user's intent. The understanding may be useful in refining the process of converting a user's intent to lighting fixture controls, such as by adjusting a data set that facilitates mapping a user's intent to lighting controls. Referring to FIG. 47, a flow diagram is depicted for generating a candidate set of light sources based on attributes of a desired bloom effect being compared to light source features. A bloom effect description 4702, such as a data set of bloom luminance values and the like, may be retrieved by a processor that analyzes the data set to detect features of the bloom 4706 that might align with light source features 4708, such as color, spread of light, intensity, and the like. The processor may access a library of light sources 4704 to retrieve light features 4708 for a plurality of lights and compare them in a comparison step 4714 to the bloom features detected. Values 4710 for the light features that match with the detected bloom features may be retrieved from the library 4704 and compared to values for the detected bloom features for the bloom 4702. Values that sufficiently match may indicate candidate light sources 4712 for producing the desired bloom 4702. A set of candidate light sources 4718 may be produced for use in a user interface to view a comparison of the desired bloom effect and bloom effects from the candidate lights.

Figure 48:
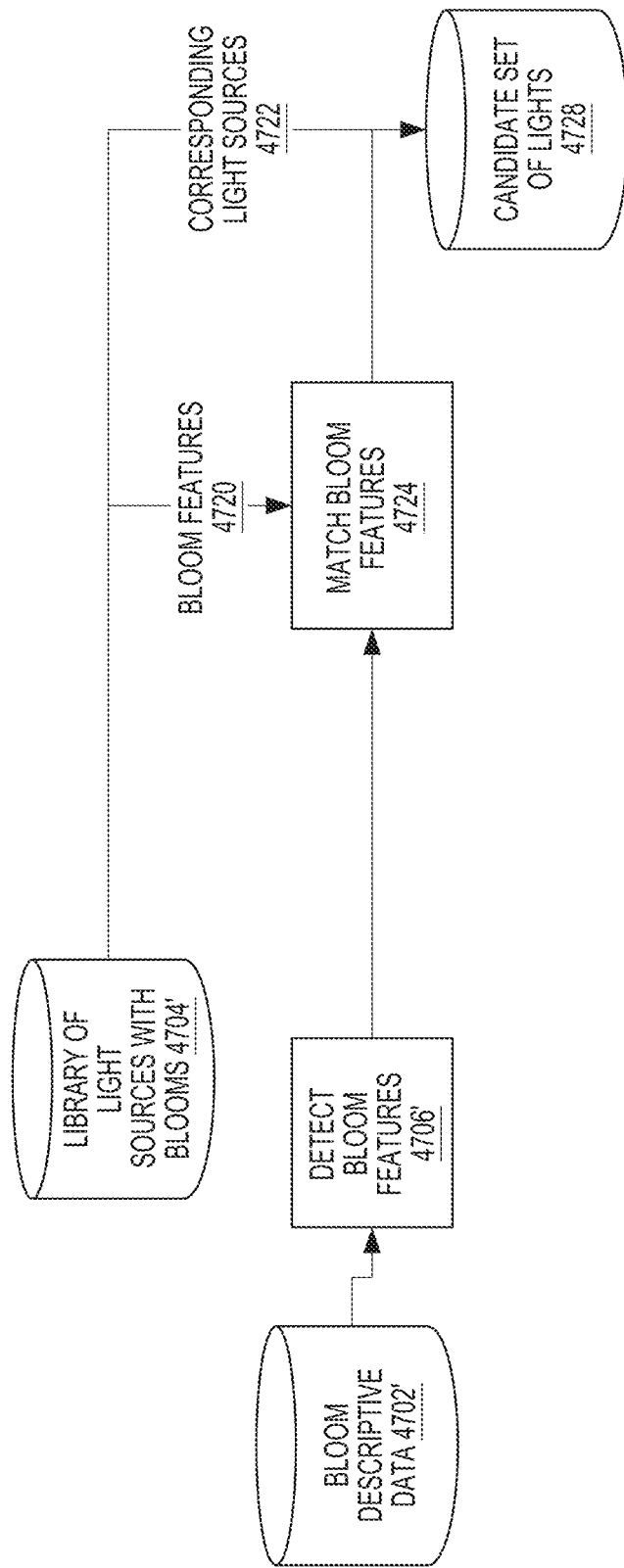
FIG. 48 is a diagrammatic view that includes a flow diagram that depicts generating a candidate set of light sources based on a comparison of a desired bloom effect to light bloom effects stored in a library of light sources in accordance with the embodiments of the present disclosure.

Referring to FIG. 48, a flow diagram is depicted for generating a candidate set of light sources based on a comparison of a desired bloom effect to light bloom effects stored in a library of light sources. A bloom effect description 4702', such as a data set of bloom luminance values and the like, may be retrieved by a processor that analyzes the data set to detect features of the bloom 4706', such as color, spread of light, intensity, and the like. A library of light sources with bloom effects 4704' may be accessed by the processor to match bloom features 4720 for light sources in the library with the detected bloom features 4706'. Matches may be used to identify corresponding light sources 4722 for the matching blooms. The candidate light sources 4722 may be saved as a set of candidate lights 4728 for use in a user interface to view a comparison of the desired bloom effect and bloom effects from the candidate lights.

Near Field: Metrics

In embodiments, methods and systems for capturing illumination in a near field for light sources and generating data sets that represent near field illumination are described herein. Processing near field illumination data may yield metrics that may be beneficial for various light matching, selection, and modeling methods and systems described herein. Generating metrics of near field illumination data may involve pattern matching, artifact detection, light quality rating, brightness classification, color classification, spectral characterization, and the like.

In embodiments, metrics associated with patterns and/or artifacts may be generated by counting occurrences thereof, determining size and or scale of artifacts and patterns, and aggregating measures related to the artifacts and patterns, such as size of patterns or artifacts, scale of patterns or artifacts, occurrences of patterns or artifacts and the like. In embodiments, pattern detection, artifact detection and the like may be performed through processing near field data, such as images, off-axis slices through a near field volume data, and the like with image analysis algorithms that employ feature detection techniques and the like. A pattern may be detected through proximity detection techniques that may be triggered off a detected artifact, such as a localized substantive change in intensity, and the like. Nearby data values in a near field volume data set may be evaluated for the presence of and/or continuation of a similar artifact which may indicate a pattern. Aggregating the measures may produce at least one of a plurality of distinct near field metrics for a light source. In embodiments, metrics may further include a mixing distance metric, a scale of artifacts metric, a contrast in the near field metric, a light quality metric, an output color metric, a brightness output metric, a spectral range metric and the like. A mixing distance metric may be a measure of distance from a light source at which a magnitude of artifacts drops below a threshold of artifact visibility.

In embodiments, patterns and artifacts may be measured cooperatively, such as by detecting an indication of size, scale and frequency of occurrence of artifacts in a detected light pattern produced by the light source. A contrast metric may likewise be based on detected patterns and artifacts in that it may be an indication of the intensity of at least one of patterns and artifacts detectable proximal to the light source. Such an indication of intensity may be represented as a ratio of at least one of the detectable patterns and the detectable artifacts. A greater number of detectable patterns and artifacts may indicate a greater contrast ratio metric. Whereas fewer detectable patterns and artifacts may indicate a lower contrast ratio. In embodiments, calculating metrics of near field light volume data may include processing luminance data such as values of theta and phi for a range of positions in the light volume. In embodiments, machine learning algorithms may play a role in calculating near field metrics by being applied to improve algorithms that associate candidate metrics with data values from a plurality of near field data sets.

Augmented Reality: Lighting Methods

In embodiments, augmented reality lighting emulation may include a three-dimensional model for an environment, where a position (and optionally direction) for a lighting fixture can be specified, such as in a user interface of the model, such that known lighting characteristics of the lighting fixture can be modeled (such as illumination effects on surfaces in the model) and presented to a user in an augmented reality format that includes a representation of the environment (such as a photo, animation, or video) with overlays that display the illumination effects created by one or more lighting fixtures, including ones based on near field and far field characteristics, and interactions thereof (such as based on illumination models that account for interference, reflection and the like). Thus, the user experiences an augmented version of the environment that demonstrates the effect a particular set of the lighting fixture(s) would have on or in the environment. In embodiments, augmented reality lighting emulation may include a combination of mobile devices. In embodiments, a user may select a light fixture with an interface or application of the first device and position the first device in the environment, such as against a wall of a room where a wall sconce might be desired, so that the augmented reality system can understand, such as from positioning data obtained from the first device, where the lighting fixture is to be positioned for purposes of augmented reality rendering of the fixture. The lighting fixture itself, as well as the physical location and orientation of the emulated light in the room, can be determined, such as using the various techniques described throughout this disclosure, and a corresponding model of the selected lighting fixture can be used to emulate an impact of the emulated lighting fixture in the room (e.g., in the near field and far field areas of the room relative to the lighting fixture). By detecting or retrieving a type of lighting fixture being emulated, and a location and an orientation of the device emulating the light in the environment, a lighting model of the emulated light fixture may be applied in an augmented reality setting to a portion of the environment in which the first mobile device is disposed. In embodiments, a second device may be an augmented reality device (e.g., AR glasses, a smartphone with AR display elements placed over a visual representation of an environment (such as a photo or video of the environment), and/or an AR headset (such as a headset configured to hold a smartphone near the eyes of the user) that a user may wear or hold in the environment. The environment may be captured and modeled in a space lighting modeling function using the position and orientation information of the emulated light fixture. A result may be a rendering of the impact of the emulated light fixture on surfaces and objects in the augmented reality view of the environment. In embodiments, the second device may be a smartphone, tablet or the like. In embodiments, the second device may be located outside of the environment and may receive information, such as images of the environment from the first device, and process the images with the lighting model of the selected light fixture to produce a variant of the images impacted by the emulated light.

In embodiments, a system for augmented reality rendering of an impact of a light fixture on an environment may include a first mobile computing device, such as a smartphone or the like representing a light source (e.g., light fixture). The position and orientation of the first mobile device in the environment may be detectable by a second computing device in the environment. The position and orientation may be detected through image analysis of images of the environment that include the first device. The position and orientation may be detected by the second device (such as by GPS, by triangulation to local beacons or access points, or the like) and communicated through a wireless or other network transmission, such as cellular, Bluetooth™, WiFi, and the like, that facilitates communicating the first device information to the second device or another device, such as a lighting modelling server and the like. In embodiments, the second device may capture an image of a portion of the environment based on the detected position and orientation of the first device. In embodiments, the second device may detect that the orientation of the first device has the screen of the user device facing a specific wall in the environment, such as to emulate the selected light illuminating the wall. The second device may indicate to a user of the second device to capture an image of the specific wall. In embodiments, the second device may access a set of images of the environment that were previously captured and, based on the first device position and orientation, select one or more images from the set that includes the specific wall. The second device may communicate the captured image and optionally the first device position and orientation information to a lighting modeling server that may access a lighting model of the emulated light source and digitally model an interaction of the light source with elements of the environment detected in the captured image, such as the specific wall and the like. The second device may receive the modeled interaction from the lighting modeling server and render the modeled interaction on its electronic display, which may be an augmented reality display. In embodiments, the second device may perform the lighting model access and modeling of interaction independent of access to a light modeling server. Changes in position and/or orientation of the first device may be detected, and optionally tracked so that the modeled interaction may be updated as the device is repositioned. In embodiments, a user of the first device may provide an indication, such as by holding the first device stably for a minimum duration of time or through voice or manual entry, that the light emulated by the first device is ready to be modeled. In embodiments, a user of the first device may position and optionally orient the first device in the environment temporarily while indicating, such as through the user interface of the device, via a gesture, via voice command and the like to use the location and orientation of the device for emulation. The user may then move the first device at will without impacting the resulting emulation and modeling of interactions with portions of the environment.

In embodiments, at least one of the first device and the second device may include a user interface that facilitates access to a library of light fixtures from which a user can select a light fixture to emulate.

In embodiments, a multi-device emulation of lighting interactions with an environment may include two devices interacting with the environment and each other. A first of the two devices may be disposed in the environment with an image of a selected light fixture rendered on its user interface display. Position and optionally orientation information about the first device relative to features in the environment may be available, such as by the first device using its position and orientation sensors to determine where in the environment it is located. The first device may communicate, such as over a wireless network its position information, orientation information, or both so that at least one of the other devices participating in the multi-device emulation may use the first device location information for modeling interactions of the emulated light with the environment. In embodiments, the second device participating in the multi-device emulation may render in its user interface an illumination effect of the selected light fixture on a target portion of the environment in response to a combination of a model of luminance of the selected light fixture, at least one of surfaces and objects in the target portion of the environment, and the location and orientation information of the first device. The second device may be an augmented reality processing device that may render an illumination effect of the selected light fixture based at least in part on a position and orientation of the second device in the environment. The target position may be captured, such as by using a camera feature of the second device. In embodiments, changes in location and/or orientation of the first device may result in near real time changes in interaction modeling and rendering on the second device.

In embodiments, the luminance model of the emulated light fixture may incorporate at least one of near-field luminance characterization of the light fixture and far-field luminance characterization.

In embodiments, a multi-device emulation of lighting interactions may include the first device, the second device and a lighting space modeling server that generates a data set that describes the illumination effect of the selected light fixture on the portion of the environment that the second device uses for rendering.

In embodiments, augmented reality techniques may be used in an embodiment of lighting design. A method for such use may include processing an augmented reality image to detect light sources, such as actual and/or emulated light sources. The method may also include processing the augmented reality image to detect surfaces (e.g., walls, windows, ceilings, floors, and the like) and/or objects (e.g., furniture, vehicles, artwork, plantings, staircases, and the like). A user, such as a lighting designer may be facilitated by a lighting design system in disposing of at least one virtual light source in the augmented reality image. Further processing of the updated augmented reality image may include processing near-field luminance data, far-field luminance data, and the like of the disposed virtual light source with a lighting space model. In response to the processing, the augmented reality image may be updated to depict illumination of portions of the augmented reality image in response to the lighting space model. If the detected surfaces and/or objects are present in the portion of the environment impacted by the illumination, interactions between the illumination model and the detected surfaces and/or objects may be rendered.

Figure 49:
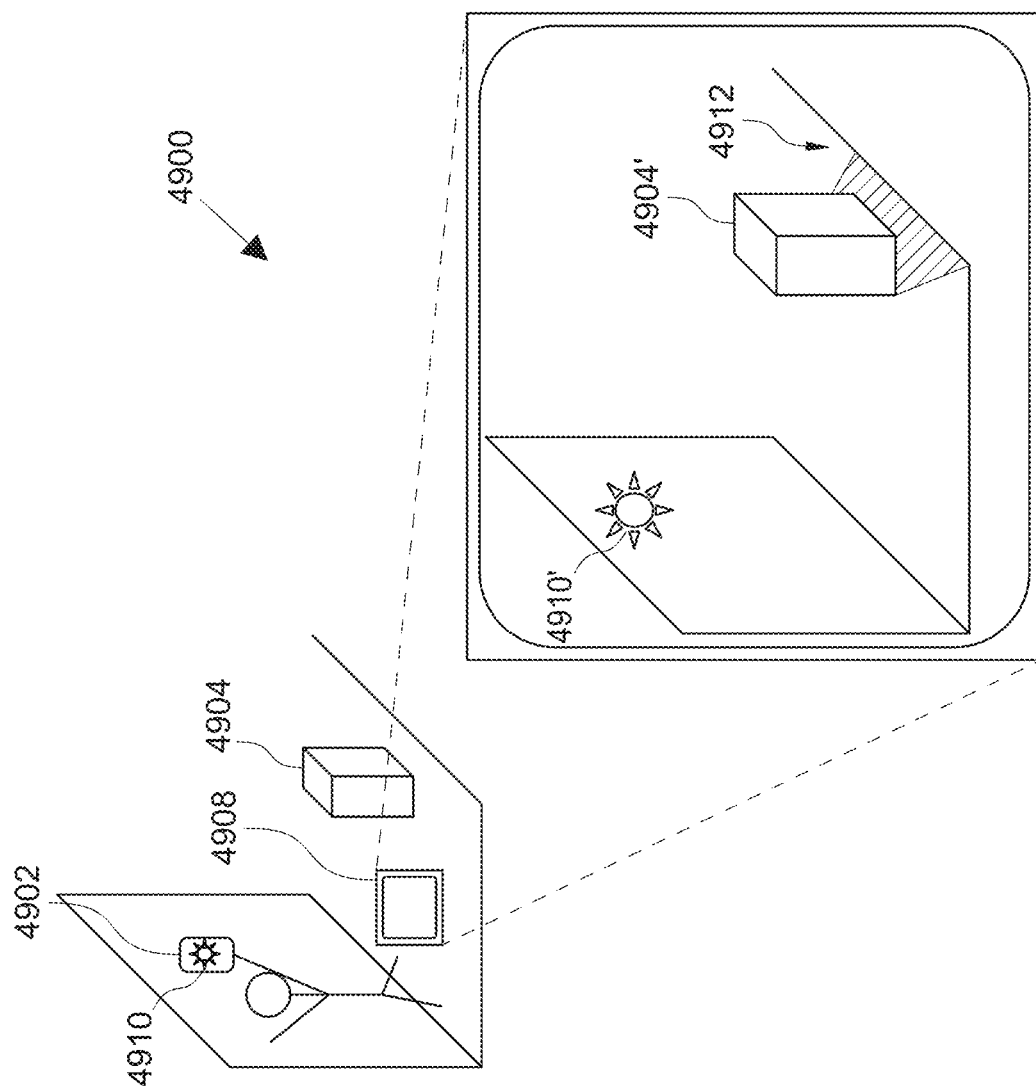
FIG. 49 is a diagrammatic view that depicts embodiments of the multi-device virtual/augmented reality light modeling methods and systems in accordance with the embodiments of the present disclosure.

Referring to FIG. 49, embodiments of the multi-device virtual/augmented reality light modeling methods and systems 4900 are depicted. A user may hold an emulation device 4902 that represents a selected light source 4910 in a specific position and orientation in an environment. The space may include surfaces and objects 4904 that may be impacted in a modeling of lighting of the selected light source. A second device 4908 may be used in the multi-device virtual/augmented reality modeling approach to render an effect of the selected light 4910 based on a position and/or orientation of the emulation device 4902 that may be a smartphone or the like. The exploded view of device 4908 depicts a rendering of a modeling of an impact on the environment of the selected light source based on a model of the selected light source 4910'. In this variation, object 4904' may be illuminated on a top surface by the light 4910' and may cause shadowing of a back surface of the object 4904' and a region of shadow 4912 caused by the object 4904' based on the position and orientation of the selected light source 4910.

K: Color: Skyglow

In embodiments, design of lighting in an environment may be configured to emulate natural light effects, such as sunrise, sunset, and the like. Additionally, lighting design may emulate other natural light effects, such as sunlight impacting a window or skylight and the like. Accomplishing specific effects, such as these natural effects may involve controlling one or more lights in an environment, optionally in coordination. To emulate sky color, for example, on a ceiling of a room may require coordinating control of lights that are directed at least in part at the ceiling (e.g., uplights) and other lights that are directed at least in part at walls, floors, or the like (e.g., downlights) in the space. To emulate a physical effect of light impacting a window, as a person inside the space may perceive it, light directed at a wall or at a ceiling for a skylight may be controlled to produce an effect similar to external sunlight impacting the window or skylight. Control of lights that coordinate with a time of day (e.g., the path of the sun through the sky), a weather forecast (e.g., clouds, full sunshine, partial sunshine, and the like), and the like may further enhance emulating a natural effect of exterior sunlight.

In embodiments, a method of emulating exterior sunlight effects in a space may include controlling a plurality of lights, such as first light and a second light for illuminating the space. The first controlled light may be disposed to illuminate a first region of the environment, such as to mimic sky color. Factors that may impact control of the light may include a user input, such as a preferred effect, a time of day, such as to emulate how the sunlight may impact the space at the specified time of day, and the like. The second controlled light may coordinate with the first light to maintain a preferred level of illumination throughout the space. In embodiments, while the first light may illuminate a ceiling of the space with a mid-day sun color, the second light may illuminate portions of the space to enhance shadowing and the like that may be caused by sunlight shining through a skylight and the like. In embodiments, the second light may be controlled to mimic a window, such as on a vertical wall in the space. The control of aspects such as color and intensity may be coordinated between the two lights so that the overall effect of illumination in the space is consistent. In embodiments, a sky color on the ceiling may be coordinated with a sky color of a window on a wall in the environment, and the like. In embodiments, a portion of the ceiling, such as may be representative of a skylight, or even a plurality of skylights on the ceiling may be the target illumination space of the first light. Emulating skylight effects, such as color and the like may automatically adjust throughout the day to emulate how natural sunlight might look on the target surface region. In embodiments, in addition to adapting light color and the like based on time of day, lighting color may be controlled to emulate moonlight (e.g., sunlight reflected off the moon) based on a position of the moon and time of day/night. In embodiments, specific objectives of emulating skylight may include producing effects in the space, such as a melanopic effect with a flux ratio of at least 10:1 for a portion of the environment, or a circadian action and the like. Other specific objectives may include generating cove lighting that emulates natural skylight, or graze lighting that compliments overhead skylight emulation and the like.

In embodiments, coordinated control of uplights and downlights may facilitate emulating skylight in a space for a specific purpose, such as performing certain tasks and the like. While an uplight may be controlled to emulate a skylight or the color and intensity of the sky in general, a second light may be controlled to provide light that is suitable for a specific purpose, such as office activity (e.g., a workspace), manufacturing activity and the like. Other desired effects, such as emulating a skylight, window, lunar illumination, time-of-day coordinated illumination, cove lighting, graze lighting and the like as described above and elsewhere herein may be achieved using control methods and systems also described herein while meeting a lighting plan for the space for the specific purpose.

In embodiments, controlling illumination of a space to emulate skylight, such as color, direction, and intensity may include controlling a downlight to mimic sky color for a time of day, such as sunrise, mid-day, and sunset timing. This may be coordinated with controlling an uplight in response to the downlight control so that illumination in the space produces, for example, a melanopic flux ratio of at least 10:1 in a portion of the environment, or a circadian action and the like. Depending on the type of controls available for the lights, controlling may include adjusting one, two, or more channels of a multi-channel light. Light control channels may include color, intensity, and the like.

In embodiments, control of light in space may, when coordinated with skylight lighting effects generation may facilitate shifting a bias of light in the space toward a side of the space, a central portion, and the like. Shifting the bias of light in the space may be coordinated with, for example, a position of the sun in the sky throughout the day, so that as the sun would naturally cause shadows to move in response to the sun traveling through the sky, the lighting in the space would be adjusted to be directed progressively less from the East throughout the first half of the daylight and progressively more from the West throughout the second half of daylight. Shifting light bias in a space coordinated with the position of the sun may emulate the movement of the sun, even on cloudy days when the sun may not be distinctly visible.

Main: Data Integration with Non-Traditional Sources

In embodiments, lighting design and control may benefit from the use of data sources that are not directly related to lighting, such as sources that indicate activity of an individual, use patterns in a space, collaborative filtered data, and the like. Such information may be gathered in a range of ways including, without limitation, directly from users, from their electronic calendars, their social media feeds (e.g., SPOTIFY, PANDORA, NETFLIX, YOUTUBE, and the like), social media feeds of others in which a user is tagged, wearable sensors that may produce biomarkers and the like about a user, activity monitors, motion tracking in an environment, data gathered from groups of similar users, and the like.

In embodiments, time zone information about a user, such as recent time zone changes and/or upcoming time zone changes may be useful in control of lights in the user's environment to, for example, assist the user's natural adjustment of his body clock to the new time zone. When upcoming time zone changes are detected, such as by a user's travel plans that may be recorded in the user's calendar and the like, lighting control may optionally be adjusted to assist the user getting ready for the new time zone, such as adjusting timing of lighting in the user's environment over a transition period to emulate the new time zone. In embodiments, when a user finds himself in a new time zone with different natural light timing, a lighting control system may adjust lighting in the user's environment, such as color and the like to facilitate adjusting to the new time zone.

In embodiments, light control may be centralized for an environment or distributed to at least a portion of the lights in the environment, such as for smart lights with integrated controllers and the like. Interfaces, such as communication networks and the like between external data sources, such as wearable sensors, and light control, whether it is centralized or distributed may facilitate control of lights in response to the interpretation of data from the wearable sensors. Interpretation of wearable sensors and the like may include detection of fatigue, anxiety, and the like that may be input into an adaptive lighting control algorithm that can adjust light color, intensity, direction, and the like to facilitate mitigating effects such as fatigue, anxiety and the like.

In embodiments, lighting design control may benefit from access to information about users, groups, their likes, preferences, habits, prior lighting environments (e.g., at a former employer or at home) and the like. Aligning, for example lighting preferences for a target group of users with a similar group of users for which lighting preferences are not directly accessible may enable predicting lighting preferences for the target group of users. In embodiments, predictions regarding lighting preferences and the like may be improved through use of feedback from users and machine learning applied thereto. In embodiments, gathering feedback from individual users, groups of users, such as customers, experts and the like may contribute to improvements in lighting design guidance that may be made available to a lighting designer in an intelligent lighting plan and design system.

In embodiments, lighting design may further be enhanced through integration of data sources, such as architectural plans, including material choices, line of sight aspects, building orientation, impacts on natural light from nearby buildings and the like may be combined with light source specific information such as near field characterization data and the like to develop a multi-dimensional understanding of factors that impact a lighting design plan for a space.

3D Structures: On-the-Fly Building of Architectural Elements for Lighting Simulation In embodiments, simulating lighting and lighting effects in an environment may include processing light source models to generate illumination in the environment and may include processing models of elements in the environment, such as walls, objects (e.g., furniture, appliances, windows, and the like) to determine, among other things, an impact of the generated illumination on elements in the environment, such a surfaces that may be illuminated, others that may be shadowed, yet others that may reflect illumination, such as shiny surfaces and the like. A lighting simulation model of an environment may include one or more lighting effect impacting models of elements in the environment. When simulating lighting and lighting effects of a live environment, lighting effect impacting models of elements in the live environment may need to be accessed. While some may exist, such as in a library of lighting models and the like, others may need to be generated. In embodiments, generating lighting models for simulating lighting effects in an environment may include building models or architectural elements and the like from images of an environment, such as may be generated through live capture of the environment such as through an augmented reality system.

In embodiments, configuring a three-dimensional space for lighting simulation may involve capturing information descriptive of physical aspects of an environment (e.g., walls, objects, such as tables, chairs, desks, plants, household objects, vehicles, and the like). In embodiments, the captured information may be stored as a three-dimensional point-cloud representation of elements in the environment. To transform the descriptive information into architectural elements for which lighting effect impacting models may be referenced during simulation, machine learning may be applied to the descriptive information to facilitate identifying the elements and therefore their corresponding models. In embodiments, machine learning may, for example, help distinguish a free-standing object from an object that is placed against a wall in the environment, and the like. In embodiments, light modeling aspects of the detected architectural elements and features may be determined based on the machine learning, such as by matching a model in a library of element lighting models based on similarity of the three-dimensional information in the point-cloud that represents an element. Alternatively, a model for an object may be generated on-the-fly based on detected properties of the three-dimensional object, such as may be determined from image analysis and the like. Light modeling aspects of the detected architectural features may include reflectance by the feature of light coming from a known angle relative to the architectural feature. Light modeling aspects of the detected architectural features may include a surface type for at least one surface of the feature, such as reflective, and the like. In embodiments, light modeling aspects of the detected features may be stored in a library of elements suitable for use in a light space model. A lighting space model for the three-dimensional space for lighting simulation may be configured by incorporating the detected architectural features/elements and their corresponding light modeling aspects. In embodiments, a lighting space model for the three-dimensional space for lighting simulation may be configured by referencing the library of architectural features and incorporating corresponding light models for architectural features referenced in the library.

In embodiments, information descriptive of the physical environment may be captured by using a digital camera, a three-dimensional sensor, a camera-equipped personal computing device, and the like. Capturing and processing the three-dimensional descriptive information may include generating measurements of elements in the environment and distances between the elements. In embodiments, the use of machine learning may include processing point clouds of the environment through a machine learning process. In embodiments, it may be desirable to include a floor plan of the environment; therefore, generating a floor plan or a reflected ceiling plan of the environment may be included when configuring a three-dimensional space for lighting simulation.

In embodiments, other user interface technology may be used including without limitation, artificial reality, and the like.

In embodiments, configuring a lighting space model may include detecting at least one light source in the environment, and incorporating light modeling aspects of the light source, such as a light source model and the like.

In embodiments, configuring a three-dimensional space for lighting simulation may involve capturing visual information representative of a physical environment (e.g., walls, objects, such as tables, chairs, desks, plants, household objects, vehicles, and the like). In embodiments, the captured information may be stored as a three-dimensional visual representation of elements in the environment. To transform the descriptive information into architectural elements for which lighting effect impacting models may be referenced during simulation, machine learning may be applied to the descriptive information to facilitate detecting either surfaces, edges between surfaces, or a combination thereof. In embodiments, machine learning may, for example, help distinguish a free-standing object from an object that is placed against a wall in the environment, and the like. In embodiments, light modeling aspects of the detected architectural elements and features may be determined based on the machine learning, such as by matching a model in a library of element lighting models based on similarity of the three-dimensional information in the point-cloud that represents an element. In embodiments, machine learning may include applying machine learning to an output of the analyzing an impact of illumination on at least one of the surfaces and the edges to improve generating the reflective model. Alternatively, a model for an object may be generated on-the-fly based on detected properties of the three-dimensional object, such as may be determined from image analysis and the like. Light modeling aspects of the detected surfaces and/or edges may include reflectance by the surface and/or edge of light coming from a known angle relative to the surface. Light modeling aspects of the detected architectural features may include a surface type for at least one surface of the feature, such as reflective, and the like. Physical relationships among the detected surfaces and edges, such as which combinations of surfaces and edges make up an architectural object may include information that facilitates determining a relative orientation of a plurality of the detected surfaces. An exemplary approach to generating a reflective model of the detected surfaces and edges may include analyzing an impact of illumination on at least a portion of the detected surfaces and edges. A lighting space model for the three-dimensional space for lighting simulation may be configured by incorporating the detected surfaces, edges, their relative orientation and a corresponding reflective model for the incorporated surfaces and edges.

In embodiments, visual information representative of the physical environment may include one or more images that may be captured by using a digital camera, a three-dimensional sensor, a camera-equipped personal computing device, and the like. Capturing and processing the three-dimensional visual information may include generating measurements of elements in the environment and distances between the elements. An element in the environment may include at least one surface and at least one edge between surfaces. In embodiments, the use of machine learning may include processing visual information of the environment through a machine learning process. In embodiments, it may be desirable to include a floor plan of the environment; therefore, generating a floor plan or a reflected ceiling plan of the environment may be included when configuring a three-dimensional space for lighting simulation.

In embodiments, other user interface technology may be used including without limitation, artificial reality, and the like.

In embodiments, configuring a lighting space model may include detecting at least one light source in the environment, and incorporating light modeling aspects of the light source, such as a light source model and the like.

In embodiments, a reflective model of surfaces and/or edges in the environment may include reflectance by the surface and/or edge of light directed at a first angle relative to the surface and/or edge.

In embodiments, when generating a light impacting and/or reflectance model of an object detected in an environment via machine learning and the like, features of the object, such as a surface type and the like may be used to identify one or more candidate models in a library of object lighting models may be used to facilitate generating the new object model for use in simulating effects of lighting in the environment. A model of an object in the library that substantially matches surface type with an object in the environment, aspects of the library object model may be automatically adapted to comply with the object in the environment, such as any of the dimensions of the object, the orientation of the object surfaces as defined by the model, and the like. A newly generated lighting/reflectance model may be classified and stored in the library to facilitate its use in other environments, and the like.

Rendering Pipeline: Low Res on the Device and High Res Streamed Through Cloud

In embodiments, lighting simulation of an environment, such as rendering an impact of a near field illumination of a light source on objects in an environment may be rendered for a user to view how a selected light source may appear and may illuminate an environment such as the user's home and the like. Rendering may be based on a three-dimensional and the like models of the light source, its near field illumination, objects and features of the environment and the like. To facilitate efficient use of computing and network resources, and the like, rendering may be different for different target viewing devices. Additionally, rendering one or more images for display at different resolutions may be performed on different computing devices, so that, for example, high resolution rendering may be performed by a computing server that may have greater computing power for such rendering than a mobile device. Therefore, a pipeline of rendering may be configured and may include at least one rendering server and at least one mobile device. Depending on the amount of data to be rendered, effectively the resolution of the image being rendered, one of the computing devices in the rendering pipeline may be selected. In embodiments, rendering of a portion of an environment may begin on a mobile device to facilitate providing a quick look at the simulated lighting environment. The resolution of the rendered portion of the environment may be increased while the portion of the environment remains on the display of the device. When the resolution of the portion reaches a server-based rendering minimum threshold, rendering may be moved along the pipeline from the mobile device to the server. Determination of when a server is used for rendering and when another device in the pipeline is used for rendering may be based on aspects such as processing bandwidth of devices in the rendering pipeline, availability of high resolution rendering data, time since a portion of an environment has been identified for rendering, and the like.

In embodiments, security of data in the rendering pipeline may further be enabled through features such as key-based compression, encoding, blockchain and the like.

In embodiments, a rendering pipeline may facilitate rendering lighting effects based on a near field light source illumination model. Rendering along a rendering pipeline for near field lighting effects may include rendering a first image, such as a low resolution image to provide a quick, initial view of the effect of a light placed in an environment (e.g., such as in an augmented and/or virtual reality display and the like).

In embodiments, rendering may include simulating lighting effects within a virtual environment. In embodiments, rendering may include converting data produced by simulating lighting effects within an environment into displayable data. Data produced by simulating lighting effects may be processed by a rendering feature to produce a range of resolution images, such as low resolution images (e.g., for rapid rendering on lower power computing devices) and high resolution images (e.g., for high fidelity display), and the like. In embodiments, a low resolution rendered image may be suitable for use in a rapidly changing environment, such as a video game experience. A high resolution rendered image may be suitable for use when a more photorealistic effect is desired. A rendering pipeline may receive an indication of the type of use of lighting effect simulation output data and determine a device along the pipeline that is best suited for rendering an image that is compatible with the type of use indicated.

In embodiments, a multi-device rendering pipeline may be implemented by a first device in the pipeline receiving, such as from a server, a blockchain-secured digital image that may include content representative of a low-resolution simulated lighting image of an environment; and rendering the low-resolution image with the first device, which may be a mobile device, such as a smartphone and the like. The rendering may include processing the received content to generate a visualization of an impact of a light disposed at a first location and oriented in a first orientation in the environment on elements in the environment. Rendering may be moved along the rendering pipeline to a different device in the pipeline based on an indication received through a user interface of the first device of a portion of the environment (e.g., a subset of the rendered low-resolution image, and the like) to render in high resolution. In embodiments, the resolution to render is greater than a server-rendering threshold. In embodiments, communication between and among devices in the rendering pipeline may be secured through a blockchain-based security protocol. In embodiments, the first device may be a smartphone. In embodiments, the different device may be a networked server and the like. In embodiments, the high resolution image rendered on the server device in the rendering pipeline may be received as a blockchain-secured message delivered in the pipeline and displayed by a mobile device, such as a smartphone, tablet and the like. In embodiments, the digital image content representative of the subset may include a full geometric model of the indicated subset. In embodiments, rendering may be based on a full geometric model of at least one of the environment, a light source, an object in the environment, and the like. In embodiments, rendering may be performed by a device type in the pipeline such as a virtual reality capable device, an augmented reality capable device and the like. In embodiments, digital image content may include at least one of a near field illumination model of illumination produced by a light source and a far field illumination model of illumination produced by the light source. In embodiments, the blockchain may secure a low resolution image of a portion of the environment rendered on a mobile device in the rendering pipeline and a high resolution image of the portion of the environment rendered on a computing server device in the pipeline.

In embodiments, a rendering pipeline for rendering lighting effects of a light source may rely on security features, such as blockchain and the like. A method of incrementally increasing resolution rendering of an effect of lighting may start by receiving a first blockchain-secured message that may include digital image content representative of an output of simulation of lighting effect on an environment and rendering, via processing the content of the message, a first resolution version of an impact on elements in the environment, such as of a light disposed at a first location and oriented in a first orientation in the environment. Subsequent blockchain-secured messages of digital image content of the simulated lighting effect (e.g., additional content that may enable increasing the rendering resolution) may be received and combined with the most recently rendered image to produce an incrementally increased resolution image. These method steps may be repeated to incrementally increase resolution. In embodiments, the first resolution version may be rendered by a mobile device. As the effective resolution of combining the previously rendered image and the subsequent content increases, when the effective resolution exceeds a resolution for which the mobile device can properly render the image, subsequent rendering activity may be performed by a second device in the rendering pipeline, such as a networked server and the resulting image may be streamed to the mobile device for display. In embodiments, the digital image content in any of the blockchain-secured messages may include a full geometric model. In embodiments, all digital image content may be derived from a full geometric model of the environment.

In embodiments, a rendering pipeline may also be applied to rendering a near-field illumination effect as the near-field effect is captured by an indirect near field illumination capture device. Such a device may be moved incrementally in three dimensions relative to a light source to capture several multi-dimensional images of the near field. As each multi-dimensional image is captured, an increased resolution image of the near field illumination effect may be rendered. Based at least in part on the resolution resulting from combining all prior multi-dimensional images, different computing devices within a rendering pipeline may be used for the rendering.

In embodiments, rendering a near field illumination effect with a rendering pipeline of computing devices may include receiving at a first computing device a first multi-dimensional image of illumination produced by a light source and captured with an indirect near field illumination multi-dimensional image capture device and rendering a first resolution representation of the near field illumination (e.g., for display on a user interface of the first computing device). Additional position differentiated multi-dimensional images of illumination from the light source captured by the indirect near field capture device may be received and combined into increasingly higher resolution renderings of the near field illumination. The rendering pipeline may manage data flow to the rendering device to provide only the amount of information (e.g., a maximum count of position-differentiated multi-dimensional images) that the rendering device can effectively render; in other words when the resulting resolution of sending an additional position-differentiated multi-dimensional image would exceed a rendering threshold for the device, further multi-dimensional images may not be delivered up the rendering pipeline to the device. Rather, a different device in the pipeline may be activated to render subsequent images with resolution that exceeds the rendering device rendering threshold. In embodiments, blockchain security may be applied to this near field rendering process. In embodiments, each of the first and subsequent multi-dimensional images may be blockchain-secured.

Color: Programmable "Modes"

In embodiments, control of a multi-channel programmable light source may enable achieving a consistent CIE map location (e.g., a consistent "x" and "y" in the map) while adjusting spectral content, such as by adjusting individual channel intensities. Therefore, there may be several ways to control a multi-channel programmable light to achieve a given effect. Various modes that may be achieved include color quality mode, (e.g., maximizing CRI or TM-30), efficacy mode, which may include maximizing lumens/watt, circadian model that may focus on maximizing equivalent melanopic lux (EML), color bias mode that may include oversaturating a single color (e.g., red, green, or blue) as a spectral component of an "x" and "y" mapped point on the CIE color map, rest model that may include minimizing blue/EML content, and the like.

In embodiments, maintaining a consistent CIE point for a light source while changing the focus at that point may include adjusting a single channel intensity, such as red to facilitate improving the red color response of cameras and the like capturing images of objects illuminated by the light source.

In embodiments, light sources with four or more light producing elements or channels (e.g., individual Light Emitting Diodes (LEDs)) can generate a single output color in nearly an infinite number of ways. This may be enabled by combining different amounts of the light output from the individual LEDs/channels. While a resulting color remains consistent between these combinations, the spectral power distribution of the generated light can be significantly different. This may result in significant variation for the various features of the output light such as color rendering, health impacts, and power efficiency. Therefore, in LED light sources with four or more channels, several color modes can be defined to give the user the flexibility of choosing their feature of interest. In embodiments, select color modes may be designed and implemented in several stages. At a first stage, the spectral power distribution and electrical power characteristics of the individual LEDs may be measured. This stage may be carried out in an optics laboratory using a measurements device called an integrating sphere. Next, the data acquired in the first stage is used to formulate and solve an optimization problem to obtain the individual LED channel intensities for each of the target colors and each of the color modes. In embodiments, mathematical models that define lighting effects and features of a color mode may be used in this second stage to calculate corresponding LED channel intensities in each case (e.g., for each color mode). In embodiments, the intensity information of the light source may be downloaded for simulation, such as in the form of a table, and the like. The luminaire firmware may be developed such that at each point in time, the LED channel intensities are determined based on the user's choice of the target color and color mode. In embodiments, computational density in microcontrollers may allow for these calculations to be done in real-time at the fixture level rather than requiring intensity information tables to be used.

In embodiments, color control, such as with a multi-channel programmable light source may include generating programmable color tuning curves, for example, to facilitate producing consistent color across a range of channel intensities and the like. Producing a color tuning curve may include controlling four color channels, such as a pair of secondary control channels that the CIE point by one of the pairs controlling the "x" index and the other of the pair controlling the "y" index. In embodiments, the other two color channels that may be controlled may include a primary control input that maps to a combination of "x" and "y" and a third control channel that facilitates controlling a dim value for the intensity of at least one of the channels of the light source, such as one of a plurality of LEDs in the light source, and the like. In embodiments, the color tuning curve may be deployed (e.g., impact lighting rendered) in an augmented reality lighting simulation environment. In embodiments, a lighting effect in a three-dimensional space produced by the use of the color tuning curve may be rendered in a simulation thereof. Simulation of a lighting effect produced from controlling a model of a light source based on the produced color tuning curve may include accounting for effects relating to physical characteristics of the light source (e.g., bulb type, bulb count, bulb orientation, shades, filters, and the like). In embodiments, the simulation may include rendering distance-based light source intensity for a range of color tuning curves and the like. Rendering distance-based light source intensity may also include handling light source intensity falloff over the distance from the light source for a set of ray-traces. In embodiments, multi-channel light control may also be achieved through a user interface that facilitates a user selecting a lighting fixture to control to produce the color tuning curve. In embodiments, the user interface may facilitate a user selecting among a plurality of color tuning factors including a programmable dimming curve, programmable color tuning curve, a tuning curve start point, a tuning curve end point, a tuning curve dimming path that may be responsive to a level of dimming, a color tuning path that may be responsive to a level of dimming, and the like. In embodiments, producing the color tuning curve may be responsive to a user selection of a tuning curve start point, tuning curve end point and at least one tuning curve waypoint between the start and end points.

In embodiments, producing a consistent color across a plurality of color modes may be performed by a system that includes a multi-channel light emitting diode (LED) illumination source, such as a four channel LED light fixture and the like. Each of the four channels may be independently controllable for at least an amount of light output by an LED in the illumination source that corresponds to a channel. In embodiments, the system may also include a set of mathematical models that define features of each of a plurality of the color modes that, when processed with a map of LED illumination source channel control values for a plurality of target illumination colors by a processor, produces a set of intensity information for each of the plurality of target illumination colors. In embodiments, the system may include a computing architecture that receives an indication of a target color and a color mode and controls the four channels of the illumination source to produce the target color based on the set of intensity information and the indicated color mode. In embodiments, a target color produced in a power efficiency color mode may be substantially indistinguishable from the same target color produced in a full power color mode. In embodiments, the system may produce a consistent target color for a range of color modes including, without limitation, a color quality mode, an efficacy mode, a circadian mode, a color bias mode, a rest mode, and the like. In embodiments, these modes may include a color quality mode, (e.g., maximizing CRI or TM-30), an efficacy mode, which may include maximizing lumens/watt, a circadian model that may focus on maximizing equivalent melanopic lux (EML), a color bias mode that may include oversaturating a single color (e.g., red, green, or blue) as a spectral component of an "x" and "y" mapped point on the CIE color map, a rest model that may include minimizing blue/EML content, and the like. In embodiments, producing a circadian mode may be achieved independently of third-party metrics, such as through the use of a daylight similarity metric, and the like. In embodiments, the circadian mode may be achieved based on circadian metrics, such as Circadian Stimulus and the like.

Near Field: Model-Based Rendering

In embodiments, lighting effect rendering may include model-based rendering of near field effects of a light source. Model-based rendering may include modeling of light source emissions as a set of direction-specific light ray-traces. Data at a plurality of positions of the modeled light emissions along a portion of the ray-traces may be extracted and stored in a computer accessible memory. The stored data may be configured as three-dimensional light volume data, and the like. The light volume data may describe a three dimensional space; however not all positions in the three-dimensional space may be included in the light volume data; therefore, some points in the three-dimensional space may be interpolated, such as based on nearest neighbor techniques. Rendering may further include determining interactions among the ray-traces, such as due to the ray traces overlapping in the three-dimensional space, and the like. Lighting effect model-based rendering may also include a step of presenting the modeled data to a user, such as by rendering in an electronic display near field effects of the light source, the effects may be derived from a lighting space model that incorporates the light volume-data, the interpolated plurality of points and the interactions among the ray-traces, essentially a superset of data associated with model based rendering as described herein this embodiment.

In embodiments, the lighting space model may enable determining an impact of illumination from the light source by taking into account element lighting-related elements such as, light transparency, absorption, and reflection. In embodiments, near field model-based rendering may work with a virtual reality controller, an augmented reality controller, and conventional two-dimensional devices, such as a smart phone, tablet, and the like. Near field rendering may include rendering near field lighting artifacts throughout a three-dimensional space, such as a room in which a user is attempting to determine which type and location of lighting may produce a desired lighting effect. Such rendering may also consider physical characteristics of a light source, such as type, location, orientation, and count of individual bulbs (e.g., individual light sources). In embodiments, each individual bulb or lighting element may be associated with a corresponding set of ray traces and rendering may include rendering effects from each of the plurality of distinct light elements (e.g., individual LEDs, bulbs, lenses, and the like). Use of three-dimensional light volume data may facilitate detecting a shape of a lighting effect, properties of the lighting effect, such as a shape at a specified distance from the light source, and the like. In embodiments, such a shape may be substantially continuous or discontinuous. Light volume data may include light color, reflections of the light from objects in the embodiments, and the like.

In embodiments, model-based rendering of near field illumination effects from a light source may include capturing a set of data representing, for example, a three-dimensional space proximal to a light source (e.g., a near field of the light source), the data set may include data representing illuminance values of light at each of a plurality of locations in the three-dimensional space, such as may be generated by an indirect near field illumination collection system. In embodiments, a portion of the set of data, such as a three-dimensional portion that references a volume of space proximal to the light source, may be extracted and used to generate a geometric model of the portion that facilitates modelling an impact of the illuminance of the light source on objects disposed in the space proximal to the light source. For portions of the three-dimensional space that is not fully characterized by light values, a plurality of additional illuminances value may be interpolated and used for model-based rendering. In addition to indirectly captured illumination from the light source, the three-dimensional data set may include reflections from surfaces in the space; thereby facilitating rendering bot a light field and an impact of the light field on objects in an environment.

Augmented Reality: Floor Planner

In embodiments, planning lighting deployments may benefit from lighting simulation and interactive technologies such as augmented reality, and the like. Developing a floor plan in an augmented reality lighting design system may further help with rendering lighting simulations. In embodiments, planning lighting in an augmented reality environment may include representing physical features of an environment as a point cloud data structure. The point cloud data may be processed with machine learning to generate a lighting space model of the environment, which may be used to produce a floor plan, a reflected ceiling plan, and the like of the environment. In embodiments, virtual measuring techniques, such as a virtual ruler in an augmented reality display may be used when producing a floor plan and the like. By coupling the lighting space model with an augmented reality view of the environment light sources (e.g., fixtures and the like) may be added to the lighting space model by a user placing lighting source elements (e.g., icons and the like) in the augmented reality view of the environment. The environment with the placed light sources, lighting space model and the like may be rendered in the augmented reality view and may include simulated lighting effects of the placed light sources, such as based on near field illumination characterization of the placed light sources. In embodiments, rendering in the augmented reality view may include accounting for aspects such as transparency, absorption, reflection and the like of the elements in the environment. Rendering of a floor-plan-based lighting environment may include accounting for physical effects of the elements in the floor plan as well as physical characteristics of the modeled light source, such as quantity, type, orientation, and shading of individual light elements that make up the light source (e.g., a light fixture with multiple bulbs, and the like). In embodiments, lighting models for light fixtures with multiple bulbs may be configured to facilitate rendering effects from each of the individual bulbs and the like. In embodiments, lighting effects simulated may be based on an area-source model of the placed lights that may not account for effects from individual lighting elements of the light source. In embodiments, the lighting floor plan may be at least partially configured through a user interface that allows a user to select light sources from a library of lights, indicate a position and orientation of the selected light sources, and optionally define a portion of the environment for inclusion in the floor plan. In embodiments, rendering for a floor-plan-based lighting environment may be performed by a volumetric renderer.

In embodiments, planning lighting in an augmented reality environment may include representing physical features of an environment as surfaces and edges. The surface and edge data may be processed with machine learning to generate a lighting space model of the environment, which may be used to produce a floor plan, a reflected ceiling plan, and the like of the environment. By coupling the lighting space model with an augmented reality view of the environment light sources (e.g., fixtures and the like) may be added to the lighting space model by a user placing lighting source elements (e.g., icons and the like) in the augmented reality view of the environment. The environment with the placed light sources, output of the lighting space model and the like may be rendered in the augmented reality view and may include simulated lighting effects of the placed light sources, such as based on near field illumination characterization of the placed light sources. In embodiments, rendering in the augmented reality view may include accounting for aspects such as transparency, absorption, reflection and the like of the surfaces and/or edges in the environment. Rendering of a floor-plan-based lighting environment may include accounting for physical effects of the surfaces and edges in the floor plan as well as physical characteristics of the modeled light source, such as quantity, type, orientation, and shading of individual light elements that make up the light source (e.g., a light fixture with multiple bulbs, and the like). In embodiments, lighting models for light fixtures with multiple bulbs may be configured to facilitate rendering effects from each of the individual bulbs and the like. In embodiments, lighting effects simulated may be based on an area-source model of the placed lights that may not account for effects from individual lighting elements of the light source. In embodiments, the lighting floor plan may be at least partially configured through a user interface that allows a user to select light sources from a library of lights, indicate a position and orientation of the selected light sources, and optionally define a portion of the environment for inclusion in the floor plan. In embodiments, rendering for a floor-plan-based lighting environment may be performed by a volumetric renderer.

Augmented Reality: Floor Planner+Project Level AR=Mini-Schedule

In embodiments, developing a floor plan, such as for lighting sources and the like may be combined with an order management system that may facilitate integrated planning, client assessment, and order preparation. In embodiments, such an integrated approach may include representing physical features of an environment as a point cloud data structure. The point cloud data may be processed with machine learning to generate a lighting space model of the environment, which may be used to produce a floor plan, a reflected ceiling plan, and the like of the environment. By coupling the lighting space model with an augmented reality view of the environment light sources (e.g., fixtures and the like) may be added to the lighting space model by a user placing lighting source elements (e.g., icons and the like) in the augmented reality view of the environment. The user may select a model for a light source from a catalog of light sources that may be presented in the augmented reality view. The environment with the placed light sources, lighting space model and the like may be rendered in the augmented reality view and may include simulated lighting effects of the placed light sources, such as based on near field illumination characterization of the placed light sources. In embodiments, rendering may include rendering near-field lighting effects in the environment of the placed light sources based on a near-file illumination model of the light source. In embodiments, the lighting floor plan may be at least partially configured through a user interface that allows a user to select light sources from a library of lights, indicate a position and orientation of the selected light sources, and optionally define a portion of the environment for inclusion in the floor plan. Integration with an order management system may include populating a data object, such as may represent an order form and the like with lighting source item identification information that may be useful for ordering the placed lights. Further integration may include automatically placing at least one order into a supply chain of lighting sources for the at least one placed light source. In embodiments, identification information for ordering a light source may be retrieved from the catalog of light sources. A user may indicate which of the placed light sources to order through the augmented reality interface. Other objects in the environment may be identified and automatically ordered, such as light switches, floor lamps, and the like by populating an order data object similarly to ordering a light source. In embodiments, a lighting installation plan may be configured based on the generated floor plan and the position and orientation of the placed light sources. In embodiments, rendering in the augmented reality view may include accounting for aspects such as transparency, absorption, reflection and the like of the elements in the environment. Rendering of a floor-plan-based lighting environment may include accounting for physical effects of the elements in the floor plan as well as physical characteristics of the modeled light source, such as quantity, type, orientation, and shading of individual light elements that make up the light source (e.g., a light fixture with multiple bulbs, and the like). In embodiments, lighting models for light fixtures with multiple bulbs may be configured to facilitate rendering effects from each of the individual bulbs and the like. In embodiments, lighting effects simulated may be based on an area-source model of the placed lights that may not account for effects from individual lighting elements of the light source. In embodiments, the lighting floor plan may be at least partially configured through a user interface that allows a user to select light sources from a library of lights, indicate a position and orientation of the selected light sources, and optionally define a portion of the environment for inclusion in the floor plan. In embodiments, rendering for a floor-plan-based lighting environment may be performed by a volumetric renderer.

In embodiments, an integrated plan, simulate, and order lighting design approach may include representing physical features of an environment as surfaces and edges. The surface and edge data may be processed with machine learning to generate a lighting space model of the environment, which may be used to produce a floor plan, a reflected ceiling plan, and the like of the environment. By coupling the lighting space model with an augmented reality view of the environment light sources (e.g., fixtures and the like) may be added to the lighting space model by a user placing lighting source elements (e.g., icons and the like) in the augmented reality view of the environment. The user may select a model for a light source from a catalog of light sources that may be presented in the augmented reality view. The environment with the placed light sources, lighting space model and the like may be rendered in the augmented reality view and may include simulated lighting effects of the placed light sources, such as based on near field illumination characterization of the placed light sources. In embodiments, rendering may include rendering near-field lighting effects in the environment of the placed light sources based on a near-file illumination model of the light source. In embodiments, the lighting floor plan may be at least partially configured through a user interface that allows a user to select light sources from a library of lights, indicate a position and orientation of the selected light sources, and optionally define a portion of the environment for inclusion in the floor plan. Integration with an order management system may include populating a data object, such as may represent an order form and the like with lighting source item identification information that may be useful for ordering the placed lights. Further integration may include automatically placing at least one order into a supply chain of lighting sources for the at least one placed light source. In embodiments, identification information for ordering a light source may be retrieved from the catalog of light sources. A user may indicate which of the placed light sources to order through the augmented reality interface. Other objects in the environment may be identified and automatically ordered, such as light switches, floor lamps, and the like by populating an order data object similarly to ordering a light source. In embodiments, a lighting installation plan may be configured based on the generated floor plan and the position and orientation of the placed light sources. In embodiments, rendering in the augmented reality view may include accounting for aspects such as transparency, absorption, reflection and the like of the surfaces and/or edges in the environment. Rendering of a floor-plan-based lighting environment may include accounting for physical effects of the surfaces and edges in the floor plan as well as physical characteristics of the modeled light source, such as quantity, type, orientation, and shading of individual light elements that make up the light source (e.g., a light fixture with multiple bulbs, and the like). In embodiments, lighting models for light fixtures with multiple bulbs may be configured to facilitate rendering effects from each of the individual bulbs and the like. In embodiments, lighting effects simulated may be based on an area-source model of the placed lights that may not account for effects from individual lighting elements of the light source. In embodiments, the lighting floor plan may be at least partially configured through a user interface that allows a user to select light sources from a library of lights, indicate a position and orientation of the selected light sources, and optionally define a portion of the environment for inclusion in the floor plan. In embodiments, rendering for a floor-plan-based lighting environment may be performed by a volumetric renderer.

Augmented Reality: Control of AR Objects—UX/UI

In embodiments, augmented reality objects, such as light sources and the like may be controlled with various virtual control features that may be represented in a computer interface, such as an augmented reality interface. In embodiments, configuring an interface to facilitate control of modeled light sources in a computer user interface, such as an augmented reality interface may include coupling lighting space models of an environment in, for example, an augmented reality view of the environment so that a user of the computer may place light sources in the environment. The environment and simulations of lighting effects of the placed lighting sources in the environment may be rendered based on a model of illumination of the placed light sources, such as a near field illumination characterization of the placed light sources. In the user interface, a plurality of virtual lighting controls may be rendered to control illumination from at least one of the placed light sources. In embodiments, the plurality of virtual lighting controls may include user interface elements for controlling at least one of light intensity (e.g., dimming color and/or finish of a fixture, beam angles of a fixture, light color, and light color temperature to allow a user to adjust how the environment might look under these different conditions. In embodiments, the plurality of virtual lighting controls may include user interface elements for controlling at least one of rotation and tilt of the placed light sources to allow a user to adjust, for example how a light fixture may be positioned in a room and pointed toward a portion of the room such as a wall, floor, doorway and the like.

In addition to computer user interface-based virtual controls, the lights in the simulation environment may be controlled through wearable sensors that a user, such as a user in the augmented reality environment, may wear to detect motion and the like of the user. The detected motion and the like may be converted into control sequences to control simulated light sources such as to dim a light, reposition a light, change its orientation, and the like. Aspects such as intensity, color, color temperature, position, orientation, tilt, rotation and the like may each be controlled through interpretation of the wearable sensors. Augmented reality controls may include virtual controls for selecting light sourced from a marketplace of light sources.

Virtual controls in an augmented reality environment may include controls such as an adjustable dial that represents a range of lighting effects producible by a placed light source. When a user interacts with the adjustable dial, the lighting effect (e.g., color mode and the like) may be changed in the simulation, which may result in changes in the interaction with elements in the environment. As a user changes the dial settings, the augmented reality display of the lighting effects on the environment may be updated in real time or near real time. In embodiments, the techniques described above for an augmented reality view device may be implemented with a combination of an augmented reality device for lighting space modeling and lighting effect interactions with an environment and a handheld computing device, such as a smartphone and the like for controlling lights placed in the augmented reality environment. The controls for color, intensity, position, tilt, rotation, placement relative to elements in the environment, and the like may be implemented in the handheld device, that may in embodiments be operated by a user in the environment.

In embodiments, a handheld device, such as a smartphone and the like may be used in place of wearable motion sensors to indicate control of the light sources. Movement of the handheld device may be detected by motion sensors of the device and reported to the augmented reality environment as inputs to virtual controls on the lights. Moving the handheld device to a new position in the environment may be detected as an indication of a new position for a light source being placed in the environment by the user. Rotating the handheld device may indicate a user's desire to increase or decrease light output and the like. These are merely examples of how motion data, may be used to perform lighting control functions in an augmented reality lighting simulation environment.

A method for planning lighting in an augmented reality display having a machine learning-based lighting space model of an environment in an augmented reality lighting design interface through which user selected light sources are automatically added to a light source supply chain order. A method for planning lighting in an augmented reality display having a machine learning-based lighting space model of an environment in an augmented reality lighting design interface through which user selected light sources are automatically added to a light source supply chain order and having a pattern matching system that facilitates identifying a light source that produces a desired bloom effect based on similarity of bloom effect-specific light source properties with properties of characterized light sources. A method for planning lighting in an augmented reality display having a machine learning-based lighting space model of an environment in an augmented reality lighting design interface through which user selected light sources are automatically added to a light source supply chain order and having use of a system for determining interactions among ray-traces through light volume data that characterizes illumination from a light source and objects in a three-dimensional space in which the light volume data is rendered. A method for planning lighting in an augmented reality display having a machine learning-based lighting space model of an environment in an augmented reality lighting design interface through which user selected light sources are automatically added to a light source supply chain order and having an emotional content data structure for lighting design that is populated with machine learning optimized factors that contribute to emotional effects of lighting. A method for planning lighting in an augmented reality display having a machine learning-based lighting space model of an environment in an augmented reality lighting design interface through which user selected light sources are automatically added to a light source supply chain order and having techniques for determining light source characteristics from a desired lighting effect data set that are used to identify candidate light sources for producing the desired lighting effect. A method for planning lighting in an augmented reality display having a machine learning-based lighting space model of an environment in an augmented reality lighting design interface through which user selected light sources are automatically added to a light source supply chain order and having a lighting space model configured with lighting models of machine learning-based architectural elements detected in a point cloud representative of a physical environment. A method for planning lighting in an augmented reality display having a machine learning-based lighting space model of an environment in an augmented reality lighting design interface through which user selected light sources are automatically added to a light source supply chain order and having machine learning generate a lighting space model of an environment from a point cloud representation of the environment for use in an augmented reality lighting design interface and using the lighting space model to generate a floor plan of the space based on light sources placed by a user in the augmented reality interface. A method for planning lighting in an augmented reality display having a machine learning-based lighting space model of an environment in an augmented reality lighting design interface through which user selected light sources are automatically added to a light source supply chain order and having a lighting space model of an environment in an augmented reality interface through which a user controls lights placed in the environment via virtual lighting control features presented in the augmented reality interface. A method for planning lighting in an augmented reality display having a machine learning-based lighting space model of an environment in an augmented reality lighting design interface through which user selected light sources are automatically added to a light source supply chain order and having use of an indirect illumination collection facility that is disposable throughout a three-dimensional region proximal to a light source that captures a plurality of multi-dimensional light source illumination images. A method for planning lighting in an augmented reality display having a machine learning-based lighting space model of an environment in an augmented reality lighting design interface through which user selected light sources are automatically added to a light source supply chain order and having a custom tuning profile that coordinates changes in color and light output of a programmable light source to match lighting characteristics of a legacy light fixture. A method for planning lighting in an augmented reality display having a machine learning-based lighting space model of an environment in an augmented reality lighting design interface through which user selected light sources are automatically added to a light source supply chain order and having an indirect illumination collection facility that captures near field multi-dimensional illumination indirectly from a light source by varying distance and orientation of the collection facility relative to the light source throughout the near field space of the light source. A method for planning lighting in an augmented reality display having a machine learning-based lighting space model of an environment in an augmented reality lighting design interface through which user selected light sources are automatically added to a light source supply chain order and having algorithms for calculating light quality, intensity, color range, and spectral characteristic metrics of a light source from illumination values collected at a plurality of theta and phi differentiated positions in the light source's near field space. A method for planning lighting in an augmented reality display having a machine learning-based lighting space model of an environment in an augmented reality lighting design interface through which user selected light sources are automatically added to a light source supply chain order and having a light source emulating device positioned by a user in a three-dimensional space that is presented in an augmented reality lighting design system that uses the position and orientation of the emulating device to model a lighting effect in the space. A method for planning lighting in an augmented reality display having a machine learning-based lighting space model of an environment in an augmented reality lighting design interface through which user selected light sources are automatically added to a light source supply chain order and having a color map to control a multi-channel light thereby producing consistent color across a range of color modes by adjusting a plurality of the channels based on the color map. A method for planning lighting in an augmented reality display having a machine learning-based lighting space model of an environment in an augmented reality lighting design interface through which user selected light sources are automatically added to a light source supply chain order and having a near field dataset characterizing a light source, generating a geometric model from the data set that facilitates modeling an impact of the light source on objects disposed in the near field. A method for planning lighting in an augmented reality display having a machine learning-based lighting space model of an environment in an augmented reality lighting design interface through which user selected light sources are automatically added to a light source supply chain order and having algorithms that construct three-dimensional illumination data sets from a plurality of distinct two-dimensional illumination data arrays that are captured throughout a near field space of a light source. A method for planning lighting in an augmented reality display having a machine learning-based lighting space model of an environment in an augmented reality lighting design interface through which user selected light sources are automatically added to a light source supply chain order and having a system for adapting light controls based on machine learning from data representing user activity including user time zone travel, user activities in an environment illuminated by a light being controlled, wearable sensor biomarker user data, and feedback from users in the environment. A method for planning lighting in an augmented reality display having a machine learning-based lighting space model of an environment in an augmented reality lighting design interface through which user selected light sources are automatically added to a light source supply chain order and having a rendering pipeline in a lighting design system that allocates rendering to devices in the pipeline based on a correspondence between the device rendering capability and a resolution of image content to be rendered. A method for planning lighting in an augmented reality display having a machine learning-based lighting space model of an environment in an augmented reality lighting design interface through which user selected light sources are automatically added to a light source supply chain order and having coordinated control of uplights and downlights to achieve a lighting effect in an environment that mimics a sky color for a given time of day A system for identifying a desired lighting source having a pattern matching system that facilitates identifying a light source that produces a desired bloom effect based on similarity of bloom effect-specific light source properties with properties of characterized light sources. A system for identifying a desired lighting source having a pattern matching system that facilitates identifying a light source that produces a desired bloom effect based on similarity of bloom effect-specific light source properties with properties of characterized light sources and having use of a system for determining interactions among ray-traces through light volume data that characterizes illumination from a light source and objects in a three-dimensional space in which the light volume data is rendered. A system for identifying a desired lighting source having a pattern matching system that facilitates identifying a light source that produces a desired bloom effect based on similarity of bloom effect-specific light source properties with properties of characterized light sources and having an emotional content data structure for lighting design that is populated with machine learning optimized factors that contribute to emotional effects of lighting. A system for identifying a desired lighting source having a pattern matching system that facilitates identifying a light source that produces a desired bloom effect based on similarity of bloom effect-specific light source properties with properties of characterized light sources and having techniques for determining light source characteristics from a desired lighting effect data set that are used to identify candidate light sources for producing the desired lighting effect. A system for identifying a desired lighting source having a pattern matching system that facilitates identifying a light source that produces a desired bloom effect based on similarity of bloom effect-specific light source properties with properties of characterized light sources and having a lighting space model configured with lighting models of machine learning-based architectural elements detected in a point cloud representative of a physical environment. A system for identifying a desired lighting source having a pattern matching system that facilitates identifying a light source that produces a desired bloom effect based on similarity of bloom effect-specific light source properties with properties of characterized light sources and having machine learning generate a lighting space model of an environment from a point cloud representation of the environment for use in an augmented reality lighting design interface and using the lighting space model to generate a floor plan of the space based on light sources placed by a user in the augmented reality interface. A system for identifying a desired lighting source having a pattern matching system that facilitates identifying a light source that produces a desired bloom effect based on similarity of bloom effect-specific light source properties with properties of characterized light sources and having a lighting space model of an environment in an augmented reality interface through which a user controls lights placed in the environment via virtual lighting control features presented in the augmented reality interface. A system for identifying a desired lighting source having a pattern matching system that facilitates identifying a light source that produces a desired bloom effect based on similarity of bloom effect-specific light source properties with properties of characterized light sources and having use of an indirect illumination collection facility that is disposable throughout a three-dimensional region proximal to a light source that captures a plurality of multi-dimensional light source illumination images. A system for identifying a desired lighting source having a pattern matching system that facilitates identifying a light source that produces a desired bloom effect based on similarity of bloom effect-specific light source properties with properties of characterized light sources and having a custom tuning profile that coordinates changes in color and light output of a programmable light source to match lighting characteristics of a legacy light fixture. A system for identifying a desired lighting source having a pattern matching system that facilitates identifying a light source that produces a desired bloom effect based on similarity of bloom effect-specific light source properties with properties of characterized light sources and having an indirect illumination collection facility that captures near field multi-dimensional illumination indirectly from a light source by varying distance and orientation of the collection facility relative to the light source throughout the near field space of the light source. A system for identifying a desired lighting source having a pattern matching system that facilitates identifying a light source that produces a desired bloom effect based on similarity of bloom effect-specific light source properties with properties of characterized light sources and having algorithms for calculating light quality, intensity, color range, and spectral characteristic metrics of a light source from illumination values collected at a plurality of theta and phi differentiated positions in the light source's near field space. A system for identifying a desired lighting source having a pattern matching system that facilitates identifying a light source that produces a desired bloom effect based on similarity of bloom effect-specific light source properties with properties of characterized light sources and having a light source emulating device positioned by a user in a three-dimensional space that is presented in an augmented reality lighting design system that uses the position and orientation of the emulating device to model a lighting effect in the space. A system for identifying a desired lighting source having a pattern matching system that facilitates identifying a light source that produces a desired bloom effect based on similarity of bloom effect-specific light source properties with properties of characterized light sources and having a color map to control a multi-channel light thereby producing consistent color across a range of color modes by adjusting a plurality of the channels based on the color map. A system for identifying a desired lighting source having a pattern matching system that facilitates identifying a light source that produces a desired bloom effect based on similarity of bloom effect-specific light source properties with properties of characterized light sources and having a near field dataset characterizing a light source, generating a geometric model from the data set that facilitates modeling an impact of the light source on objects disposed in the near field. A system for identifying a desired lighting source having a pattern matching system that facilitates identifying a light source that produces a desired bloom effect based on similarity of bloom effect-specific light source properties with properties of characterized light sources and having algorithms that construct three-dimensional illumination data sets from a plurality of distinct two-dimensional illumination data arrays that are captured throughout a near field space of a light source. A system for identifying a desired lighting source having a pattern matching system that facilitates identifying a light source that produces a desired bloom effect based on similarity of bloom effect-specific light source properties with properties of characterized light sources and having a system for adapting light controls based on machine learning from data representing user activity including user time zone travel, user activities in an environment illuminated by a light being controlled, wearable sensor biomarker user data, and feedback from users in the environment. A system for identifying a desired lighting source having a pattern matching system that facilitates identifying a light source that produces a desired bloom effect based on similarity of bloom effect-specific light source properties with properties of characterized light sources and having a rendering pipeline in a lighting design system that allocates rendering to devices in the pipeline based on a correspondence between the device rendering capability and a resolution of image content to be rendered. A system for identifying a desired lighting source having a pattern matching system that facilitates identifying a light source that produces a desired bloom effect based on similarity of bloom effect-specific light source properties with properties of characterized light sources and having coordinated control of uplights and downlights to achieve a lighting effect in an environment that mimics a sky color for a given time of day A method of electronic display rendering of lighting distribution in a three-dimensional space having use of a system for determining interactions among ray-traces through light volume data that characterizes illumination from a light source and objects in a three-dimensional space in which the light volume data is rendered. A method of electronic display rendering of lighting distribution in a three-dimensional space having use of a system for determining interactions among ray-traces through light volume data that characterizes illumination from a light source and objects in a three-dimensional space in which the light volume data is rendered and having an emotional content data structure for lighting design that is populated with machine learning optimized factors that contribute to emotional effects of lighting. A method of electronic display rendering of lighting distribution in a three-dimensional space having use of a system for determining interactions among ray-traces through light volume data that characterizes illumination from a light source and objects in a three-dimensional space in which the light volume data is rendered and having techniques for determining light source characteristics from a desired lighting effect data set that are used to identify candidate light sources for producing the desired lighting effect. A method of electronic display rendering of lighting distribution in a three-dimensional space having use of a system for determining interactions among ray-traces through light volume data that characterizes illumination from a light source and objects in a three-dimensional space in which the light volume data is rendered and having a lighting space model configured with lighting models of machine learning-based architectural elements detected in a point cloud representative of a physical environment. A method of electronic display rendering of lighting distribution in a three-dimensional space having use of a system for determining interactions among ray-traces through light volume data that characterizes illumination from a light source and objects in a three-dimensional space in which the light volume data is rendered and having machine learning generate a lighting space model of an environment from a point cloud representation of the environment for use in an augmented reality lighting design interface and using the lighting space model to generate a floor plan of the space based on light sources placed by a user in the augmented reality interface. A method of electronic display rendering of lighting distribution in a three-dimensional space having use of a system for determining interactions among ray-traces through light volume data that characterizes illumination from a light source and objects in a three-dimensional space in which the light volume data is rendered and having a lighting space model of an environment in an augmented reality interface through which a user controls lights placed in the environment via virtual lighting control features presented in the augmented reality interface. A method of electronic display rendering of lighting distribution in a three-dimensional space having use of a system for determining interactions among ray-traces through light volume data that characterizes illumination from a light source and objects in a three-dimensional space in which the light volume data is rendered and having use of an indirect illumination collection facility that is disposable throughout a three-dimensional region proximal to a light source that captures a plurality of multi-dimensional light source illumination images. A method of electronic display rendering of lighting distribution in a three-dimensional space having use of a system for determining interactions among ray-traces through light volume data that characterizes illumination from a light source and objects in a three-dimensional space in which the light volume data is rendered and having a custom tuning profile that coordinates changes in color and light output of a programmable light source to match lighting characteristics of a legacy light fixture. A method of electronic display rendering of lighting distribution in a three-dimensional space having use of a system for determining interactions among ray-traces through light volume data that characterizes illumination from a light source and objects in a three-dimensional space in which the light volume data is rendered and having an indirect illumination collection facility that captures near field multi-dimensional illumination indirectly from a light source by varying distance and orientation of the collection facility relative to the light source throughout the near field space of the light source. A method of electronic display rendering of lighting distribution in a three-dimensional space having use of a system for determining interactions among ray-traces through light volume data that characterizes illumination from a light source and objects in a three-dimensional space in which the light volume data is rendered and having algorithms for calculating light quality, intensity, color range, and spectral characteristic metrics of a light source from illumination values collected at a plurality of theta and phi differentiated positions in the light source's near field space. A method of electronic display rendering of lighting distribution in a three-dimensional space having use of a system for determining interactions among ray-traces through light volume data that characterizes illumination from a light source and objects in a three-dimensional space in which the light volume data is rendered and having a light source emulating device positioned by a user in a three-dimensional space that is presented in an augmented reality lighting design system that uses the position and orientation of the emulating device to model a lighting effect in the space. A method of electronic display rendering of lighting distribution in a three-dimensional space having use of a system for determining interactions among ray-traces through light volume data that characterizes illumination from a light source and objects in a three-dimensional space in which the light volume data is rendered and having a color map to control a multi-channel light thereby producing consistent color across a range of color modes by adjusting a plurality of the channels based on the color map. A method of electronic display rendering of lighting distribution in a three-dimensional space having use of a system for determining interactions among ray-traces through light volume data that characterizes illumination from a light source and objects in a three-dimensional space in which the light volume data is rendered and having a near field dataset characterizing a light source, generating a geometric model from the data set that facilitates modeling an impact of the light source on objects disposed in the near field. A method of electronic display rendering of lighting distribution in a three-dimensional space having use of a system for determining interactions among ray-traces through light volume data that characterizes illumination from a light source and objects in a three-dimensional space in which the light volume data is rendered and having algorithms that construct three-dimensional illumination data sets from a plurality of distinct two-dimensional illumination data arrays that are captured throughout a near field space of a light source. A method of electronic display rendering of lighting distribution in a three-dimensional space having use of a system for determining interactions among ray-traces through light volume data that characterizes illumination from a light source and objects in a three-dimensional space in which the light volume data is rendered and having a system for adapting light controls based on machine learning from data representing user activity including user time zone travel, user activities in an environment illuminated by a light being controlled, wearable sensor biomarker user data, and feedback from users in the environment. A method of electronic display rendering of lighting distribution in a three-dimensional space having use of a system for determining interactions among ray-traces through light volume data that characterizes illumination from a light source and objects in a three-dimensional space in which the light volume data is rendered and having a rendering pipeline in a lighting design system that allocates rendering to devices in the pipeline based on a correspondence between the device rendering capability and a resolution of image content to be rendered. A method of electronic display rendering of lighting distribution in a three-dimensional space having use of a system for determining interactions among ray-traces through light volume data that characterizes illumination from a light source and objects in a three-dimensional space in which the light volume data is rendered and having coordinated control of uplights and downlights to achieve a lighting effect in an environment that mimics a sky color for a given time of day A method of using emotional filters for lighting design having an emotional content data structure for lighting design that is populated with machine learning optimized factors that contribute to emotional effects of lighting. A method of using emotional filters for lighting design having an emotional content data structure for lighting design that is populated with machine learning optimized factors that contribute to emotional effects of lighting and having techniques for determining light source characteristics from a desired lighting effect data set that are used to identify candidate light sources for producing the desired lighting effect. A method of using emotional filters for lighting design having an emotional content data structure for lighting design that is populated with machine learning optimized factors that contribute to emotional effects of lighting and having a lighting space model configured with lighting models of machine learning-based architectural elements detected in a point cloud representative of a physical environment. A method of using emotional filters for lighting design having an emotional content data structure for lighting design that is populated with machine learning optimized factors that contribute to emotional effects of lighting and having machine learning generate a lighting space model of an environment from a point cloud representation of the environment for use in an augmented reality lighting design interface and using the lighting space model to generate a floor plan of the space based on light sources placed by a user in the augmented reality interface. A method of using emotional filters for lighting design having an emotional content data structure for lighting design that is populated with machine learning optimized factors that contribute to emotional effects of lighting and having a lighting space model of an environment in an augmented reality interface through which a user controls lights placed in the environment via virtual lighting control features presented in the augmented reality interface. A method of using emotional filters for lighting design having an emotional content data structure for lighting design that is populated with machine learning optimized factors that contribute to emotional effects of lighting and having use of an indirect illumination collection facility that is disposable throughout a three-dimensional region proximal to a light source that captures a plurality of multi-dimensional light source illumination images. A method of using emotional filters for lighting design having an emotional content data structure for lighting design that is populated with machine learning optimized factors that contribute to emotional effects of lighting and having a custom tuning profile that coordinates changes in color and light output of a programmable light source to match lighting characteristics of a legacy light fixture. A method of using emotional filters for lighting design having an emotional content data structure for lighting design that is populated with machine learning optimized factors that contribute to emotional effects of lighting and having an indirect illumination collection facility that captures near field multi-dimensional illumination indirectly from a light source by varying distance and orientation of the collection facility relative to the light source throughout the near field space of the light source. A method of using emotional filters for lighting design having an emotional content data structure for lighting design that is populated with machine learning optimized factors that contribute to emotional effects of lighting and having algorithms for calculating light quality, intensity, color range, and spectral characteristic metrics of a light source from illumination values collected at a plurality of theta and phi differentiated positions in the light source's near field space. A method of using emotional filters for lighting design having an emotional content data structure for lighting design that is populated with machine learning optimized factors that contribute to emotional effects of lighting and having a light source emulating device positioned by a user in a three-dimensional space that is presented in an augmented reality lighting design system that uses the position and orientation of the emulating device to model a lighting effect in the space. A method of using emotional filters for lighting design having an emotional content data structure for lighting design that is populated with machine learning optimized factors that contribute to emotional effects of lighting and having a color map to control a multi-channel light thereby producing consistent color across a range of color modes by adjusting a plurality of the channels based on the color map. A method of using emotional filters for lighting design having an emotional content data structure for lighting design that is populated with machine learning optimized factors that contribute to emotional effects of lighting and having a near field dataset characterizing a light source, generating a geometric model from the data set that facilitates modeling an impact of the light source on objects disposed in the near field. A method of using emotional filters for lighting design having an emotional content data structure for lighting design that is populated with machine learning optimized factors that contribute to emotional effects of lighting and having algorithms that construct three-dimensional illumination data sets from a plurality of distinct two-dimensional illumination data arrays that are captured throughout a near field space of a light source. A method of using emotional filters for lighting design having an emotional content data structure for lighting design that is populated with machine learning optimized factors that contribute to emotional effects of lighting and having a system for adapting light controls based on machine learning from data representing user activity including user time zone travel, user activities in an environment illuminated by a light being controlled, wearable sensor biomarker user data, and feedback from users in the environment. A method of using emotional filters for lighting design having an emotional content data structure for lighting design that is populated with machine learning optimized factors that contribute to emotional effects of lighting and having a rendering pipeline in a lighting design system that allocates rendering to devices in the pipeline based on a correspondence between the device rendering capability and a resolution of image content to be rendered. A method of using emotional filters for lighting design having an emotional content data structure for lighting design that is populated with machine learning optimized factors that contribute to emotional effects of lighting and having coordinated control of uplights and downlights to achieve a lighting effect in an environment that mimics a sky color for a given time of day. A method having techniques for determining light source characteristics from a desired lighting effect data set that are used to identify candidate light sources for producing the desired lighting effect. A method having techniques for determining light source characteristics from a desired lighting effect data set that are used to identify candidate light sources for producing the desired lighting effect and having a lighting space model configured with lighting models of machine learning-based architectural elements detected in a point cloud representative of a physical environment. A method having techniques for determining light source characteristics from a desired lighting effect data set that are used to identify candidate light sources for producing the desired lighting effect and having machine learning generate a lighting space model of an environment from a point cloud representation of the environment for use in an augmented reality lighting design interface and using the lighting space model to generate a floor plan of the space based on light sources placed by a user in the augmented reality interface. A method having techniques for determining light source characteristics from a desired lighting effect data set that are used to identify candidate light sources for producing the desired lighting effect and having a lighting space model of an environment in an augmented reality interface through which a user controls lights placed in the environment via virtual lighting control features presented in the augmented reality interface. A method having techniques for determining light source characteristics from a desired lighting effect data set that are used to identify candidate light sources for producing the desired lighting effect and having use of an indirect illumination collection facility that is disposable throughout a three-dimensional region proximal to a light source that captures a plurality of multi-dimensional light source illumination images. A method having techniques for determining light source characteristics from a desired lighting effect data set that are used to identify candidate light sources for producing the desired lighting effect and having a custom tuning profile that coordinates changes in color and light output of a programmable light source to match lighting characteristics of a legacy light fixture. A method having techniques for determining light source characteristics from a desired lighting effect data set that are used to identify candidate light sources for producing the desired lighting effect and having an indirect illumination collection facility that captures near field multi-dimensional illumination indirectly from a light source by varying distance and orientation of the collection facility relative to the light source throughout the near field space of the light source. A method having techniques for determining light source characteristics from a desired lighting effect data set that are used to identify candidate light sources for producing the desired lighting effect and having algorithms for calculating light quality, intensity, color range, and spectral characteristic metrics of a light source from illumination values collected at a plurality of theta and phi differentiated positions in the light source's near field space. A method having techniques for determining light source characteristics from a desired lighting effect data set that are used to identify candidate light sources for producing the desired lighting effect and having a light source emulating device positioned by a user in a three-dimensional space that is presented in an augmented reality lighting design system that uses the position and orientation of the emulating device to model a lighting effect in the space. A method having techniques for determining light source characteristics from a desired lighting effect data set that are used to identify candidate light sources for producing the desired lighting effect and having a color map to control a multi-channel light thereby producing consistent color across a range of color modes by adjusting a plurality of the channels based on the color map. A method having techniques for determining light source characteristics from a desired lighting effect data set that are used to identify candidate light sources for producing the desired lighting effect and having a near field dataset characterizing a light source, generating a geometric model from the data set that facilitates modeling an impact of the light source on objects disposed in the near field. A method having techniques for determining light source characteristics from a desired lighting effect data set that are used to identify candidate light sources for producing the desired lighting effect and having algorithms that construct three-dimensional illumination data sets from a plurality of distinct two-dimensional illumination data arrays that are captured throughout a near field space of a light source. A method having techniques for determining light source characteristics from a desired lighting effect data set that are used to identify candidate light sources for producing the desired lighting effect and having a system for adapting light controls based on machine learning from data representing user activity including user time zone travel, user activities in an environment illuminated by a light being controlled, wearable sensor biomarker user data, and feedback from users in the environment. A method having techniques for determining light source characteristics from a desired lighting effect data set that are used to identify candidate light sources for producing the desired lighting effect and having a rendering pipeline in a lighting design system that allocates rendering to devices in the pipeline based on a correspondence between the device rendering capability and a resolution of image content to be rendered. A method having techniques for determining light source characteristics from a desired lighting effect data set that are used to identify candidate light sources for producing the desired lighting effect and having coordinated control of uplights and downlights to achieve a lighting effect in an environment that mimics a sky color for a given time of day A method of configuring a three-dimensional space for lighting simulation having a lighting space model configured with lighting models of machine learning-based architectural elements detected in a point cloud representative of a physical environment. A method of configuring a three-dimensional space for lighting simulation having a lighting space model configured with lighting models of machine learning-based architectural elements detected in a point cloud representative of a physical environment and having machine learning generate a lighting space model of an environment from a point cloud representation of the environment for use in an augmented reality lighting design interface and using the lighting space model to generate a floor plan of the space based on light sources placed by a user in the augmented reality interface. A method of configuring a three-dimensional space for lighting simulation having a lighting space model configured with lighting models of machine learning-based architectural elements detected in a point cloud representative of a physical environment. and having a lighting space model of an environment in an augmented reality interface through which a user controls lights placed in the environment via virtual lighting control features presented in the augmented reality interface. A method of configuring a three-dimensional space for lighting simulation having a lighting space model configured with lighting models of machine learning-based architectural elements detected in a point cloud representative of a physical environment. and having use of an indirect illumination collection facility that is disposable throughout a three-dimensional region proximal to a light source that captures a plurality of multi-dimensional light source illumination images. A method of configuring a three-dimensional space for lighting simulation having a lighting space model configured with lighting models of machine learning-based architectural elements detected in a point cloud representative of a physical environment. and having a custom tuning profile that coordinates changes in color and light output of a programmable light source to match lighting characteristics of a legacy light fixture. A method of configuring a three-dimensional space for lighting simulation having a lighting space model configured with lighting models of machine learning-based architectural elements detected in a point cloud representative of a physical environment. and having an indirect illumination collection facility that captures near field multi-dimensional illumination indirectly from a light source by varying distance and orientation of the collection facility relative to the light source throughout the near field space of the light source. A method of configuring a three-dimensional space for lighting simulation having a lighting space model configured with lighting models of machine learning-based architectural elements detected in a point cloud representative of a physical environment. and having algorithms for calculating light quality, intensity, color range, and spectral characteristic metrics of a light source from illumination values collected at a plurality of theta and phi differentiated positions in the light source's near field space. A method of configuring a three-dimensional space for lighting simulation having a lighting space model configured with lighting models of machine learning-based architectural elements detected in a point cloud representative of a physical environment. and having a light source emulating device positioned by a user in a three-dimensional space that is presented in an augmented reality lighting design system that uses the position and orientation of the emulating device to model a lighting effect in the space. A method of configuring a three-dimensional space for lighting simulation having a lighting space model configured with lighting models of machine learning-based architectural elements detected in a point cloud representative of a physical environment. and having a color map to control a multi-channel light thereby producing consistent color across a range of color modes by adjusting a plurality of the channels based on the color map. A method of configuring a three-dimensional space for lighting simulation having a lighting space model configured with lighting models of machine learning-based architectural elements detected in a point cloud representative of a physical environment. and having a near field dataset characterizing a light source, generating a geometric model from the data set that facilitates modeling an impact of the light source on objects disposed in the near field. A method of configuring a three-dimensional space for lighting simulation having a lighting space model configured with lighting models of machine learning-based architectural elements detected in a point cloud representative of a physical environment. and having algorithms that construct three-dimensional illumination data sets from a plurality of distinct two-dimensional illumination data arrays that are captured throughout a near field space of a light source. A method of configuring a three-dimensional space for lighting simulation having a lighting space model configured with lighting models of machine learning-based architectural elements detected in a point cloud representative of a physical environment. and having a system for adapting light controls based on machine learning from data representing user activity including user time zone travel, user activities in an environment illuminated by a light being controlled, wearable sensor biomarker user data, and feedback from users in the environment. A method of configuring a three-dimensional space for lighting simulation having a lighting space model configured with lighting models of machine learning-based architectural elements detected in a point cloud representative of a physical environment. and having a rendering pipeline in a lighting design system that allocates rendering to devices in the pipeline based on a correspondence between the device rendering capability and a resolution of image content to be rendered. A method of configuring a three-dimensional space for lighting simulation having a lighting space model configured with lighting models of machine learning-based architectural elements detected in a point cloud representative of a physical environment. and having coordinated control of uplights and downlights to achieve a lighting effect in an environment that mimics a sky color for a given time of day.

A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having a lighting space model of an environment in an augmented reality interface through which a user controls lights placed in the environment via virtual lighting control features presented in the augmented reality interface. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having use of an indirect illumination collection facility that is disposable throughout a three-dimensional region proximal to a light source that captures a plurality of multi-dimensional light source illumination images. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having a custom tuning profile that coordinates changes in color and light output of a programmable light source to match lighting characteristics of a legacy light fixture. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having an indirect illumination collection facility that captures near field multi-dimensional illumination indirectly from a light source by varying distance and orientation of the collection facility relative to the light source throughout the near field space of the light source. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having algorithms for calculating light quality, intensity, color range, and spectral characteristic metrics of a light source from illumination values collected at a plurality of theta and phi differentiated positions in the light source's near field space. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having a light source emulating device positioned by a user in a three-dimensional space that is presented in an augmented reality lighting design system that uses the position and orientation of the emulating device to model a lighting effect in the space. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having a color map to control a multi-channel light thereby producing consistent color across a range of color modes by adjusting a plurality of the channels based on the color map. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having a near field dataset characterizing a light source, generating a geometric model from the data set that facilitates modeling an impact of the light source on objects disposed in the near field. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having algorithms that construct three-dimensional illumination data sets from a plurality of distinct two-dimensional illumination data arrays that are captured throughout a near field space of a light source. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having a system for adapting light controls based on machine learning from data representing user activity including user time zone travel, user activities in an environment illuminated by a light being controlled, wearable sensor biomarker user data, and feedback from users in the environment. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having a rendering pipeline in a lighting design system that allocates rendering to devices in the pipeline based on a correspondence between the device rendering capability and a resolution of image content to be rendered. A method for planning lighting in an augmented reality display having machine learning generate a lighting space model of an environment from a point cloud representation of the environment for use in an augmented reality lighting design interface and using the lighting space model to generate a floor plan of the space based on light sources placed by a user in the augmented reality interface and having coordinated control of uplights and downlights to achieve a lighting effect in an environment that mimics a sky color for a given time of day.

A method of control of modeled light sources in an augmented reality interface having a lighting space model of an environment in an augmented reality interface through which a user controls lights placed in the environment via virtual lighting control features presented in the augmented reality interface. A method of control of modeled light sources in an augmented reality interface having a lighting space model of an environment in an augmented reality interface through which a user controls lights placed in the environment via virtual lighting control features presented in the augmented reality interface and having use of an indirect illumination collection facility that is disposable throughout a three-dimensional region proximal to a light source that captures a plurality of multi-dimensional light source illumination images. A method of control of modeled light sources in an augmented reality interface having a lighting space model of an environment in an augmented reality interface through which a user controls lights placed in the environment via virtual lighting control features presented in the augmented reality interface and having a custom tuning profile that coordinates changes in color and light output of a programmable light source to match lighting characteristics of a legacy light fixture. A method of control of modeled light sources in an augmented reality interface having a lighting space model of an environment in an augmented reality interface through which a user controls lights placed in the environment via virtual lighting control features presented in the augmented reality interface and having an indirect illumination collection facility that captures near field multi-dimensional illumination indirectly from a light source by varying distance and orientation of the collection facility relative to the light source throughout the near field space of the light source. A method of control of modeled light sources in an augmented reality interface having a lighting space model of an environment in an augmented reality interface through which a user controls lights placed in the environment via virtual lighting control features presented in the augmented reality interface and having algorithms for calculating light quality, intensity, color range, and spectral characteristic metrics of a light source from illumination values collected at a plurality of theta and phi differentiated positions in the light source's near field space. A method of control of modeled light sources in an augmented reality interface having a lighting space model of an environment in an augmented reality interface through which a user controls lights placed in the environment via virtual lighting control features presented in the augmented reality interface and having a light source emulating device positioned by a user in a three-dimensional space that is presented in an augmented reality lighting design system that uses the position and orientation of the emulating device to model a lighting effect in the space. A method of control of modeled light sources in an augmented reality interface having a lighting space model of an environment in an augmented reality interface through which a user controls lights placed in the environment via virtual lighting control features presented in the augmented reality interface and having a color map to control a multi-channel light thereby producing consistent color across a range of color modes by adjusting a plurality of the channels based on the color map. A method of control of modeled light sources in an augmented reality interface having a lighting space model of an environment in an augmented reality interface through which a user controls lights placed in the environment via virtual lighting control features presented in the augmented reality interface and having a near field dataset characterizing a light source, generating a geometric model from the data set that facilitates modeling an impact of the light source on objects disposed in the near field. A method of control of modeled light sources in an augmented reality interface having a lighting space model of an environment in an augmented reality interface through which a user controls lights placed in the environment via virtual lighting control features presented in the augmented reality interface and having algorithms that construct three-dimensional illumination data sets from a plurality of distinct two-dimensional illumination data arrays that are captured throughout a near field space of a light source. A method of control of modeled light sources in an augmented reality interface having a lighting space model of an environment in an augmented reality interface through which a user controls lights placed in the environment via virtual lighting control features presented in the augmented reality interface and having a system for adapting light controls based on machine learning from data representing user activity including user time zone travel, user activities in an environment illuminated by a light being controlled, wearable sensor biomarker user data, and feedback from users in the environment. A method of control of modeled light sources in an augmented reality interface having a lighting space model of an environment in an augmented reality interface through which a user controls lights placed in the environment via virtual lighting control features presented in the augmented reality interface and having a rendering pipeline in a lighting design system that allocates rendering to devices in the pipeline based on a correspondence between the device rendering capability and a resolution of image content to be rendered. A method of control of modeled light sources in an augmented reality interface having a lighting space model of an environment in an augmented reality interface through which a user controls lights placed in the environment via virtual lighting control features presented in the augmented reality interface and having coordinated control of uplights and downlights to achieve a lighting effect in an environment that mimics a sky color for a given time of day.

A method of generating a data structure that characterizes the near field illumination pattern generated by a light source having use of an indirect illumination collection facility that is disposable throughout a three-dimensional region proximal to a light source that captures a plurality of multi-dimensional light source illumination images. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having a custom tuning profile that coordinates changes in color and light output of a programmable light source to match lighting characteristics of a legacy light fixture. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having an indirect illumination collection facility that captures near field multi-dimensional illumination indirectly from a light source by varying distance and orientation of the collection facility relative to the light source throughout the near field space of the light source. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having algorithms for calculating light quality, intensity, color range, and spectral characteristic metrics of a light source from illumination values collected at a plurality of theta and phi differentiated positions in the light source's near field space. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having a light source emulating device positioned by a user in a three-dimensional space that is presented in an augmented reality lighting design system that uses the position and orientation of the emulating device to model a lighting effect in the space. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having a color map to control a multi-channel light thereby producing consistent color across a range of color modes by adjusting a plurality of the channels based on the color map. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having a near field dataset characterizing a light source, generating a geometric model from the data set that facilitates modeling an impact of the light source on objects disposed in the near field. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having algorithms that construct three-dimensional illumination data sets from a plurality of distinct two-dimensional illumination data arrays that are captured throughout a near field space of a light source. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having a system for adapting light controls based on machine learning from data representing user activity including user time zone travel, user activities in an environment illuminated by a light being controlled, wearable sensor biomarker user data, and feedback from users in the environment. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having a rendering pipeline in a lighting design system that allocates rendering to devices in the pipeline based on a correspondence between the device rendering capability and a resolution of image content to be rendered. A method of generating a data structure that characterizes the near field illumination pattern generated by a light source having use of an indirect illumination collection facility that is disposable throughout a three-dimensional region proximal to a light source that captures a plurality of multi-dimensional light source illumination images and having coordinated control of uplights and downlights to achieve a lighting effect in an environment that mimics a sky color for a given time of day.

A system for enabling custom tuning a lighting object having a custom tuning profile that coordinates changes in color and light output of a programmable light source to match lighting characteristics of a legacy light fixture. A system for enabling custom tuning a lighting object having a custom tuning profile that coordinates changes in color and light output of a programmable light source to match lighting characteristics of a legacy light fixture and having an indirect illumination collection facility that captures near field multi-dimensional illumination indirectly from a light source by varying distance and orientation of the collection facility relative to the light source throughout the near field space of the light source. A system for enabling custom tuning a lighting object having a custom tuning profile that coordinates changes in color and light output of a programmable light source to match lighting characteristics of a legacy light fixture and having algorithms for calculating light quality, intensity, color range, and spectral characteristic metrics of a light source from illumination values collected at a plurality of theta and phi differentiated positions in the light source's near field space. A system for enabling custom tuning a lighting object having a custom tuning profile that coordinates changes in color and light output of a programmable light source to match lighting characteristics of a legacy light fixture and having a light source emulating device positioned by a user in a three-dimensional space that is presented in an augmented reality lighting design system that uses the position and orientation of the emulating device to model a lighting effect in the space. A system for enabling custom tuning a lighting object having a custom tuning profile that coordinates changes in color and light output of a programmable light source to match lighting characteristics of a legacy light fixture and having a color map to control a multi-channel light thereby producing consistent color across a range of color modes by adjusting a plurality of the channels based on the color map. A system for enabling custom tuning a lighting object having a custom tuning profile that coordinates changes in color and light output of a programmable light source to match lighting characteristics of a legacy light fixture and having a near field dataset characterizing a light source, generating a geometric model from the data set that facilitates modeling an impact of the light source on objects disposed in the near field. A system for enabling custom tuning a lighting object having a custom tuning profile that coordinates changes in color and light output of a programmable light source to match lighting characteristics of a legacy light fixture and having algorithms that construct three-dimensional illumination data sets from a plurality of distinct two-dimensional illumination data arrays that are captured throughout a near field space of a light source. A system for enabling custom tuning a lighting object having a custom tuning profile that coordinates changes in color and light output of a programmable light source to match lighting characteristics of a legacy light fixture and having a system for adapting light controls based on machine learning from data representing user activity including user time zone travel, user activities in an environment illuminated by a light being controlled, wearable sensor biomarker user data, and feedback from users in the environment. A system for enabling custom tuning a lighting object having a custom tuning profile that coordinates changes in color and light output of a programmable light source to match lighting characteristics of a legacy light fixture and having a rendering pipeline in a lighting design system that allocates rendering to devices in the pipeline based on a correspondence between the device rendering capability and a resolution of image content to be rendered. A system for enabling custom tuning a lighting object having a custom tuning profile that coordinates changes in color and light output of a programmable light source to match lighting characteristics of a legacy light fixture and having coordinated control of uplights and downlights to achieve a lighting effect in an environment that mimics a sky color for a given time of day.

A near-field characterization system having an indirect illumination collection facility that captures near field multi-dimensional illumination indirectly from a light source by varying distance and orientation of the collection facility relative to the light source throughout the near field space of the light source. A near-field characterization system having an indirect illumination collection facility that captures near field multi-dimensional illumination indirectly from a light source by varying distance and orientation of the collection facility relative to the light source throughout the near field space of the light source and having algorithms for calculating light quality, intensity, color range, and spectral characteristic metrics of a light source from illumination values collected at a plurality of theta and phi differentiated positions in the light source's near field space. A near-field characterization system having an indirect illumination collection facility that captures near field multi-dimensional illumination indirectly from a light source by varying distance and orientation of the collection facility relative to the light source throughout the near field space of the light source and having a light source emulating device positioned by a user in a three-dimensional space that is presented in an augmented reality lighting design system that uses the position and orientation of the emulating device to model a lighting effect in the space. A near-field characterization system having an indirect illumination collection facility that captures near field multi-dimensional illumination indirectly from a light source by varying distance and orientation of the collection facility relative to the light source throughout the near field space of the light source and having a color map to control a multi-channel light thereby producing consistent color across a range of color modes by adjusting a plurality of the channels based on the color map. A near-field characterization system having an indirect illumination collection facility that captures near field multi-dimensional illumination indirectly from a light source by varying distance and orientation of the collection facility relative to the light source throughout the near field space of the light source and having a near field dataset characterizing a light source, generating a geometric model from the data set that facilitates modeling an impact of the light source on objects disposed in the near field. A near-field characterization system having an indirect illumination collection facility that captures near field multi-dimensional illumination indirectly from a light source by varying distance and orientation of the collection facility relative to the light source throughout the near field space of the light source and having algorithms that construct three-dimensional illumination data sets from a plurality of distinct two-dimensional illumination data arrays that are captured throughout a near field space of a light source. A near-field characterization system having an indirect illumination collection facility that captures near field multi-dimensional illumination indirectly from a light source by varying distance and orientation of the collection facility relative to the light source throughout the near field space of the light source and having a system for adapting light controls based on machine learning from data representing user activity including user time zone travel, user activities in an environment illuminated by a light being controlled, wearable sensor biomarker user data, and feedback from users in the environment. A near-field characterization system having an indirect illumination collection facility that captures near field multi-dimensional illumination indirectly from a light source by varying distance and orientation of the collection facility relative to the light source throughout the near field space of the light source and having a rendering pipeline in a lighting design system that allocates rendering to devices in the pipeline based on a correspondence between the device rendering capability and a resolution of image content to be rendered. A near-field characterization system having an indirect illumination collection facility that captures near field multi-dimensional illumination indirectly from a light source by varying distance and orientation of the collection facility relative to the light source throughout the near field space of the light source and having coordinated control of uplights and downlights to achieve a lighting effect in an environment that mimics a sky color for a given time of day A method of near field metrics for evaluating light sources having algorithms for calculating light quality, intensity, color range, and spectral characteristic metrics of a light source from illumination values collected at a plurality of theta and phi differentiated positions in the light source's near field space. A method of near field metrics for evaluating light sources having algorithms for calculating light quality, intensity, color range, and spectral characteristic metrics of a light source from illumination values collected at a plurality of theta and phi differentiated positions in the light source's near field space and having a light source emulating device positioned by a user in a three-dimensional space that is presented in an augmented reality lighting design system that uses the position and orientation of the emulating device to model a lighting effect in the space. A method of near field metrics for evaluating light sources having algorithms for calculating light quality, intensity, color range, and spectral characteristic metrics of a light source from illumination values collected at a plurality of theta and phi differentiated positions in the light source's near field space and having a color map to control a multi-channel light thereby producing consistent color across a range of color modes by adjusting a plurality of the channels based on the color map. A method of near field metrics for evaluating light sources having algorithms for calculating light quality, intensity, color range, and spectral characteristic metrics of a light source from illumination values collected at a plurality of theta and phi differentiated positions in the light source's near field space and having a near field dataset characterizing a light source, generating a geometric model from the data set that facilitates modeling an impact of the light source on objects disposed in the near field. A method of near field metrics for evaluating light sources having algorithms for calculating light quality, intensity, color range, and spectral characteristic metrics of a light source from illumination values collected at a plurality of theta and phi differentiated positions in the light source's near field space and having algorithms that construct three-dimensional illumination data sets from a plurality of distinct two-dimensional illumination data arrays that are captured throughout a near field space of a light source. A method of near field metrics for evaluating light sources having algorithms for calculating light quality, intensity, color range, and spectral characteristic metrics of a light source from illumination values collected at a plurality of theta and phi differentiated positions in the light source's near field space and having a system for adapting light controls based on machine learning from data representing user activity including user time zone travel, user activities in an environment illuminated by a light being controlled, wearable sensor biomarker user data, and feedback from users in the environment. A method of near field metrics for evaluating light sources having algorithms for calculating light quality, intensity, color range, and spectral characteristic metrics of a light source from illumination values collected at a plurality of theta and phi differentiated positions in the light source's near field space and having a rendering pipeline in a lighting design system that allocates rendering to devices in the pipeline based on a correspondence between the device rendering capability and a resolution of image content to be rendered. A method of near field metrics for evaluating light sources having algorithms for calculating light quality, intensity, color range, and spectral characteristic metrics of a light source from illumination values collected at a plurality of theta and phi differentiated positions in the light source's near field space and having coordinated control of uplights and downlights to achieve a lighting effect in an environment that mimics a sky color for a given time of day.

A method of augmented reality-based lighting design having a light source emulating device positioned by a user in a three-dimensional space that is presented in an augmented reality lighting design system that uses the position and orientation of the emulating device to model a lighting effect in the space. A method of augmented reality-based lighting design having a light source emulating device positioned by a user in a three-dimensional space that is presented in an augmented reality lighting design system that uses the position and orientation of the emulating device to model a lighting effect in the space and having a color map to control a multi-channel light thereby producing consistent color across a range of color modes by adjusting a plurality of the channels based on the color map. A method of augmented reality-based lighting design having a light source emulating device positioned by a user in a three-dimensional space that is presented in an augmented reality lighting design system that uses the position and orientation of the emulating device to model a lighting effect in the space and having a near field dataset characterizing a light source, generating a geometric model from the data set that facilitates modeling an impact of the light source on objects disposed in the near field. A method of augmented reality-based lighting design having a light source emulating device positioned by a user in a three-dimensional space that is presented in an augmented reality lighting design system that uses the position and orientation of the emulating device to model a lighting effect in the space and having algorithms that construct three-dimensional illumination data sets from a plurality of distinct two-dimensional illumination data arrays that are captured throughout a near field space of a light source. A method of augmented reality-based lighting design having a light source emulating device positioned by a user in a three-dimensional space that is presented in an augmented reality lighting design system that uses the position and orientation of the emulating device to model a lighting effect in the space and having a system for adapting light controls based on machine learning from data representing user activity including user time zone travel, user activities in an environment illuminated by a light being controlled, wearable sensor biomarker user data, and feedback from users in the environment. A method of augmented reality-based lighting design having a light source emulating device positioned by a user in a three-dimensional space that is presented in an augmented reality lighting design system that uses the position and orientation of the emulating device to model a lighting effect in the space and having a rendering pipeline in a lighting design system that allocates rendering to devices in the pipeline based on a correspondence between the device rendering capability and a resolution of image content to be rendered. A method of augmented reality-based lighting design having a light source emulating device positioned by a user in a three-dimensional space that is presented in an augmented reality lighting design system that uses the position and orientation of the emulating device to model a lighting effect in the space and having coordinated control of uplights and downlights to achieve a lighting effect in an environment that mimics a sky color for a given time of day.

A method of producing a color tuning curve having a color map to control a multi-channel light thereby producing consistent color across a range of color modes by adjusting a plurality of the channels based on the color map. A method of producing a color tuning curve having a color map to control a multi-channel light thereby producing consistent color across a range of color modes by adjusting a plurality of the channels based on the color map and having a near field dataset characterizing a light source, generating a geometric model from the data set that facilitates modeling an impact of the light source on objects disposed in the near field. A method of producing a color tuning curve having a color map to control a multi-channel light thereby producing consistent color across a range of color modes by adjusting a plurality of the channels based on the color map and having algorithms that construct three-dimensional illumination data sets from a plurality of distinct two-dimensional illumination data arrays that are captured throughout a near field space of a light source. A method of producing a color tuning curve having a color map to control a multi-channel light thereby producing consistent color across a range of color modes by adjusting a plurality of the channels based on the color map and having a system for adapting light controls based on machine learning from data representing user activity including user time zone travel, user activities in an environment illuminated by a light being controlled, wearable sensor biomarker user data, and feedback from users in the environment. A method of producing a color tuning curve having a color map to control a multi-channel light thereby producing consistent color across a range of color modes by adjusting a plurality of the channels based on the color map and having a rendering pipeline in a lighting design system that allocates rendering to devices in the pipeline based on a correspondence between the device rendering capability and a resolution of image content to be rendered. A method of producing a color tuning curve having a color map to control a multi-channel light thereby producing consistent color across a range of color modes by adjusting a plurality of the channels based on the color map and having coordinated control of uplights and downlights to achieve a lighting effect in an environment that mimics a sky color for a given time of day.

A method of model-based rendering near-field effects of a light source having a near field dataset characterizing a light source, generating a geometric model from the data set that facilitates modeling an impact of the light source on objects disposed in the near field. A method of model-based rendering near-field effects of a light source having a near field dataset characterizing a light source, generating a geometric model from the data set that facilitates modeling an impact of the light source on objects disposed in the near field and having algorithms that construct three-dimensional illumination data sets from a plurality of distinct two-dimensional illumination data arrays that are captured throughout a near field space of a light source. A method of model-based rendering near-field effects of a light source having a near field dataset characterizing a light source, generating a geometric model from the data set that facilitates modeling an impact of the light source on objects disposed in the near field and having a system for adapting light controls based on machine learning from data representing user activity including user time zone travel, user activities in an environment illuminated by a light being controlled, wearable sensor biomarker user data, and feedback from users in the environment. A method of model-based rendering near-field effects of a light source having a near field dataset characterizing a light source, generating a geometric model from the data set that facilitates modeling an impact of the light source on objects disposed in the near field and having a rendering pipeline in a lighting design system that allocates rendering to devices in the pipeline based on a correspondence between the device rendering capability and a resolution of image content to be rendered. A method of model-based rendering near-field effects of a light source having a near field dataset characterizing a light source, generating a geometric model from the data set that facilitates modeling an impact of the light source on objects disposed in the near field and having coordinated control of uplights and downlights to achieve a lighting effect in an environment that mimics a sky color for a given time of day.

A method for characterizing a near field illumination effect of a light source having algorithms that construct three-dimensional illumination data sets from a plurality of distinct two-dimensional illumination data arrays that are captured throughout a near field space of a light source. A method for characterizing a near field illumination effect of a light source having algorithms that construct three-dimensional illumination data sets from a plurality of distinct two-dimensional illumination data arrays that are captured throughout a near field space of a light source and having a system for adapting light controls based on machine learning from data representing user activity including user time zone travel, user activities in an environment illuminated by a light being controlled, wearable sensor biomarker user data, and feedback from users in the environment. A method for characterizing a near field illumination effect of a light source having algorithms that construct three-dimensional illumination data sets from a plurality of distinct two-dimensional illumination data arrays that are captured throughout a near field space of a light source and having a rendering pipeline in a lighting design system that allocates rendering to devices in the pipeline based on a correspondence between the device rendering capability and a resolution of image content to be rendered. A method for characterizing a near field illumination effect of a light source having algorithms that construct three-dimensional illumination data sets from a plurality of distinct two-dimensional illumination data arrays that are captured throughout a near field space of a light source and having coordinated control of uplights and downlights to achieve a lighting effect in an environment that mimics a sky color for a given time of day.

A lighting control system having a system for adapting light controls based on machine learning from data representing user activity including user time zone travel, user activities in an environment illuminated by a light being controlled, wearable sensor biomarker user data, and feedback from users in the environment. A lighting control system having a system for adapting light controls based on machine learning from data representing user activity including user time zone travel, user activities in an environment illuminated by a light being controlled, wearable sensor biomarker user data, and feedback from users in the environment and having a rendering pipeline in a lighting design system that allocates rendering to devices in the pipeline based on a correspondence between the device rendering capability and a resolution of image content to be rendered. A lighting control system having a system for adapting light controls based on machine learning from data representing user activity including user time zone travel, user activities in an environment illuminated by a light being controlled, wearable sensor biomarker user data, and feedback from users in the environment and having coordinated control of uplights and downlights to achieve a lighting effect in an environment that mimics a sky color for a given time of day.

A method having a rendering pipeline in a lighting design system that allocates rendering to devices in the pipeline based on a correspondence between the device rendering capability and a resolution of image content to be rendered. A method having a rendering pipeline in a lighting design system that allocates rendering to devices in the pipeline based on a correspondence between the device rendering capability and a resolution of image content to be rendered and having coordinated control of uplights and downlights to achieve a lighting effect in an environment that mimics a sky color for a given time of day. A method of illumination in an environment having coordinated control of uplights and downlights to achieve a lighting effect in an environment that mimics a sky color for a given time of day.

Detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The terms "a" or "an," as used herein, are defined as one or more than one. The term "another," as used herein, is defined as at least a second or more. The terms "including" and/or "having," as used herein, are defined as comprising (i.e., open transition).

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like. The processor may be or may include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, Internet server, intranet server, cloud server, and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, Internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or intangible items from one state to another. The methods and systems described herein may also transform data representing physical and/or intangible items from one state to another.

The elements described and depicted herein, including in flowcharts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flowchart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium. The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples but is to be understood in the broadest sense allowable by law.

The use of the terms "a" and "an" and "the" and similar referents in the context of describing the disclosure (especially in the context of the following claims) is to be construed to cover both the singular and the plural unless otherwise indicated herein or clearly contradicted by context. The terms "comprising," "having," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one skilled in the art to make and use what is considered presently to be the best mode thereof, those skilled in the art will understand and appreciate the existence of variations, combinations, and equivalents of the specific embodiment, method, and examples herein. The disclosure should therefore not be limited by the above-described embodiment, method, and examples, but by all embodiments and methods within the scope and spirit of the disclosure.

Any element in a claim that does not explicitly state "means for" performing a specified function, or "step for" performing a specified function, is not to be interpreted as a "means" or "step" clause as specified in 35 U.S.C. § 112(f). In particular, any use of "step of" in the claims is not intended to invoke the provision of 35 U.S.C. § 112(f).

Persons skilled in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

We claim:

1. A method for characterizing a near field illumination effect of a light source, the method comprising:
capturing, and correlating with a distance- and orientation-specific location of a multi-dimensional image sensor set relative to a light source, a set of illumination values forming an image of the light source and including an illumination value for each one of a plurality of image sensing elements in the image sensor set, and repeating the capturing and correlating for a plurality of different distance- and orientation-specific locations of the image sensor set relative to the light source;

storing, in a processor accessible electronic memory, a plurality of the images of the light source each including a set of the illumination values and being correlated with a one of the plurality of distance- and orientation-specific locations;

producing a multi-dimensional representation of a near-field light distribution of the light source by processing the stored images and their correlated distance- and orientation-specific locations relative to the light source, utilizing a multi-dimensional near-field illumination reconstruction algorithm that defines a plurality of point sources that collectively represent the light source and that define relative contributions of each one of the point sources to the image of the light source; and storing the multi-dimensional representation in the processor accessible electronic memory.

2. The method of claim 1, wherein the multi-dimensional image sensor set is a two-dimensional array of the image sensing elements.

3. The method of claim 1, wherein the multi-dimensional representation includes four dimensions consisting of a first dimension of a two-dimensional array of the image sensing elements, a second dimension of the two-dimensional array of the image sensing elements, and two dimensions collectively representing illumination values of luminous flux from each of the point sources.

4. The method of claim 1, wherein the multi-dimensional representation includes five dimensions consisting of a first dimension of a two-dimensional array of the image sensing elements, a second dimension of the two-dimensional array of the image sensing elements, a value representing the distance- and orientation-specific location of the image sensor set relative to the light source, and two dimensions collectively representing illumination values of luminous flux from each of the point sources.

5. The method of claim 1, wherein producing the multi-dimensional representation includes applying the Kaczmarz method, numerical methods, machine learning methods, neural networks, or linear algebra.

6. The method of claim 1, wherein the multi-dimensional image sensor set includes a smartphone camera.

7. The method of claim 1, wherein producing the multi-dimensional representation includes producing a model of an illumination pattern of the light source.

8. The method of claim 1, further including controlling with the processor, the plurality of the distance- and orientation-specific locations of the multi-dimensional image sensor set relative to the light source.

9. The method of claim 1, wherein the capturing includes capturing a light pattern visible on a secondary side of a translucent intermediate screen disposed between the light source and the image sensor set.

10. The method of claim 7, wherein producing the model of the illumination pattern of the light source includes recognizing a presence of an additional light source, and wherein producing the multi-dimensional representation includes determining relative contributions of the light source and the additional light source to the illumination values of the image sensor set for a plurality of different distance- and orientation-specific locations of the image sensor set relative to the light sources.

11. A method for characterizing a near field illumination effect of a light source, the method comprising:

capturing, and correlating with a distance- and orientation-specific location of a multi-dimensional image sensor set relative to a light source, a set of illumination values forming an image of the light source and including an illumination value for each one of a plurality of image sensing elements in the image sensor set, and repeating the capturing and correlating for a plurality of different distance- and orientation-specific locations of the image sensor set relative to the light source;

storing, in a processor accessible electronic memory, a plurality of the images of the light source each including a set of the illumination values and being correlated with a one of the plurality of distance- and orientation-specific locations;

producing a multi-dimensional representation of a near-field light distribution of the light source by processing the stored images and their correlated distance- and orientation-specific locations relative to the light source, utilizing a multi-dimensional near-field illumination reconstruction algorithm that generates a volume data set linking one or more illumination values in one or more ones of the stored images with one or more other illumination values in one or more other ones of the stored images to facilitate processing the resulting volume data set; and storing the multi-dimensional representation in the processor accessible electronic memory.

12. The method of claim 11, wherein the multi-dimensional image sensor set is a two-dimensional array of the image sensing elements.

13. The method of claim 11, wherein the multi-dimensional representation includes four dimensions consisting of a first dimension of a two-dimensional array of the image sensing elements, a second dimension of the two-dimensional array of the image sensing elements, and two dimensions collectively representing luminous flux of the linked illumination values of the volume data set.

14. The method of claim 11, wherein the multi-dimensional representation includes five dimensions consisting of a first dimension of a two-dimensional array of the image sensing elements, a second dimension of the two-dimensional array of the image sensing elements, a value representing the distance- and orientation-specific location of the image sensor set relative to the light source, and two dimensions collectively representing luminous flux of the linked illumination values of the volume data set.

15. The method of claim 11, wherein producing the multi-dimensional representation includes applying the Kaczmarz method, numerical methods, machine learning methods, neural networks, or linear algebra.

16. The method of claim 11, wherein the multi-dimensional image sensor set includes a smartphone camera.

17. The method of claim 11, wherein producing the multi-dimensional representation includes producing a model of an illumination pattern of the light source.

18. The method of claim 11, further including controlling with the processor, the plurality of the distance- and orientation-specific locations of the multi-dimensional image sensor set relative to the light source.

19. The method of claim 11, wherein the capturing includes capturing a light pattern visible on a secondary side of a translucent intermediate screen disposed between the light source and the image sensor set.

20. The method of claim 17, wherein producing the model of the illumination pattern of the light source includes recognizing a presence of an additional light source, and wherein producing the multi-dimensional representation includes determining relative contributions of the light source and the additional light source to the illumination values of the image sensor set for a plurality of different distance- and orientation-specific locations of the image sensor set relative to the light sources.

\* \* \* \* \*